US011780834B2

(12) United States Patent
Chung et al.

(10) Patent No.: US 11,780,834 B2
(45) Date of Patent: Oct. 10, 2023

(54) SOLID FORMS OF 3-((1R,3R)-1-(2,6-DIFLUORO-4-((1-(3-FLUOROPROPYL)AZETIDIN-3-YL)AMINO)PHENYL)-3-METHYL-1,3,4,9-TETRAHYDRO-2H-PYRIDO[3,4-B]INDOL-2-YL)-2,2-DIFLUOROPROPAN-1-OL AND PROCESSES FOR PREPARING FUSED TRICYCLIC COMPOUNDS COMPRISING A SUBSTITUTED PHENYL OR PYRIDINYL MOIETY, INCLUDING METHODS OF THEIR USE

(71) Applicants: Hoffmann-La Roche Inc., Little Falls, NJ (US); GENENTECH, INC., South San Francisco, CA (US)

(72) Inventors: Cheol Keun Chung, South San Francisco, CA (US); Jie Xu, South San Francisco, CA (US); Hans Iding, Basel (CH); Kyle Clagg, South San Francisco, CA (US); Michael Dalziel, South San Francisco, CA (US); Alec Fettes, Basel (CH); Francis Gosselin, South San Francisco, CA (US); Ngiap-Kie Lim, South San Francisco, CA (US); Andrew McClory, South San Francisco, CA (US); Haiming Zhang, South San Francisco, CA (US); Paroma Chakravarty, South San Francisco, CA (US); Karthik Nagapudi, South San Francisco, CA (US); Sarah Robinson, South San Francisco, CA (US)

(73) Assignees: Genentech, Inc., South San Francisco, CA (US); Hoffmann-La Roche Inc., Little Falls, NJ (US)

(*) Notice: Subject to any disclaimer, the term of this patent is extended or adjusted under 35 U.S.C. 154(b) by 143 days.

(21) Appl. No.: 17/110,607

(22) Filed: Dec. 3, 2020

(65) Prior Publication Data
US 2022/0041587 A1 Feb. 10, 2022

Related U.S. Application Data

(62) Division of application No. 16/443,515, filed on Jun. 17, 2019, now Pat. No. 10,954,234.

(60) Provisional application No. 62/719,896, filed on Aug. 20, 2018, provisional application No. 62/687,930, filed on Jun. 21, 2018.

(51) Int. Cl.
C07D 471/04 (2006.01)
C07D 403/14 (2006.01)

(52) U.S. Cl.
CPC ......... C07D 471/04 (2013.01); C07D 403/14 (2013.01); C07B 2200/13 (2013.01)

(58) Field of Classification Search
CPC .. C07D 471/04; C07D 403/14; C07D 205/04; C07D 209/14; C07D 401/12; C07B 2200/13; A61P 35/00; A61K 31/437; C07C 213/10; C07C 215/08; C07C 253/32; C07C 255/26; C07C 2601/02
See application file for complete search history.

(56) References Cited

U.S. PATENT DOCUMENTS

| | | | |
|---|---|---|---|
| 5,206,377 A | 4/1993 | McAfee et al. | |
| 5,635,528 A | 6/1997 | Audia et al. | |
| 5,861,425 A | 1/1999 | Audia et al. | |
| 6,951,961 B2 | 10/2005 | Protopopova et al. | |
| 8,053,442 B2 | 11/2011 | Ang et al. | |
| 8,133,992 B2 | 3/2012 | Martin et al. | |
| 8,703,810 B2 | 4/2014 | Kahraman et al. | |
| 8,853,423 B2 | 10/2014 | Govek et al. | |
| 9,139,821 B2 | 9/2015 | Nazor et al. | |
| 9,292,307 B2 | 3/2016 | Yamamoto | |
| 9,388,395 B2 | 7/2016 | Nazor et al. | |
| 9,598,712 B2 | 3/2017 | Crowe et al. | |
| 9,708,588 B2 | 7/2017 | Nazor et al. | |
| 2005/0282849 A1 | 12/2005 | Moon et al. | |
| 2007/0254878 A1 | 11/2007 | Cao et al. | |
| 2008/0064683 A1 | 3/2008 | Cao et al. | |
| 2010/0249153 A1 | 9/2010 | Tandon et al. | |
| 2013/0116232 A1 | 5/2013 | Kahraman et al. | |
| 2013/0137746 A1 | 5/2013 | Govek et al. | |
| 2014/0364427 A1 | 12/2014 | Smith et al. | |
| 2016/0090377 A1 | 3/2016 | Govek et al. | |
| 2016/0090378 A1 | 3/2016 | Kahraman et al. | |
| 2016/0175284 A1 | 6/2016 | Labadie et al. | |
| 2016/0175289 A1 | 6/2016 | Labadie et al. | |

FOREIGN PATENT DOCUMENTS

| | | |
|---|---|---|
| CA | 2485909 | 12/2003 |
| EP | 2682119 | 1/2014 |
| GB | 2122617 A1 | 1/1984 |
| RU | 2387652 C2 | 4/2010 |
| RU | 014873 B1 | 2/2011 |

(Continued)

OTHER PUBLICATIONS

Wuts, P.G.M., Greene's Protective Groups in Organic Synthesis, Chapter 4, Fourth Edition, 2007 p. 431-532; p. 431 and 439 excerpt provided.*

(Continued)

Primary Examiner — John M Mauro
(74) Attorney, Agent, or Firm — GENENTECH, INC.; Kevin M. Clark

(57) ABSTRACT

Provided herein are solid forms, salts, and formulations of 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol, processes and synthesis thereof, and methods of their use in the treatment of cancer.

72 Claims, 31 Drawing Sheets
Specification includes a Sequence Listing.

(56) References Cited

FOREIGN PATENT DOCUMENTS

| | | |
|---|---|---|
| SU | 665804 A3 | 5/1979 |
| WO | 2002/062339 A1 | 8/2002 |
| WO | 2002/064590 A2 | 8/2002 |
| WO | 2003/099821 A1 | 12/2003 |
| WO | 2004/089470 A1 | 10/2004 |
| WO | 2005/034857 A2 | 4/2005 |
| WO | 2005/089764 A1 | 9/2005 |
| WO | 2006/015035 A1 | 2/2006 |
| WO | 2007/002051 A1 | 1/2007 |
| WO | 2007/077570 A1 | 7/2007 |
| WO | 2008/127714 A1 | 10/2008 |
| WO | 2008/127715 A1 | 10/2008 |
| WO | 2010/013758 A1 | 2/2010 |
| WO | 2010/015815 A2 | 2/2010 |
| WO | 2010/015816 A2 | 2/2010 |
| WO | 2010/029313 A1 | 3/2010 |
| WO | 2010/049678 A2 | 5/2010 |
| WO | 2010/075282 A1 | 7/2010 |
| WO | 2010/075286 A1 | 7/2010 |
| WO | 2010/107485 A1 | 9/2010 |
| WO | 2010/138652 A1 | 12/2010 |
| WO | 2010/138659 A1 | 12/2010 |
| WO | 2010/138685 A1 | 12/2010 |
| WO | 2010/138695 A1 | 12/2010 |
| WO | 2010/138706 A1 | 12/2010 |
| WO | 2010/138758 A1 | 12/2010 |
| WO | 2015/082990 A1 | 6/2011 |
| WO | 2011/150162 A1 | 12/2011 |
| WO | 2011/156518 A2 | 12/2011 |
| WO | 2011/159769 A2 | 12/2011 |
| WO | 2012/084711 A1 | 6/2012 |
| WO | 2013/090829 A1 | 6/2013 |
| WO | 2013/090836 A1 | 6/2013 |
| WO | 2014/083529 A1 | 6/2014 |
| WO | 2014/183532 A1 | 11/2014 |
| WO | 2014/191726 A1 | 12/2014 |
| WO | 2014/205136 A1 | 12/2014 |
| WO | 2015/039348 A1 | 3/2015 |
| WO | 2015/066019 A1 | 5/2015 |
| WO | 2015/136016 A2 | 9/2015 |
| WO | 2015/136017 A1 | 9/2015 |
| WO | 2015/197861 A1 | 12/2015 |
| WO | 2016/097071 A1 | 6/2016 |
| WO | 2016/097072 A1 | 6/2016 |
| WO | 2016/097073 A1 | 6/2016 |
| WO | 2017/059139 A1 | 4/2017 |
| WO | 2017/136688 A1 | 8/2017 |
| WO | 2017/216280 A1 | 12/2017 |
| WO | WO-2017216279 A1 * | 12/2017 ......... A61K 31/4355 |
| WO | 2019/245974 A1 | 12/2019 |

OTHER PUBLICATIONS

Baselga, J., et al., "Everolimus in Postmenopausal Hormone-Receptor-Positive Advanced Breast Cancer" New Engl J Med 366(6):520-529 (Feb. 9, 2012).
Bentrem et al., "Molecular Mechanism of Action at Estrogen Receptor α of a New Clinically Relevant Antiestrogen (GW7604) Related to Tanoxifen" Endocrinology 142(2):838-846 (Feb. 1, 2001).
Blizzard et al., "Estrogen receptor ligands. Part 14: Application of novel antagonist side chains to exisiting platforms" Bioorg Med Chem Lett 15(23):5124-5128 (Dec. 1, 2005).
CAS Registry Database, CAS Reg. No. 404925-92-4, pp. 1 (CAS Registry Database, CAS Reg. No. 404925-92-4 Apr. 10, 2002).
CAS Registry Database, CAS Reg. No. 404930-10-5, pp. 1 (CAS Registry Database, CAS Reg. No. 404930-10-5 Apr. 10, 2002).
Chatman, L., et al., "A Strategy for Risk Management of Drug-Induced Phospholipids" Toxicol Pathol 37:997-1005 (Dec. 14, 2009).
Dardes, R. et al., "Effects of a New Clinically Relevant Antiestrogen (GW5638) Related to Tamoxifen on Breast and Endometrial Cancer Growth in Vivo [1]" Clin Cancer Res 88(6):1995-2001 (Jun. 1, 2002).
Di Leo, A., et al., "Results of the Confirm Phase III Trial Comparing Fulvestrant 250 mg With Fluvestrant 500 mg in Postmenopausal Women With Estrogen Receptor—Positive Advanced Breast Cancer" J Clin Oncol 28(30):4594-4600 (Sep. 20, 2010).
"International Search Report—PCT/US2019/037492":1-19 (dated Sep. 20, 2019).
Jones, W., et al., "Pharmaceutical CoCrystals: An Emerging Approach to Physical Property Enhancement" MRS BULL 31:875-879 (Nov. 1, 2006).
Komm, B., et al., "An Overview of Current and Emerging SERMs" J Steroid Biochem Mol Biol 143:207-222 (Mar. 22, 2014).
Li, Shunqiang, et al., "Endocrine-Therapy-Resistant ESR 1 Variants Revealed by Genomic Charcterization of Breast-Cancer-Derived Xenografts" Cell Reports 4(6):1116-1130 (Sep. 26, 2013).
Lumachi, F., "Treatment of Estrogen Receptor-Positive Breast Cancer" Curr Med Chem 20(5):596-604 (Jan. 1, 2013).
Miller et al., "Hyperactivation oh phosphatidylinositol-3 kinase promotes escape from hormone dependence in estrogen receptor-positive human breast cancer" J Clin Invest 120(7):2406-2413 (Jul. 2010).
Mueller M., et al., "Regulation of vascular endothelial growth factor (VEGF) gene transcription by estrogen receptors a and b" PNAS 97(20):10972-10977 (Sep. 26, 2000).
Reasor, M., et al., "Drug-induced phospholipidosis: issues and future directions" Expert Opin Drug Saf 5(4):567-583 (Jul. 1, 2006).
Robinson, D., et al., "Activating ESR1 mutations in hormone-resistant metastatic breast cancer" Nat Genet 45(12):1446-1453 (Dec. 1, 2013).
Segal, C.V., et al., "Estrogen Receptor Mutations in Breast Cancer—New Focus on an Old Target" Clin Cancer Res 20(7):1724-1726 (Apr. 1, 2014).
Shewale, S., et al., "Pharmaceutical Cocrystals: Design, Development and Characterization" Am J Pharmatech Res 5(4):90-107 (Jan. 1, 2015).
Toy et al., "ESR 1 ligand-binding domain mutations in hormone-resistant breast cancer" Nat Genet 45(12):1439-45 (Dec. 2013).
Van Tine, B., et al., "Understanding the Estrogen Receptor-Positive Breast Cancer Genome: Not Even the End of the Beginning" J Natl Cancer I 103(7):1-2 (Apr. 6, 2011).
Willson, T., et al., "3-[4-(1,2-Diphenylbut-1-enyl) phenyl]acrylic Acid: A Non-Steroidal Estrogen with Functional Selectivity for Bone Over Uterus in Rats" J Med Chem 37(11):1550-1552 (May 27, 1994).
Zanardi, E., et al., "Better Together: Targeted Combination Therapies in Breast Cancer" Semin Oncol 42(6):887-895 (Dec. 1, 2015).
Zhang, C., et al., "Facile Formation of Cyclic Animals through Brønsted Acid-Promoted Redox Process" J Org Chem 74(1):419-422 (Jan. 2, 2009).
Belikov, V.G. Pharmaceutical Chemistry—Tutorial "Part I: General Pharmaeutical Chemistry" (Extract—Eng. Translation), Fourth, Revised edition, Moscow-RU:MEDPress-Inform,:27-29 ( 2007).
Caira, M.R. Design of Organic Solids—Topics in Chemistry "Chapter 5: Crystalline Polymorphism of Organic Compounds" Weber, E., Aoyama, Y., Caira, M.R., eds., Berlin, Heidelberg-DE:Springer, vol. 198:163-208 (Jan. 1, 1998).
Dyson, G., et al. Chemistry of Synthetic Medicinial Substances (Russian w/Eng. Translation), Moscow::12-19 (Jan. 1, 1964).
Melentieva, G.A. et al. Medicine "Pharmaceutical Chemistry: Sources and Reasons of Poor Quality of Medicinal Substances. General Requirements to Pharmaceutical Preparations with Regard to Purity Thereof" (Russian w/Eng. Transl.), Moscow, Russia:Med Press Inform,:21-23 ( 1985).
Sarma, B., et al., "Solid forms of pharmaceuticals: Polymorphs, salts and cocrystals" Korean J Chem Eng 28(2):315-322 (Jan. 31, 2011).
Serajuddon, A., "Salt Formation to Imrpove Drug Stability" Adv Drug Deliv Rev 59(7):603-616 (Jul. 30, 2007).

* cited by examiner

SOLID FORMS OF 3-((1R,3R)-1-(2,6-DIFLUORO-4-((1-(3-FLUOROPROPYL)AZETIDIN-3-YL)AMINO)PHENYL)-3-METHYL-1,3,4,9-TETRAHYDRO-2H-PYRIDO[3,4-B]INDOL-2-YL)-2,2-DIFLUOROPROPAN-1-OL AND PROCESSES FOR PREPARING FUSED TRICYCLIC COMPOUNDS COMPRISING A SUBSTITUTED PHENYL OR PYRIDINYL MOIETY, INCLUDING METHODS OF THEIR USE

CROSS REFERENCE TO RELATED APPLICATIONS

This application is a divisional of U.S. application Ser. No. 16/443,515, filed Jun. 17, 2019, which claims the benefit of U.S. Provisional Patent Application No. 62/687,930, filed Jun. 21, 2018, and U.S. Provisional Patent Application No. 62/719,896, filed Aug. 20, 2018, each of which is incorporated herein by reference in its entirety and for all purposes.

SEQUENCE LISTING

This application incorporates by reference a Sequence Listing submitted with this application as text file entitled P34807US3_SeqList.txt created on Nov. 4, 2020 and having a size of 16.5 kilobytes.

FIELD OF THE INVENTION

Provided herein are solid forms of 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol, and methods of their use in the treatment of cancer. Further described herein are processes for preparing fused tricyclic compounds comprising a substituted phenyl or pyridinyl moiety.

BACKGROUND

Fused tricyclic compounds comprising a substituted phenyl or pyridinyl moiety within the scope of the present disclosure are useful as estrogen receptor ("ER") targeting agents.

The ER is a ligand-activated transcriptional regulatory protein that mediates induction of a variety of biological effects through its interaction with endogenous estrogens. Endogenous estrogens include 17β (beta)-estradiol and estrones. ER has been found to have two isoforms, ER-α (alpha) and ER-β (beta). Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions. ER-α targeting agents have particular activity in the setting of metastatic disease and acquired resistance. ER-α targeting agents are disclosed in U.S. Publication Number 2016/0175289.

Useful processes for preparing fused tricyclic compounds comprising a substituted phenyl or pyridinyl moiety are disclosed in U.S. Publication Number 2016/0175289. However, there is a need for improved processes for preparing ER-α targeting agents.

There exists significant complexity surrounding the identification and selection of a solid form of a pharmaceutical compound. The differences in solid forms of such compounds affects both physical and chemical properties and may alter the processing, stability, bioavailability, formulation, and storage of pharmaceutical compounds. There is no reliable predictability of the solid form and its usefulness as a crystalline solid or amorphous solid. Crystalline solids may be considered useful, for example, for physical or chemical stability whereas amorphous solids may be considered useful, for example, for enhanced dissolution and increased bioavailability.

Mixtures of crystalline materials arises from polymorphism. It is not possible to predict, a priori, if crystalline forms of a compound exist, much less whether crystalline forms can be prepared or isolated. Jones et al., 2006, Pharmaceutical Cocrystals: An Emerging Approach to Physical Property Enhancement," MRS Bulletin 31:875-879 (At present it is not generally possible to computationally predict the number of observable polymorphs of even the simplest molecules). The number of possible solid forms results in differing chemical and physical properties for a pharmaceutical compound and can greatly affect development, stability, and marketing of the product.

The estrogen receptor ("ER") is a ligand-activated transcriptional regulatory protein that mediates induction of a variety of biological effects through its interaction with endogenous estrogens. Endogenous estrogens include 17β (beta)-estradiol and estrones. ER has been found to have two isoforms, ER-α (alpha) and ER-β (beta). Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions. There is a need for new ER-α targeting agents that have activity in the setting of metastatic disease and acquired resistance. Accordingly, there remains a need for cancer therapies having particular solid forms.

SUMMARY

Provided herein are solutions to the problems above and other problems in the art.

In one aspect provided herein is a compound, Compound B, having the name 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol tartrate, as described herein.

In another aspect provided herein is a crystal form of Compound B having an X-ray powder diffraction pattern comprising peaks at 19.32, 20.26, 21.63, 23.28, or 24.81±0.1° 2θ (±0.1° 2θ).

In another aspect provided herein is a crystal form of Compound B having an X-ray powder diffraction pattern comprising peaks at 11.49, 12.54, 19.16, 19.42, or 24.67±0.1° 2θ (±0.1° 2θ).

In another aspect provided herein is a crystal form of Compound B having an X-ray powder diffraction pattern substantially as shown in FIG. 10 or FIG. 14.

In another aspect provided herein is a crystal form of Compound B having an X-ray powder diffraction pattern comprising peaks at 11.31, 15.70, 16.54, 19.10, or 22.76±0.1° 2θ.

In another aspect provided herein is a crystal form of Compound B having an X-ray powder diffraction pattern comprising peaks at 12.52, 15.90, 19.66, 20.65, or 24.99±0.1° 2θ.

In another aspect provided herein is a crystal form of Compound B having an X-ray powder diffraction pattern comprising peaks at 11.46, 12.51, 19.29, 19.42, or 20.23±0.1° 2θ.

In another aspect provided herein is an amorphous solid comprising Compound A.

Further provided herein are pharmaceutical compositions comprising Compound B or a crystal salt thereof. Such compounds and pharmaceutical compositions can be used in methods of treating cancer as set forth herein.

In another aspect provided herein is a process for preparing a compound of formula (IV) or a salt thereof as set forth herein. The process comprises (1) reacting a reaction mixture comprising a compound of formula (I) as described herein, an organic solvent and thionyl chloride to form a compound of formula (IIa) as described herein and (2) reacting a reaction mixture comprising the compound of formula (IIa), a catalyst, an oxidant and a solvent to form a compound of formula (II) as described herein. The process further comprises reacting a reaction mixture comprising the compound of formula (II) and a compound of formula (III) as described herein in an organic solvent to form a compound of formula (IV) or a salt thereof as described herein.

In another aspect provided herein is a process for preparing a compound of formula (VIII) or a pharmaceutically acceptable salt thereof as described herein. The process comprises reacting a reaction mixture comprising a compound of formula (IV) as described herein, a compound of formula (V) as described herein or a compound of formula (X) as described herein, and an organic solvent to form a compound of formula (VI) as described herein. The process further comprises reacting a reaction mixture comprising the compound of formula (VI), an organic solvent, and a compound of formula (VII) as described herein or a salt thereof to form a compound of formula (VIII) or a salt thereof.

In another aspect provided herein is a process for preparing a compound of formula (VIII) or a pharmaceutically acceptable salt thereof as described herein. The process comprises reacting a reaction mixture comprising a compound of formula (IX) as described herein or a compound of formula (X) as described herein, a compound of formula (IV) as described herein and an organic solvent to form the compound of formula (VIII) or a salt thereof as described herein.

In still another aspect provided herein is a process for preparing a compound of formula (IX) or a salt thereof as described herein. The process comprises reacting a reaction mixture comprising a compound of formula (X) as described herein, a compound of formula (VII), or a salt thereof, as described herein an organic solvent and a catalyst to form a compound of formula (XI) or a salt thereof as described herein.

In yet another aspect provided herein is a process for preparing a compound of formula (III) or a salt thereof as described herein. The process comprises reacting a reaction mixture comprising a compound of formula (XII) s described herein, a compound B and an organic solvent to form the compound of formula (XIII) as described herein.

In yet another aspect provided herein is a compound of formula (XVI) as described herein.

Still further provided herein is a process for preparing a compound having formula (XX) is provided, where the process comprises contacting a compound of formula (XXI) as described herein with a protein transaminase to form a compound of formula (3). The compound of formula (3) is contacted with a compound of formula (II) as described herein to form compound formula (XX).

The present embodiments can be understood more fully by reference to the detailed description and examples, which are intended to exemplify non-limiting embodiments.

DETAILED DESCRIPTION

Figure 1:
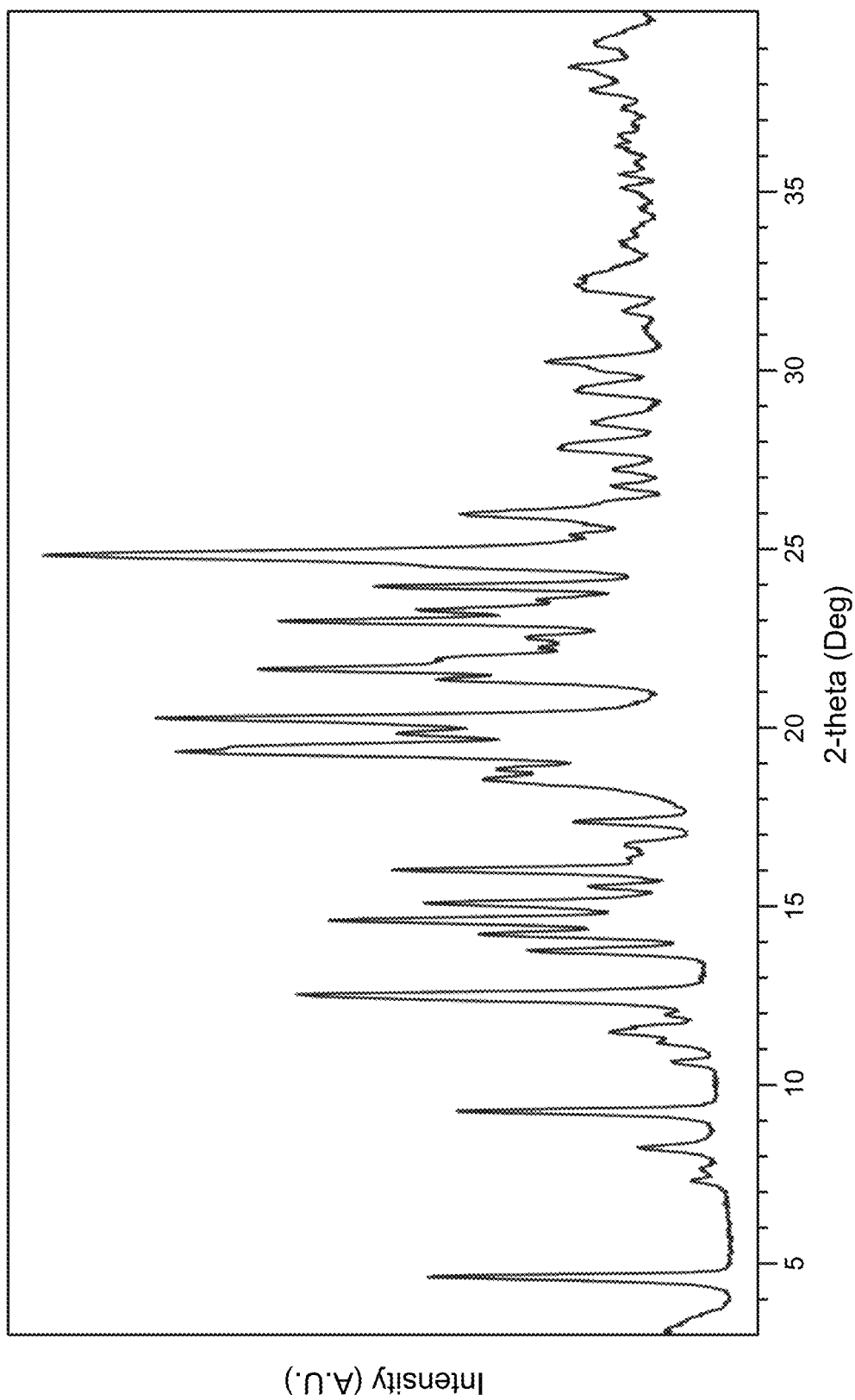
FIG. 1 depicts the XRPD pattern for Compound B Form A.

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

As used herein, and unless otherwise specified, the terms "about" and "approximately," when referring to a numeric value or range of values used for characterization of a particular solid form described herein (e.g., XRPD peak values) indicate that the value or range of values may deviate from a given value to an extent deemed reasonable to one of ordinary skill in the art while still describing the solid form. In one embodiment, the value of an XRPD peak position may vary by up to ±0.1° 2θ (or 0.05 degree 2θ) while still describing the particular XRPD peak.

As used herein, and unless otherwise specified, a crystalline that is "pure," i.e., substantially free of other crystalline or amorphous solids or other chemical compounds, and contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by, for example, diffraction analysis, thermal analysis, elemental combustion analysis and/or spectroscopic analysis. The detection of other chemical compounds can be accomplished by, for example, mass spectrometry analysis, spectroscopic analysis, thermal analysis, elemental combustion analysis and/or chromatographic analysis.

Unless otherwise specified, the terms "solvate" and "solvated," as used herein, refer to a solid form of a substance which contains solvent. The terms "hydrate" and "hydrated" refer to a solvate wherein the solvent is water. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

The term "pharmaceutically acceptable," refers to a diluent, excipient, or carrier in a formulation compatible with the other ingredient(s) of the formulation and not deleterious to the recipient thereof.

Compound A refers to the compound having the structure:

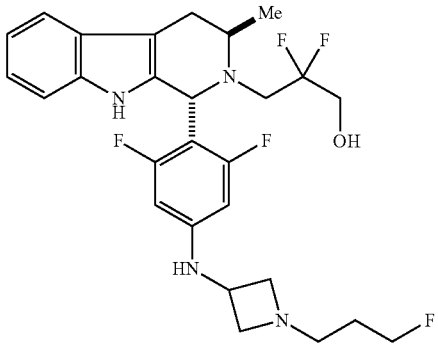

and having the name 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol, including a pharmaceutically acceptable salt thereof. Compound A can be a tartaric acid salt as described herein (e.g. Compound B). Compound A can be a fumaric acid salt as described herein (e.g. Compound C). Compound A can be a malonate salt as described herein (e.g. Compound D).

The term "solid form" refers to a physical form which is not predominantly in a liquid or a gaseous state. A solid form may be a crystalline form or a mixture thereof. In certain embodiments, a solid form may be a liquid crystal. In certain embodiments, the solid form of Compound A is Form A, Form B, Form C, Form D, Form E, Form F, Form G, Form 1, or Form 2, an amorphous solid, or a mixture thereof. In one embodiment, the solid form of Compound A is a tartrate salt. In another embodiment, the solid form of Compound A is a fumarate salt or a mixture thereof. A solid form may be a crystal form as defined herein.

The term "crystal form" or "crystalline form" refers to a solid form that is crystalline. In certain embodiments, a crystal form of a compound described herein may be substantially free of amorphous solids and/or other crystal forms. In certain embodiments, a crystal form of a compound described herein may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous solids and/or other crystal forms. In certain embodiments, a crystal form described herein is pure. In certain embodiments, a crystal form of a compound described herein may be about 99%, 98%, 97%, 96%, 95%, 94%, 93%, 92%, 91%, or 90% pure.

The term "amorphous" or "amorphous solid" refers to a solid form that not substantially crystalline as determined by X-ray diffraction. In particular, the term "amorphous solid"

describes a disordered solid form, i.e., a solid form lacking long range crystalline order. In certain embodiments, an amorphous solid of a compound described herein may be substantially free of other amorphous solids and/or crystal forms. In certain embodiments, an amorphous solid may be pure. In certain embodiments, an amorphous solid of a compound described herein may be about 99%, 98%, 97%, 96%, 95%, 94%, 93%, 92%, 91%, or 90% pure.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a cancer.

The term "effective amount" or "therapeutically effective amount" refers to an amount of a compound described herein capable of treating or preventing a disorder, disease or condition, or symptoms thereof, disclosed herein.

"Patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like, in one embodiment a mammal, in another embodiment a human. In one embodiment, a subject is a human having or at risk for cancer.

As used herein, the terms "moiety" and "substituent" refer to an atom or group of chemically bonded atoms that is attached to another atom or molecule by one or more chemical bonds thereby forming part of a molecule.

As used herein, the term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms. Alkyl groups may be optionally substituted independently with one or more substituents described herein.

As used herein, the term "substituted" refers to the replacement of at least one of hydrogen atom of a compound or moiety with another substituent or moiety. Examples of such substituents include, without limitation, halogen, —OH, —CN, oxo, alkoxy, alkyl, alkylene, aryl, heteroaryl, haloalkyl, haloalkoxy, cycloalkyl and heterocycle. For example, the term "haloalkyl" refers to the fact that one or more hydrogen atoms of an alkyl (as defined below) is replaced by one or more halogen atoms (e.g., trifluoromethyl, difluoromethyl, fluoromethyl, chloromethyl, etc.). In one embodiment, substituted as used herein can refer to replacement of at least one hydrogen atom of a compound or moiety described herein with halogen or alkyl.

As used herein, the term "alkylene" as used herein refers to a linear or branched saturated divalent hydrocarbon radical of one to twelve carbon atoms, and in another aspect one to six carbon atoms, wherein the alkylene radical may be optionally substituted independently with one or more substituents described herein. Examples include, but are not limited to, methylene, ethylene, propylene, 2-methylpropylene, pentylene, and the like.

As used herein, the term "alkoxy" refers to a group of the formula —O—R', wherein R' is an alkyl group. Alkoxy groups may be optionally substituted independently with one or more substituents described herein. Examples of alkoxy moieties include methoxy, ethoxy, isopropoxy, and tert-butoxy.

As used herein, the term "aryl" refers to a cyclic aromatic hydrocarbon moiety having a mono-, bi- or tricyclic aromatic ring of 5 to 16 carbon ring atoms. Bicyclic aryl ring systems include fused bicyclics having two fused five-membered aryl rings (denoted as 5-5), having a five-membered aryl ring and a fused six-membered aryl ring (denoted as 5-6 and as 6-5), and having two fused six-membered aryl rings (denoted as 6-6). The aryl group can be optionally substituted as defined herein. Examples of aryl moieties include, but are not limited to, phenyl, naphthyl, phenanthryl, fluorenyl, indenyl, pentalenyl, azulenyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted.

As used herein, the term "heteroaryl" refers to an aromatic heterocyclic mono-, bi- or tricyclic ring system of 5 to 16 ring atoms, comprising 1, 2, 3 or 4 heteroatoms selected from N, O and S, the remaining ring atoms being carbon. In some embodiments, monocyclic heteroaryl rings may be 5-6 membered. Bicyclic heteroaryl ring systems include fused bicyclics having two fused five-membered heteroaryl rings (denoted as 5-5), having a five-membered heteroaryl ring and a fused six-membered heteroaryl ring (denoted as 5-6 and 6-5), and having two fused six-membered heteroaryl rings (denoted as 6-6). The heteroaryl group can be optionally substituted as defined herein. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, benzothiophenyl, indolyl, aza-indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, pyrrolopyridinyl, furopyridinyl, thienopyridinyl, pyrrolopyridazinyl, pyrrolopyrimidinyl, pyrrolopyrazinyl, thienopyridazinyl, thienopyrimidinyl, thienopyrazinyl, furopyridazinyl, furopyrimidinyl, and furopyrazinyl.

As used herein, the terms "halo", "halogen" and "halide", which may be used interchangeably, refer to a substituent fluorine, chlorine, bromine, or iodine.

As used herein, the term "haloalkyl" refers to an alkyl group wherein one or more of the hydrogen atoms of the alkyl group has been replaced by the same or different halogen atoms, particularly fluorine and/or chlorine atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl or trifluoromethyl.

As used herein, the term "hydroxyalkyl" refers to an alkyl group wherein one or more of the hydrogen atoms of the alkyl group have been replaced by a hydroxyl moiety. Examples include alcohols and diols As used herein, the term "heteroalkyl" refers to a straight- or branched-chain alkyl as defined herein having from 2 to 14 carbons, from 2 to 10 carbons, or from 2 to 6 carbons in the chain, one or more of which has been replaced by a heteroatom selected from S, O, P and N. Non-limiting examples of heteroalkyls include alkyl ethers, secondary and tertiary alkyl amines, amides, and alkyl sulfides.

As used herein, the term "cycloalkyl" means a saturated or partially unsaturated carbocyclic moiety having mono-, bi- (including bridged bicyclic) or tricyclic rings and 3 to 10 carbon atoms in the ring. The cycloalkyl moiety can optionally be substituted with one or more substituents. In particular embodiments cycloalkyl contains from 3 to 8 carbon atoms (i.e., ($C_3$-$C_8$)cycloalkyl). In other particular embodiments cycloalkyl contains from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl), bicyclo[3.1.0]hexanyl, bicyclo[3.1.0]hexenyl, bicyclo[3.1.1]heptanyl, and bicyclo[3.1.1]heptenyl. The cycloalkyl moiety can be attached in a "spirocycloalkyl" fashion such as "spirocyclopropyl":

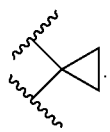 [SMILES: *C1(*)CC1]

As used herein, the terms "heterocycle" or "heterocyclyl" refer to a 4, 5, 6 and 7-membered monocyclic, 7, 8, 9 and 10-membered bicyclic (including bridged bicyclic) or 10, 11, 12, 13, 14 and 15-membered bicyclic heterocyclic moiety that is saturated or partially unsaturated, and has one or more (e.g., 1, 2, 3 or 4 heteroatoms selected from oxygen, nitrogen and sulfur in the ring with the remaining ring atoms being carbon. In some embodiments, the heterocycle is a heterocycloalkyl. In particular embodiments heterocycle or heterocyclyl refers to a 4, 5, 6 or 7-membered heterocycle. When used in reference to a ring atom of a heterocycle, a nitrogen or sulfur may also be in an oxidized form, and a nitrogen may be substituted with one or more ($C_1$-$C_6$)alkyl or groups. The heterocycle can be attached to its pendant group at any heteroatom or carbon atom that results in a stable structure. Any of the heterocycle ring atoms can be optionally substituted with one or more substituents described herein. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, azabicyclo[2.2.1]heptanyl, azabicyclo[3.1.0]hexanyl, azabicyclo[3.1.1]heptanyl, octahydroindolyl, or tetrahydroquinolinyl.

Unless otherwise indicated, the term "hydrogen" or "hydro" refers to the moiety of a hydrogen atom (—H) and not $H_2$.

As used herein, the term "organic solvent" refers to any non-aqueous polar aprotic solvent, polar protic solvent, and non-polar solvent.

As used herein, the term "polar organic solvent" refers to both polar aprotic solvents and polar protic solvents, excluding water.

As used herein, the term "polar aprotic solvent" refers to any polar solvent not having a proton-donating ability. Examples include, without any limitation, 2-methyltetrahydrofuran, tetrahydrofuran, ethyl acetate, propyl acetate (e.g., isopropyl acetate), acetone, dimethylsulfoxide, N,N-dimethylformamide, acetonitrile, N,N-dimethylacetamide, N-methylpyrrolidone, hexamethylphosphoramide, and propylene carbonate.

As used herein, the term "polar protic solvent" refers to any polar solvent having a proton-donating ability. Examples include, without limitation, methanol, ethanol, 1-propanol, 2-propanol, 1-butanol, formic acid, nitromethane and acetic acid. An organic polar protic solvent excludes any effective amount of water.

As used herein, the term "non-polar solvent" refers to solvents that contain bonds between atoms with similar electronegativities, such as carbon and hydrogen, such that the electric charge on the molecule is evenly distributed. Non-polar solvents are characterized as having a low dielectric constant. Examples include, without limitation, pentane, hexane, heptane, cyclopentane, methyl tert-butyl ether (MTBE), diethyl ether, toluene, benzene, 1,4-dioxane, carbon tetrachloride, chloroform and dichloromethane (DCM). In some embodiments, the non-polar solvent has a dielectric constant of less than 2, examples of which include, without limitation, pentane, hexane and heptane. As compared to other non-polar solvents, DCM exhibits some degree of polarity at the bond level (i.e., between carbon and chlorine), but only a small degree of polarity at the molecular level due to symmetry-based cancellation of polarity.

As used herein, the term "anti-solvent" refers to a solvent in which the referenced compound is poorly soluble and which induces precipitation or crystallization of said compound from solution.

As used herein, the term "acid catalyst" refers to an acid catalyst such as, but not limited to, a Brönsted acid, a Lewis acid or a Brönsted-Lowry catalyst. Non-limiting examples of acid catalysts include acetic acid, glacial acetic acid, trifluoroacetic acid, benzoic acid, pivalic acid, diphenyl phosphoric acid, triflic acid, formic acid, tartaric acid, fumaric acid, malonic acid, salicyclic acid, p-toluene sulfonic acid, sulfuric acid, hydrochloric acid, phosphoric acid, methanesulfonic acid, camphor sulfonic acid, naphthalene sulfonic acid, clay-based montmorillonite K-10 and resin based amberlyst, and combinations thereof.

As used herein, the term "amine protecting group" refers to any known protecting group that that blocks or protects the functionality of amines. Amine protecting groups within the scope of the disclosure include, without limitation, 1-chloroethyl carbamate (ACD); 4-methoxybenzenesulfonamide; acetamide (Ac); benzylamine (Bn); benzyloxy carbamate (CBz); formamide; methyl carbamate; trifluoroacetamide; tert-butoxy carbamate (Boc); p-methoxybenzyl carbonyl (MeOZ); 9-fluorenylmethoxycarbonyl (FMOC); bezoyl (Bz); p-methoxybenzyl (PMB); 3,4-dimethoxybenzyl (DMPM); p-methoxyphenyl (PMP); Tosyl (Ts); and trichloroethyl chloroformate (Troc). For a description of amine protecting groups and their use, see P. G. M. Wuts and T. W. Greene, Greene's Protective Groups in Organic Synthesis 4$^{th}$ edition, Wiley-Interscience, New York, 2006

As used herein, the term "aldehyde protecting group" refers to any known substituent attached to an aldehyde group that blocks or protects the carbonyl group of the aldehyde functionality. Suitable protecting groups of the aldehyde functionality include, but are not limited to (a) cyclic acetals and ketals, (b) cyclic mono or di-thio acetals or ketals or other derivatives such as imines, hydrazones, cyanohydrin, oximes or semicarbazones, for example, dialkyl or diaryl acetals or 1,3 dithiane, (c) cyclic imines such as substituted methylene derivatives or N,N'-dimethylimidazolidine. Some non-limiting examples of aldehyde protecting groups include 1,3-dithiane, 1,3-dithiolane, diethyl acetal, dimethyl acetal, ethylene glycol acetal, neopentyl glycol acetal, trimethylsilyl cyanohydrin, and trialkyl orthoformates such as triethyl orthoformate. For a description of aldehyde protecting groups and their use, see, Wuts and Greene.

As used herein, "leaving group" refers to an atom or a group of atoms that is displaced in a chemical reaction as stable species. Suitable leaving groups are well known in the art, e.g., see, March's Advanced Organic Chemistry, 5.sup.th Ed., Ed.: Smith, M. B. and March, J., John Wiley & Sons, New York: 2001 and T. W. Greene, *Protective Groups in Organic Synthesis*, John Wiley & Sons, New York, 1991, the entire contents of each are hereby incorporated by reference. Such leaving groups include, but are not limited to, halogen, alkoxy, sulphonyloxy, optionally substituted alkylsulphonyl, optionally substituted alkenylsulfonyl, optionally substituted arylsulfonyl, and diazonium moieties. Examples of some leaving groups include chloro, iodo, bromo, fluoro, methanesulfonyl (mesyl), tosyl, triflate, nitro-phenylsulfonyl (nosyl), and bromo-phenylsulfonyl (brosyl).

"Transition metal catalysts" within the scope of the disclosure include, without limitation, palladium, platinum, gold, ruthenium, rhodium, and iridium catalysts. Non-limiting examples of suitable catalysts include: (2-Biphenyl)di-tert-butylphosphine gold(I) chloride ("JohnPhos"), 2-Dicyclohexylphosphino-2',4',6'-triisopropylbiphenyl gold(I) chloride ("XPhos AuCl"), 2-Dicyclohexylphosphino-2',4',6'-triisopropylbiphenyl gold(I) bis(trifluoromethanesulfonyl)imide ("XPhos AuNTf2"), Chloro(2-dicyclohexylphosphino-2',4',6'-triisopropyl-1,1'-biphenyl)[2-(2-aminoethyl)phenyl)]palladium(II) ("XPhos Palladacycle"), Chloro(2-dicyclohexylphosphino-2',6'-dimethoxy-1,1'-biphenyl)[2-(2-aminoethylphenyl)]palladium(II)-methyl-t-butyl ether adduct ("SPhos Palladacycle"), t-BuXPhos palladium(II) phenethylamine chloride ("tBuXPhos Pd G1"), Chloro(2-dicyclohexylphosphino-2',4',6'-triisopropyl-1,1'-biphenyl)[2-(2'-amino-1,1'-biphenyl)]palladium(II) ("Xphos Pd G2"), Chloro(2-dicyclohexylphosphino-2',6'-dimethoxy-1,1'-biphenyl)[2-(2'-amino-1,1'-biphenyl)]palladium(II) ("SPhos Pd G2"), Chloro(2-dicyclohexylphosphino-2',6'-diisopropoxy-1,1'-biphenyl)[2-(2'-amino-1,1'-biphenyl)]palladium(II) ("RuPhos Pd G2"), Chloro[(2-dicyclohexylphosphino-2',6'-bis(N,N-dimethylamino)-1,1'-biphenyl)-2-(2'-amino-1,1'-biphenyl)]palladium(II) ("CPhos-Pd-G2"), [(2-Dicyclohexylphosphino-2',6'-bis(N,N-dimethylamino)-1,1'-biphenyl)-2-(2'-amino-1,1'-biphenyl)]palladium(II) methanesulfonate ("CPhos-Pd-G3"), [(2-Di-tert-butylphosphino-2',4',6'-triisopropyl-1,1'-biphenyl)-2-(2'-amino-1,1'-biphenyl)]palladium(II)methanesulfonate ("tBuXPhos-Pd-G3"), (2-Dicyclohexylphosphino-2',6'-diisopropoxy-1,1'-biphenyl)[2-(2'-amino-1,1'-biphenyl)]palladium(II) methanesulfonate ("RuPhos-Pd-G3"), (2-Dicyclohexylphosphino-2',4',6'-triisopropyl-1,1'-biphenyl)[2-(2'-amino-1,1'-biphenyl)]palladium(II) methanesulfonate ("XPhos-Pd-G3"), [(2-Di-cyclohexylphosphino-3,6-dimethoxy-2',4',6'-triisopropyl-1,1'-biphenyl)-2-(2'-amino-1,1'-biphenyl)]palladium(II) methanesulfonate ("BrettPhos-Pd-G3"), [(2-{Bis[3,5-bis(trifluoromethyl)phenyl]phosphine-3,6-dimethoxy-2',4',6'-triisopropyl-1,1'-biphenyl)-2-(2'-amino-1,1'-biphenyl)]palladium(II) methanesulfonate ("JackiePhos-Pd-G3"), tert-butyl BrettPhos-Pd-G3, [tert-butyl BrettPhos-Pd (allyl)]OTf), and combinations thereof.

As used herein, "inorganic acids" refer to acids such as, but not limited to, hydrochloric acid, hydrobromic acid, hydroiodic acid, sulfuric acid, sulfamic acid, nitric acid, boric acid, phosphoric acid, and combinations thereof.

As used herein, "organic acids" refer to acids such as, but not limited to: acetic acid; trifluoroacetic acid; phenylacetic acid; propionic acid; stearic acid; lactic acid; ascorbic acid; maleic acid; hydroxymaleic acid; isethionic acid; succinic acid; valeric acid; fumaric acid; malonic acid; pyruvic acid; oxalic acid; glycolic acid; salicylic acid; oleic acid; palmitic acid; lauric acid; a pyranosidyl acid, such as glucuronic acid or galacturonic acid; an alpha-hydroxy acid, such as mandelic acid, citric acid, or tartaric acid; cysteine sulfinic acid; an amino acid, such as aspartic acid, glutaric acid or glutamic acid; an aromatic acid, such as benzoic acid, 2-acetoxybenzoic acid, naphthoic acid, or cinnamic acid; a sulfonic acid, such as laurylsulfonic acid, p-toluenesulfonic acid, methanesulfonic acid, benzenesulfonic acid or ethanesulfonic acid; cysteine sulfonic acid; and combinations thereof.

As used herein, "inorganic bases" refer to bases such as, but not limited to, sodium hydroxide, potassium hydroxide, lithium hydroxide, ammonium hydroxide, magnesium hydroxide, sodium carbonate, potassium carbonate, and combinations thereof.

As used herein, the term "organic base" refers to an organic compound containing one or more nitrogen atoms, and which acts as a base. Examples of organic bases include, but are not limited to, tertiary amine bases. Examples of organic bases include, but are not limited to, 1,8-Diazabicyclo[5.4.0]undec-7-ene ("DBU"), N-methyl-morpholine (NMM), diisopropylethylamine (DIPEA), triethylamine (TEA), a t-butoxide (e.g., sodium, potassium, calcium or magnesium tert-butoxide).

Compounds of the present disclosure may present in a salt form which encompasses pharmaceutically acceptable salts and non-pharmaceutically acceptable salts. As used herein, the term "pharmaceutically acceptable salts" refers to those salts which retain the biological effectiveness and properties of the free bases or free acids, which are not biologically or otherwise undesirable. In addition to pharmaceutically acceptable salts, the compounds of the present disclosure may be in the form of non-pharmaceutically acceptable salts which can be useful as an intermediate for isolating or purifying said compounds.

Exemplary acid salts of the compounds of the present disclosure include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Exemplary base salts of the compounds of the present disclosure include, but are not limited to, inorganic salts formed from sodium, potassium, ammonium, calcium, magnesium, iron, zinc, copper, manganese, and aluminum cations. Organic salts formed from cations including primary, secondary, and tertiary amines; substituted amines including naturally occurring substituted amines; cyclic amines; basic ion exchange resins; isopropylamine; trimethylamine; diethylamine; trimethylamine; tripropylamine; ethanolamine; 2-diethylaminoethanol; trimethamine; dicyclohexylamine; lysine; arginine; histidine; caffeine; procaine; hydrabamine; choline; betaine; ethylenediamine; glucosamine; methylglucamine; theobromine; purines; piperazine; piperidine; N-ethylpiperidine; and polyamine resins.

The compounds of the present disclosure can also be solvated, i.e. hydrated. The solvation can be effected in the course of the manufacturing process or can take place i.e. as a consequence of hygroscopic properties of an initially anhydrous compounds. As herein, "solvate" refers to an association or complex of one or more solvent molecules and a compound of the invention. Non-limiting examples of solvents that form solvates include, but are not limited to, water, isopropanol, ethanol, methanol, DMSO, ethyl acetate (EtOAc), acetic acid (AcOH), and ethanolamine.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present disclosure possess asymmetric carbon atoms (optical centers) or double bonds; the racemates, diastereomers, regioisomers and individual isomers (e.g., separate enantiomers) are all intended to be encompassed within the scope of the present disclosure.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Many organic compounds exist in optically active forms, i.e., they have the ability to rotate the plane of plane polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative while stereochemistry is definitively established, such as from x-ray crystallographic data.

As used herein, "essentially" refers to at least 90%, at least 95%, at least 98% or at least 99%.

In the description herein, if there is a discrepancy between a depicted structure and a name given to that structure, then the depicted structure controls. Additionally, if the stereochemistry of a structure or a portion of a structure is not indicated with, for example, bold wedged, or dashed lines, the structure or portion of the structure is to be interpreted as encompassing all stereoisomers of it. In some cases, however, where more than one chiral center exists, the structures and names may be represented as single enantiomers to help describe the relative stereochemistry.

Unless otherwise indicated, the terms "a compound of the formula" or "a compound of formula" or "compounds of the formula" or "compounds of formula" refer to any compound selected from the genus of compounds as defined by the formula (including any pharmaceutically acceptable salt of any such compound if not otherwise noted).

In one aspect provided herein is a process for preparing a compound of formula (IV), or a salt thereof:

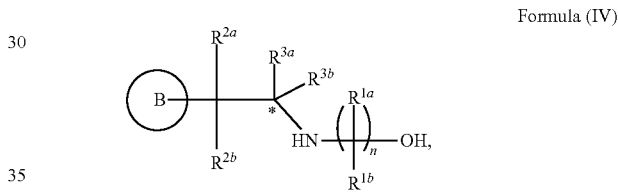

Formula (IV)

where the process comprises the steps:
(a) reacting a reaction mixture comprising a compound of formula (I), an organic solvent and thionyl chloride to form a compound of formula (IIa) according to step 1 below, and reacting a reaction mixture comprising the compound of formula (IIa), a catalyst, an oxidant and a solvent to form a compound of formula (II) according to step 2 below

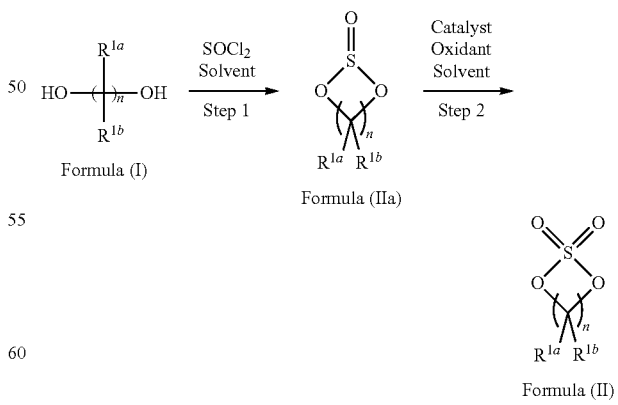

wherein
each of $R^{1a}$ and $R^{1b}$ is independently hydrogen, halogen, $C_{1-3}$ alkyl, $C_{1-3}$ haloalkyl, $C_{1-3}$ alkoxy, —CN, $C_{3-6}$ cycloalkyl, or $C_{3-6}$ spirocycloalkyl, and n is an integer of 2 or 3; and (b) reacting a reaction mixture comprising the compound of formula (II) and a compound of formula (III) in an organic solvent to form a compound of formula (IV) or a salt thereof according to step 3 below

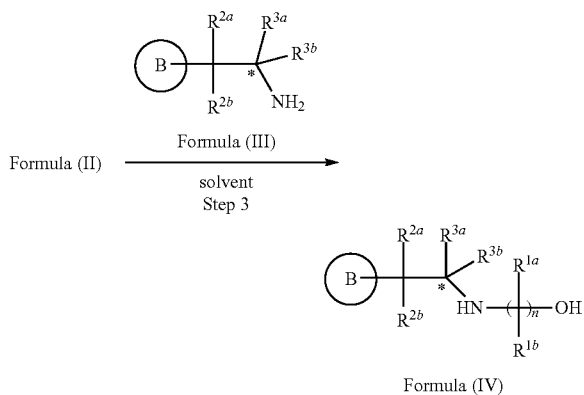

wherein B is substituted or unsubstituted indolyl, benzofuranyl, benzothiophenyl, indazolyl, aza-indolyl, benzimidazolyl, pyrrolopyridinyl, furopyridinyl, thienopyridinyl, pyrrolopyridazinyl, pyrrolopyrimidinyl, pyrrolopyrazinyl, thienopyridazinyl, thienopyrimidinyl, thienopyrazinyl, furopyridazinyl, furopyrimidinyl, or furopyrazinyl, each of $R^{2a}$ and $R^{2b}$ is independently hydrogen, halogen, —OH, $C_{1-3}$ alkyl, $C_{1-3}$ haloalkyl, $C_{1-3}$ alkoxy, $C_{1-3}$ hydroxyalkyl, —CN, $C_{3-6}$ cycloalkyl, or $C_{3-6}$ spirocycloalkyl, $R^{3a}$ and $R^{3b}$ are independently hydrogen, $C_{1-3}$ alkyl, $C_{1-3}$ haloalkyl, $C_{1-3}$ hydroxyalkyl, —CN, $C_{3-6}$ cycloalkyl, $C_{3-6}$ heterocycloalkyl, phenyl, $C_{3-6}$ heteroaryl, or $C_{3-6}$ spirocycloalkyl, and the asterisk represents a chiral center when $R^{3a}$ and $R^{3b}$ are different.

In one embodiment, B is substituted indolyl, benzofuranyl, benzothiophenyl, indazolyl, aza-indolyl, benzimidazolyl, pyrrolopyridinyl, furopyridinyl, thienopyridinyl, pyrrolopyridazinyl, pyrrolopyrimidinyl, pyrrolopyrazinyl, thienopyridazinyl, thienopyrimidinyl, thienopyrazinyl, furopyridazinyl, furopyrimidinyl, or furopyrazinyl.

In another embodiment, B is unsubstituted indolyl, benzofuranyl, benzothiophenyl, indazolyl, aza-indolyl, benzimidazolyl, pyrrolopyridinyl, furopyridinyl, thienopyridinyl, pyrrolopyridazinyl, pyrrolopyrimidinyl, pyrrolopyrazinyl, thienopyridazinyl, thienopyrimidinyl, thienopyrazinyl, furopyridazinyl, furopyrimidinyl, or furopyrazinyl.

In one embodiment, B is a substituted or unsubstituted indolyl, benzofuranyl, or benzothiophenyl. In another embodiment, B is a indolyl, benzofuranyl, or benzothiophenyl substituted with one or more halogen or $C_{1-3}$ alkyl as described herein. In still another embodiment, B is a substituted or unsubstituted pyrrolopyridazinyl, pyrrolopyrimidinyl, or pyrrolopyrazinyl. In another embodiment, B is a pyrrolopyridazinyl, pyrrolopyrimidinyl, or pyrrolopyrazinyl substituted with one or more halogen or $C_{1-3}$ alkyl as described herein. In yet another embodiment, B is a substituted or unsubstituted indolyl. In one preferred embodiment, B is unsubstituted indolyl. In one embodiment, B is substituted indolyl (e.g. substituted with one or more halogen or $C_{1-3}$ alkyl as described herein). In another preferred embodiment, B is substituted indolyl comprising substitution with at least one moiety selected from the group consisting of methyl, Cl, and F. In still another embodiment, B is a benzofuranyl or a substituted benzofuranyl comprising substitution with at least one moiety selected from the group comprising methyl, Cl, and Fl.

B may suitably be substituted with one or two substituents independently selected from the group consisting of fluorine, chlorine, $C_{1-3}$ alkyl, $C_{1-3}$ haloalkyl, —CN, —OH, $C_{1-3}$ alkoxy and $C_{1-3}$ hydroxyalkyl. In one embodiment, B is indolyl substituted with halogen (e.g. F or Cl).

In one embodiment, $R^{1a}$ and $R^{1b}$ are each independently hydrogen, halogen, $C_{1-3}$ alkyl, $C_{1-3}$ haloalkyl, $C_{1-3}$ alkoxy, —CN, or $C_{3-6}$ cycloalkyl. In another embodiment, $R^{1a}$ and $R^{1b}$ are each independently hydrogen, —F, —Cl, —OH, —CN, —CH$_3$, —CF$_3$, —CHF$_2$, —CH$_2$F, or spirocyclopropyl. In one embodiment, $R^{1a}$ and $R^{1b}$ are independently F or hydrogen. In a preferred embodiment, $R^{1a}$ and $R^{1b}$ are each independently hydrogen, —F, or —CH$_3$. In another preferred embodiment, $R^{1a}$ and $R^{1b}$ are each independently hydrogen, —F, or cyclopropyl. In one embodiment, n is 3.

In one embodiment:

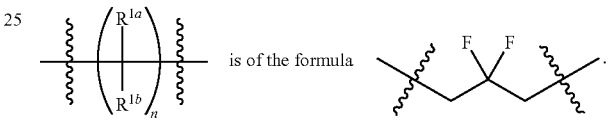

$R^{2a}$ and $R^{2b}$ are each independently hydrogen, halogen, —OH, $C_{1-3}$ alkyl, $C_{1-3}$ haloalkyl, $C_{1-3}$ alkoxy, $C_{1-3}$ hydroxyalkyl, —CN, or $C_{3-6}$ cycloalkyl. In some embodiments, $R^{2a}$ and $R^{2b}$ are each hydrogen. In one embodiment, $R^{1a}$ and $R^{1b}$ are each independently —F or CH$_3$ and $R^{2a}$ and $R^{2b}$ are each independently hydrogen. In one embodiment, B is a indolyl, benzofuranyl, or benzothiophenyl, $R^{1a}$ and $R^{1b}$ are each independently —F or CH$_3$, and $R^{2a}$ and $R^{2b}$ are each independently hydrogen.

$R^{3a}$ and $R^{3b}$ are each independently hydrogen, $C_{1-3}$ alkyl, $C_{1-3}$ haloalkyl, $C_{1-3}$ hydroxyalkyl, —CN, $C_{3-6}$ cycloalkyl, $C_{3-6}$ heterocycloalkyl, phenyl, or $C_{3-6}$ heteroaryl. In one embodiment, $R^{3a}$ and $R^{3b}$ are each independently hydrogen or —CH$_3$.

The asterisk in formula (IV) represents a chiral center when $R^{3a}$ and $R^{3b}$ are different. In some embodiments, therefore, $R^{3a}$ and $R^{3b}$ are different and are hydrogen or —CH$_3$.

In one embodiment, the compound of formula (I) is:

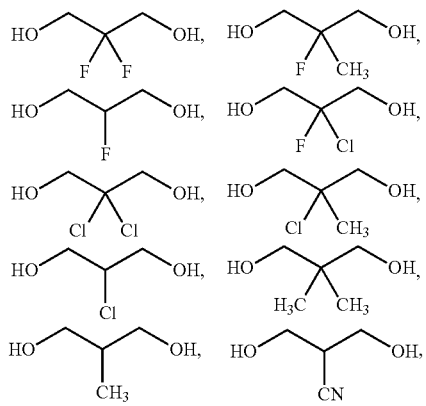

-continued

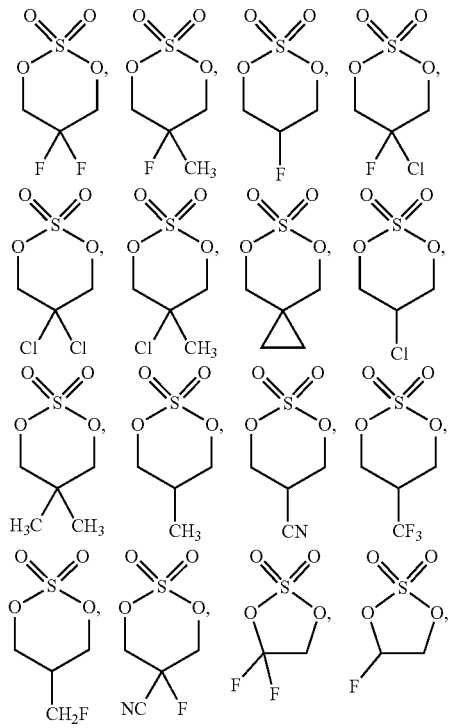

including stereoisomers thereof.

In a particular embodiment, the compound of formula (I) is:

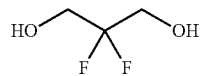
(1)

In another embodiment, the compound of formula (I) is:

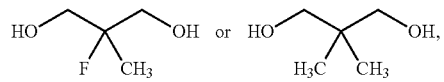

including stereoisomers thereof.

In one embodiment, the compound of formula (II) is:

-continued

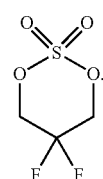 or 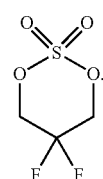

including stereoisomers thereof.

In a particular embodiment, formula (II) is:

(2)

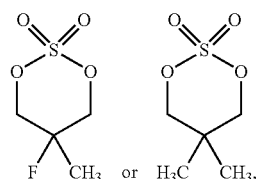

In some particular embodiments, the compound of formula (II) is:

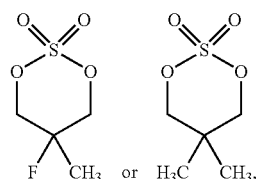

including stereoisomers thereof.

In one embodiment, the compound of formula (III) is:

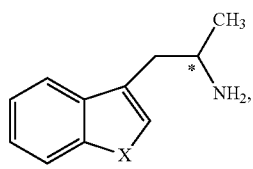

including stereoisomers thereof, where X is —NH—, —N—$C_1$-$C_3$ unsubstituted alkyl, —O— or —S—.

In a particular embodiment, the compound of formula (III) is:

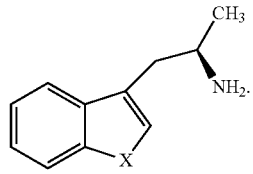

In another particular embodiment, the compound of formula (III) is:

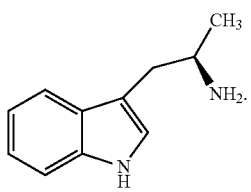
(3)

In one embodiment, the compound of formula (IV) is:

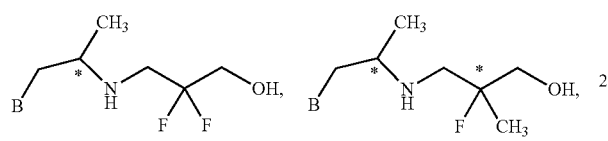
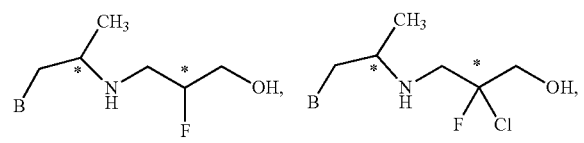
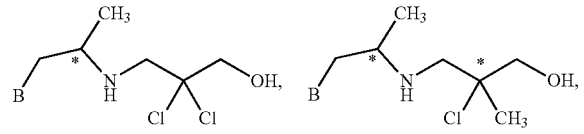
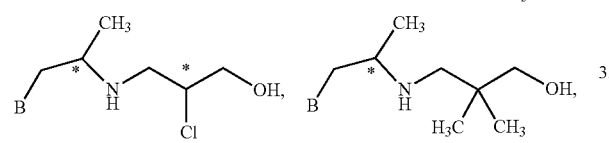
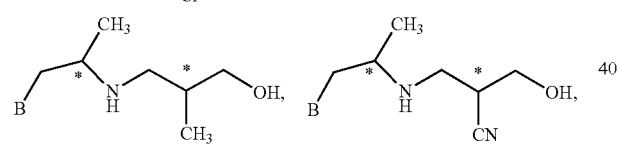
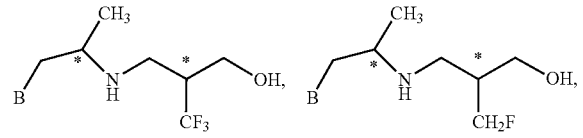
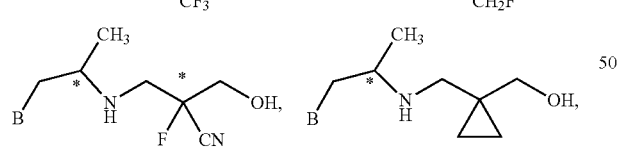
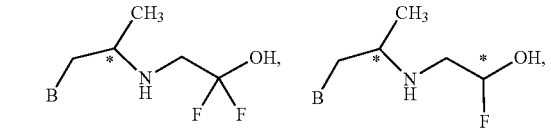
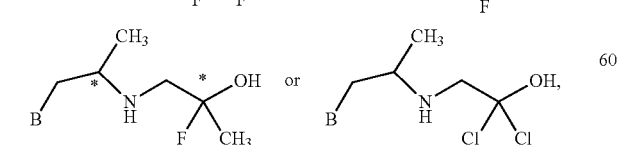

or salt thereof, including stereoisomers thereof; and wherein the asterisk denotes a chiral center.

In a particular embodiment, formula (IV) is:

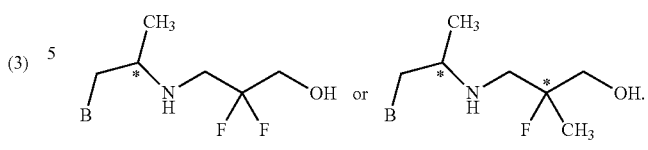

In another particular embodiment, formula (IV) is:

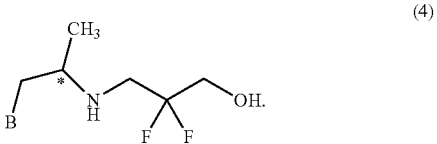
(4)

In a particular embodiment, the compound of formula (I) is:

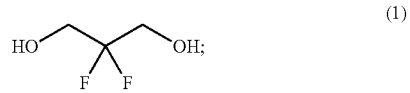
(1)

the compound of formula (II) is

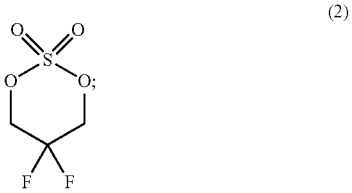
(2)

the compound of formula (III) is

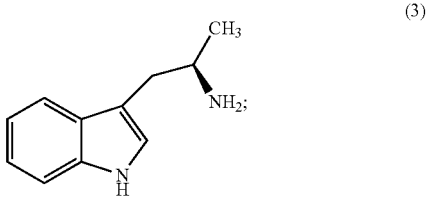
(3)

and
the compound of formula (IV) is

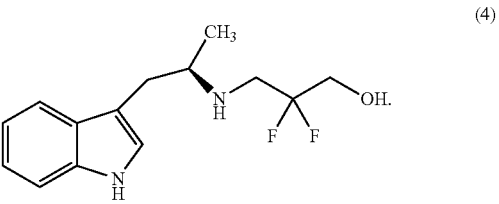 [SMILES: C[C@H](Cc1c[nH]c2ccccc12)NCC(F)(F)CO]
(4)

In step 1, a reaction mixture comprising a compound of formula (I), an organic solvent and thionyl chloride is reacted to form a compound of formula (IIa). In one embodiment, the compound of formula (I) is compound 1. In one embodiment, the organic solvent is a non-polar solvent or a polar solvent. In one embodiment, the solvent is non-polar. Non-limiting examples of suitable non-polar solvents include pentane, cyclopentane, hexane, cyclohexane, benzene, toluene, 1,4-dioxane, chloroform, diethyl ether, dichloromethane ("DCM"), and combinations thereof. In one embodiments, the solvent is DCM. In one embodiment, the concentration of formula (I) in the solvent may suitably be about 25 g/L, about 50 g/L, about 100 g/L, about 150 g/L, about 200 g/L, about 250 g/L, and up to a concentration approaching saturation at the reaction temperature, and ranges constructed from those concentrations, such as from about 100 g/L to about 250 g/L. The equivalent ratio of thionyl chloride to the compound of formula (I) is suitably about 1:1, about 1.1:1, about 1.2:1, about 1.3:1, about 1.5:1 or about 2:1, and ranges constructed from those ratios, such as from about 1.1:1 to about 1.5:1. In one embodiment, the reaction temperature is below the reaction mixture reflux temperature. In one embodiment, the reaction is run at reflux. For instance, where the solvent is DCM, the reaction temperature may suitably be from about 25° C. to about 40° C. The reaction time is not narrowly limited and the reaction is typically continued until the conversion of formula (I) to formula (IIa) is essentially complete such as determined by chromatography (e.g., TLC, GC or HPLC).

Upon reaction completion, the reaction mixture may be quenched. In some such embodiments, the reaction mixture may be quenched with cold water. In such embodiments, the phases may be separated into an aqueous phase and organic phase comprising the compound of formula (IIa). The aqueous phase may be extracted one or more times with organic solvent to recover additional compound formula (IIa).

In step 2, a reaction mixture comprising the compound of formula (IIa), a catalyst, an oxidant and a solvent is reacted to form a compound of formula (II). In one embodiment, the organic phase or combined organic phases from step 1, comprising formula (IIa), is used as the source of formula (IIa) for step 2. In one embodiment, the catalyst is a redox active metal catalyst. Non-limiting examples of suitable catalysts include $NiCl_2$, $RuCl_3$, $CoCl_2$, $FeCl_3$, $FeCl_2$, and $MnCl_2$. Non-limiting examples of suitable oxidants include $NaIO_4$, NaOCl, and Oxone. Suitable organic solvents include non-polar and polar solvents as discussed elsewhere herein. In general, the oxidant is in equivalent excess to compound formula (IIa), for instance, the ratio of oxidant to compound formula (IIa) may be 1.1:1, 1.5:1, 2:1, 2.5:1, 3:1, 3.5:1, 4:1, 4.5:1 or 5:1. The step 2 reaction mixture may further comprise water. In such embodiments, the volume ratio of water to organic solvent used in the step 1 reaction mixture may be about 9:1, about 5:1, about 3:1, about 2:1, about 1:1, about 1:2, about 1:3, about 1:5 or about 1:9, and ranges constructed therefrom, such from about 2:1 to about 1:2. The step 2 reaction temperature may suitably be about 25° C., about 15° C., about 5° C., about 0° C., about −5° C. or about −10° C., and ranges constructed therefrom, such as from about −10° C. to about 10° C. In one embodiment, the organic phase(s) comprising formula (IIa), catalyst, and water are combined and cooled to a reaction temperature. The oxidant is then added over a period of time while maintaining the temperature around the reaction temperature.

Upon reaction completion, the step 2 reaction mixture may be separated into an aqueous phase and organic phase comprising the compound of formula (II) in solution. In some optional embodiments, the reaction mixture may be filtered, such as through a filter aid (e.g., celite) prior to phase separation. The aqueous phase may be extracted one or more times with organic solvent to recover additional compound formula (II).

In another embodiment, the step 2 organic phase(s) may be worked up by methods known to those skilled in the art. For instance, the organic phases may be washed with a base, such as with an aqueous solution of $Na_2SO_3$. The organic phases may further optionally be dried, such as with a brine solution and/or by the addition of a solid drying agent such as $CaCl_2$, $MgSO_4$ or $Na_2SO_4$. Solid desiccants may suitably be removed by filtration. In one embodiment, the compound formula (II) solution may be used for subsequent reaction. In one embodiment, compound formula (II) may be isolated from the solution by methods known in the art such as by distillation, concentration, precipitation (such as by addition of an anti-solvent or pH adjustment) and/or crystallization. In some such embodiments, the organic phase(s) may be concentrated by distillation or stripping to reduce the volume, such as by at least 25%, 50%, 100% or more. Compound formula (II) may then be precipitated/crystallized from solution by addition of an anti-solvent followed by optional further concentration. In one embodiment, the anti-solvent is a $C_{4-8}$ nonionic solvent such as pentane, hexane or heptane. Compound formula (II) solids may be collected by methods known in the art such as filtration or centrifugation. The solids may be dried, such as under partial vacuum, to yield solid compound formula (II). The yield to compound formula (II) from compound formula (I) for steps 1 and 2 is at least 60%, at least 70%, or at least 75%. In one embodiment, the compound of formula (II) is compound 2.

In step 3, a reaction mixture comprising the compound of formula (II), a compound of formula (III), and an organic solvent is reacted to form a compound of formula (IV). In one embodiment, the organic solvent is a polar aprotic solvent. Non-limiting examples of suitable solvents include tetrahydrofuran, ethyl acetate, acetone, dimethylformamide, acetonitrile ("ACN"), dimethyl sulfoxide, nitromethane and propylene carbonate. In one embodiment, the solvent is ACN. The mole ratio of compound formula (II) to compound formula (III) is suitably about 1:1, about 1.1:1, about 1.2:1, about 1.3:1, about 1.4:1, about 1.5:1, or greater, and ranges constructed from those ratios, such as between 1:1 and 1.3:1. The concentration of compound formula (II) in the solvent is suitably about 10 g/L, about 25 g/L, about 50 g/L, about 75 g/L, about 100 g/L, about 125 g/L, about 150 g/L, and up to a concentration approaching saturation at the reaction temperature, and ranges constructed from those concentrations, such as from about 50 g/L to about 150 g/L. The acid catalyst may be an acid catalyst as described elsewhere herein. In some embodiments, the acid catalyst is sulfuric acid, p-toluene sulfonic acid (p-TsOH), or methansulfonic acid, or combinations thereof. In one embodiment, the acid catalyst is p-toluene sulfonic acid. The equivalent ratio of acid catalyst to compound formula (II) is suitably about 0.75:1, about 0.9:1, about 1:1, about 1.05:1, about 1.1:1, about 1.2:1, about 1.3:1, about 1.4:1, about 1.5:1, or greater, and ranges constructed therefrom, such as from about 1:1 to about 1.2:1. In one embodiment, the compound of formula (III) is compound 3.

In some step 3 embodiments, compound formula (II), compound formula (III), the organic solvent and a base are combined to form an admixture. The base may suitably be a moderate base, non-limiting examples of which include potassium tert-butoxide, trimethylamine, sodium bicarbonate, potassium bicarbonate, sodium carbonate, potassium carbonate, sodium hydroxide, ammonium hydroxide, and combinations thereof. The admixture may be heated with agitation to a reaction temperature, typically a temperature of from 2° C. to about 30° C. below the reflux temperature up to the reflux temperature, and held for a time sufficient to essentially complete the formation of a reaction product comprising compound formula (III). In the case of ACN solvent, the reaction temperature is suitably about 65° C., about 70° C., about 75° C., or about 80° C. The reaction product mixture may then be cooled, such as to less than 50° C., than 40° C., or than 30° C., and optionally filtered to remove solid impurities. The solids may be optionally washed with the solvent to recover additional reaction product. Acid (e.g., p-TsOH) and water are then added. The volume ratio of organic solvent to water may be 25:1, 15:1, 10:1, 5:1, 2:1 or 1:1, and ranges constructed therefrom, such as from about 15:1 to about 5:1. The admixture may be heated with agitation to a reaction temperature, typically at a temperature of from 2° C. to about 20° C. below the reflux temperature to the reflux temperature, and held for a time sufficient to essentially complete the formation of compound formula (IV) such as determined by chromatography (e.g., TLC, GC or HPLC). Upon reaction completion, the reaction mixture may be quenched, such as with cold water (e.g., less than 10° C. or less than 5° C.). The pH of the quenched reaction mixture may then be adjusted with a base to greater than 7, such as about pH 8, about pH 9, about pH 10 or about pH 11. In one embodiment, the base is an aqueous base such as sodium bicarbonate, potassium bicarbonate, sodium carbonate, potassium carbonate, sodium hydroxide, or ammonium hydroxide.

Upon reaction completion, the step 3 reaction mixture may be separated into an aqueous phase and organic phase comprising the compound of formula (IV) in solution. In some optional embodiments, the reaction mixture may be filtered, such as through a filter aid (e.g., celite) prior to phase separation. The aqueous phase may be extracted one or more times with organic solvent to recover additional compound formula (IV). In one embodiment, the solvent is aprotic. In a particular embodiment, the extracting solvent is suitably isopropyl acetate ("i-PrOAc").

In some embodiments, the step 3 organic phase(s) may be worked up by, for instance, washing the organic phases with water. The organic phases may optionally be dried, such as with a brine solution and/or by the addition of a solid drying agent such as $CaCl_2$, $MgSO_4$ or $Na_2SO_4$. Solid desiccants may suitably be removed by filtration, and the collected desiccant may optionally be washed with solvent to recover compound formula (IV) therefrom. In such embodiments, the organic phase(s) may be concentrated by distillation under partial vacuum or stripping to form compound formula (IV) residue. The compound formula (IV) residue may then be dissolved in organic solvent at a temperature below the reflux temperature. Anti-solvent, such as a non-polar organic solvent as described elsewhere herein, may then be added to the compound formula (IV) solution while cooling, such as to less than about 10° C., to precipitate/crystallize compound formula (IV) from solution. Compound formula (IV) solids may be collected by methods known in the art such as filtration or centrifugation, and optionally washed with anti-solvent. The solids may be dried, such as under partial vacuum, to yield solid compound formula (IV). The yield to compound formula (IV) from compound formula (II) for step 3 is at least 80%, at least 85%, at least 90%, at least 95%, at least 96% or at least 97%. Compound formula (IV) purity is at least 95%, at least 98%, or at least 99%.

One aspect of the disclosure is directed to a process for preparing a compound of formula (VIII) or a salt thereof:

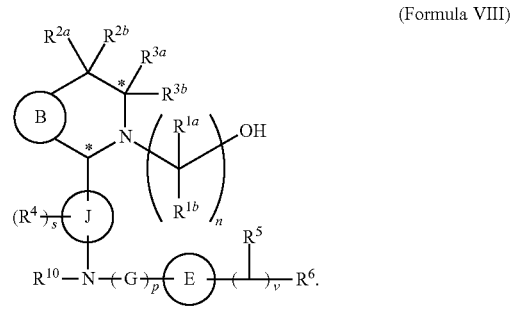

(Formula VIII)

where the process comprises the steps of:
(a) reacting a reaction mixture comprising a compound of formula (IV), a compound of formula (V) or a compound of formula (X), and an organic solvent to form a compound of formula (VI) according to step 1 below

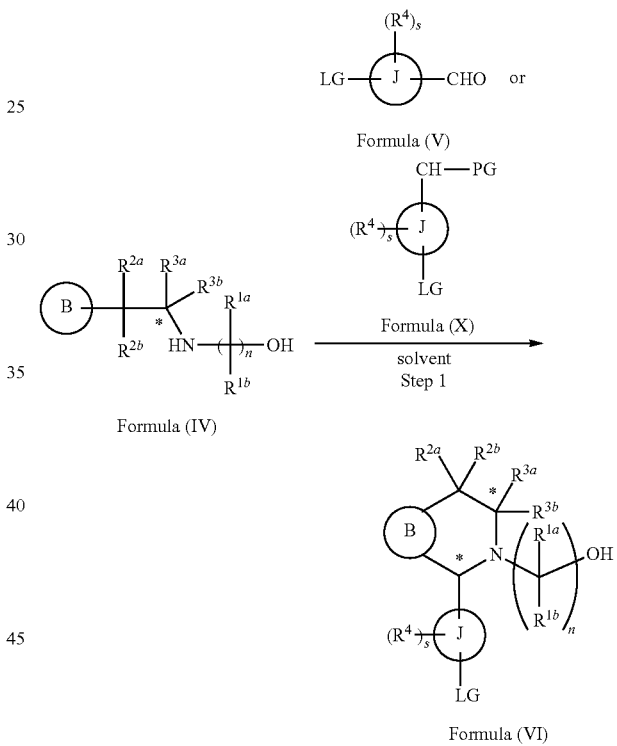

wherein
B is substituted or unsubstituted indolyl, benzofuranyl, benzothiophenyl, aza-indolyl, indazolyl, benzimidazolyl, pyrrolopyridinyl, furopyridinyl, thienopyridinyl, pyrrolopyridazinyl, pyrrolopyrimidinyl, pyrrolopyrazinyl, thienopyridazinyl, thienopyrimidinyl, thienopyrazinyl, furopyridazinyl, furopyrimidinyl, or furopyrazinyl;

each of $R^{1a}$ and $R^{1b}$ is independently hydrogen, fluorine, chlorine, —OH, $C_{1-3}$ alkyl, $C_{1-3}$ haloalkyl, $C_{1-3}$ alkoxy, $C_{1-3}$ hydroxyalkyl, and —CN, $C_{3-6}$ cycloalkyl, or $C_{3-6}$ spirocycloalkyl, n is an integer of 2 or 3, each of $R^{2a}$ and $R^{2b}$ is independently hydrogen, halogen, —OH, $C_{1-3}$ alkyl, $C_{1-3}$ haloalkyl, $C_{1-3}$ alkoxy, $C_{1-3}$ hydroxyalkyl, —CN, $C_{3-6}$ cycloalkyl, or $C_{3-6}$ spirocycloalkyl, $R^{3a}$ and $R^{3b}$ are independently hydrogen, $C_{1-3}$ alkyl, $C_{1-3}$ haloalkyl, $C_{1-3}$ alkoxy, —CN, $C_{3-6}$ cycloalkyl, $C_{3-6}$ heterocycloalkyl, phenyl, $C_{3-6}$ heteroaryl, or $C_{3-6}$ spirocycloalkyl, J is phenyl or pyridinyl;
each $R^4$ is independently hydrogen, halogen or $C_{1-3}$ alkyl,
s is an integer from 0 to 2,
LG is a leaving group,
LG and CHO are located in the para position with respect to each other on J on the compound of formula (V),
PG is an aldehyde protecting group,
LG and CH-PG are located in the para position with respect to each other on J on the compound formula (X), and
each asterisk independently represents a chiral center wherein the carbon bearing $R^{3a}$ and $R^{3b}$ is a chiral center when $R^{3a}$ and $R^{3b}$ are different; and
(b) reacting a reaction mixture comprising the compound of formula (VI), an organic solvent, and a compound of formula (VII) or a salt thereof to form a compound of formula (VIII) or a salt thereof according to step 2 below

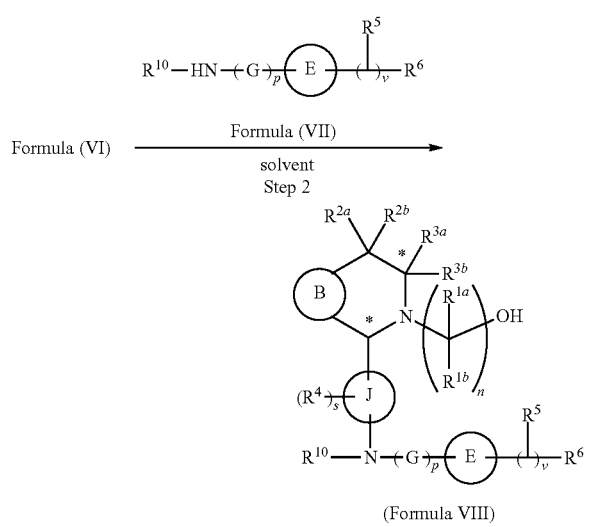

wherein
G is $C_{1-3}$ alkyl,
p is 0 or 1,
E is substituted or unsubstituted azetidinyl or pyrrolidinyl,
each $R^5$ is independently hydrogen, halogen, —OH, —CN, $C_{1-5}$ alkoxy, or $C_{1-5}$ hydroxyalkyl,
v is an integer from 1 to 5,
$R^6$ is halogen or —CN; and
$R^{10}$ is hydrogen or $C_{1-3}$ alkyl.
B, $R^{1a}$, $R^{1b}$, n, $R^{2a}$, $R^{2b}$, $R^{3a}$, $R^{3b}$ and the asterisk (*) are as defined herein.

In one preferred embodiment, J is phenyl. In another embodiment, J is pyridinyl.

In one embodiment, each $R^4$ is independently hydrogen or halogen. In a preferred embodiment, each $R^4$ is fluorine. In one embodiment, s is 1 or 2. In one embodiment, s is 2. In one preferred embodiment, each $R^4$ is fluorine and s is 2.

In one embodiment, G is methylene or ethylene.

In one embodiment, p is 0.

In one embodiment, each $R^5$ is independently hydrogen, halogen, —OH, or —CN. In one preferred embodiment, each $R^5$ is hydrogen. In one embodiment, v is 2. In another embodiment, v is 3. In another embodiment, v is 5. In a preferred embodiment, each $R^5$ is hydrogen and v is 3.

In one preferred embodiment, $R^6$ is halogen. In one embodiment, $R^6$ is F. In another embodiment, $R^6$ is —CN.

In one embodiment, $R^{10}$ is hydrogen or methyl. In a preferred embodiment, $R^{10}$ is hydrogen In one embodiment, E is azetidinyl. In another embodiment, E is pyrrolidinyl.

In one embodiment, E has the following structure:

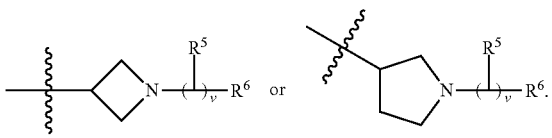

In one embodiment, E is azetidinyl of the following structure:

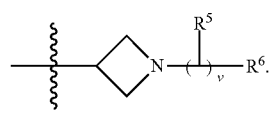

In one embodiment, E is of the following structure:

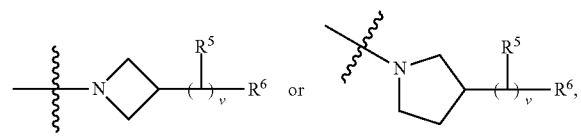

where $R^5$ is H, v is 2 or 3, and $R^6$ is halogen.

In one embodiment, E is azetidinyl of the following structure:

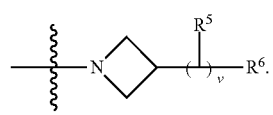

In one embodiment, formula (VIII) is an acid salt. Such acid salt can be a pharmaceutically acceptable salt. In some such embodiments, formula (VIII) is a salt of a pharmaceutically acceptable acid. In some particular embodiments, formula (VIII) is a salt of a pharmaceutically acceptable organic acid. In a preferred embodiment, formula (VIII) is a pharmaceutically acceptable salt of tartaric acid. In one embodiment, the compound of formula (VIII) is Compound A as described herein. In another embodiment, the compound of formula (VIII) is Compound A (tartrate salt) of Compound A described herein. In another embodiment, formula (VIII) is a pharmaceutically acceptable salt of fumaric acid. In still another embodiment, the compound of formula (VIII) is Compound B (fumarate salt) of Compound A as described herein.

In one embodiment, formula (VIII) is of any one of the following structures, or a pharmaceutically acceptable salt thereof:
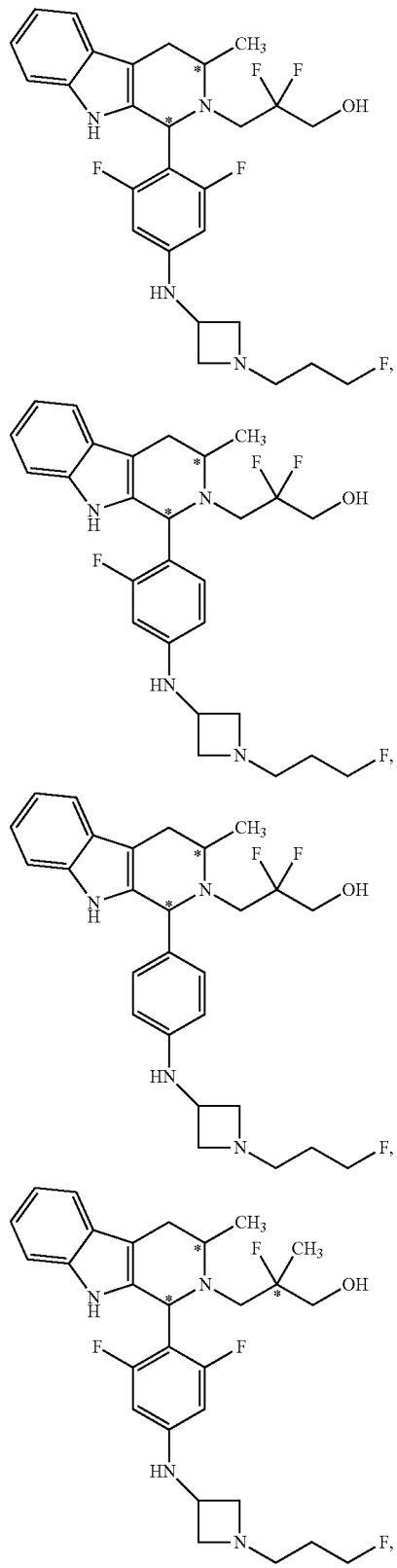
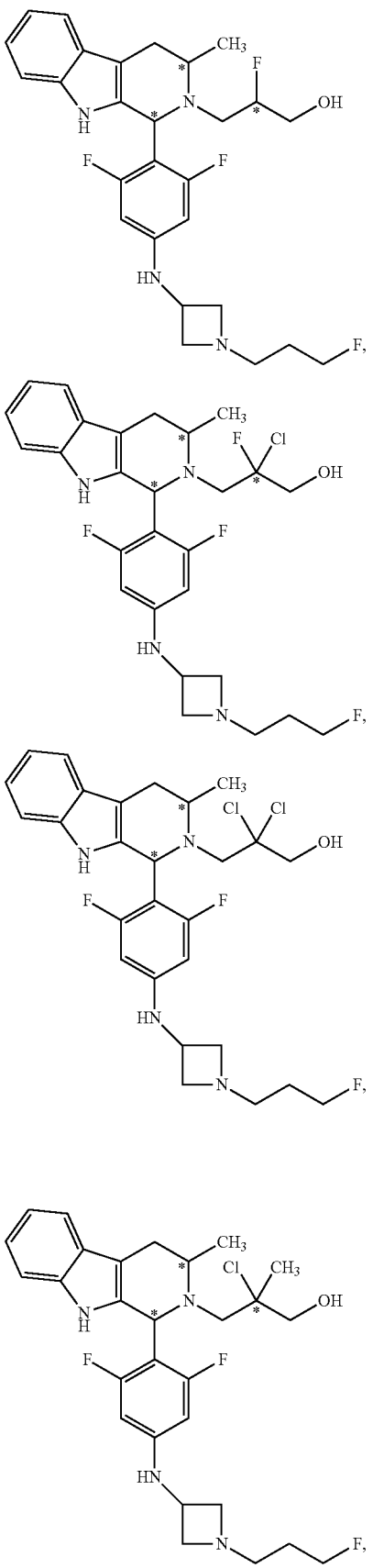

29
-continued
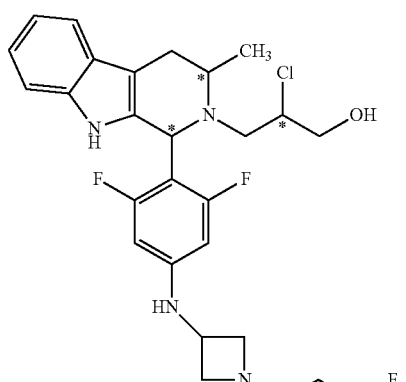
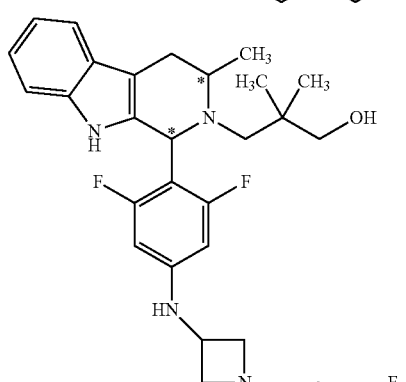
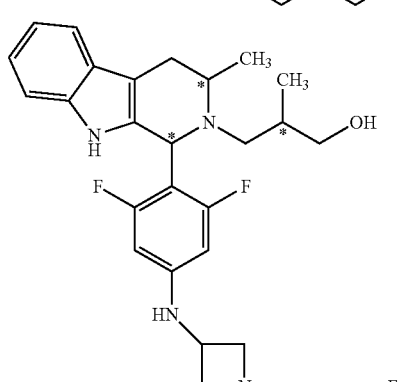
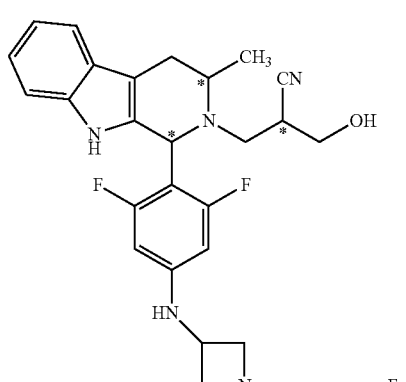
30
-continued
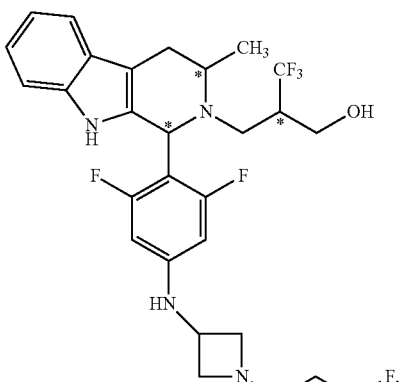
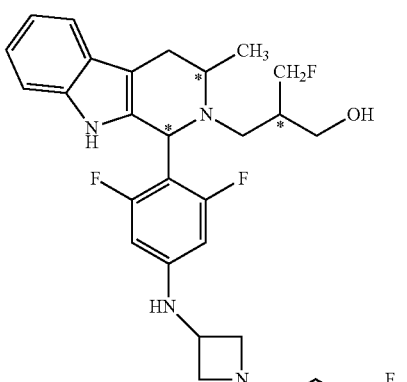
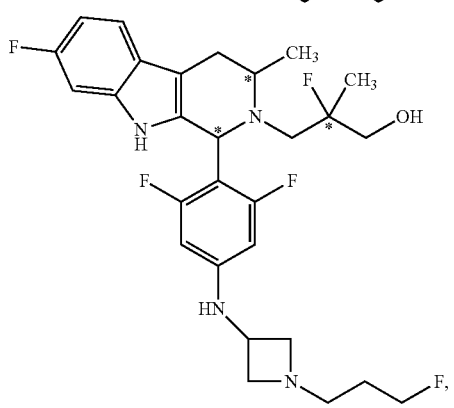
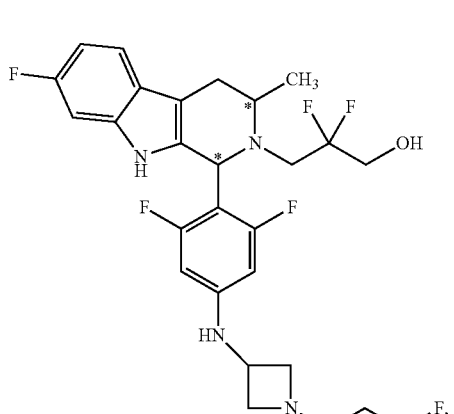

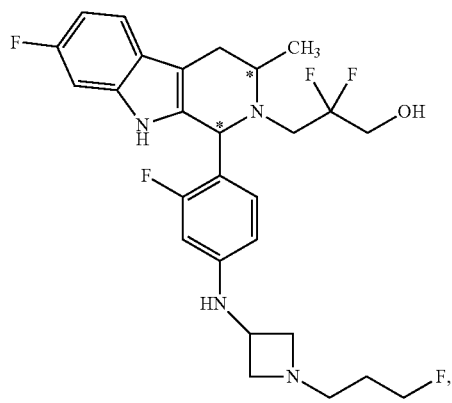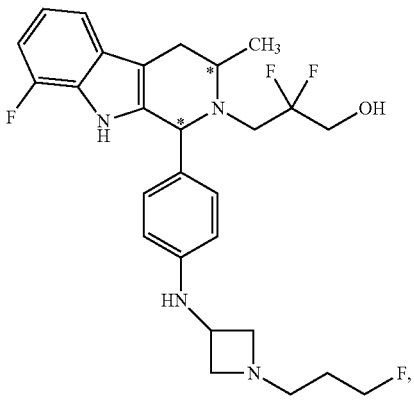

33
-continued
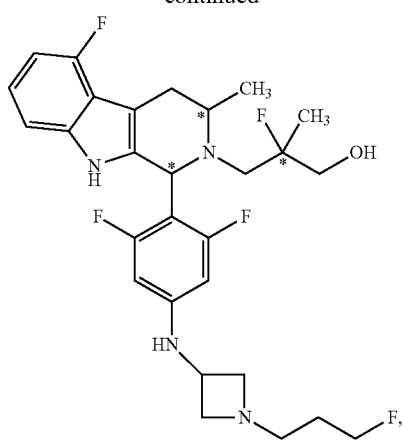
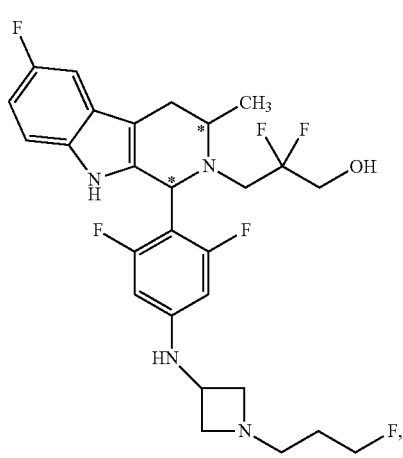 [SMILES: CC1Cc2c([nH]c3ccc(F)cc23)C(c2c(F)cc(NC3CN(CCCF)C3)cc2F)N1CC(C)(F)CO]
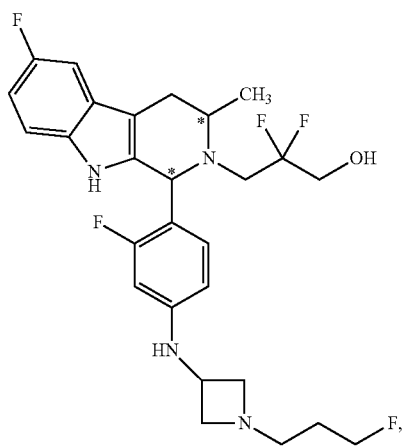
34
-continued
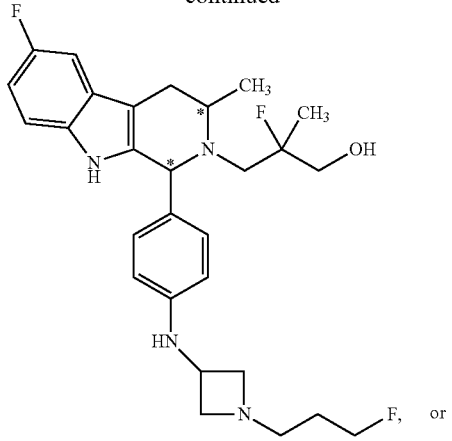
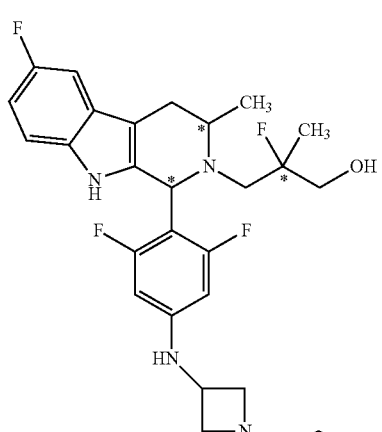
or a pharmaceutically acceptable salt thereof and including stereoisomers thereof.
In one embodiment, formula (VIII) is of the following structure, or a pharmaceutically acceptable salt thereof:
(Compound A)
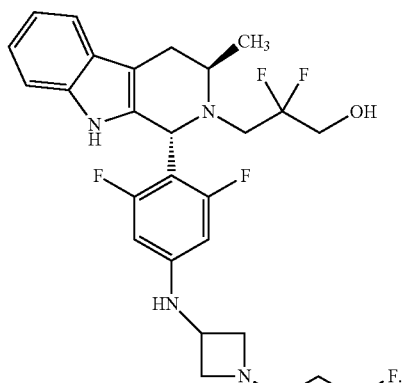

In one embodiment, formula (VIII) is of the following structure:

(Compound B)

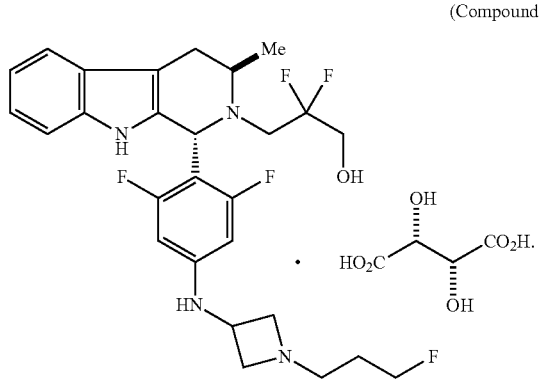

In one embodiment, formula (VIII) is of the following structure:

(Compound C)

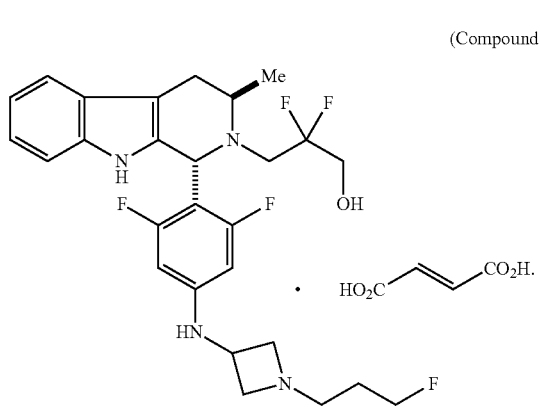

Step 1 of the process to synthesize compounds of formula (VIII) comprises reacting a reaction mixture comprising a compound of formula (IV), a compound of formula (V) or a compound of formula (X), and an organic solvent to form a compound of formula (VI) as set forth herein. In one embodiment, LG is bromine. In a preferred embodiment, when reacting with compounds of formula (IV) and formula (V), LG and CHO are located on J in the para position with respect to each other. In a preferred embodiment, when reacting compounds of formula (IV) and formula (X), LG and CH-PG are located in the para position with respect to each other on J.

The compound of formula (IV) is as described herein.

In one embodiment, the compound of formula (V) is of any one of the following compounds, or a salt thereof:

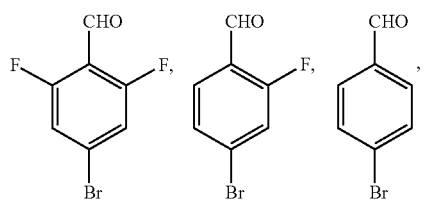

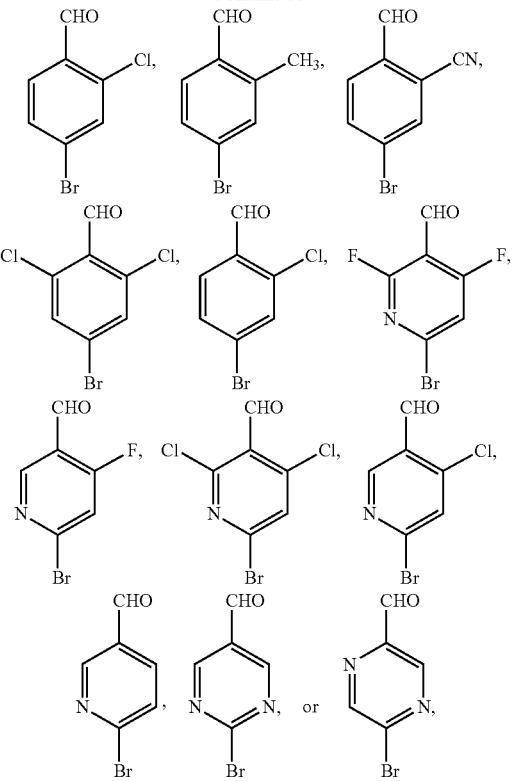

or a salt thereof.

In some embodiments, formula (X) corresponds to any of the above formula (V) structure, or a salt thereof, but where the aldehyde (—CHO) is a protected moiety of the structure —CH-PG where PG is an aldehyde protecting group as defined elsewhere herein.

In some embodiments, formula (VI) is of any one of the following structures:

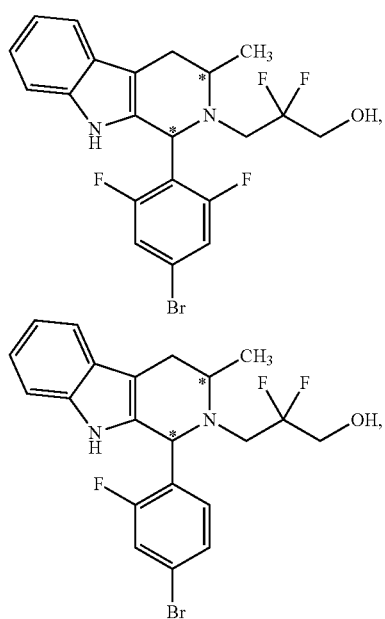

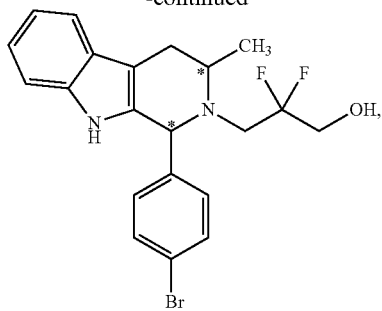
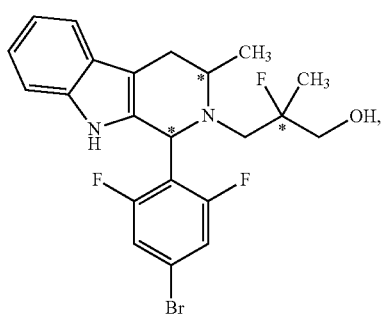
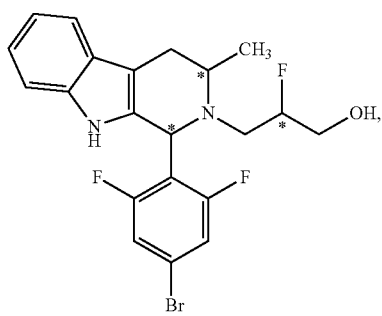
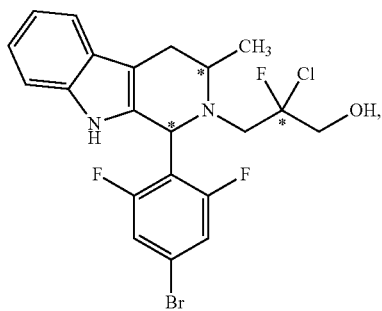
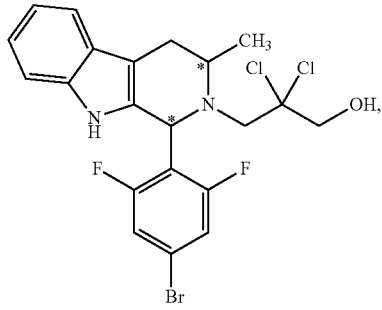
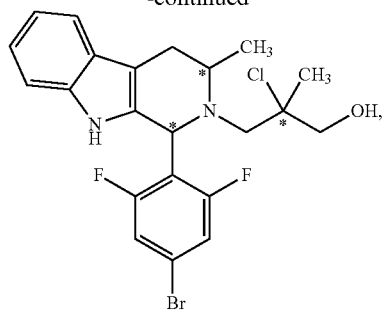
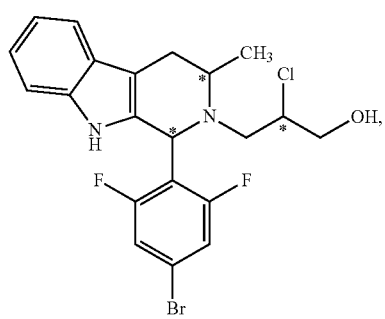
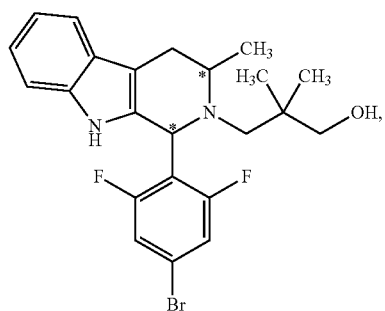
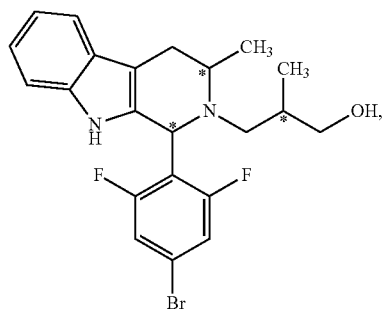
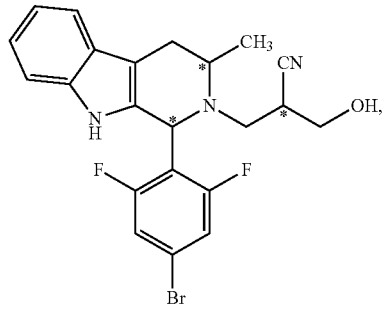

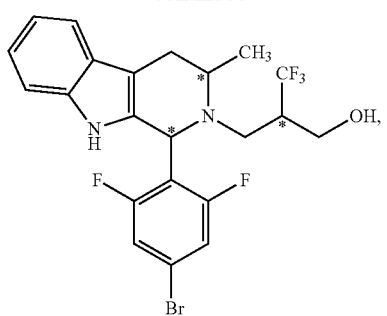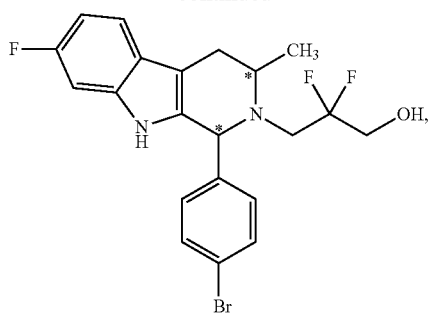

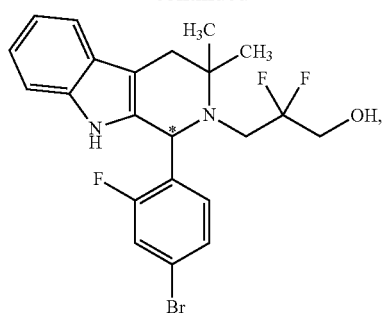
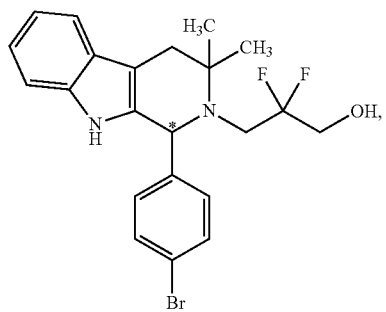
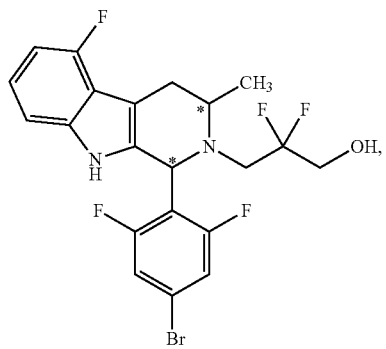
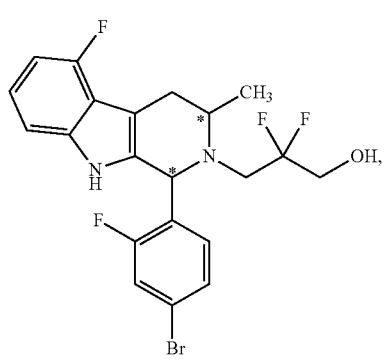
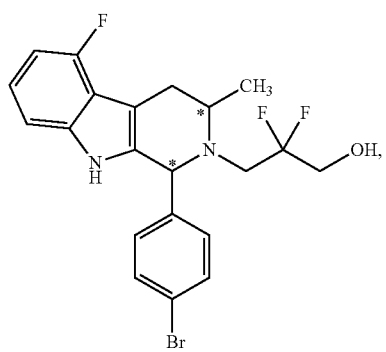
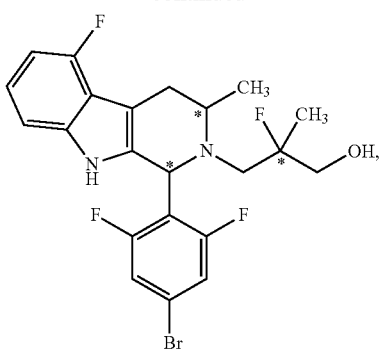
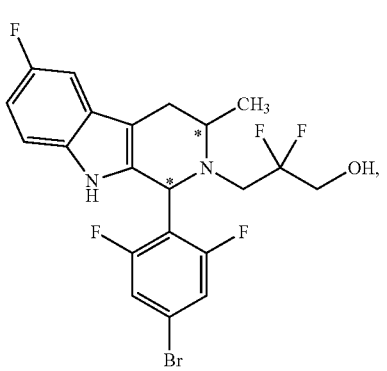
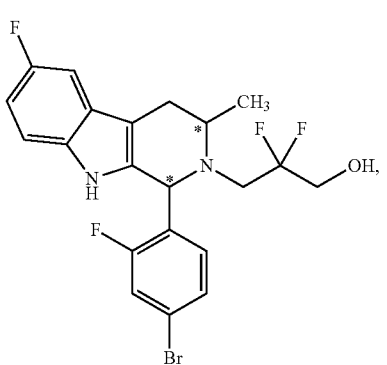
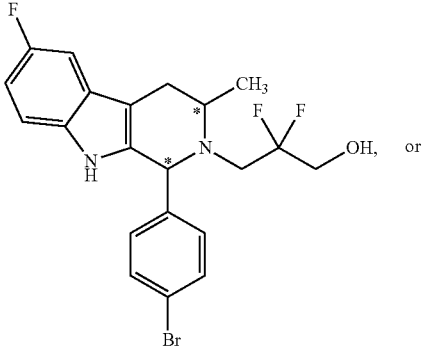, or -continued

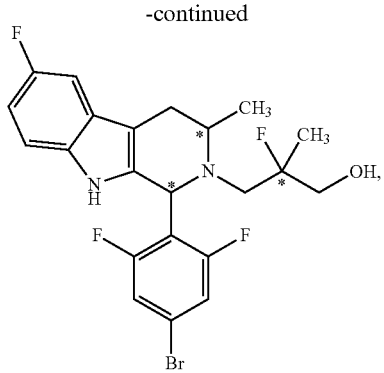

or a salt thereof, including stereoisomers thereof.

In step 2 of the synthesis of compounds of formula (VIII) set forth herein, the compound of formula (VII) can be any one of the following structures:

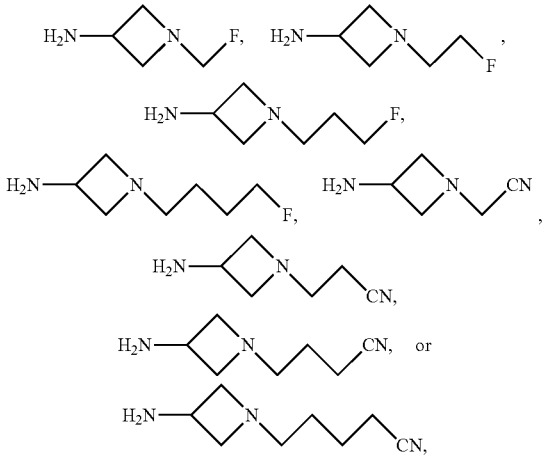

or a salt thereof.

In one embodiment, the salt is an ethane-disulfonate (e.g. a salt of ethane-1,2-disulfonate).

In one embodiment, the compound of formula (VII) has structure

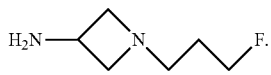

(7)

Compound (7) can be prepared according to the examples provided herein, such as, for example, Example 4 or Example 4a.

In one embodiment, Compound 7 is prepared according to the scheme below:

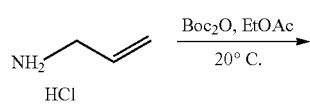

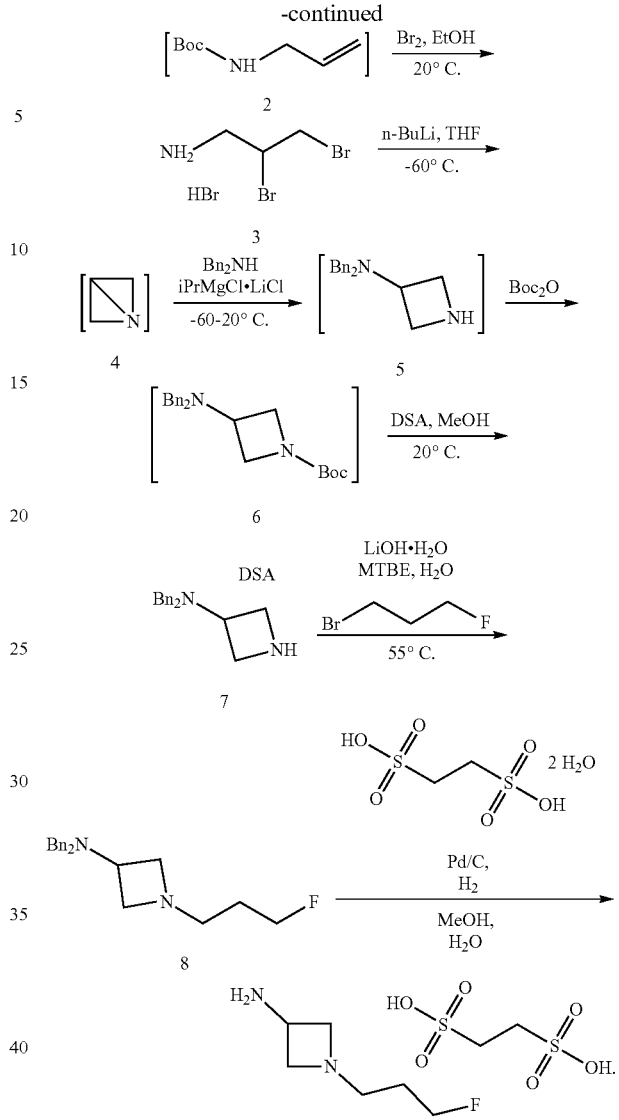

In step 1, a reaction mixture comprising a compound of formula (IV), a compound of formula (V) or a compound of formula (X), and an organic solvent are reacted to form a compound of formula (VI). In one embodiment, the organic solvent is a polar protic solvent, a non-polar solvent, a polar aprotic solvent, or a combination thereof, as described elsewhere herein. In some non-limiting embodiments, the solvent is toluene. In one embodiment, the solvent is acetonitrile, methyl ethyl ketone, or methyltetrahydrofuran. In one embodiment, the step 1 reaction mixture further comprises an acid catalyst as described elsewhere herein. In some such non-limiting embodiments, the acid catalyst is acetic acid. The mole ratio of compound (IV) to compound (V) or compound (X) is from about 0.95:1 to about 1.05:1, stoichiometric amounts, or, in some embodiments, compound (V) or compound (X) is in slight molar excess. The acid catalyst is generally present in stoichiometric excess, such as in an equivalent ratio to compound formula (IV) of about 1.1:1, about 1.2:1, about 1.3:1, about 1.4:1, about 1.5:1, about 1.6:1, about 1.7:1, about 1.8:1, about 2:1, or greater, and ranges constructed therefrom, such as from about 1.2:1 to about 1.8:1.

In some step 1 embodiments, the reaction mixture may be heated with agitation to a reaction temperature, of from 2°

C. to about 30° C. below the reflux temperature to the reflux temperature, and held for a time sufficient to essentially complete the reaction to compound formula (VI) such as determined by chromatography (e.g., TLC, GC or HPLC). In the case of toluene solvent, the reaction temperature is suitably about 65° C., about 70° C., about 75° C., or about 80° C. The reaction product mixture may then be cooled and optionally diluted with additional solvent. The reaction product mixture may then be quenched with a base, such as an aqueous solution of a base as described elsewhere herein. A step 1 reaction product mixture organic phase comprising the compound of formula (VI) may then be isolated and, in some embodiments, worked up by methods known in the art such as washing with water and/or a brine solution as described elsewhere herein followed by product isolation as a solid. In one embodiment, the reaction product mixture may be treated with activated charcoal, followed by filtration and optional washing of the activated charcoal filter cake with solvent. As described elsewhere herein: (i) the organic phase(s) containing compound formula (VI) may be concentrated by distillation or stripping to reduce the volume, such as by at least 25%, 50%, 100% or more; and (ii) compound formula (IV) may then be precipitated/crystallized from solution by addition of an anti-solvent followed by optional further concentration.

In some other step 1 embodiments, the step 1 reaction mixture is heated at reflux for a time to essentially complete the reaction such as determined by chromatography (e.g., TLC, GC or HPLC). The reaction mixture may then be cooled and pH-adjusted with a base, such as an aqueous solution of a base, to a pH at which compound formula (VI) precipitates from solution.

In any of the various step 1 embodiments, compound formula (VI) solids may be collected by methods known in the art such as filtration or centrifugation. The solids may be dried, such as under partial vacuum, to yield solid compound formula (VI). The yield to compound formula (VI) from compound formula (V) for steps 1 and 2 is at least 65%, at least 70%, at least 75%, at least 80%, at least 85%, at least 90%, or at least 95%.

In step 2, a reaction mixture comprising a compound of formula (VI), a compound of formula (VII) and an organic solvent are reacted to form a compound of formula (VIII). In some embodiments, the organic solvent is a polar aprotic solvent as described elsewhere herein. In some non-limiting embodiments, the solvent is ACN. The step 2 reaction mixture may further comprise a base, such as an organic base. Non-limiting examples of organic bases include DBU, NMM, DIPEA, and TEA. In some such embodiments, the base is DBU. The step 2 reaction mixture may further comprise a catalyst, such as a transition metal catalyst. In some embodiments the catalyst is a Pd catalyst. The mole ratio of compound (VII) to compound (VI) is about 0.95:1, about 1:1, about 1.05:1, about 1.1:1, about 1.2:1, about 1.3:1, about 1.4:1 or about 1.5:1, and ranges constructed therefrom, such as from about 1:1 to about 1.4:1. The base is generally present in stoichiometric excess, such as in an equivalent ratio to compound formula (VI) of about 1.1:1, about 2:1, about 3:1, about 4:1, about 5:1, about 6:1, about 7:1, or about 8:1, and ranges constructed therefrom, such as from about 3:1 to about 7:1. The reaction mixture may be heated with agitation to a reaction temperature, typically a temperature of from 2° C. to about 30° C. below the reflux temperature up to the reflux temperature, and held for a time sufficient to essentially complete the reaction such as determined by chromatography (e.g., TLC, GC or HPLC). In the case of ACN solvent, the reaction temperature is suitably about 65° C., about 70° C., about 75° C., or about 80° C.

After completion the reaction product mixture may suitably be cooled and optionally diluted with an organic solvent. In one embodiment, the reaction product mixture is diluted with a non-polar solvent as described elsewhere herein. One non-limiting example of a suitable non-polar solvent is MTBE. The step 2 reaction product mixture may be worked up by methods known to those skilled in the art including water wash and brine wash. In some such non-limiting embodiments, the work-up may include washing with an aqueous solution of ammonium chloride, brine and water. In some embodiments, the step 2 reaction product mixture may be contacted with a metal scavenger known in the art, such as for instance and without limitation, SiliaMetS Thiol. The reaction product mixture may then be filtered to remove solids prior to isolation of compound formula (VIII) therefrom.

In some embodiments, the step 2 reaction product mixture may be concentrated, such as by vacuum distillation or stripping, and diluted with an organic solvent, such as an alcohol (e.g., ethanol), such as in a solvent exchange step. An acid may then be added to the diluted solution of compound formula (VIII) followed by cooling to crystallize compound formula (VIII) as an acid salt. In some particular embodiments, the acid is tartaric acid and compound formula (VIII) is the tartaric salt. In some such embodiments, the acid is (2R-3R)-tartaric acid (L-(+)-tartaric acid). In another aspect, the acid is (2S-3S)-tartaric acid (D-(−)-tartaric acid). In some such embodiments, the solvent comprises an organic solvent. The crystalline material may be collected by centrifugation or filtration, optionally washed with solvent, and optionally dried.

In some other embodiments, compound formula (VIII) may be isolated from the step 2 reaction product mixture using methods described elsewhere herein including: (i) distillation, concentration, precipitation (such as by addition of an anti-solvent or pH adjustment) and/or crystallization; (ii) solids collection by centrifugation or filtration; (iii) optional washing of the collected solids; (iv) and drying.

The step 2 yield of compound formula (VIII) either as a free base or acid salt is at least 80%, at least 85%, or at least 90%.

Another aspect of the disclosure is directed to a process for preparing a compound of formula (VIII) or a salt thereof, wherein compound formula (VIII) is as described elsewhere herein. The process for preparing formula (VIII) according to this embodiment comprises reaction step 1 as depicted below:

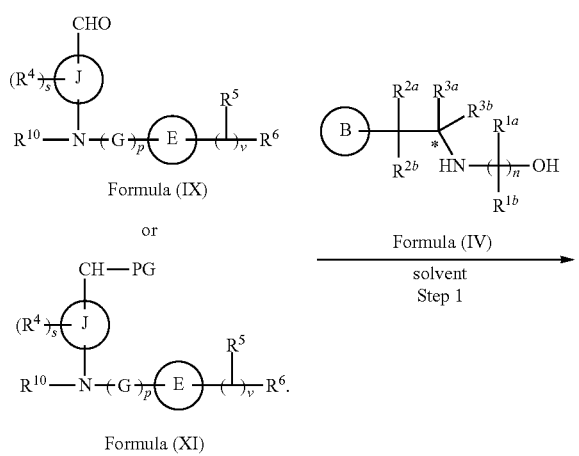

-continued

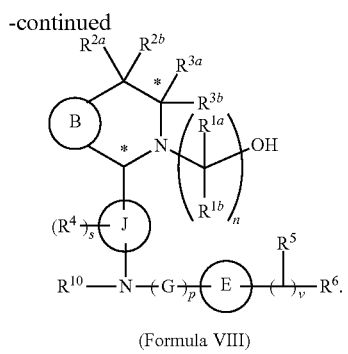

(Formula VIII)

Each of B, $R^{1a}$, $R^{1b}$, n, $R^{2a}$, $R^{2b}$, $R^{3a}$, $R^{3b}$, $R^4$, s, J, $R^5$, v, $R^6$, $R^{10}$, G, p, E, PG and the asterisk are as described elsewhere herein. The CHO moiety and the nitrogen atom linking J and G are located in the para position with respect to each other on J. The CH-PG moiety and the nitrogen atom linking J and G are located in the para position with respect to each other on J.

In one embodiment, the compound of formula (IX) is:

(8a)

(8b)

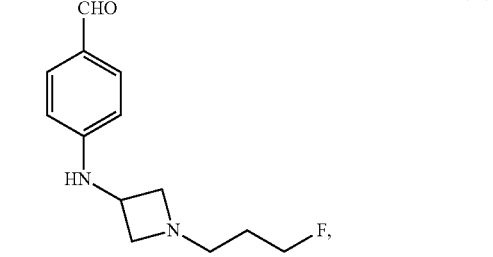
(8c)

or a salt thereof.

In one preferred embodiment, the compound of formula (IX) is compound (8a). In some embodiments, formula (XI) corresponds to any of the above formula (IX) structures, or a salt thereof, but where the aldehyde (—CHO) is a protected moiety of the structure —CH-PG where PG is an aldehyde protecting group as defined elsewhere herein.

In step 1, a reaction mixture comprising a compound of formula (IX) or of formula (XI), a compound of formula (IV) and an organic solvent is reacted to form a compound of formula (VIII), or a salt thereof. In one embodiment, the organic solvent is a polar solvent, or is a polar protic solvent. The step 1 reaction mixture further comprises an acid catalyst as described elsewhere herein. In a particular embodiment, the acid catalyst is tartaric acid or fumaric acid. In one embodiment, the acid catalyst is tartaric acid. In another embodiment, the acid catalyst is fumaric acid. Non-limiting examples of suitable solvents include n-butanol, isopropyl alcohol, n-propanol, i-propanol, ethanol, methanol, and combinations thereof. In some particular embodiments, the solvent is ethanol. In one embodiment, the concentration of formula (IX) in the solvent may suitably be about 25 g/L, about 50 g/L, about 100 g/L %, about 150 g/L, about 200 g/L, about 250 g/L, and up to a concentration approaching saturation at the reaction temperature, and ranges constructed from those concentrations, such as from about 100 g/L to about 250 g/L. The mole ratio of formula (IX) or of formula (XI) to formula (IV) is suitably about 0.25:1, about 0.3:1, about 0.4:1, about 0.5:1, about 0.6:1, about 0.7:1, about 0.8:1, about 0.9:1, about 0.95:1, about 1:1, about 1.05:1, about 1.1:1 or about 1.2:1, and ranges constructed from those ratios, such as from about 0.95:1 to about 1.05:1. In one embodiment, formula (IX) or formula (XI) and formula (IV) are present in approximately stoichiometric amounts. In one embodiment, the reaction temperature is below the reaction mixture reflux temperature. In some other embodiments, the reaction is run at reflux. For instance, where the solvent is ethanol, the reaction temperature may suitably be from about 50° C. to about 75° C. The reaction time is not narrowly limited and the reaction is typically continued until the conversion of formula (IX) or formula (XI) to formula (VIII) is essentially complete such as determined by chromatography (e.g., TLC, GC or HPLC).

In one embodiment, formula (VIII) may be formed as a salt of an acid. Suitable acids include inorganic acids and inorganic acids as described elsewhere herein. In one embodiment, the acid is an organic acid. In a preferred embodiment, the acid is tartaric acid. In another embodiment, the acid is fumaric acid. In one embodiment, formula (VIII) free base may be dissolved in a suitable solvent, such as a polar protic solvent (e.g., an alcohol such as methanol or ethanol) at an elevated temperature followed by addition of an acid. In general, the acid is in stoichiometric excess as compared to compound formula (VIII). In some such embodiments, the solution temperature and/or concentration of formula (VIII) is adjusted to keep the concentration below saturation and thereby avoid formula (VIII) precipitation and/or crystallization. Following acid addition, the solution may optionally be seeded with a crystalline formula (VIII) salt of the acid. In any of the various embodiments, the solution is cooled with stirring to form crystalline formula (VIII) salt. The salt may then be collected by methods known in the art, such as by filtration or centrifugation. In one embodiment, the salt is collected by filtration. The collected formula (VIII) salt may be optionally washed, such as with the dissolution solvent, and then dried, such as under partial vacuum.

In a particular embodiment, the step 1 reaction mixture as set forth above forth synthesis of a compound of formula (VIII) comprises tartaric acid as the acid catalyst, crystalline formula (VIII) tartaric acid, and an alcoholic solvent (e.g. ethanol); the step 1 reaction product mixture is diluted with the alcoholic solvent; and the resultant slurry is cooled with stirring to form crystalline formula (VIII) tartaric acid. In another embodiment, the step 1 reaction mixture comprises fumaric acid as the acid catalyst, crystalline formula (VIII)

fumaric acid, and a solvent. The step 1 yield of compound formula (VIII) as a tartaric acid salt is at least 70%, at least 75%, at least 80%, at least 85%, at least 90%, or at least 95%. In such embodiments, the step 1 reaction scheme is as follows:

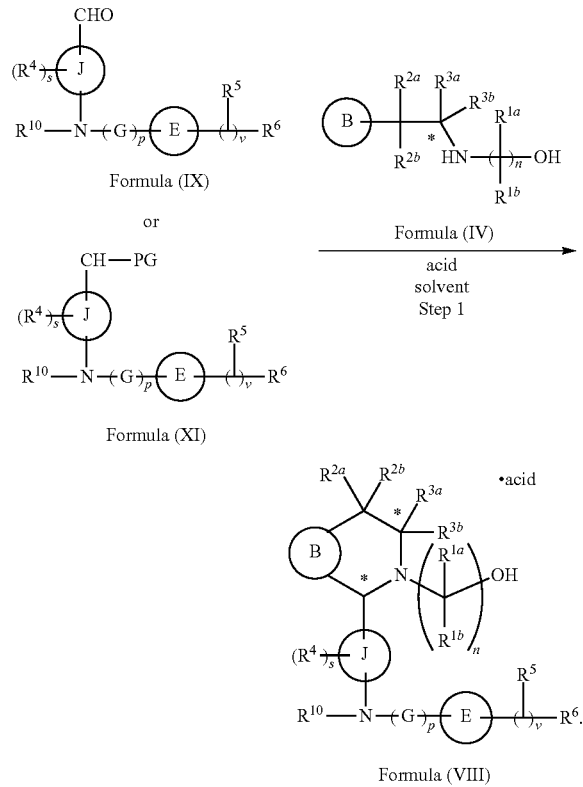

Still another aspect of the disclosure is directed to a process for preparing a compound of formula (IX) or a salt thereof. The process for preparing compound formula (IX) comprises two reaction steps as depicted below:

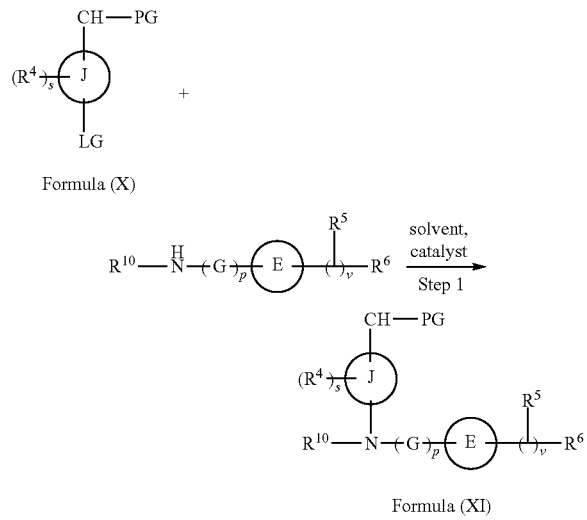

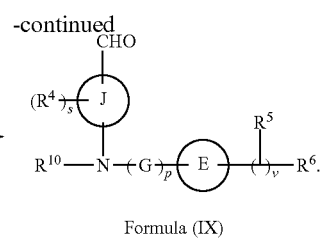

$R^4$, s, LG, PG, $R^5$, v, $R^6$, $R^{10}$, G, p, J, and E are as described elsewhere herein.

Aldehyde protecting groups are defined herein and non-limiting examples include 1,3-dithiane, 1,3-dithiolane, diethyl acetal, dimethyl acetal, ethylene glycol acetal, neopentyl glycol acetal, trimethylsilyl cyanohydrin, and triethyl orthoformate.

In step 1, a reaction mixture comprising a compound of formula (X), a compound of formula (VII) or a salt thereof, an organic solvent and a catalyst is reacted to form a compound of formula (XI). In one embodiment, the solvent is a non-polar solvent as described elsewhere herein. Non-limiting examples of suitable solvents include pentane, hexane, heptane, cyclopentane, MTBE, diethyl ether, toluene, 2-methyl tetrahydrofuran (2-MeTHF), benzene, 1,4-dioxane, carbon tetrachloride, chloroform, dichloromethane, and combinations thereof. In some examples, the solvent is toluene. In one embodiment, the catalyst is a transition metal catalyst as described herein. In one embodiment, non-limiting examples of transition metal catalysts include palladium, platinum, gold, ruthenium, rhodium, and iridium catalysts. Non-limiting examples of suitable catalysts include JohnPhos, XPhos AuCl, XPhos AuNTf2, XPhos Palladacycle, SPhos Palladacycle, tBuXPhos Pd G1, Xphos Pd G2, SPhos Pd G2, RuPhos Pd G2, CPhos-Pd-G2, CPhos-Pd-G3, tBuXPhos-Pd-G3, RuPhos-Pd-G3, XPhos-Pd-G3, BrettPhos-Pd-G3, JackiePhos-Pd-G3, tert-butyl BrettPhos-Pd-G3, [tert-butyl BrettPhos-Pd (allyl)]OTf), and combinations thereof. In some embodiments the catalyst is Brett-Phos-Pd-G3. In some embodiments, the step 1 reaction mixture further comprises an organic base as describe elsewhere herein. In some such embodiments, the base is a tert-butoxide such as sodium or potassium tert-butoxide. The mole ratio of the compound of formula (VII) to the compound of formula (X) is suitably about 1:1, about 1.1:1, about 1.2:1, about 1.3:1, about 1.5:1 or about 2:1, and ranges constructed from those ratios, such as from about 1.1:1 to about 1.5:1.

In some step 1 embodiments, the reaction mixture may be heated with agitation to a reaction temperature, of from 2° C. to about 30° C. below the reflux temperature to the reflux temperature, and held for a time sufficient to essentially complete the reaction to compound formula (XI) such as determined by chromatography (e.g., TLC, GC or HPLC). In the case of toluene solvent, the reaction temperature is suitably about 50° C., about 55° C., about 60° C., about 65° C., about 70° C., about 75° C., or about 80° C. The reaction time is not narrowly limited and the reaction is typically continued until the conversion of formulae (VII) and (X) to formula (XI) is essentially complete such as determined by chromatography (e.g., TLC, GC or HPLC). After the reaction is complete the reaction product mixture may be suitably quenched. In some embodiments, the step 1 reaction may be quenched with water. Where the reaction is quenched with water, the organic phase comprising the compound of formula (XI) in solution may be isolated and optionally washed at least once with water. In some embodiments, the step 1 reaction product mixture may be contacted with a metal scavenger known in the art, such as for instance and without limitation, SiliaMetS Thiol. The reaction product mixture may then be filtered to remove solids.

In step 2, the compound of formula (XI) is deprotected to form compound formula (IX) by combining a solution of compound (XI) in an organic solvent (e.g., toluene) with an acid and water. The acid is generally present in equivalent excess, such an equivalent ratio of acid to compound (XI) of 1.01:1, 1.05:1, 1.1:1, 1.15:1, 1.2:1, or grater. In one embodiment, the deprotection temperature is not narrowly critical and may suitably be room temperature. After deprotection, the organic phase and the aqueous phase (comprising the compound of formula (IX)) are separated. The organic phase may optionally be washed with water. The aqueous phase(s) may be treated with a base, such as an inorganic base (e.g., NaOH or KOH), combined with compound formula (IX) seed crystals. The base may suitably be added in equivalent excess. A slurry of crystalline compound formula (IX) forms with optional cooling. Compound formula (IX) solids may be collected by methods known in the art such as filtration or centrifugation. The solids may be dried, such as under partial vacuum, to yield solid compound formula (IX). The yield to compound formula (IX) from compound formula (XI) for steps 1 and 2 is at least 65%, at least 70%, at least 75%, at least 80% or, at least 85%.

One aspect of the disclosure is directed to a process for preparing a compound of formula (III) or a salt thereof. The process for preparing compound formula (III) comprises two reaction steps as depicted below:
(1) reacting a reaction mixture comprising a compound of formula (XII), a compound B and an organic solvent to form the compound of formula (XIII) according to step 1 below

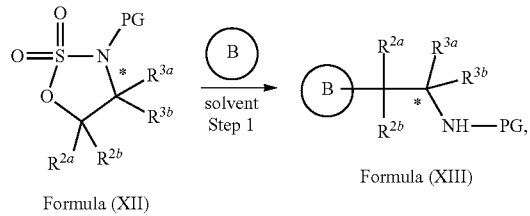

where PG is an amine protecting group; and
(2) deprotecting the compound of formula (XIII) to form the compound of formula (III) according to step 2 below

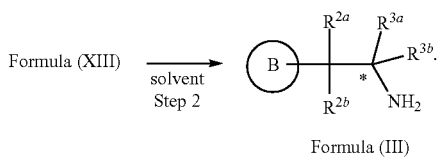

where $R^{2a}$, $R^{2b}$, $R^{3a}$, $R^{3b}$, B, and the asterisk are as described elsewhere herein.

Non-limiting examples of amine protecting groups include ACD, Ac, Bn, CBz, trifluoroacetamide, Boc, MeOZ, FMOC, Bz, PMB, DMPM, PMP, Ts and Troc. In one embodiment, PG is Boc.

In one embodiment, the compound of formula (III) is of the structure

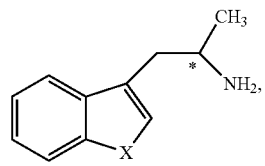

or a salt thereof as described herein.

In some other embodiments, the compound of formula (III) is of the structure

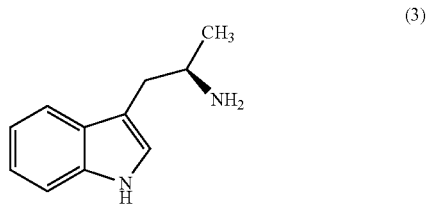

(3)

or a salt thereof as described elsewhere herein.

In step 1, a reaction mixture comprising a compound of formula (XII), B and an organic solvent is reacted to form a compound of formula (XIII). In one embodiment, the organic solvent is a non-polar solvent or a polar solvent. In one embodiment, the solvent is non-polar. Non-limiting examples of suitable solvents include pentane, cyclopentane, hexane, cyclohexane, benzene, toluene, 1,4-dioxane, chloroform, diethyl ether, DCM, and combinations thereof. In one embodiment, the solvent is DCM. In some embodiments, the concentration of B in the solvent may suitably be about 10 g/L, about 25 g/L, about 50 g/L, about 75 g/L, about 100 g/L %, about 125 g/L, about 150 g/L, about 175 g/L, or about 200 g/L, and up to a concentration approaching saturation at the reaction temperature, and ranges constructed from those concentrations, such as from about 25 g/L to about 125 g/L. The equivalent ratio of B to compound formula (XII) is about 0.75:1, about 0.9:1, about 1:1, about 1.25:1, about 1.5:1, about 1.75:1 or about 2:1, and ranges thereof, such as from about 1.25:1 to about 1.75:1. The step 1 reaction mixture may further comprise a suitable alkylating agent. Non-limiting examples of alkylating reagents include alkyl lithium (e.g., methyl lithium) such as and organomagnesium halide compounds, such as methyl magnesium chloride (e.g., in THF). The equivalent ratio of B to the alkylating reagent is suitably about 0.75:1, about 0.8:1, about 0.85:1, about 0.9:1, about 0.95:1, about 1:1, about 1.05:1, about 1.1:1, about 1.15:2, about 1.2:1, about 1.3:1, about 1.4:1, about 1.5:1 or greater, and ranges constructed therefrom, such as from about 1.1 to about 1.3:1. In one embodiment, the reaction mixture further comprises an alkylation catalyst. In some such embodiments, the catalyst is a transition metal catalyst. In some such embodiments the transition metal is copper. In a particular embodiment, the catalyst is suitably a transition metal halide, such as copper (I) halide (e.g., CuCl). In one embodiment, the reaction temperature is about 25° C., about 20° C., about 15° C., about 10° C., about 5° C., about 0° C., about −5° C., about −10° C., about −15° C., about −20° C., about −25° C., about −30° C., about −35° C., about −40° C., about −45° C., or about −50° C., and ranges constructed therefrom, such as from about −20° C. to about 0° C. In one embodiment, the reaction time is not narrowly limited and the reaction is typically continued until the conversion of B and compound formula (XII) to compound formula (XIII) is essentially complete such as determined by chromatography (e.g., TLC, GC or HPLC).

After reaction completion, the reaction may be quenched, such as for instance by the addition of aqueous acid. In one embodiment, the acid may an organic acid as described elsewhere herein, one non-limiting example of which is citric acid. The organic phase comprising the compound of formula (XIII) may then be worked up to dry the compound. In some such embodiments, the quenched reaction product mixture may be separated into an aqueous phase and an organic phase comprising the compound of formula (XIII). The aqueous phase may be washed one or more times with an organic solvent, such as the solvent used to form the reaction mixture (e.g., two washes, each with one volume of the solvent as compared to the reaction mixture volume). The organic phases may be combined and washed one or more times with brine (e.g., two brine washes, each with one volume of brine as compared to the reaction mixture volume). The washed organic phases may then be combined with stirring with activated carbon and with a solid drying agent (e.g., $Na_2SO_4$). Any activated carbon and solid drying agent may be removed by filtration or centrifugation. Any collected solids may then be optionally washed with additional solvent to recover compound formula (XIII) therefrom.

In one embodiment, the solution of compound formula (XIII) may be used as the starting material for step 2. In one embodiment, solid compound formula (XIII) may be prepared. In such embodiments, the collected solution of compound formula (XIII) in organic solvent may be concentrated under partial vacuum to form crude compound formula (XIII). Alternatively, solid compound formula (XIII) may be precipitated/crystallized from solution by the addition of an anti-solvent, such as a non-polar solvent (e.g., 2 volumes of heptane as compared to the solvent volume in the reaction mixture). The solids may be collected by filtration or centrifugation and the collected solids may be washed with anti-solvent. The solids may be dried under partial vacuum, at a temperature of less than 40° C. to provide finished compound formula (XIII). The compound formula (XIII) yield based on compound (XII) is at typically least 50%, at least 55%, at least 60%, or at least 65%. The purity by HPLC (area percent) is at least 90%, at least 95%, at least 98% or at least 99%.

In some step 1 embodiments, compound B, a metal catalyst and an alkylating agent are combined in a first volume of the solvent at the reaction temperature indicated above. The volume of solvent is suitably from about 30% to about 80% of the total volume of solvent used for step 1. Thereafter, a solution of compound formula (XII) in the remainder of the solvent is added at the reaction temperature over a time period to form the reaction mixture. The reaction mixture is then held a temperature for a time to essentially complete the formation of compound formula (XIII), followed by quenching and work-up to a solution of compound formula (XIII) or dried compound formula (XIII).

In step 2, compound formula (XIII) is deprotected to form compound formula (III). In any of the various embodiments, a solution of compound formula (XIII) is suitably deprotected by the addition of an acid. In one embodiment, solid compound formula (XIII) is dissolved in a polar protic solvent as described elsewhere herein (such as methanol, ethanol or i-propanol). The concentration of compound formula (XIII) in the solvent is about 25 g/L, about 50 g/L, about 75 g/L, about 100 g/L, about 125 g/L, about 150 g/L, about 175 g/L, or about 200 g/L, and ranges constructed therefrom, such as from about 50 g/L to about 150 g/L. Acid addition temperature is not narrowly critical.

In some step 2 embodiments, the acid is an inorganic acid as described elsewhere herein. A non-limiting example of a suitable inorganic acid is HCl. In one embodiment, the equivalent ratio of acid to compound formula (XIII) is about 1.5:1, about 2.5:1, about 5:1, about 7.5:1, about 10:1, about 12.5:1 or about 15:1 and ranges constructed therefrom, such as from about 5:1 to about 15:1. After acid addition, the solution is held at temperature with stirring until the deprotection of compound formula (XIII) to form compound formula (III) is essentially complete. In one embodiment, a solvent exchange from the polar protic solvent to a non-polar solvent (as described elsewhere herein) or a polar aprotic solvent (as described elsewhere herein) may be done. In some such embodiments, the solution of compound formula (III) may be concentrated under partial vacuum and extracted with the non-polar or polar aprotic solvent. In some such embodiments, the extraction solvent is DCM. After extraction, the pH of the aqueous phase may be adjusted to strongly basic (i.e., greater than pH 11) with a suitable base, such as aqueous sodium hydroxide. After basification, the aqueous phase may then be further extracted at least once with the extraction solvent. The organic phase(s) may then be dried, such as with brine and/or over a solid desiccant followed by filtration to remove any solids. Collected solids may be optionally washed to recover additional compound formula (III). Solid compound may be isolated from the solution in organic solvent by methods known in the art. For instance, the solution may be concentrated under partial vacuum to dryness. Alternatively, the solution may be concentrated followed by the addition of an anti-solvent to form solid compound (III) that may be collected by filtration or centrifugation, washed, and dried. The compound formula (III) yield based on compound (XIII) is at typically least 85%, at least 90%, at least 95%, or at least 97%. The purity by HPLC (area percent) is at least 90%, at least 95%, or at least 96%.

In some other step 2 embodiments, the acid is an organic acid as described elsewhere herein. Non-limiting examples of suitable organic acids include sulfonic acids and camphorsulfonic acid (CSA) (e.g., L-(−)-CSA). In the case of CSA, the equivalent ratio of CSA to compound formula (XIII) is about 1.5:1, about 2:1 about 2.5:1, about 5:1, about 7.5:1, or about 10:1, and ranges constructed therefrom, such as from about 2:1 to about 4:1. After acid addition, the solution may be heated and held at elevated temperature (e.g., about 35° C. to about 60° C.) with stirring to complete deprotection and form the acid salt of compound formula (XIII). The acid salt solution/suspension may then be cooled, such as to less than about 5° C., to form a suspension of the acid salt of compound formula (XIII). The salt may be collected by filtration or centrifugation and optionally washed wish solvent. The salt may then be dried under partial vacuum to yield the solid salt of compound of compound formula (XIII), such as the L-(−)-CSA salt thereof. The compound formula (III) salt yield based on compound formula (XIII) is at typically least 85%, at least 90%, at least 92% or at least 95%. The purity by HPLC (area percent) is at least 90%, at least 95%, at least 96%, or at least 97%. The compound formula (XIII) salt may be dissolved in water and pH-adjusted to greater than 13, such as about 14, with a strong base thereby forming a suspension comprising solid compound formula (III) free base. The solid material may be collected by filtration or centrifugation and optionally washed with chilled water. The solids may then be dried under partial vacuum to yield dried compound formula (III) free base. The compound formula (III) yield based on compound (XIII) is at typically at least 80%, at least 85%, or at least 90%. The purity by HPLC (area percent) is at least 90%, at least 95%, at least 96%, or at least 97%.

In one embodiment, a compound of formula (VIII) as prepared herein is further recrystallized. In one embodiment the recrystallization comprises recrystallizing the compound of formula (VIII) in a 2-step process. The process comprises heating a slurry comprising a compound of formula (VIII) in a mixture of methanol/ethanol, distilling with methanol, and cooling the mixture. In one embodiment, the mixture of methanol/ethanol is a 95:5, 90:10, 85:15, or 80:20 mixture of methanol/ethanol. In another embodiment, the mixture of ethanol/methanol is a 90:10 mixture of methanol/ethanol. The mixture can be headed at a temperature of >about 50° C., for example, about 55° C., 60° C., or 65° C. The cooling can be down to about room temperature. In one embodiment, the cooling is to about 20° C., 25° C., or 30° C. The solution can be filtered and dried.

In another embodiment, the recrystallization comprises recrystallizing the compound of formula (VIII) from MTBE. A base, such as NaOH or KOH is added to the slurry comprising the compound of formula (VIII) in MTBE. The mixture is stirred at, for example, 15° C., 20° C., 25° C. or 30° C., optionally filtered and distilled with ethanol.

In some embodiments of the process for preparing a compound of formula (III) or a salt thereof, the process further comprises preparing the compound of formula (XII) or a salt thereof.

The process for preparing the compound of formula (XII) comprises reaction steps 3a and 3b depicted below:

(1) reacting a reaction mixture comprising a compound of formula (XIV), thionyl chloride, and an organic solvent to form a compound of formula (XV) according to step 3a below

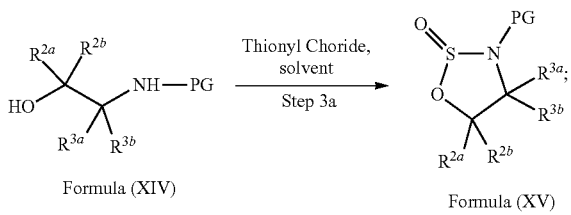

Formula (XIV)   Formula (XV)

and (2) reacting a reaction mixture comprising the compound of formula (XV), a catalyst, an oxidizing agent, and an organic solvent to form the compound of formula (XII) according to step 3b below

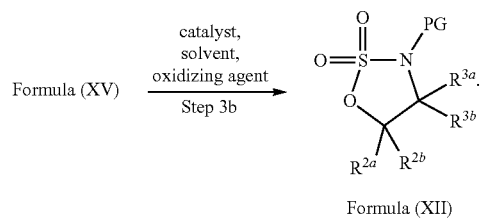

Formula (XV)   Formula (XII)

$R^{2a}$, $R^{2b}$, $R^{3a}$, $R^{3b}$, and the nitrogen protecting group PG are as described herein.

In step 3a, a reaction mixture comprising a compound of formula (XIV), thionyl chloride, and an organic solvent is reacted to form a compound of formula (XV). In one embodiment, the organic solvent is a non-polar solvent or a polar solvent as described elsewhere herein. In one embodiment, the solvent is non-polar as described elsewhere herein. Non-limiting examples of suitable solvents include pentane, cyclopentane, hexane, cyclohexane, benzene, toluene, 1,4-dioxane, chloroform, diethyl ether, DCM, and combinations thereof. In some particular embodiments, the solvent is DCM. In one embodiment, the concentration of the compound of formula (XIV) in the solvent may suitably be about 10 g/L, about 25 g/L, about 50 g/L, about 75 g/L, about 100 g/L %, about 125 g/L, about 150 g/L, about 175 g/L, or about 200 g/L, and up to a concentration approaching saturation at the reaction temperature, and ranges constructed from those concentrations, such as from about 25 g/L to about 125 g/L. The equivalent ratio of thionyl chloride to compound formula (XIV) is about 1:1, about 1.25:1, about 1.5:1, about 1.75:1, about 2:1, about 2.25:1, or about 2.5:1, and ranges thereof, such as from about 1.25:1 to about 1.75:1. In one embodiment, the reaction temperature is about 10° C., about 5° C., about 0° C., about −5° C., or about −10° C., and ranges constructed therefrom, such as from about −5° C. to about 5° C. In one embodiment, the reaction time is not narrowly limited and the reaction is typically continued until the conversion of compound formula (XIV) is essentially complete such as determined by chromatography (e.g., TLC, GC or HPLC). The step 3a reaction mixture may further comprise a base, a non-limiting example of which is imidazole. In such embodiments, the equivalent ratio of thiolation reagent to thionyl chloride may be about 1:1, about 2:1, about 3:1 or about 4:1. The step 3a reaction mixture may further comprise a base, such as an organic base as described elsewhere herein. In some such embodiments, the base may be TEA. In such embodiments, the equivalent ratio of the base to compound formula (XIV) is about 1.25:1, about 1.5:1, about 1.75:1, about 2:1, about 2.25:1, about 2.5:1, about 3:1, about 3.5:1 or about 4:1, and ranges constructed therefrom, such as from about 1.5:1 to about 2.5:1.

In some particular step 3a embodiments, a solution of the base (e.g., imidazole) in the solvent is formed to which the thionyl chloride is added with stirring while maintaining the reaction temperature. Compound formula (XIV) in the solvent may then be added with stirring while maintaining the reaction temperature, followed by addition of the base with stirring while maintaining the reaction temperature. The reaction mixture is then maintained at the reaction temperature with stirring until the conversion of compound formula (XIV) to form a reaction product mixture comprising the compound of formula (XV) is essentially complete.

In any of the various step 3a embodiments, the reaction product mixture may be worked up by methods known to those skilled in the art. For instance, the step 3a reaction mixture may be quenched with chilled water (e.g., 0.25 to 2 volumes of water per volume of organic solvent in the step 3a reaction product mixture). An organic phase comprising the compound of formula (XV) in solution may be isolated and the isolated aqueous phase may be extracted with organic solvent to recover additional compound formula (XV). The organic phases may be combined and washed with an aqueous acid solution, and aqueous base solution, and brine. A non-limiting example of an aqueous acid solution is a solution of a weak acid, such as a citric acid. A non-limiting example of a base solution is a solution of a weak base, such as sodium bicarbonate.

In step 3b, a reaction mixture comprising formula (XV) in solution in the organic solvent is combined with a catalyst and an oxidizing agent, and reacted to form a reaction product mixture comprising the compound of formula (XII). In one embodiment, the catalyst is a redox active metal catalyst as described elsewhere herein. Non-limiting examples of suitable catalysts include $NiCl_2$, $RuCl_3$, $CoCl_2$, $FeCl_3$, $FeCl_2$, and $MnCl_2$. Non-limiting examples of suitable oxidants include $NaIO_4$, NaOCl, and Oxone. In some embodiments the reaction mixture further comprises water. The volume ratio of water to organic solvent is suitably about 0.25:1, about 0.5:1, about 0.75:1, about 1:1, about 1.25:1, about 1.50:1, about 1.75:1, about 2:1 or about 2.5:1, and ranges constructed therefrom, such as from about 0.5:1 to about 1.5:1. The reaction temperature is suitably from about 5° C. to about 50° C. The reaction mixture is maintained at the reaction temperature with stirring until the conversion of compound formula (XV) to form a reaction product mixture comprising the compound of formula (XII) is essentially complete such as determined by chromatography (e.g., TLC, GC or HPLC).

The step 3b reaction product mixture may be worked up by methods known to those skilled in the art. For instance, the organic phase comprising the compound of formula (XII) in solution may be isolated and the aqueous phase may be optionally filtered and then extracted with organic solvent to recover compound formula (XII). The organic phase(s) may optionally be washed with a reducing agent (e.g., sodium thiosulfate) and with brine. The organic phase(s) may be dried with a solid desiccant (e.g., sodium sulfate) followed by filtration to remove solids and optional washing thereof with organic solvent. Solid compound formula (XII) from solution in organic solvent by methods known in the art. For instance, the solution may be concentrated under partial vacuum to dryness. Alternatively, the solution may be concentrated followed by the addition of an anti-solvent to form solid compound (XII) that may be collected by filtration or centrifugation, washed, and dried. The compound formula (XII) yield based on compound (XIV) is at typically least 85%, at least 90%, or at least 92%. The purity by HPLC (area percent) is at least 95%, at least 98%, or at least 99%.

Chiral primary amines can be produced using a stereospecific transaminase either via an asymmetric transamination of a prochiral ketone or kinetic resolution of a racemic amine. The transamination is a reaction equilibrium consisting of a pair of amines and ketones (donors and acceptors) and the reaction conditions applied shift the equilibrium to the chiral target amine. In one such aspect, the amine donor is alanine or 2-propylamine. In one embodiment, the amine acceptor is pyruvate or acetone.

Thus, further provided herein is a process for preparing a compound of formula (XX) or a salt thereof, wherein conversion of the chiral tryptamine comprises using enzymatic transformation:

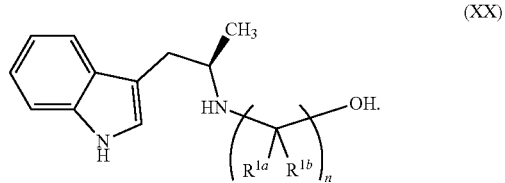

The process for preparing compound formula (XX) comprises contacting a compound of formula (XXI)

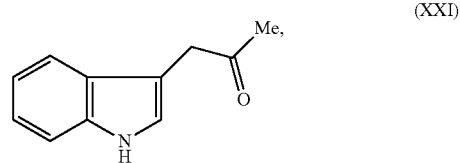 [SMILES: CC(=O)Cc1c[nH]c2ccccc12]

with a protein transaminase to form a compound of formula (3):

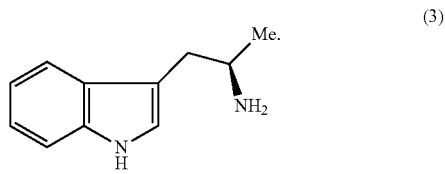 [SMILES: C[C@@H](N)Cc1c[nH]c2ccccc12]

The process further comprises the presence of one or more amine donors. In one embodiment the amine donor is alanine or iso-propyl amine.

The contacting described above can be performed in mixed aqueous organic solvent systems. For example, the transaminase reaction can be performed in aqueous buffer with an organic co-solvent such as cyclo-hexane, methyl-cyclo-hexane, iso-octane, DMSO, acetonitrile, or acetone. Such co-solvents can be present at 1, 2, 3, 4, 5, 6, 7, 8, 9, 10, 15, 20, 25, 30, 35, 40, 45, or 50% v/v.

The mixed organic/aqueous solvent system (micro-aqueous reaction system) can, in certain instances, comprise one or more organic solvents comprising a small amount of aqueous buffer. In one embodiment, the contacting is performed in TBME, dibutyl ether, CPME, toluene, ethyl acetate, butyl acetate, iso-propyl acetate, butyl butyrate, ethyl butyrate or iso-butyl acetate comprising less than 15, 14, 13, 12, 11, 10, 9, 8, 7, 6, 5, 4, 3, 2 or 1% v/v aqueous buffer. When performed in organic solvent, the transaminase can be immobilized to a solid support.

In another embodiment, the conversion of compound (XXI) to compound (3) is above at least 70%, 75%, 80%, 85%, 90%, 95%, 96%, 97%, 98%, or 99%. In another aspect, the conversion is above 90%. In another embodiment, the conversion is above 95%.

The reductive amination completed by the transaminase can yield the compound of formula (3) in at least 90, 91, 92, 93, 94, 95, 96, 97, 98, 99, or 100% enantiomeric excess (EE). In certain instances, the transaminase converts the compound of formula (XXI) to (3) at an EE greater than 99%.

In one embodiment, the asymmetric transamination of the compound of formula (XXI) is performed using the scheme below:

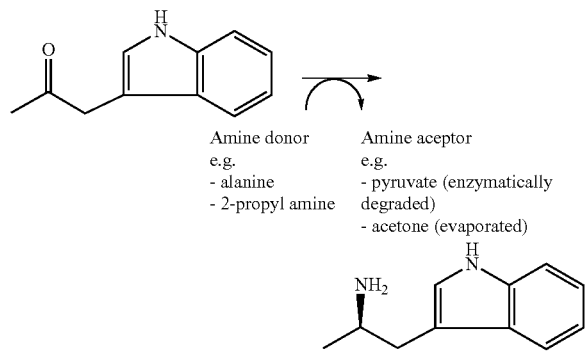

Amine donor
e.g.
- alanine
- 2-propyl amine

Amine aceptor
e.g.
- pyruvate (enzymatically degraded)
- acetone (evaporated)

The compound of formula (3) is contacted with a compound of formula (II) as described herein:

(II)

to form compound formula (XX).

$R^{1a}$, $R^{1b}$ and n are as described elsewhere herein. In one embodiment, $R^{1a}$ and $R^{1b}$ are independently fluorine.

In one embodiment, compound formula (XX) is of the structure:

The protein transaminase can be selected from Table 6. In one such aspect, the transaminase is (R)-selective. In one embodiment, the transaminase is TA-P2-A01. In one embodiment, the protein transaminase is selected from a (S)-enantioselective transaminase of SEQ ID NO:1, SEQ ID NO:2, SEQ ID NO:3, and SEQ ID NO:4.

Further provided herein are methods of enzymatically synthesizing a compound of formula (3) through kinetic resolution of a racemic amine in the presence of an amine acceptor and a transaminase. The reaction can be performed in conditions as described herein, for example, in mixed aqueous/organic solvent systems as described herein. In one such aspect, the reaction is performed in aqueous buffer comprising acetonitrile. Such kinetic resolution can yield the compound of formula (3) in an EE of at least 99%, requiring above 50% conversion rate. Kinetic resolution comprises use of an (S)-selective transaminase as described herein for performing the kinetic resolution. In one embodiment, the transaminase is selected from Table 6.

One embodiment of the disclosure is directed to a compound of formula (XVI):

(XVI)

$R^4$, s, $R^{10}$, G, and p are as defined herein.

each of $R^{7a}$, $R^{7b}$, $R^{8a}$ and $R^{8b}$ is independently hydrogen, halogen, $C_{1-3}$ alkyl, $C_{1-3}$ haloalkyl, $C_{1-3}$ hydroxyalkyl, or —CN. In one embodiment, each of $R^{7a}$, $R^{7b}$, $R^{8a}$ and $R^{8b}$ is independently hydrogen, fluorine, —$CH_3$, or —CN. In one embodiment, each of $R^{7a}$, $R^{7b}$, $R^{8a}$ and $R^{8b}$ is hydrogen.

y is an integer of 1 or 2, x is an integer of 1 or 2, and the total of x and y is 2 or 3.

M is $C_{1-5}$ alkyl;

r is 0 or 1; and $R^9$ is halogen or —CN.

In one embodiment, M is —$CH_2CH_2CH_2$—, p is 1, and $R^9$ is fluorine.

In one embodiment, M is —$CH_2CH_2CH_2$—, p is 1, and $R^9$ is —CN.

In one embodiment, the compound of formula (XVI) is:

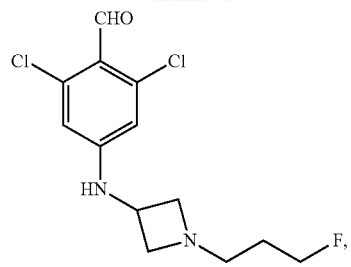
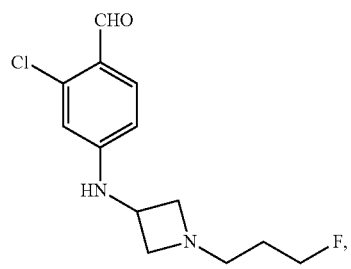
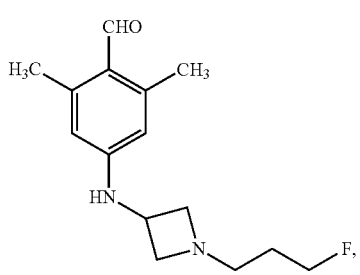
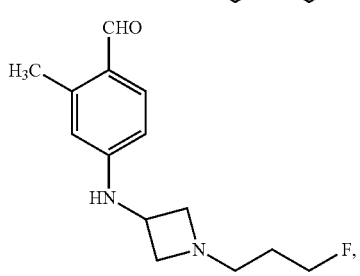
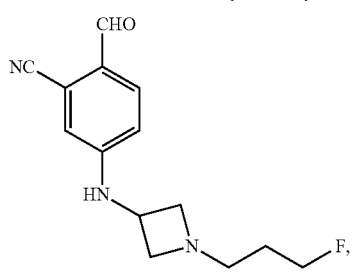
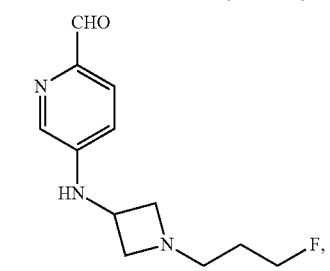
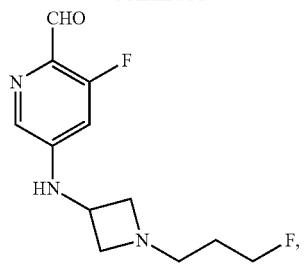
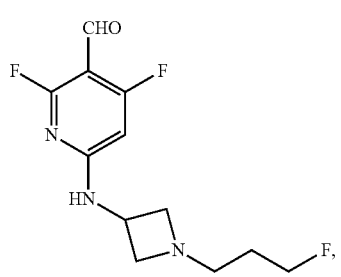
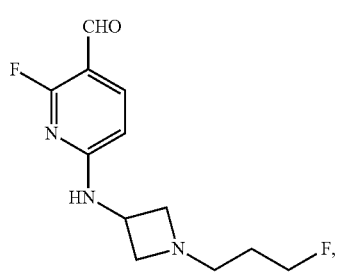
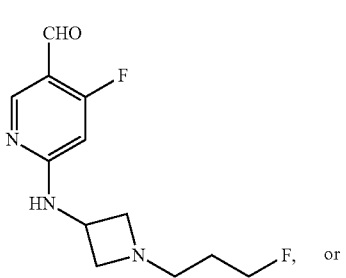
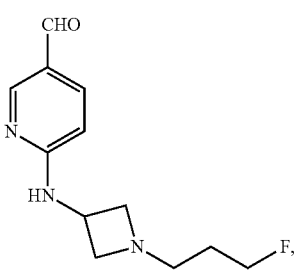
or a salt thereof.

In a particular embodiment, the compound of formula (XVI) is:

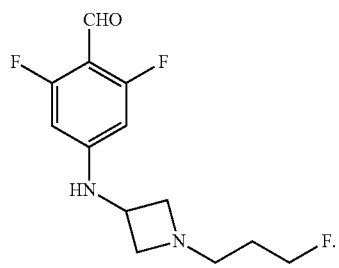 [SMILES: O=Cc1c(F)cc(NC2CN(CCCF)C2)cc1F]

In another aspect provided herein is a compound having the structure:

(Compound B)

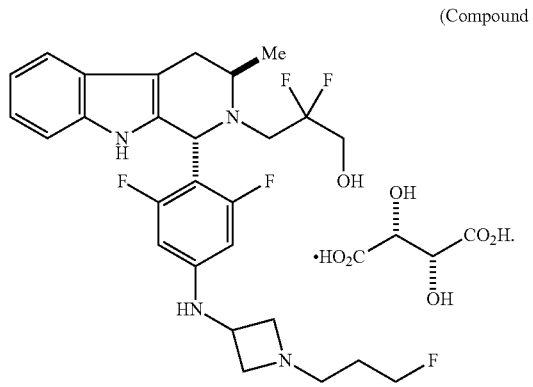

In another aspect provided herein is a process to make a compound having formula:

(B)

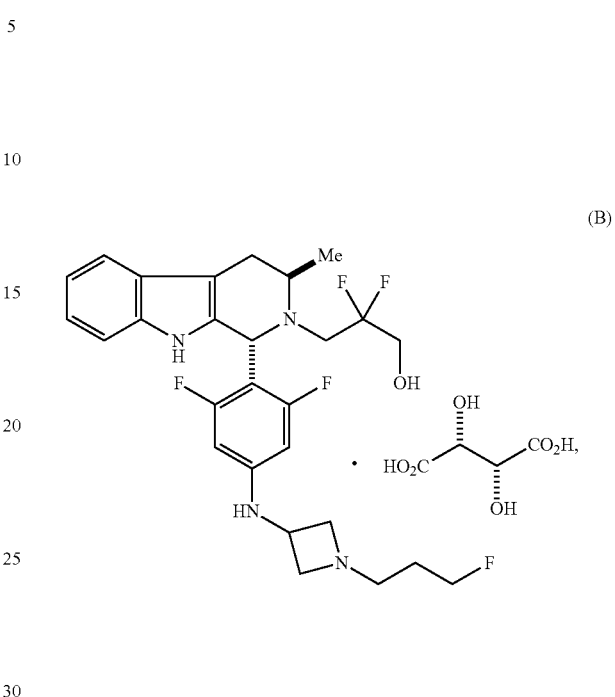

wherein the process is performed as set forth in Scheme A below and in accordance with the embodiments and embodiments provided herein.

Scheme A

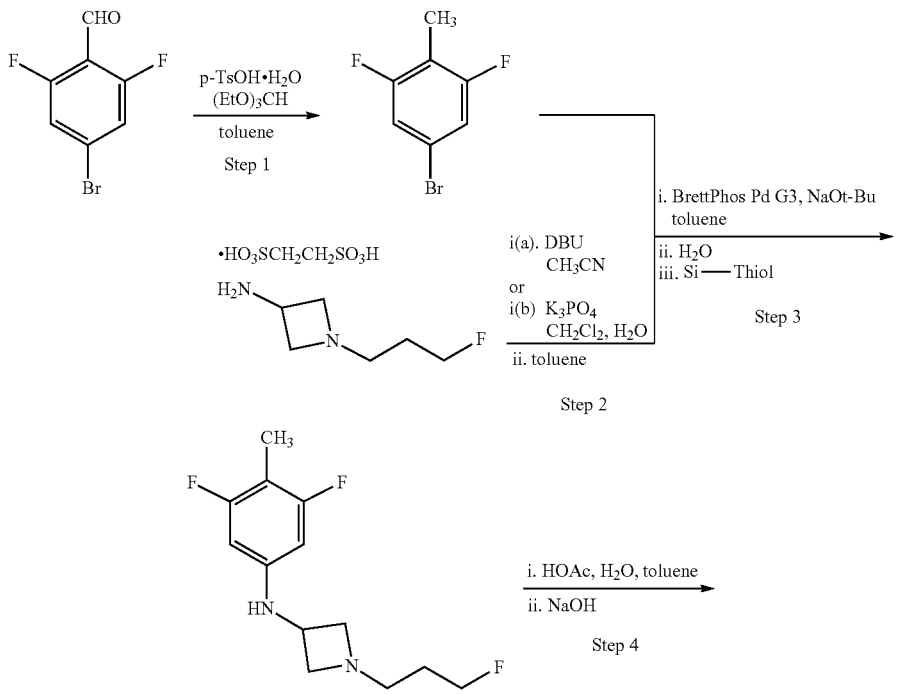

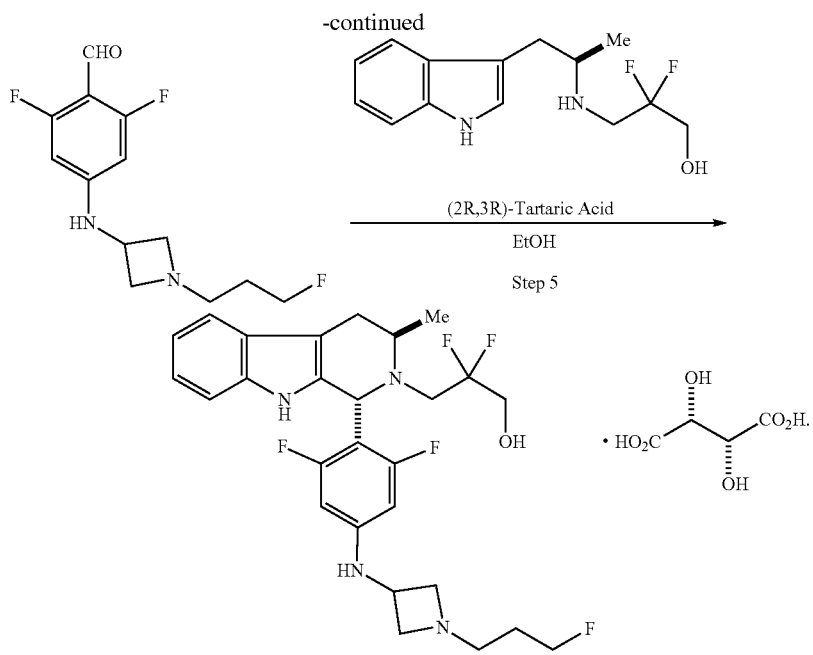

BrettPhos Pd G3=[(2-di-cyclohexylphosphino-3,6-dimethoxy-2',4',6'-triisopropyl-1,1'-biphenyl)-2-(2'-amino-1,1'-biphenyl)]palladium(II) methanesulfonate In still another embodiment, of the disclosure is a process to make a compound having formula:

(B)

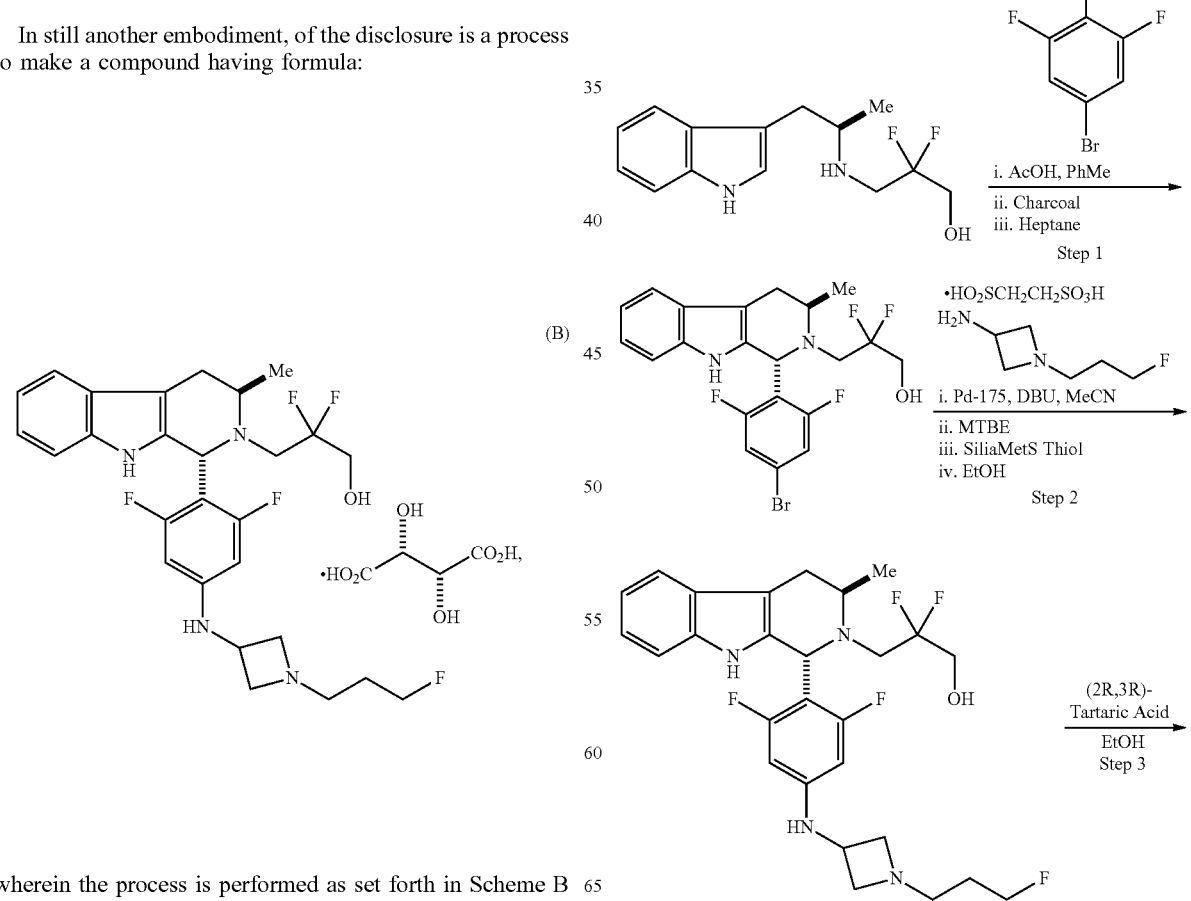

wherein the process is performed as set forth in Scheme B below and in accordance with the embodiments and embodiments provided herein.

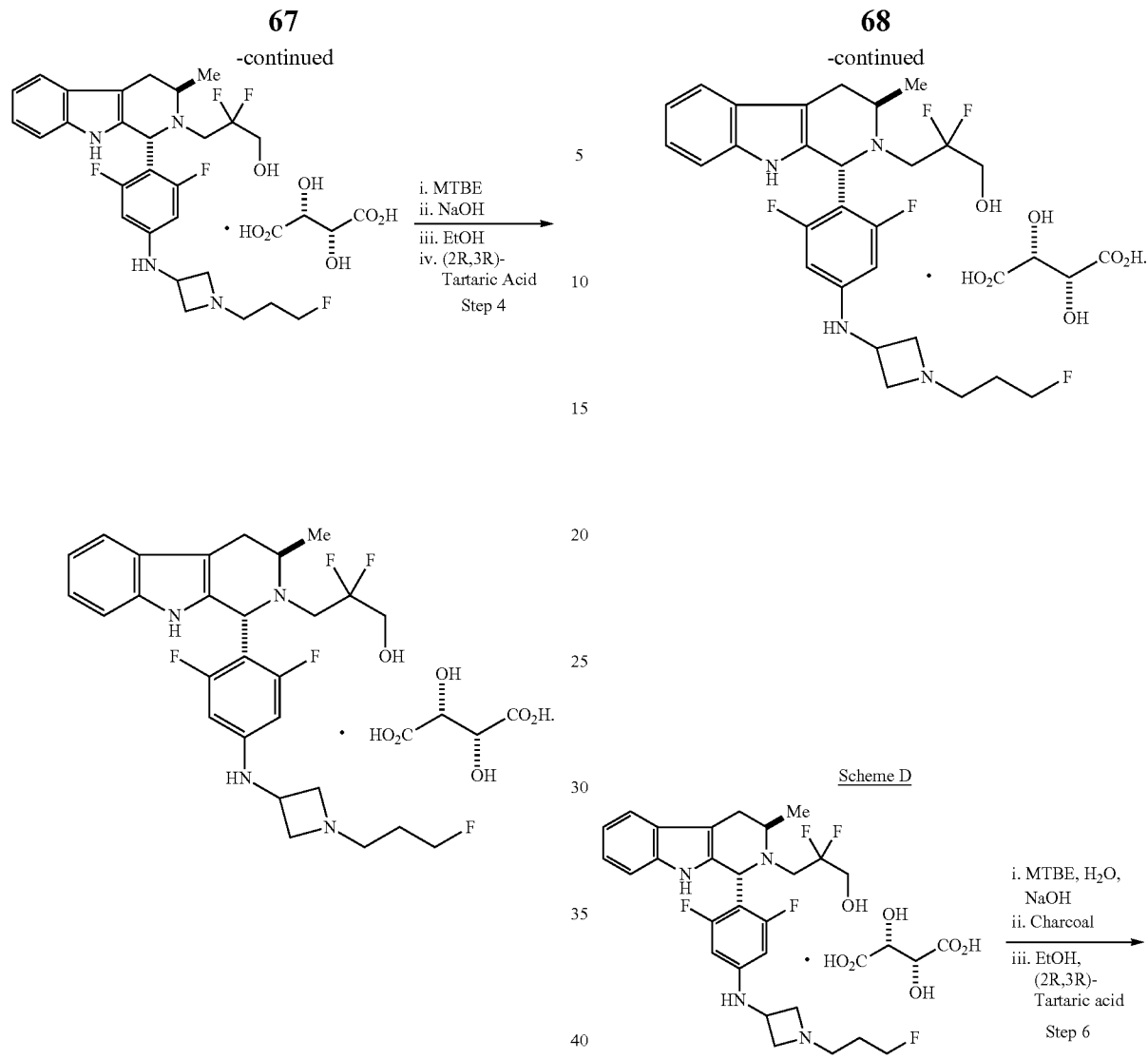

The processes for synthesis of Compound B above (e.g. Scheme A and B) can further comprise recrystallization according to Scheme C or D below:

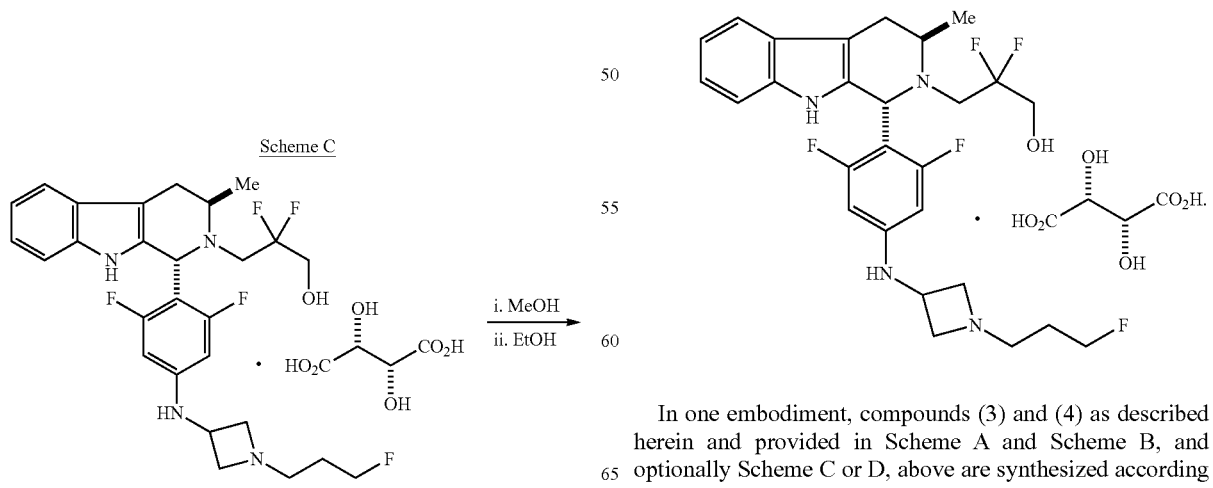

In one embodiment, compounds (3) and (4) as described herein and provided in Scheme A and Scheme B, and optionally Scheme C or D, above are synthesized according to Scheme E below and in accordance with the embodiments and embodiments provided herein.

Scheme E

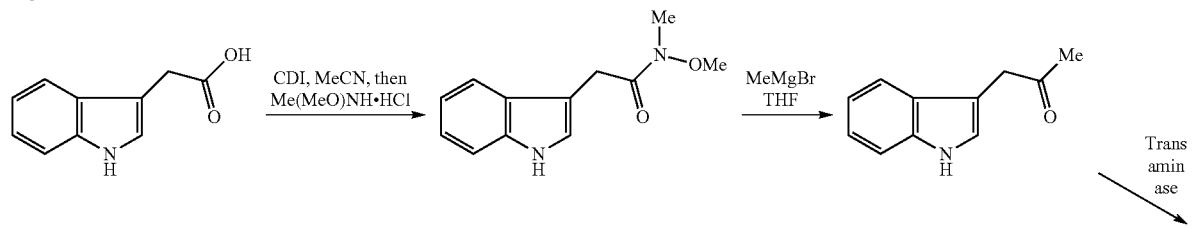

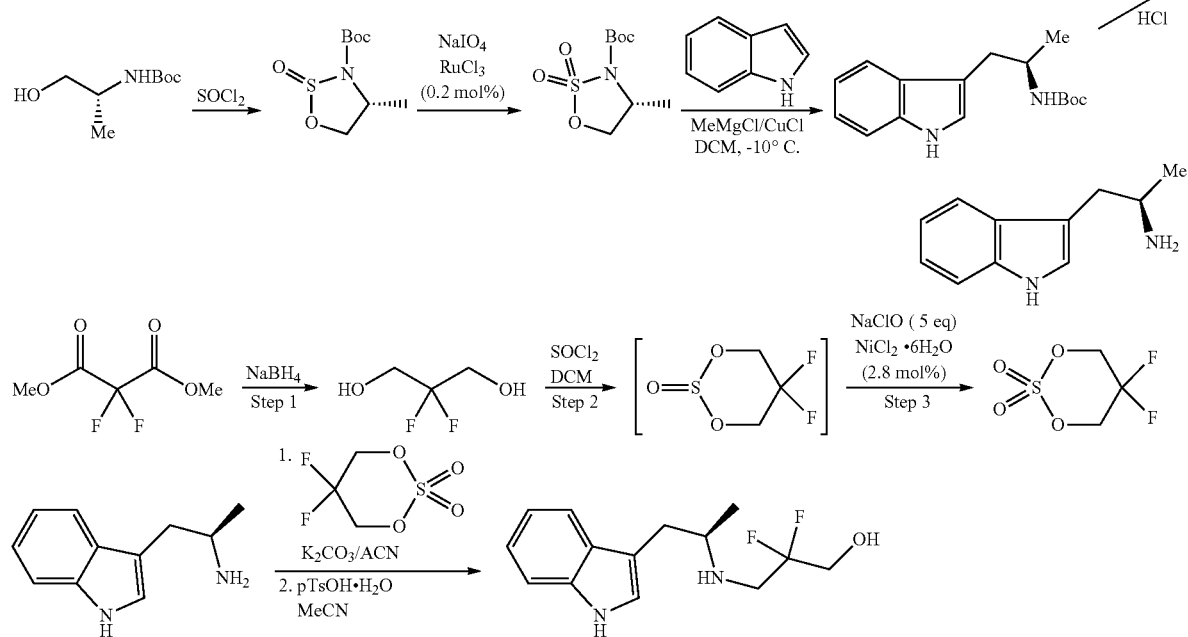

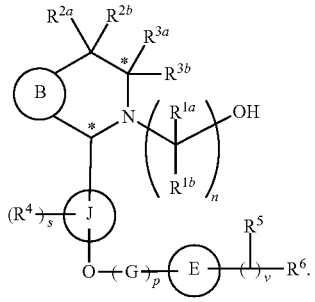

Further provided herein is a process for preparing a compound of formula (XXIII) or a salt thereof:

Formula (XXIII)

B, $R^{1a}$, $R^{1b}$, n, $R^{2a}$, $R^{2b}$, $R^{3a}$, $R^{3b}$, J, $R^4$, s, G, $R^5$, v, $R^6$, E, and the asterisks are as defined herein.

In one embodiment, the compound of formula (XXIII) is an acid salt. In such embodiments, the compound of formula (VIII) is a salt of an acid. In a preferred embodiment, the compound of formula (XXIII) is a salt of tartaric acid. In some embodiments, the compound of formula (XXIII) is a salt of fumaric acid.

In one embodiment, the compound of formula (XXIII) is of any one of the following structures, or a tartaric acid salt thereof:

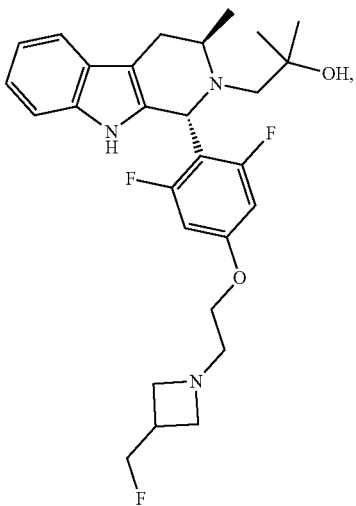

71
-continued
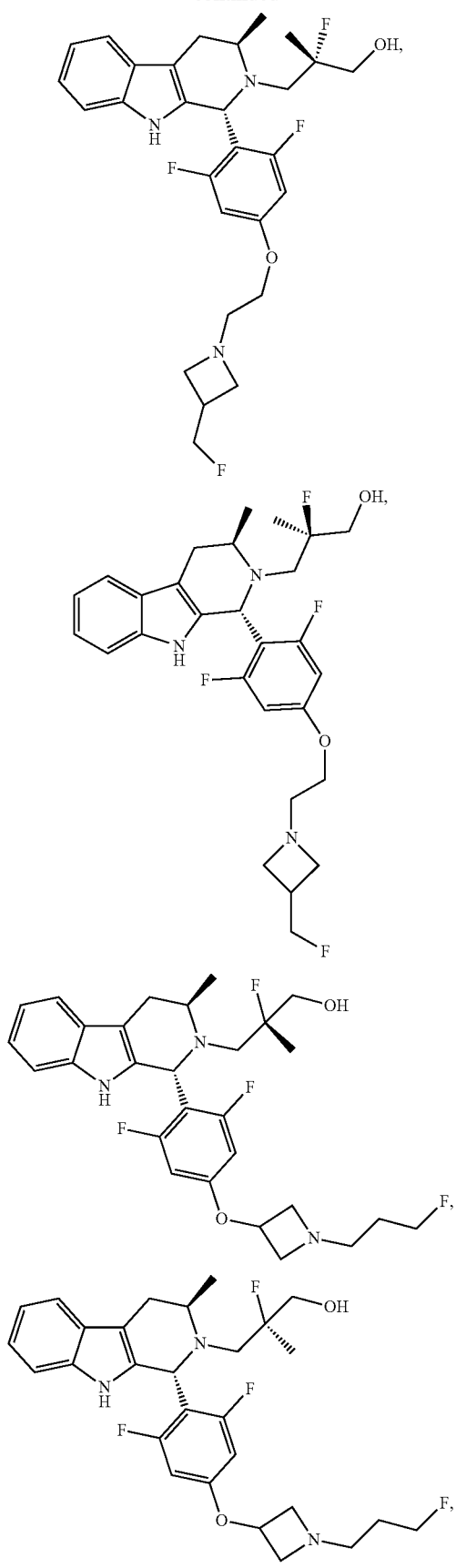
72
-continued
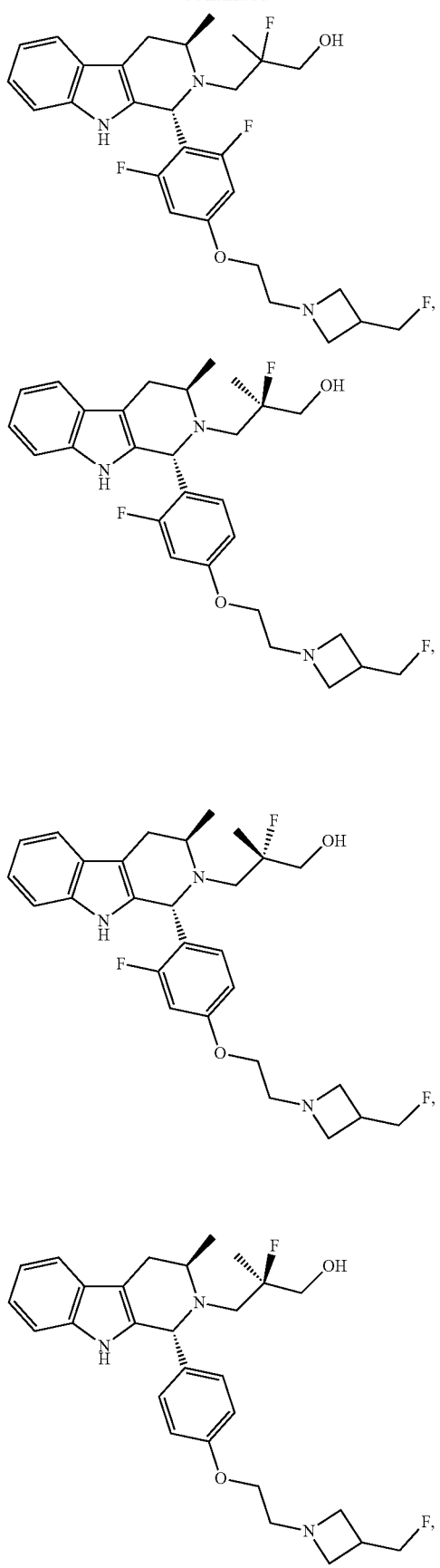

73
-continued
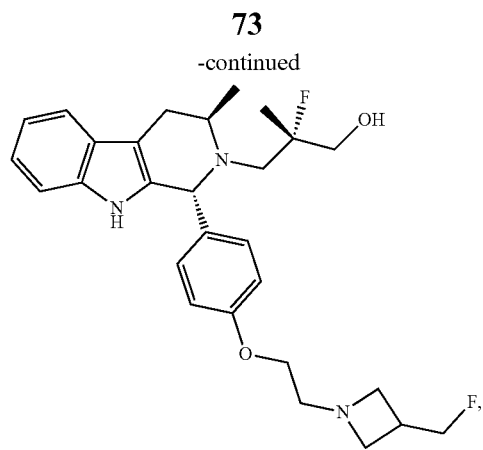
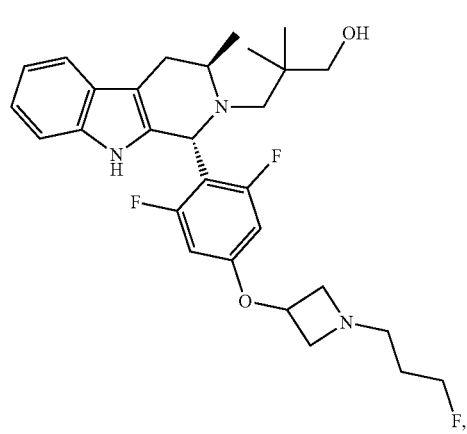
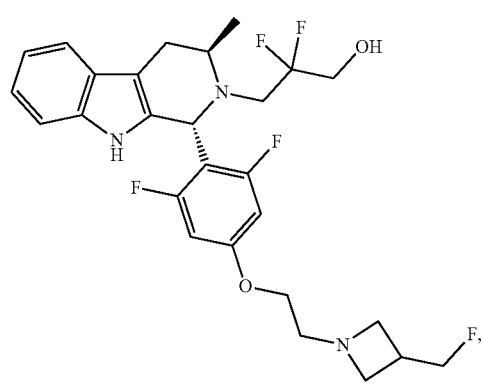
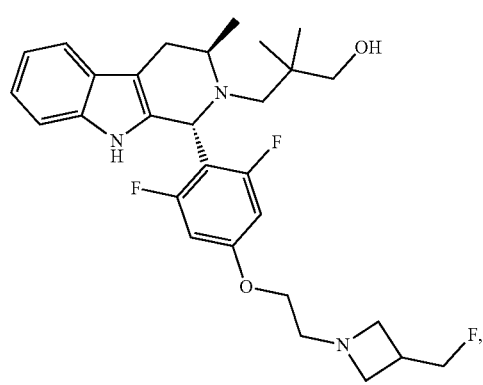
74
-continued
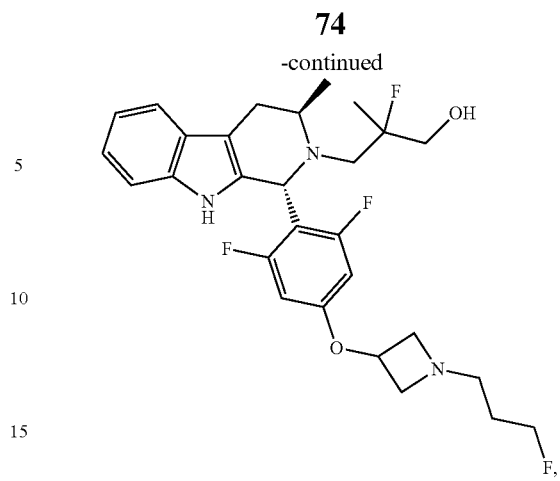
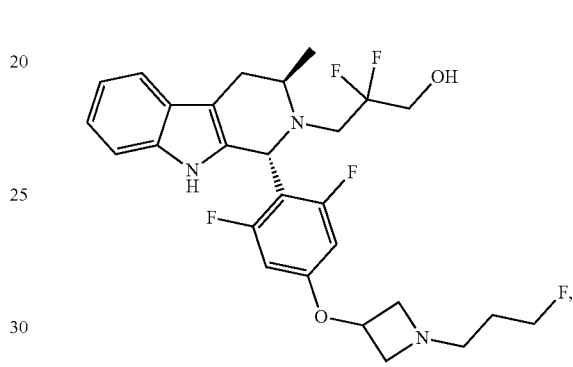
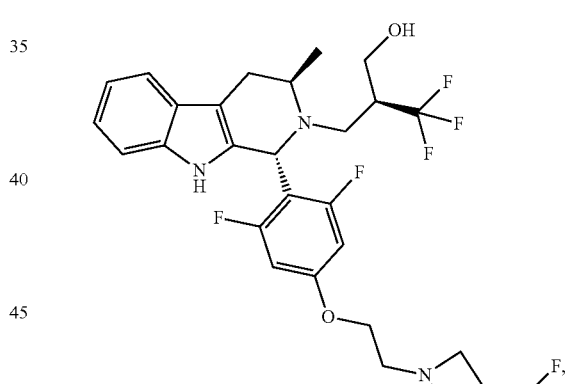
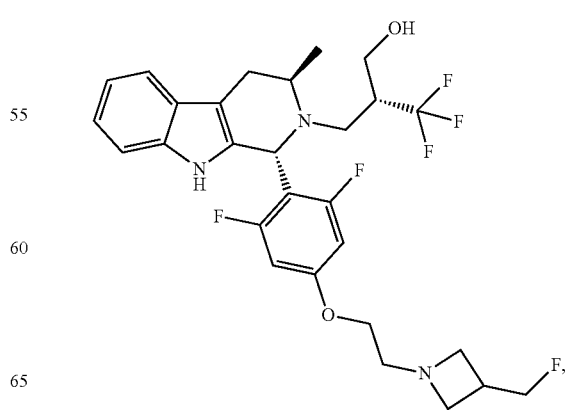

75
-continued
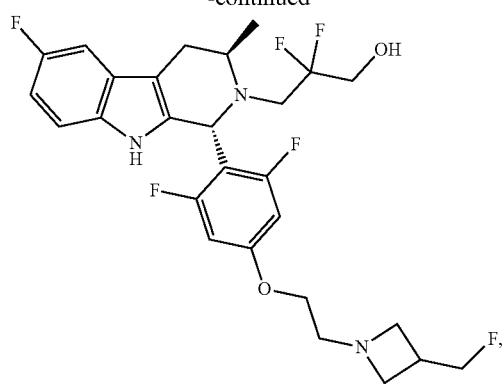
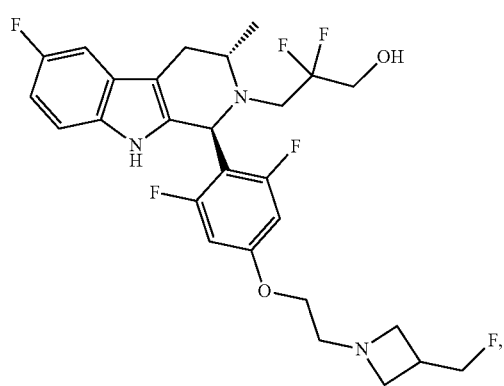
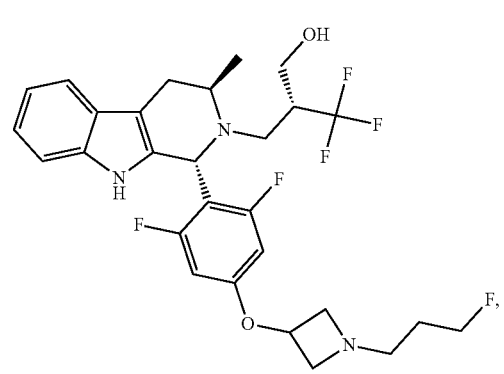
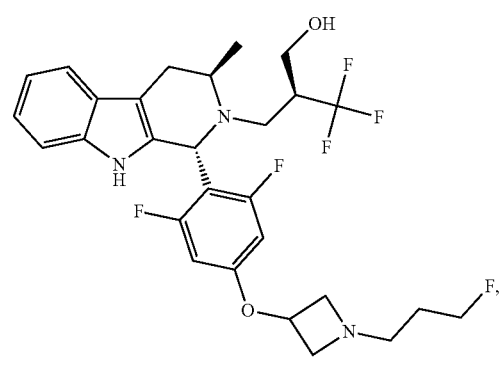
76
-continued
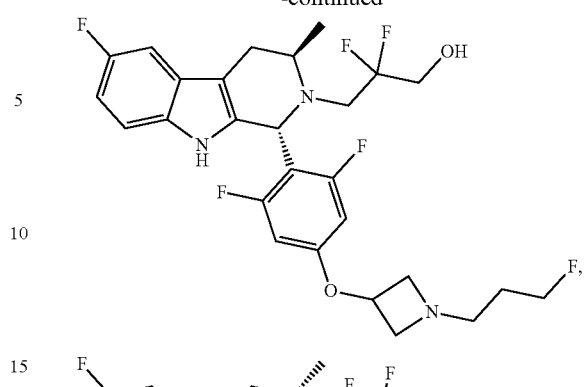
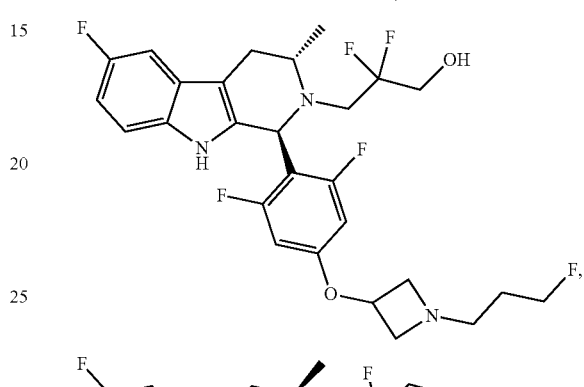
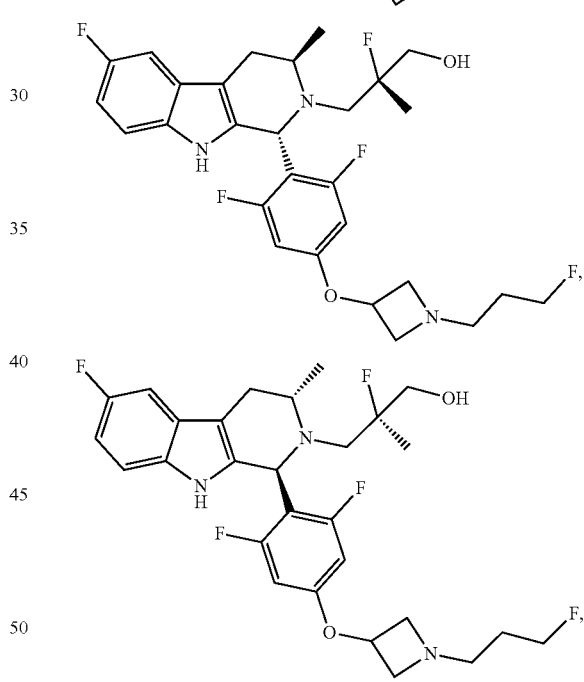
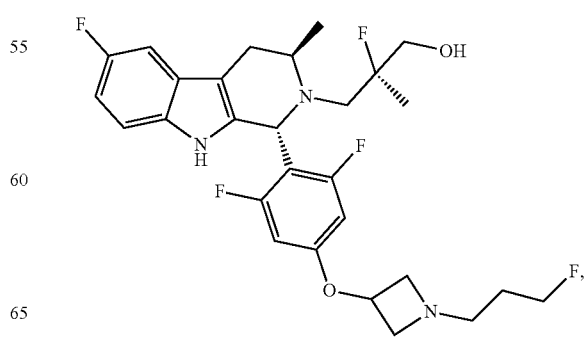

77
-continued
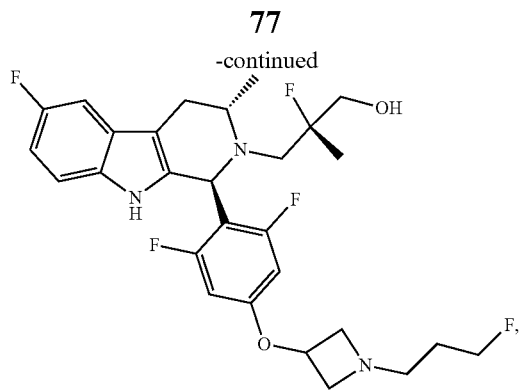
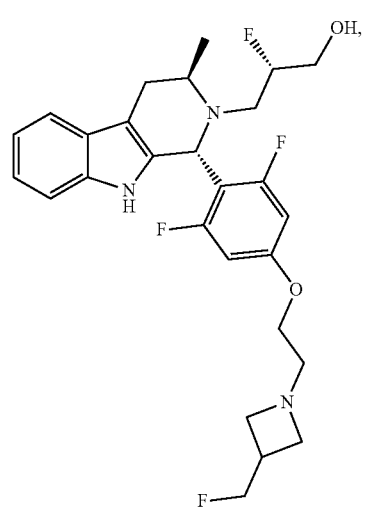
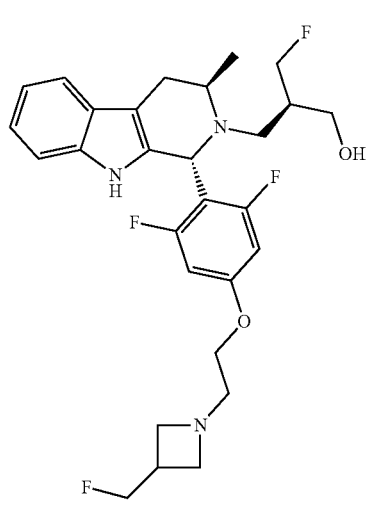
78
-continued
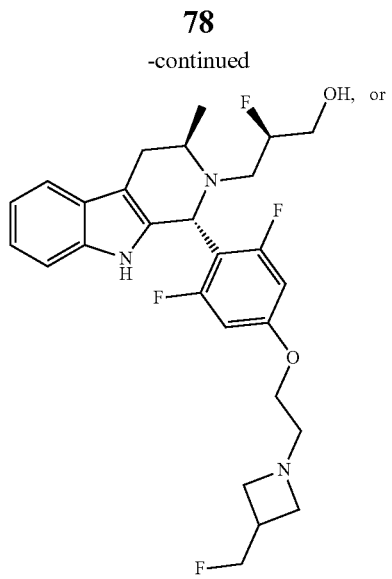
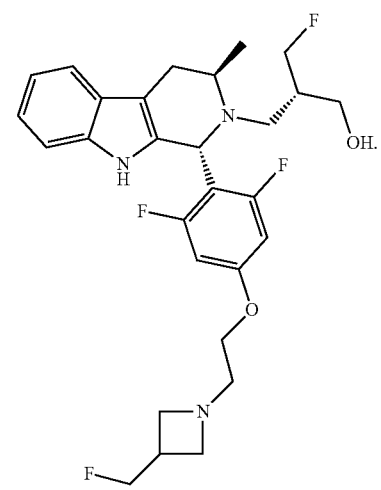 [SMILES: C[C@@H]1Cc2c([nH]c3ccccc23)[C@@H](c2c(F)cc(OCCN3CC(CF)C3)cc2F)N1C[C@@H](CO)CF]
In another embodiment, the compounds above are a fumaric acid salt.
In one embodiment, the compound of formula (XXIII) is of the following structure, or a pharmaceutically acceptable salt thereof:
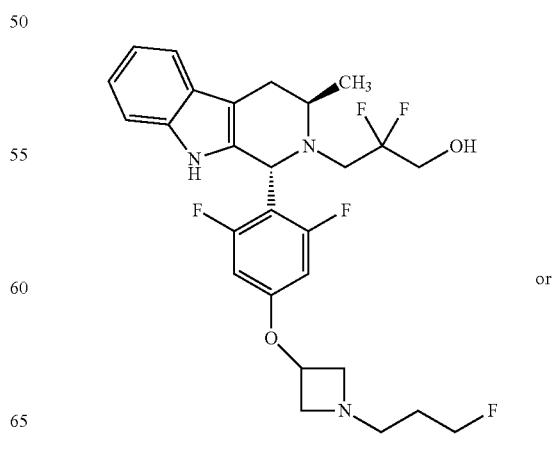
or

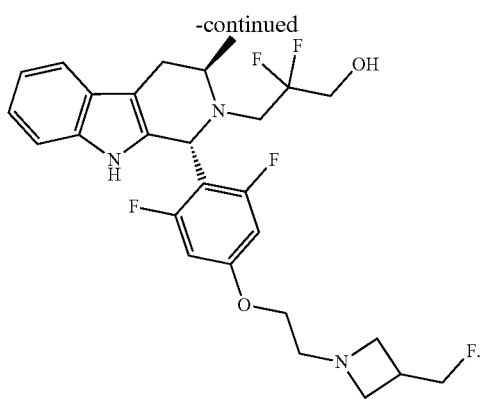

The process for preparing the compound of formula (XXIII) comprises two reaction steps as depicted below:

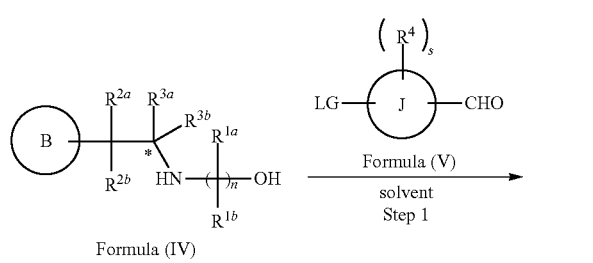

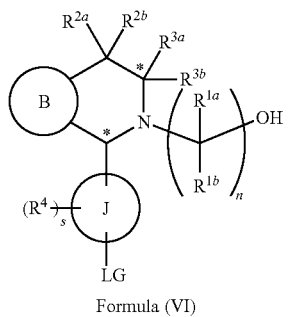

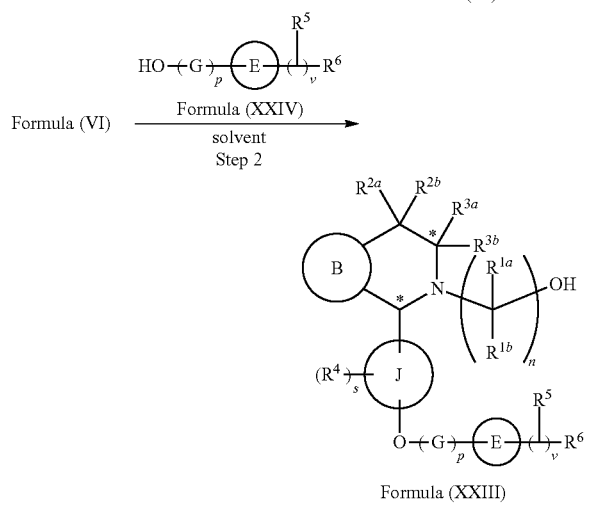

LG is as defined herein.

The variables of formulae (IV), (V) and (VI) are as described herein.

In one embodiment, the compound of formula (XXIV) is of any one of the following structures, or a salt thereof:

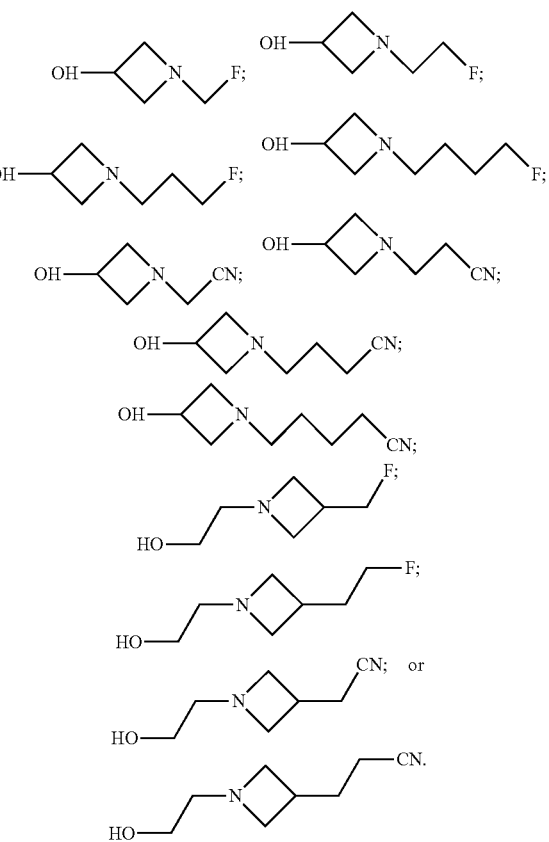

One embodiment of the disclosure is directed to a process for preparing a compound of formula (XXIII) or a salt thereof, wherein the compound of formula (XXIII) is as described herein. The process for preparing the compound of formula (XXIII) according to this embodiment comprises reaction step 1 as depicted below:

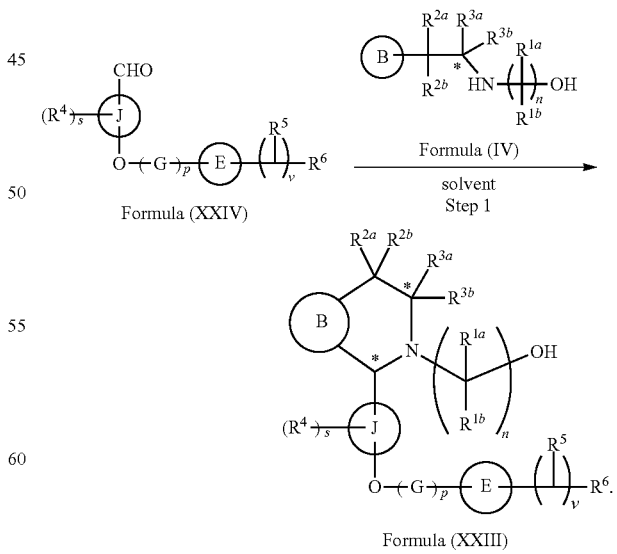

Each of B, $R^{1a}$, $R^{1b}$, n, $R^{2a}$, $R^{2b}$, $R^{3a}$, $R^{3b}$, $R^4$, s, J, $R^5$, v, $R^6$, G, p, E and the asterisk are as described elsewhere herein. The CHO moiety and the nitrogen atom linking J and G are located in the para position with respect to each other on J.

In some embodiments, compound formula (XXIV) is:

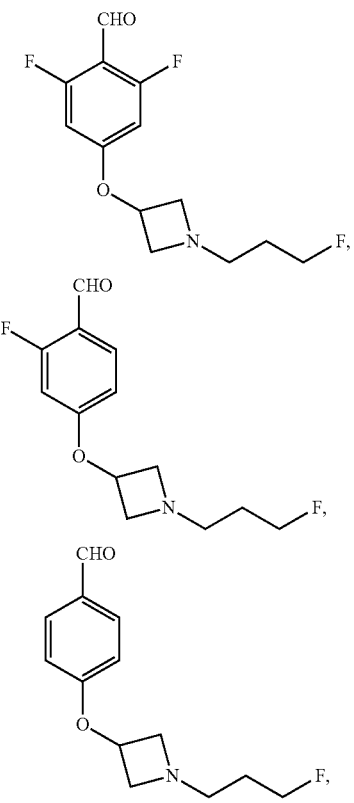

or a salt thereof

One embodiment of the disclosure is directed to a process for preparing a compound of formula (XXVII) or a salt thereof.

The process for preparing compound formula (XXVII) comprises two reaction steps as depicted below:

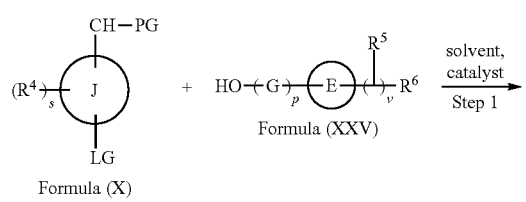

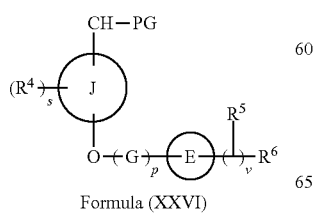

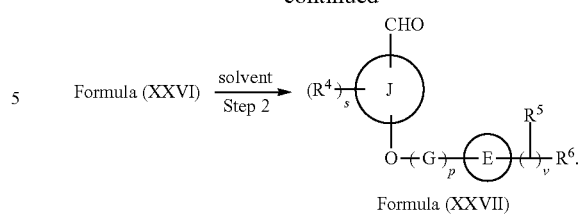

$R^4$, s, LG, $R^5$, v, $R^6$, G, p, E and PG are as described herein.

Further provided herein are solid forms, formulations comprising such solid forms, and methods of using such solid forms of Compound A:

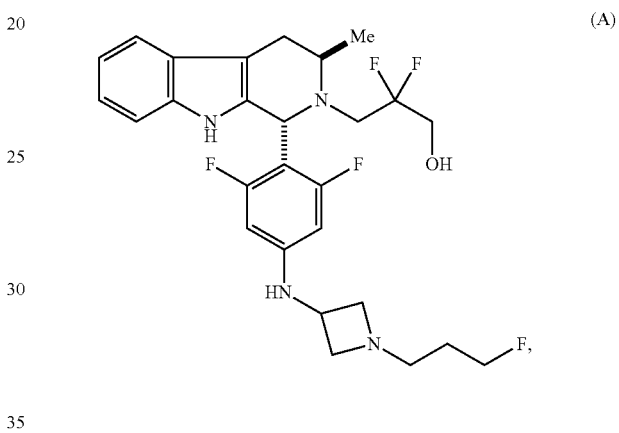

and having the name 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol, including a pharmaceutically acceptable salt thereof.

In one embodiment provided herein are solid forms of Compound A. Compound A can be a freebase as described herein existing in an amorphous solid form. In another embodiment, Compound A is a crystalline solid as described herein. In still another embodiment, Compound A is a crystalline tartrate salt having the structure:

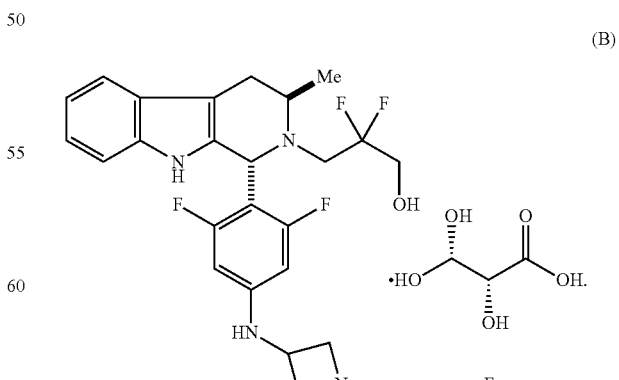

In another aspect provided herein are crystalline solid forms of Compound A as a fumarate salt having the structure:

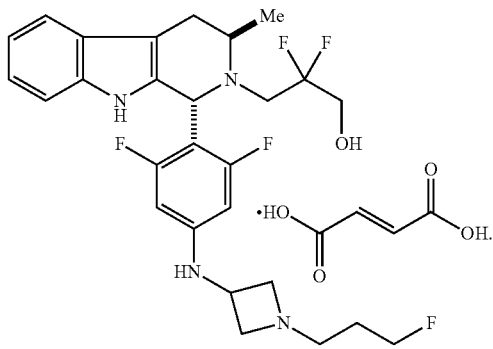

(C)

In still another aspect provided herein are solid forms of Compound A malonate salts having the structure:

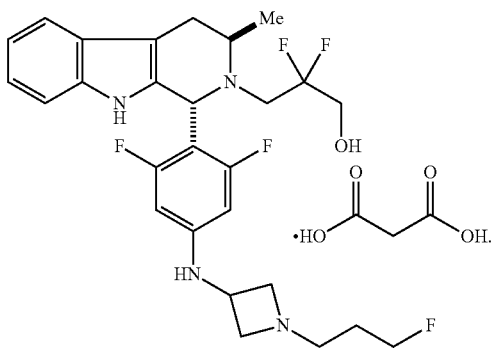

(D)

Solid forms described herein can be crystalline. In another embodiment, the solid form is a single-component solid form. Solid forms described herein can be solvates, hydrates, anhydrates, or salts as set forth herein. In one embodiment, solid forms described herein comprise tartrate salts. In another embodiment, solid forms described herein comprise anhydrates of Compound B. In another embodiment, solid forms described herein comprise fumarate salts. In still another embodiment, solid forms described herein comprise phosphate salts or other salts.

While not intending to be bound by any particular theory, solid forms can be characterized by physical properties such as, for example, stability, solubility and dissolution rate, density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein.

The solid forms described herein, including salt forms, crystalline forms, and amorphous solids can be characterized by a number of methods including, for example, single crystal X-ray diffraction, X-ray powder diffraction (XRPD), microscopy (e.g., scanning electron microscopy (SEM)), thermal analysis (e.g., differential scanning calorimetry (DSC), dynamic vapor sorption (DVS), thermal gravimetric analysis (TGA), and hot-stage microscopy), spectroscopy (e.g., infrared, Raman, and solid-state nuclear magnetic resonance), ultra-high performance liquid chromatography (UHPLC), proton nuclear magnetic resonance (spectrum.

Techniques for characterizing crystal forms and amorphous solids include, for example, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NIR) spectroscopy (including $^1$H NMR and F NMR), scanning electron microscopy (SEM), electron crystallography and quantitative analysis, particle size analysis (PSA), surface area analysis, solubility studies, and dissolution studies.

The purity of the solid forms provided herein can be determined by standard analytical methods, such as thin layer chromatography (TLC), gel electrophoresis, gas chromatography, ultra-high performance liquid chromatography (UHPLC), and mass spectrometry (MS).

Compound B, Form A:

In certain embodiments, provided herein is a solid form of Compound B designated as Form A. Form A is a crystalline solid form of Compound B. In one embodiment, Form A is an acetone solvate of Compound B. In one embodiment, Form A is a crystalline acetone solvate tartrate salt of Compound A.

In another embodiment, Form A of Compound B is obtained by slurrying in acetone followed by evaporation. Form A can prepared according to the methods and examples described herein.

In one embodiment, a solid form provided herein, e.g., Form A, is a tartrate salt of Compound A (i.e. Compound B), and is crystalline, as indicated by X-ray powder diffraction pattern (XRPD) measurements. In one embodiment, the XRPD of a solid form provided herein, e.g., Form A, is substantially as shown in FIG. 1. In another embodiment, a solid form provided herein, e.g., Form A, has one or more characteristic XRPD peaks at approximately 4.64, 8.26, 9.28, 11.18, 11.49, 11.96, 12.54, 13.77, 14.22, 14.61, 15.09, 15.56, 16.01, 17.35, 18.55, 18.84, 19.32, 19.82, 20.26, 21.34, 21.63, 21.92, 22.52, 22.97, 23.28, 23.54, 23.94, 24.81, or 25.96±0.1° 2θ, as depicted in, for example, FIG. 1 and as found in Table 16 herein. In still another embodiment, a solid form provided herein, e.g., Form A, has at least 3, at least 5, at least 7, or at least 10 XPRD peaks at approximately 4.64, 8.26, 9.28, 11.18, 11.49, 11.96, 12.54, 13.77, 14.22, 14.61, 15.09, 15.56, 16.01, 17.35, 18.55, 18.84, 19.32, 19.82, 20.26, 21.34, 21.63, 21.92, 22.52, 22.97, 23.28, 23.54, 23.94, 24.81, or 25.96 0.1° 2θ, as depicted in, for example, FIG. 1 and as found in Table 16 herein. In yet another embodiment, a solid form described herein, e.g., Form A, has one, two, three, four, five, six, seven, eight, nine, ten, eleven, twelve, thirteen, fourteen, fifteen, sixteen, seventeen, eighteen, nineteen, twenty, or all of the characteristic XRPD peaks as set forth in Table 16.

In still another embodiment, a solid form provided herein, e.g., Form A, has one, two, three, four, five, six, seven, eight, nine, or ten characteristic XRPD peaks at approximately 12.54, 14.61, 16.01, 19.32, 20.26, 21.63, 23.28, 23.54, 23.94, or 24.81±0.1° 2θ, as depicted in, for example, FIG. 1 and as found in Table 16 herein. In another embodiment, a solid form provided herein, e.g., Form A, has one, two, three, four, or five characteristic XRPD peaks at approximately 19.32, 20.26, 21.63, 23.28, or 24.81±0.1° 2θ, as depicted in, for example, FIG. 1 and as found in Table 16 herein. In another embodiment, a solid form provided herein, e.g., Form A, has one, two, three, four, or five characteristic XRPD peaks at approximately 19.32, 20.26, 21.63, 23.28, or 24.81±0.05° 2θ, as depicted in, for example, FIG. 1 and as found in Table 16 herein.

In one embodiment described herein, is a solid form, e.g., Form A, having a TGA thermograph corresponding substantially to the representative TGA thermogram as depicted in FIG. 2. In certain embodiments, the crystalline form exhibits a TGA thermogram comprising a total mass loss of approximately 7.2% of the total mass of the sample before approximately 125° C.

In another embodiment described herein, is a solid form, e.g., Form A, having a DSC thermogram substantially as depicted in FIG. 2 comprising desolvation event at about 124° C. and a melting temperature of having an onset temperature of about 164° C. and a peak maximum temperature of about 171° C.

Figure 3:
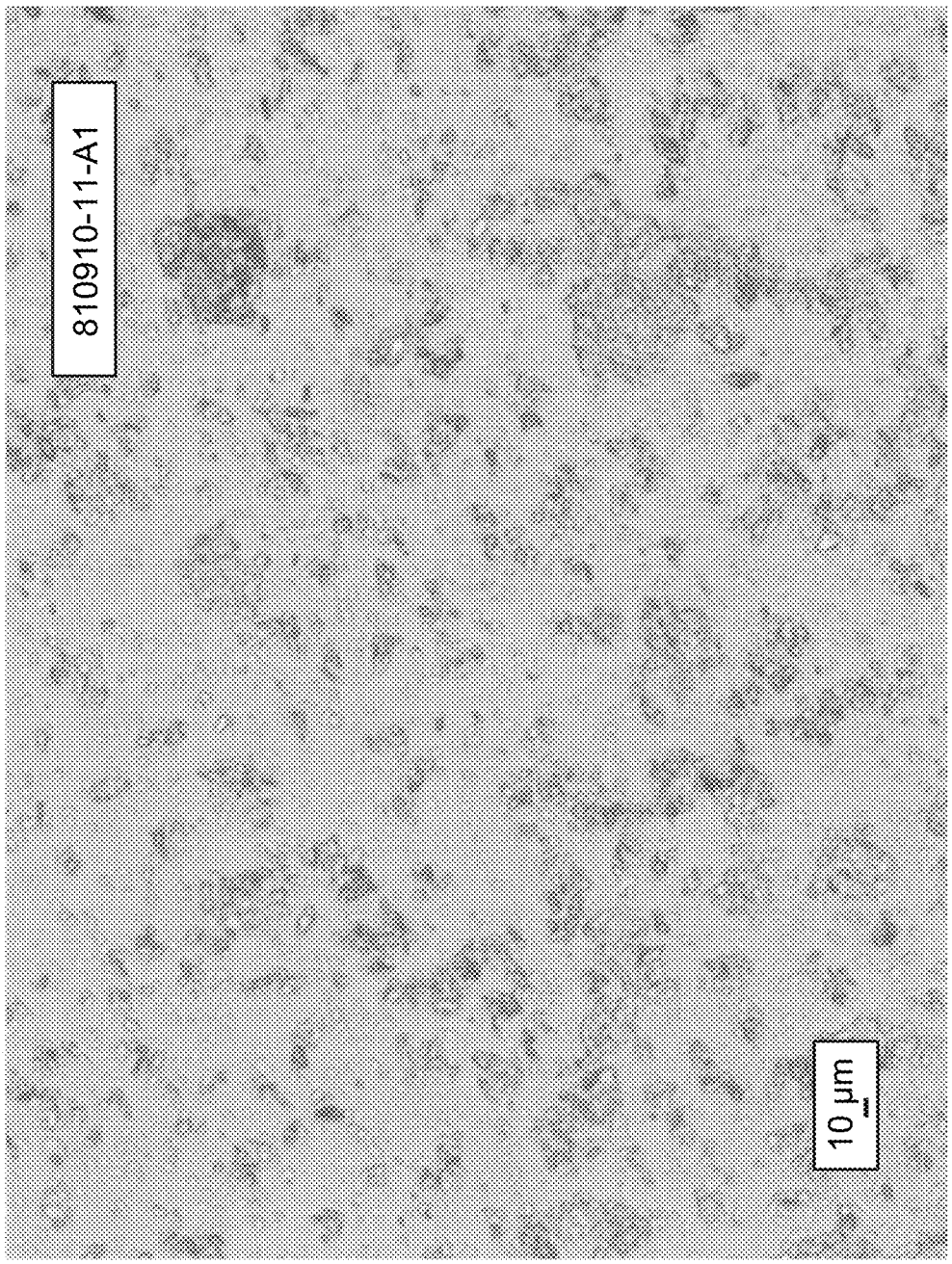
FIG. 3 depicts a PLM image for Compound B Form A.

In another embodiment described herein, is a solid form, e.g., Form A, having a Polarized Light Microscopy image as depicted in FIG. 3.

In still another embodiment, Form A is pure. In certain embodiments, pure Form A is substantially free of other solid forms, e.g., amorphous solid. In certain embodiments, the purity of Form A is no less than about 95%, no less than about 96%, no less than about 97%, no less than about 98%, no less than about 98.5%, no less than about 99%, no less than about 99.5%, or no less than about 99.9%.

Compound B, Form B:

In certain embodiments, provided herein is a solid form of Compound B designated as Form B. Form B is a crystalline solid form of Compound B. In one embodiment, Form B is an anhydrate of Compound B. In another embodiment, Form B is an anhydrate tartrate salt of Compound A.

In one embodiment, Form B of Compound B is obtained by slurrying Compound B in ethyl acetate at RT for about 24 hours. In another embodiment, Form B of Compound B is obtained by slurrying Compound B in acetone:water (e.g. 90:10, 95:5, 96:4, 97:3, 99:1 v/v) at about 50° C. for about 6 hours. In still another embodiment, Form B of Compound B is obtained by slurrying Compound B in ethanol.

In certain instances, Form B of Compound B is obtained by slurrying Compound B in a solvent system comprising ≥95% acetone (e.g. ≥95:5 acetone:water). Form B of Compound B is then isolated from the slurry by, for example, centrifugation or filtration. In another embodiment, Form B of Compound B is obtained from either Form A or Form F as described herein. In one embodiment, Form A of Compound B is reslurried in ethanol (e.g. 100% ethanol) for 10, 12, 16, or 24 hours (e.g. overnight) to obtain Form B. In one embodiment, Form F is converted to Form D as described herein in the presence of water. The mixture can then be slurried in neat ethanol (at for example about 50° C.) or 95:5 or 97:3 acetone:water (v/v) to form Form B. Mixtures can optionally be seeded with Form B crystals.

Form B can be prepared according to the methods and examples described herein. Thus, provided herein is a method of preparing Form B where the method comprises slurrying Compound B in a solvent system comprising acetone or aqueous mixtures of acetone water (e.g., 50%, 90%, 95%, 96%, 97%, 98% and 99% acetone v/v). In one embodiment, the solvent system for crystalizing Form B comprises ≥95% acetone. In one embodiment, the solvent system for Form B comprises 96:4 acetone:water. The mixtures can be slurried at RT for about 120 hrs. The mixtures can be filtered and analyzed as described herein (e.g., XRPD). In one embodiment, Form B is prepared according to the methods and/or examples set forth herein.

Figure 4:
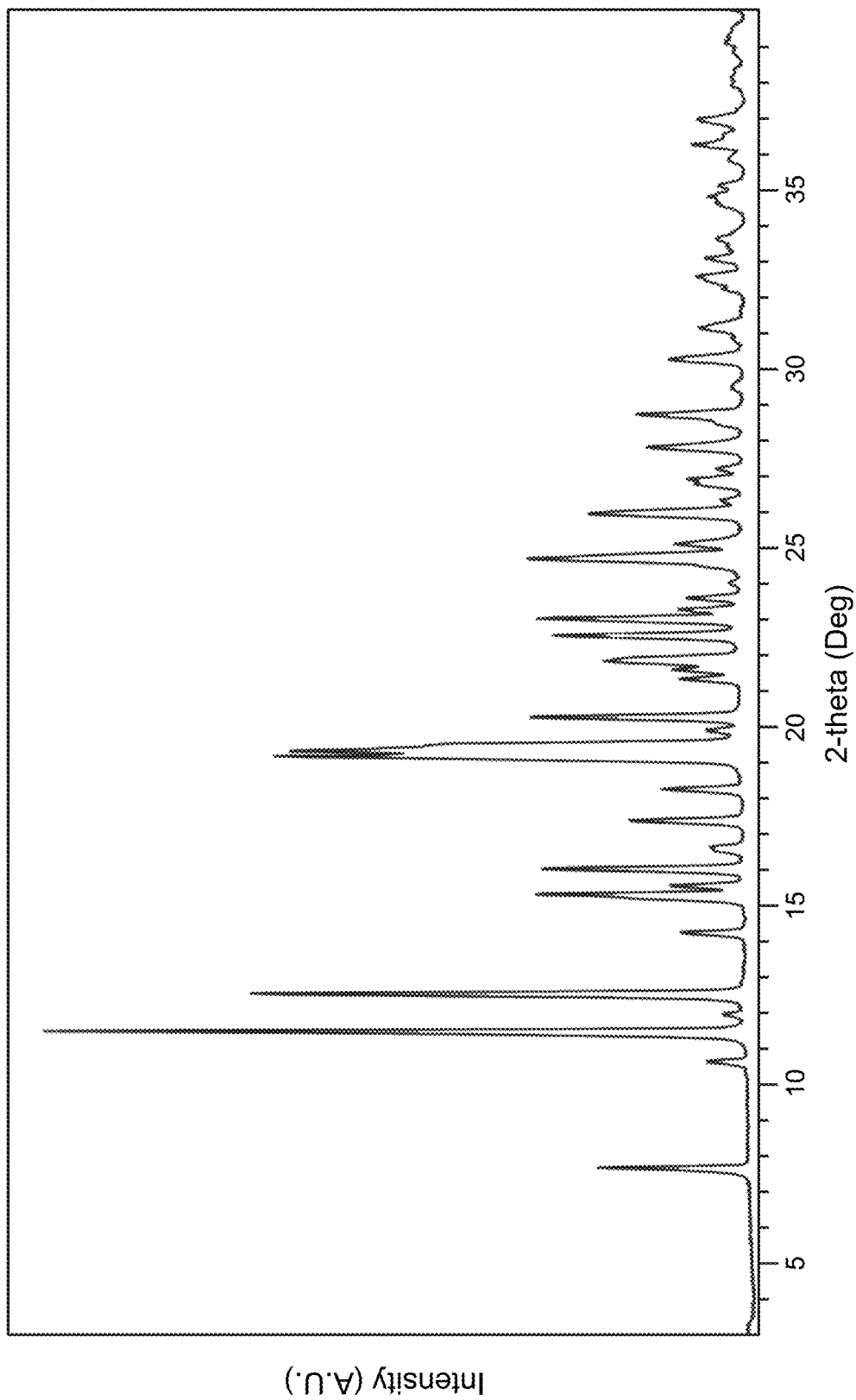
FIG. 4 depicts the XRPD pattern for Compound B Form B.

In one embodiment, a solid form provided herein, e.g., Form B, is a tartrate salt of Compound A, and is crystalline, as indicated by X-ray powder diffraction pattern (XRPD) measurements. In one embodiment, the XRPD of a solid form provided herein, e.g., Form B, is substantially as shown in FIG. 4. In another embodiment, a solid form provided herein, e.g., Form B, has one or more characteristic XRPD peaks at approximately 7.68, 11.49, 12.54, 14.24, 15.30, 15.55, 16.01, 16.63, 17.37, 18.24, 19.16, 19.42, 19.89, 20.24, 21.81, 22.52, 22.99, 23.25, 23.57, 24.67, 25.07, 25.91±0.1° 2θ, as depicted in, for example, FIG. 4 and as found in Table 17 herein. In still another embodiment, a solid form provided herein, e.g., Form B, has at least 3, at least 5, at least 7, or at least 10 characteristic XPRD peaks at approximately 7.68, 11.49, 12.54, 14.24, 15.30, 15.55, 16.01, 16.63, 17.37, 18.24, 19.16, 19.42, 19.89, 20.24, 21.81, 22.52, 22.99, 23.25, 23.57, 24.67, 25.07, 25.91±0.1° 2θ, as depicted in, for example, FIG. 4 and as found in Table 17 herein. In yet another embodiment, a solid form described herein, e.g., Form B, has one, two, three, four, five, six, seven, eight, nine, ten, eleven, twelve, thirteen, fourteen, fifteen, or all of the characteristic XRPD peaks as set forth in Table 17.

In still another embodiment, a solid form provided herein, e.g., Form B, has one, two, three, four, five, six, seven, eight, nine, or ten characteristic XRPD peaks at approximately 11.49, 12.54, 15.30, 15.55, 19.16, 19.42, 20.24, 23.25, 24.67, or 25.91±0.1° 2θ, as depicted in, for example, FIG. 4. In still another embodiment, a solid form provided herein, e.g., Form B, has one, two, three, four, or five characteristic XRPD peaks at approximately 11.49, 12.54, 19.16, 19.42, or 24.67±0.1° 2θ, as depicted in, for example, FIG. 4. In still another embodiment, a solid form provided herein, e.g., Form B, has one, two, three, four, or five characteristic XRPD peaks at approximately 11.49, 12.54, 19.16, 19.42, or 24.67±0.05° 2θ, as depicted in, for example, FIG. 4.

Figure 5:
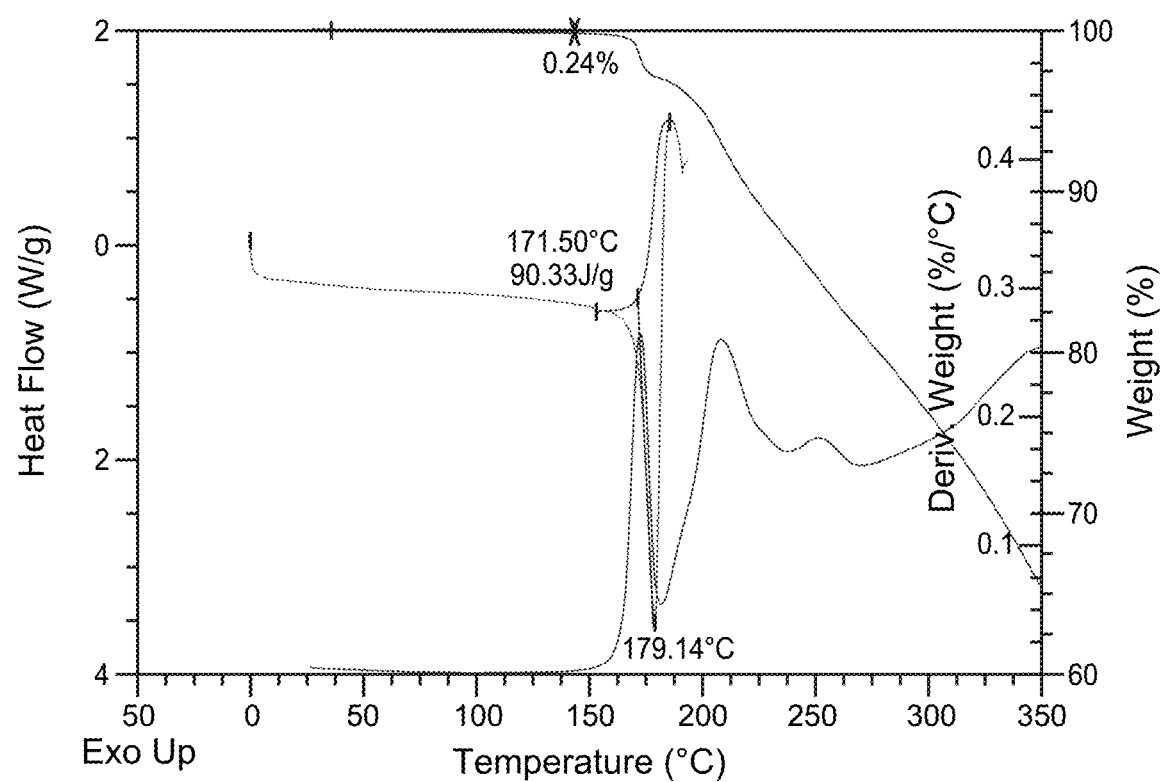
FIG. 5 depicts the TGA and DSC for Compound B Form B.

In one embodiment described herein, is a solid form, e.g., Form B, having a TGA thermograph corresponding substantially to the representative TGA thermogram as depicted in FIG. 5. In certain embodiments, the crystalline form exhibits a TGA thermogram comprising a total mass loss of approximately 3.5% of the total mass of the sample.

In another embodiment described herein, is a solid form, e.g., Form B, having a DSC thermogram substantially as depicted in FIG. 5 comprising an endothermic event with an onset temperature of about 171° C. and a peak maximum temperature of about 179° C.

Figure 6:
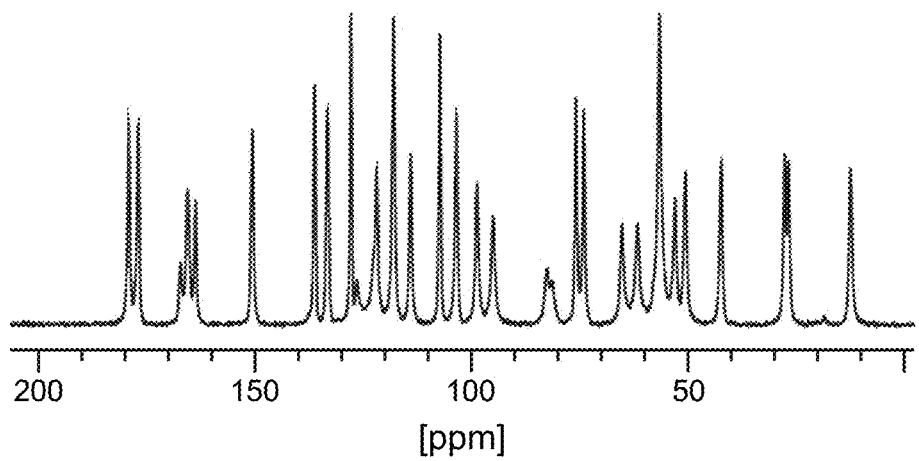
FIG. 6 depicts the $^{13}$C SSNMR for Compound B Form B.
Figure 7:
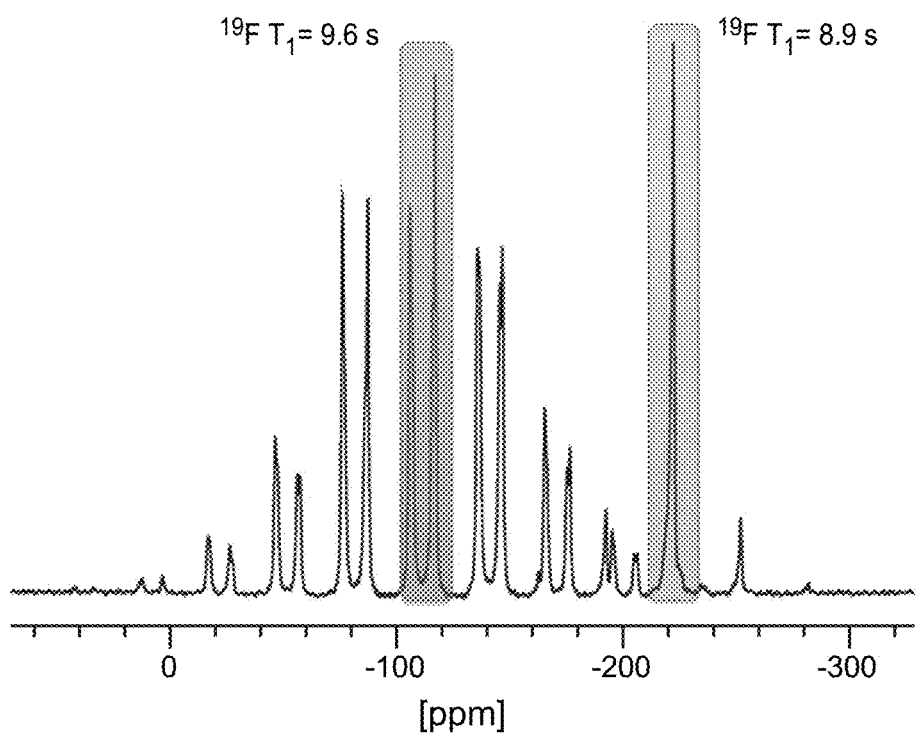
FIG. 7 depicts the $^{19}$F SSNMR for Compound B Form B.

In another embodiment described herein, is a solid form, e.g., Form B, having a $^{13}C$ and $^{19}F$ NMR spectrum substantially as depicted in FIG. 6 and FIG. 7, respectively.

Figure 8:
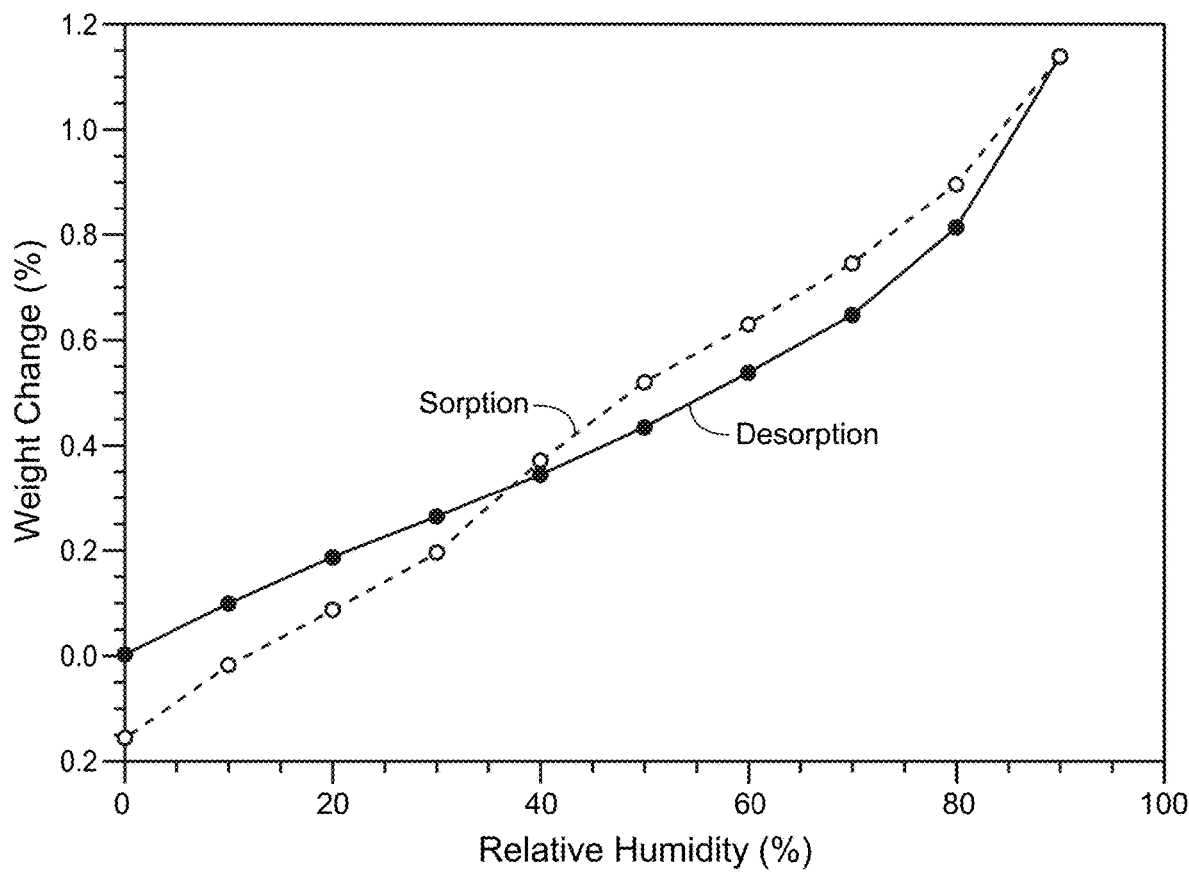
FIG. 8 depicts the water sorption/desorption plot for Compound B Form B.

In another embodiment described herein, is a solid form, e.g., Form B, having a water sorption-desorption profile as depicted in FIG. 8. The solid form, e.g., Form B of Compound B, absorbs about 1.2% w/w moisture up to 90% relative humidity (RH) at about 25° C.

Figure 9B:
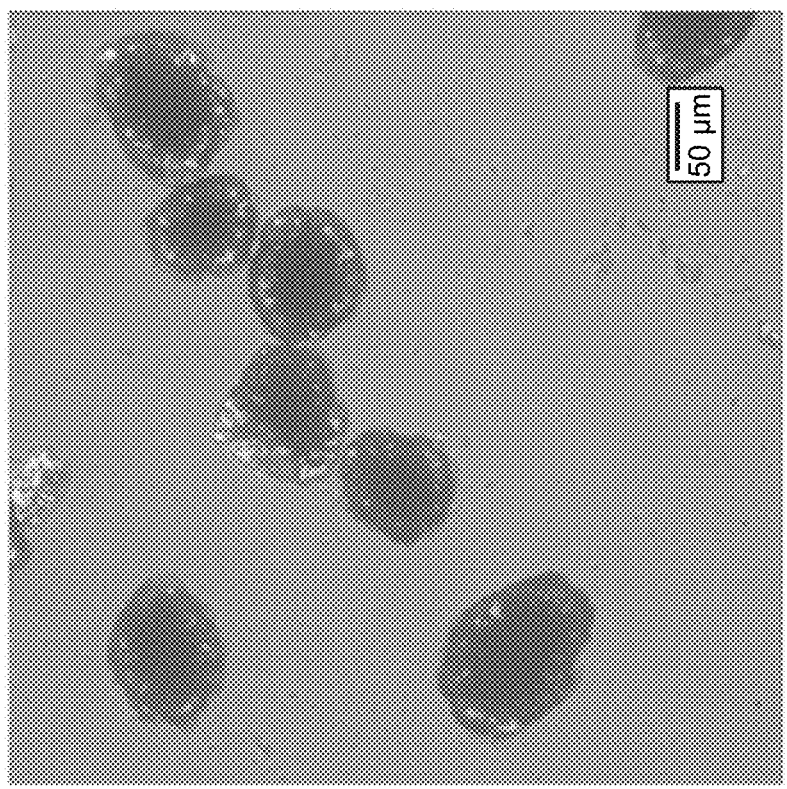
FIG. 9b depicts the PLM image for Compound B Form B.
Figure 9A:
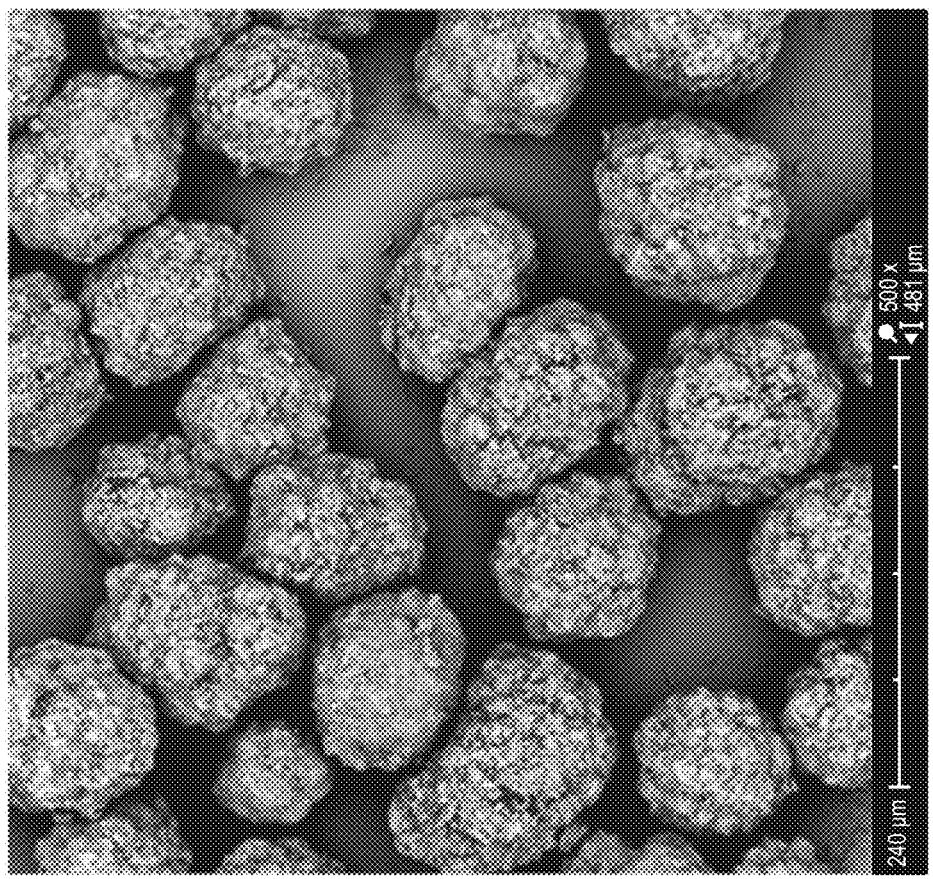
FIG. 9a depicts the SEM image.

In another embodiment described herein, is a solid form, e.g., Form B, having a Scanning Electron Microscope (SEM) image and PLM image as depicted in FIG. 9a and FIG. 9b, respectively. The sample comprises of dense spherical aggregates.

Figure 9C:
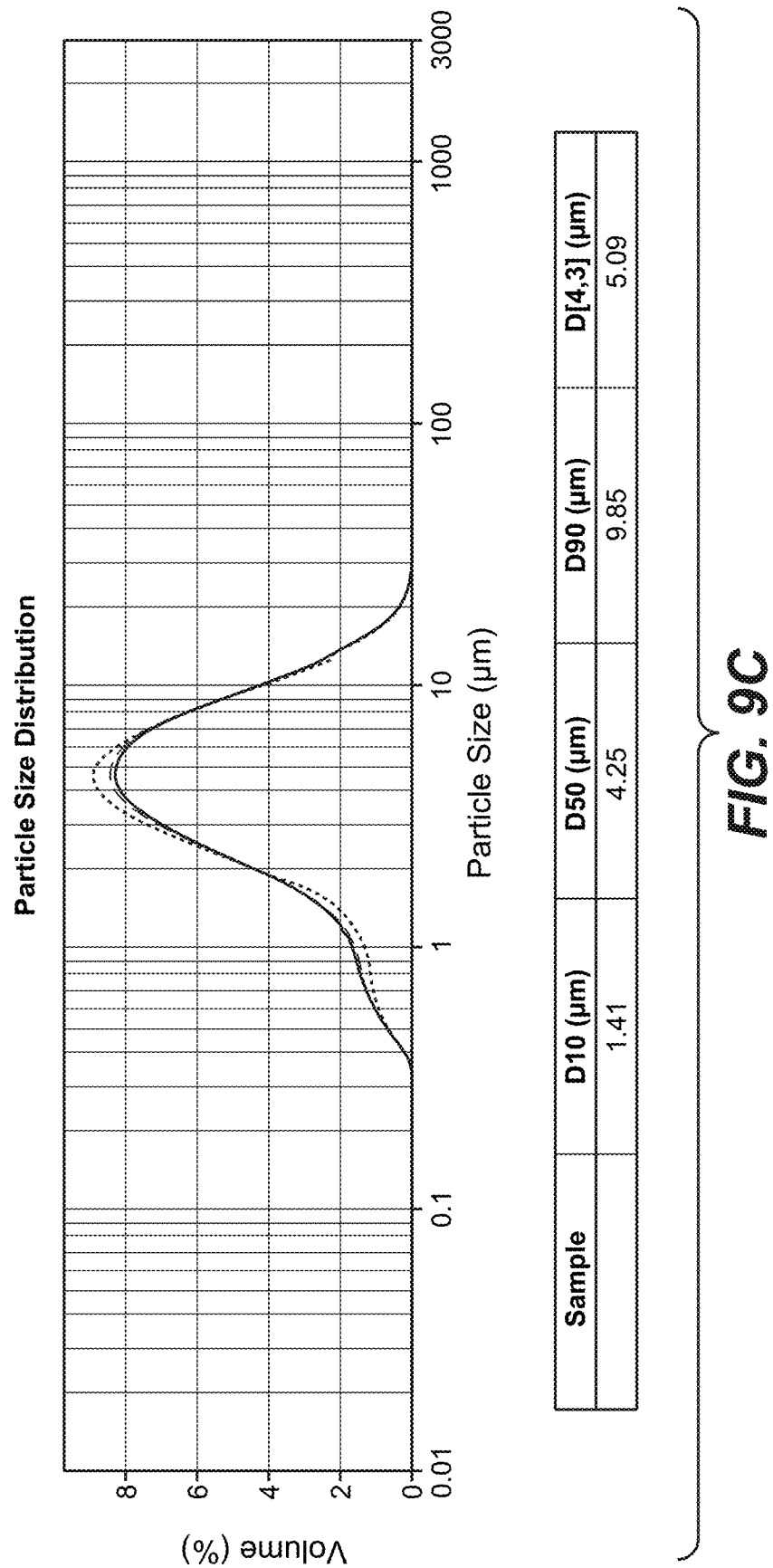
FIG. 9c depicts the particle size distribution (PSD) for Compound B Form B.

In another embodiment described herein, is a solid form, e.g., Form B, having a particle size distribution (PSD) as depicted in FIG. 9c.

Figure 22:
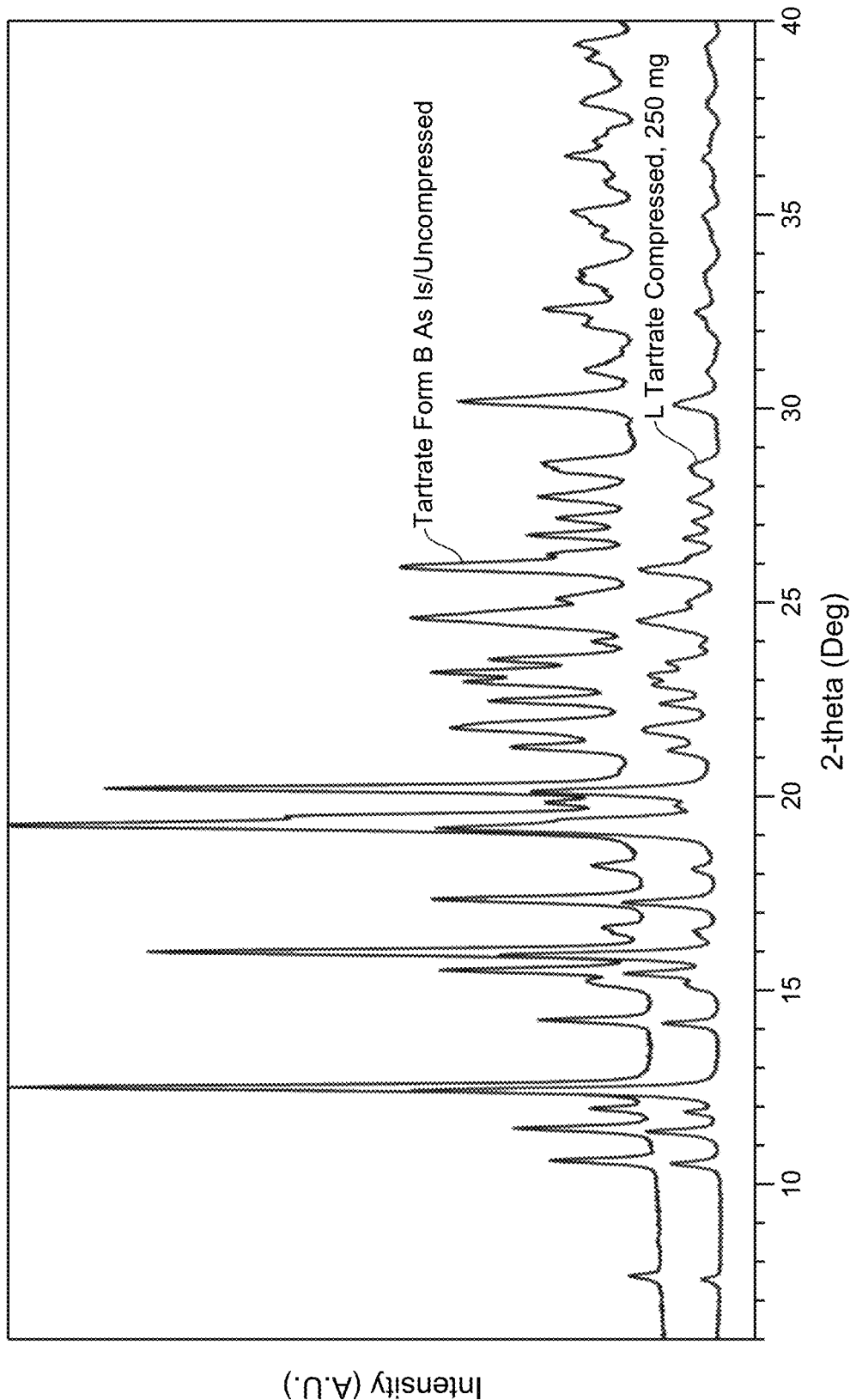
FIG. 22 depicts the XRPD for the compressibility properties for Compound B Form B.
Figure 23:
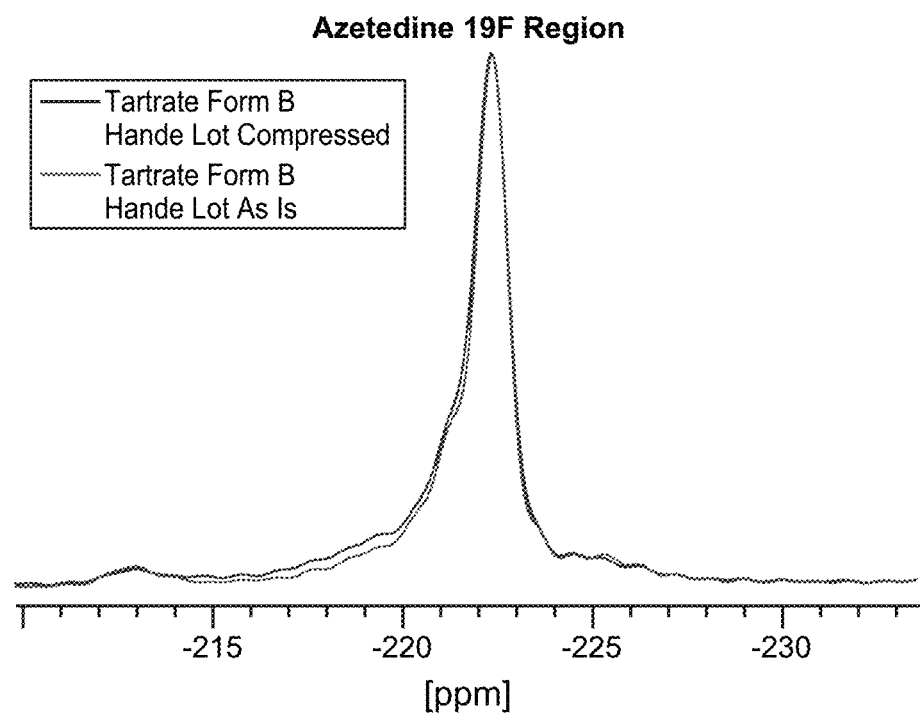
FIG. 23 depicts the $^{19}$F SSNMR for the compressibility properties for Compound B Form B.
Figure 24:
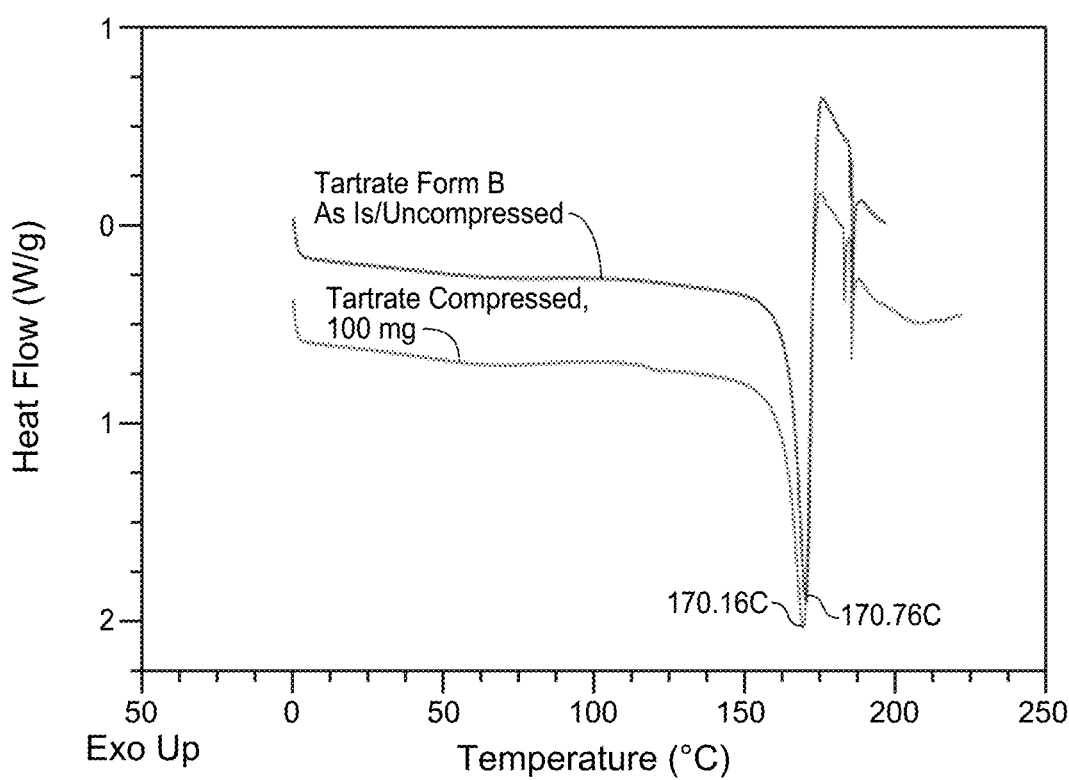
FIG. 24 depicts the DSC for the compressibility properties for Compound B Form B.

In still another embodiment, a solid form, e.g., Form B, remains substantially unchanged following compression as described herein. FIG. 22, FIG. 23, and FIG. 24, respectively show XRPD, $^{19}$F SSNMR, and DSC of Form B of Compound B and compare the compound before and after compression as described herein.

In still another embodiment, Form B is substantially pure. In certain embodiments, the pure Form B is substantially free of other solid forms, e.g., amorphous solid. In certain embodiments, the substantially pure Form B is substantially free of Form A, Form D, or Form F. In certain embodiments, the purity of Form B is no less than about 95%, no less than about 96%, no less than about 97%, no less than about 98%, no less than about 98.5%, no less than about 99%, no less than about 99.5%, or no less than about 99.9%.

Compound B, Form C:

In certain embodiments, provided herein is a solid form of Compound B designated as Form C. Form C is a crystalline solid form of Compound B. In one embodiment, Form C is a THF solvate of Compound B.

In one embodiment, Form C of Compound B is obtained by slurrying Compound B in THF. The mixture can then be filtered. Form C can be prepared according to the methods and examples described herein.

Figure 10:
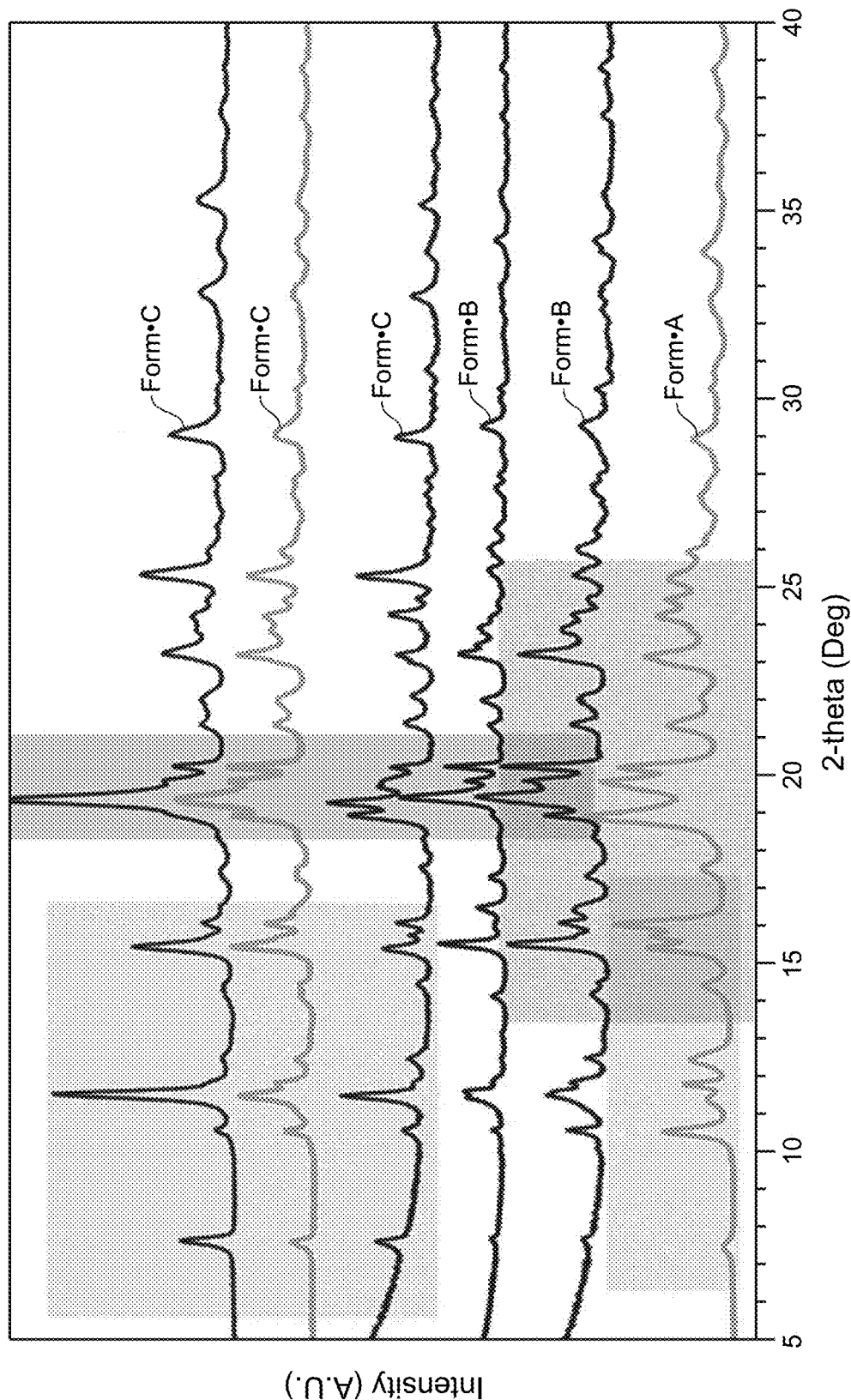
FIG. 10 depicts a comparative XRPD pattern for Compound B Form C against Form A and Form B of Compound B. Form C was found to be a mixture of Form A and Form B.

In one embodiment, a solid form provided herein, e.g., Form C, is tartrate salt of Compound A, and is substantially crystalline, as indicated by X-ray powder diffraction pattern (XRPD) measurements. In one embodiment, the XRPD is substantially as shown in FIG. 10.

Figure 11:
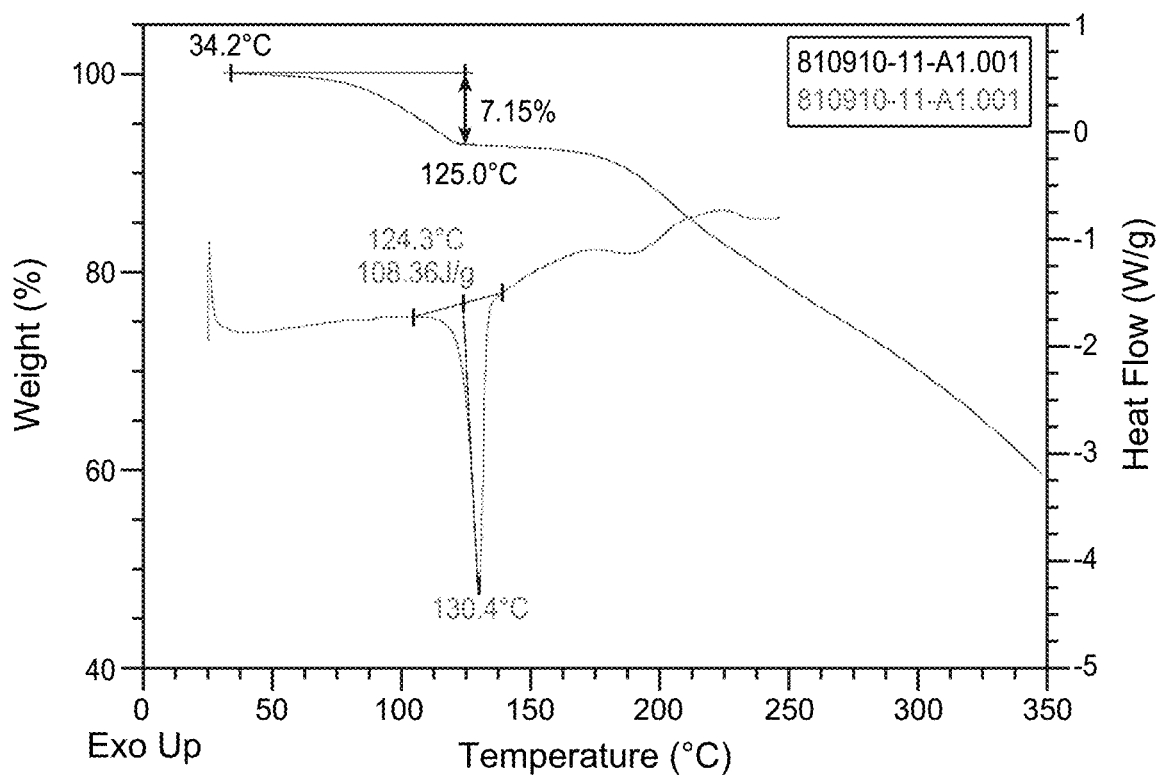
FIG. 11 depicts the TGA and DSC for Compound B Form C.

In one embodiment described herein, is a solid form, e.g., Form C, having a TGA thermograph corresponding substantially to the representative TGA thermogram as depicted in FIG. 11. In certain embodiments, the crystalline form exhibits a TGA thermogram comprising a total mass loss of approximately 6.8% of the total mass of the sample.

In another embodiment described herein, is a solid form, e.g., Form C, having a DSC thermogram substantially as depicted in FIG. 11 comprising an endothermic event with an onset temperature of about 118° C. and a peak maximum temperature of about 125° C.

In still another embodiment, Form C is pure. In certain embodiments, the purity of Form C is no less than about 95%, no less than about 96%, no less than about 97%, no less than about 98%, no less than about 98.5%, no less than about 99%, no less than about 99.5%, or no less than about 99.9%.

Compound B, Form D:

In certain embodiments, provided herein is a solid form of Compound B designated as Form D. Form D is a crystalline solid form of Compound B. In one embodiment, Form D is a hydrate of Compound B. In another embodiment, Form D is a monohydrate of Compound B.

In one embodiment, Form D of Compound B is obtained by slurrying Compound B in 100% ethanol for about 48 hours. The mixture can then be filtered.

Figure 12:
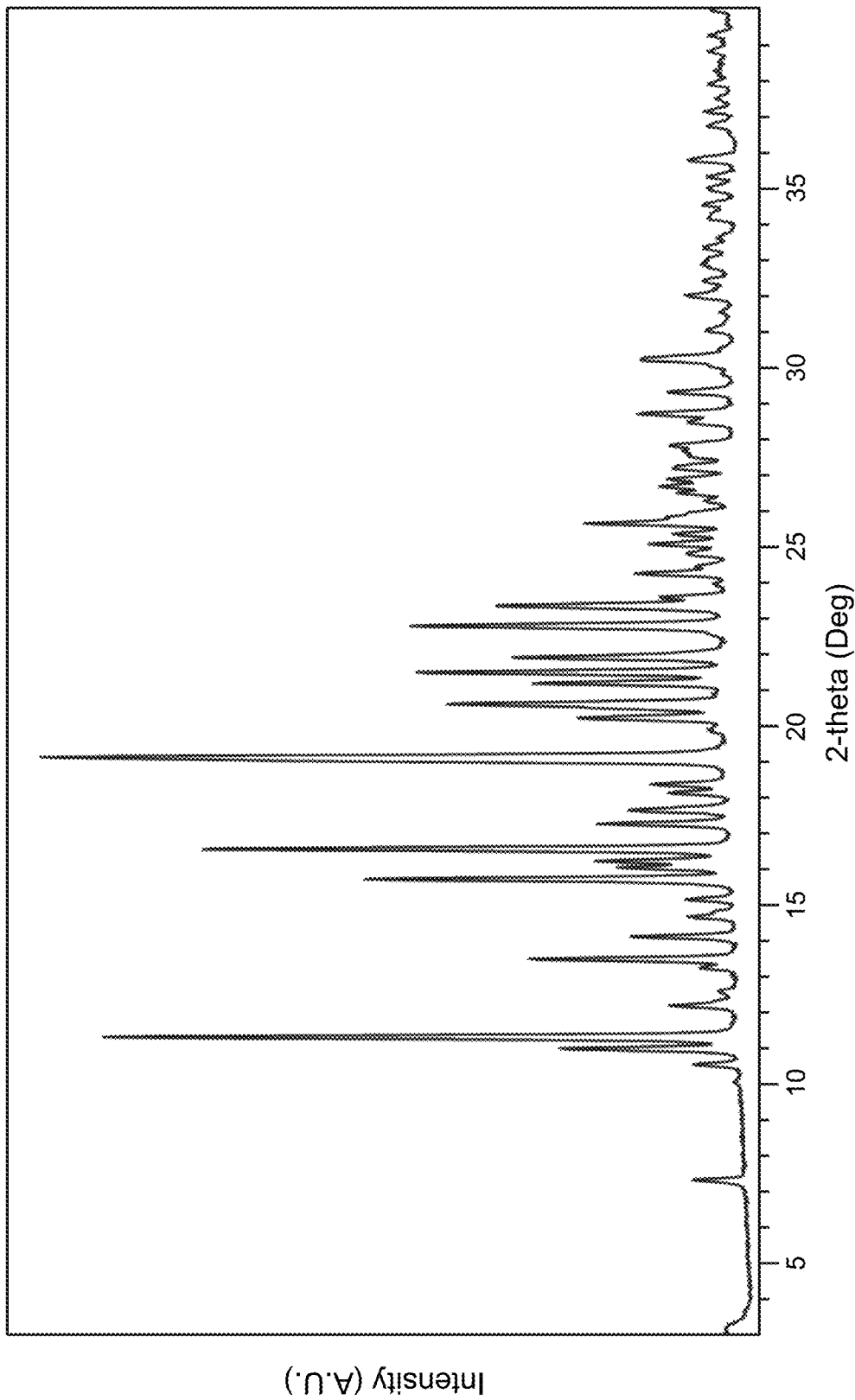
FIG. 12 depicts the XRPD pattern for Compound B Form D.

In one embodiment, a solid form provided herein, e.g., Form D, is a tartrate salt of Compound A, and is substantially crystalline, as indicated by X-ray powder diffraction pattern (XRPD) measurements. In another embodiment, Form D is a hydrate of Compound B. In one embodiment, the XRPD of a solid form provided herein, e.g., Form D, is substantially as shown in FIG. 12. In another embodiment, a solid form provided herein, e.g., Form D, has one or more characteristic XRPD peaks at approximately 7.32, 10.99, 11.31, 12.18, 13.23, 13.48, 14.11, 14.66, 15.14, 15.70, 16.03, 16.21, 16.54, 17.24, 17.63, 18.11, 18.34, 19.10, 20.20, 20.58, 21.16, 21.47, 21.89, 22.76, 23.33, or 23.56±0.1° 2θ, as depicted in, for example, FIG. 12 and as found in Table 19. In still another embodiment, a solid form provided herein, e.g., Form D, has at least 3, at least 5, at least 7, or at least 10 characteristic XRPD peaks at approximately 7.32, 10.99, 11.31, 12.18, 13.23, 13.48, 14.11, 14.66, 15.14, 15.70, 16.03, 16.21, 16.54, 17.24, 17.63, 18.11, 18.34, 19.10, 20.20, 20.58, 21.16, 21.47, 21.89, 22.76, 23.33, or 23.56±0.1° 2θ, as depicted in, for example, FIG. 12 and as found in Table 19. In yet another embodiment, a solid form described herein has one, two, three, four, five, six, seven, eight, nine, ten, eleven, twelve, thirteen, fourteen, fifteen, or all of the characteristic XRPD peaks as set forth in Table 19.

In still another embodiment, a solid form provided herein, e.g., Form D, has one, two, three, four, five, six, seven, eight, nine, or ten characteristic XRPD peaks at approximately 11.31, 15.70, 16.54, 19.10, 20.58, 21.16, 21.47, 21.89, 22.76, or 23.33±0.1° 2θ, as depicted in, for example, FIG. 12. In still another embodiment, a solid form provided herein, e.g., Form D, has one, two, three, four, or five characteristic XRPD peaks at approximately 11.31, 15.70, 16.54, 19.10, or 22.76±0.1° 2θ, as depicted in, for example, FIG. 12. In still another embodiment, a solid form provided herein, e.g., Form D, has one, two, three, four, or five characteristic XRPD peaks at approximately 11.31, 15.70, 16.54, 19.10, or 22.76±0.05° 2θ, as depicted in, for example, FIG. 12.

Figure 13:
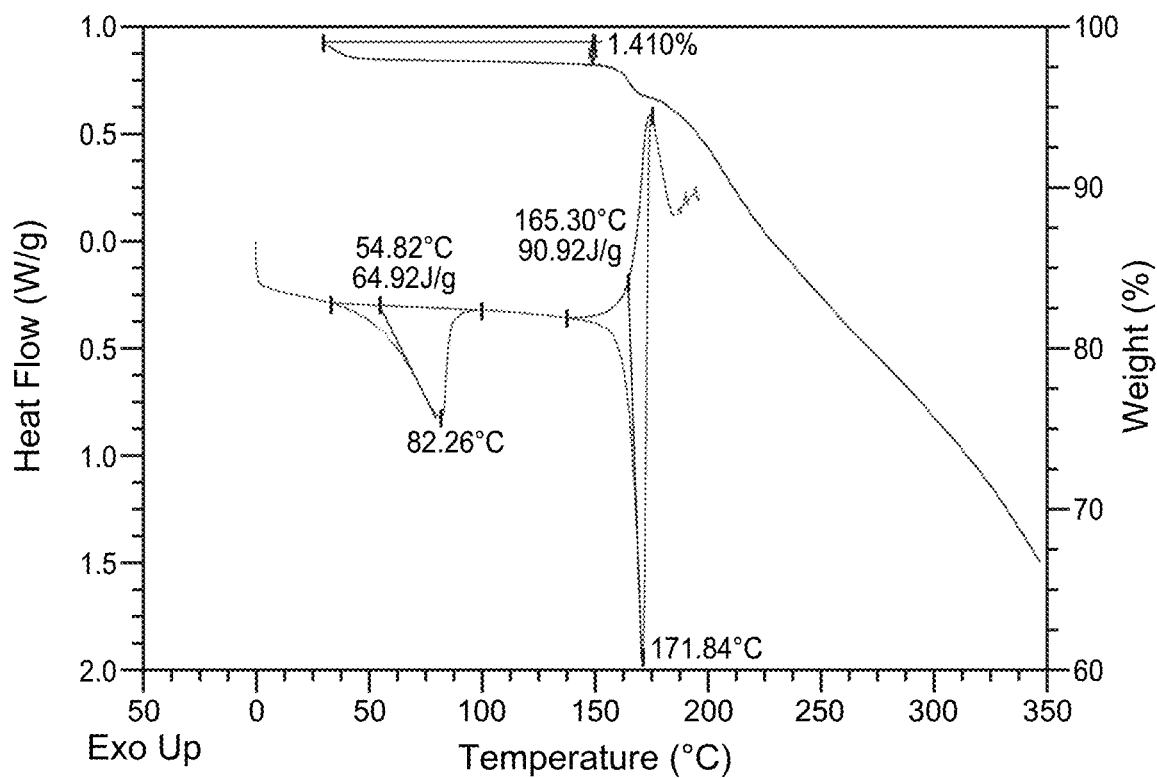
FIG. 13 depicts the TGA and DSC for Compound B Form D.

In one embodiment described herein, is a solid form, e.g., Form D, having a TGA thermograph corresponding substantially to the representative TGA thermogram as depicted in FIG. 13. In certain embodiments, the crystalline form exhibits a TGA thermogram comprising a total mass loss of approximately 1.4% of the total mass of the sample before approximately 150° C.

In another embodiment described herein, is a solid form, e.g., Form D, having a DSC thermogram substantially as depicted in FIG. 13 comprising an endothermic event having an onset temperature of about 55° C. and a peak maximum temperature of about 82° C. followed by a second endothermic event with an onset temperature of about 165° C. and a peak maximum temperature of about 172° C.

In still another embodiment, Form D is pure. In certain embodiments, Form D is substantially free of other solid forms, e.g., amorphous solid. In certain embodiments, Form D is substantially free of Form A, Form B, or Form F. In certain embodiments, the purity of Form D is no less than about 95%, no less than about 96%, no less than about 97%, no less than about 98%, no less than about 98.5%, no less than about 99%, no less than about 99.5%, or no less than about 99.9%.

Compound B, Form E:

In certain embodiments, provided herein is a solid form of Compound B designated as Form E. Form E is a solid form of Compound B. In one embodiment, Form E is a DMSO solvate of Compound B.

In one embodiment, Form E of Compound B is obtained by slurrying Compound B in DMSO and adding IPAc, for about 24 hours. The mixture can then be filtered. Form E can be prepared according to the methods and examples described herein.

Figure 14:
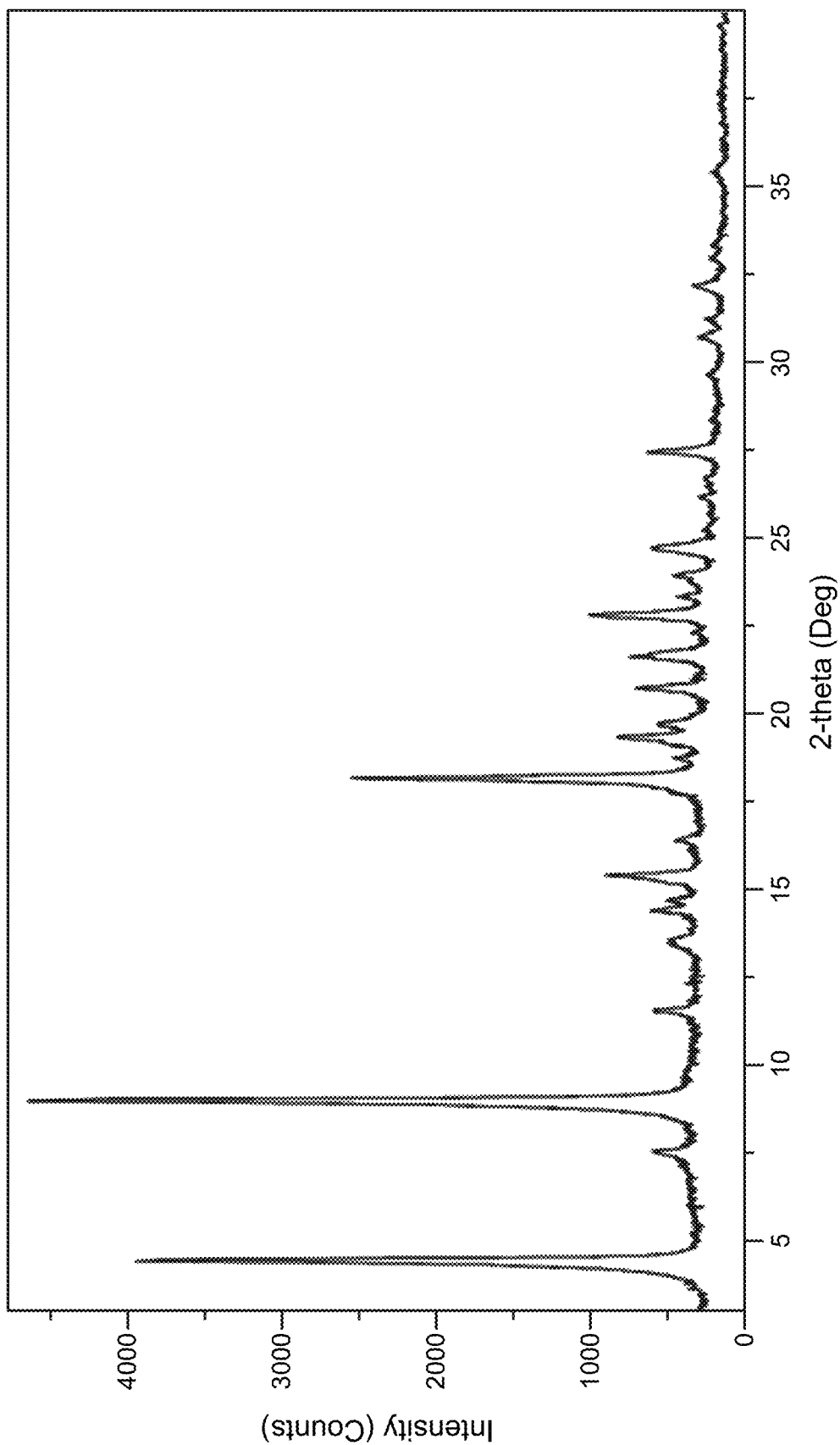
FIG. 14 depicts the XRPD pattern for Compound B Form E.

In one embodiment, a solid form provided herein, e.g., Form E, is a tartrate salt of Compound A, and is substantially crystalline, as indicated by X-ray powder diffraction pattern (XRPD) measurements. In one embodiment, the XRPD is substantially as shown in FIG. 14.

Figure 15:
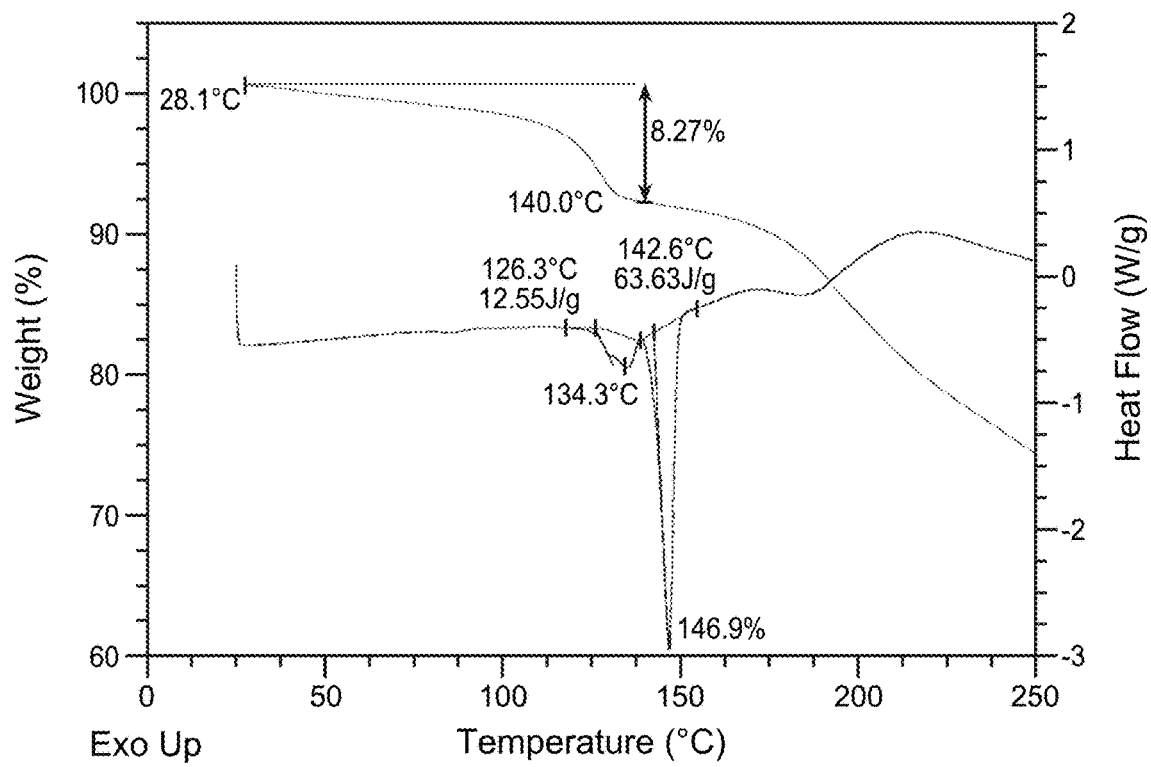
FIG. 15 depicts the TGA and DSC for Compound B Form E.

In one embodiment described herein, is a solid form, e.g., Form E, having a TGA thermograph corresponding substantially to the representative TGA thermogram as depicted in FIG. 15. In certain embodiments, the crystalline form exhibits a TGA thermogram comprising a total mass loss of approximately 8.3% of the total mass of the sample.

In another embodiment described herein, is a solid form, e.g., Form E, having a DSC thermogram substantially as depicted in FIG. 15 comprising a first endotherm with an onset temperature of about 126° C. and a peak maximum temperature of about 134° C. and a second endothermic event with an onset temperature of about 143° C. and a peak maximum temperature of about 147° C.

In still another embodiment, Form E is pure. In certain embodiments, Form E is substantially free of other solid forms, e.g., amorphous solid. In certain embodiments, the purity of Form E is no less than about 95%, no less than about 96%, no less than about 97%, no less than about 98%, no less than about 98.5%, no less than about 99%, no less than about 99.5%, or no less than about 99.9%.

Compound B, Form F:

In certain embodiments, provided herein is a solid form of Compound B designated as Form F. Form F is a crystalline solid form of Compound B. In one embodiment, Form F is an anhydrate of Compound B. In another embodiment, Form F is an anhydrate tartrate salt of Compound A.

In one embodiment, Form F of Compound B is obtained by slurrying Compound B in 100% ethanol at RT or at 50° C. for about 8, 10, 12, 15, 20, or 25 hours (e.g. overnight). In another embodiment, Form F can be obtained by slurrying Compound B in ethanol/water (e.g. 65:35 v/v). The slurry of Compound B to obtain Form F can optionally include seeding with Form B described herein. The slurry can be filtered to obtain Form F. Form F can also be obtained by slurrying at RT in 100% DI water, 1:1 acetone/water or 100% acetone. Slurries of Form F in neat solvents can be maintained at RT. In one embodiment, Form F can be obtained from 1:1 acetone:water mixture agitated at 5° C. In still another embodiment, Form F can be obtained by slurrying Compound B in 95:5 acetone:water and 97:3 acetone:water mixtures at 50° C. for about 2 hours and cooling to RT. Form F can be prepared according to the methods and examples described herein.

Figure 16:
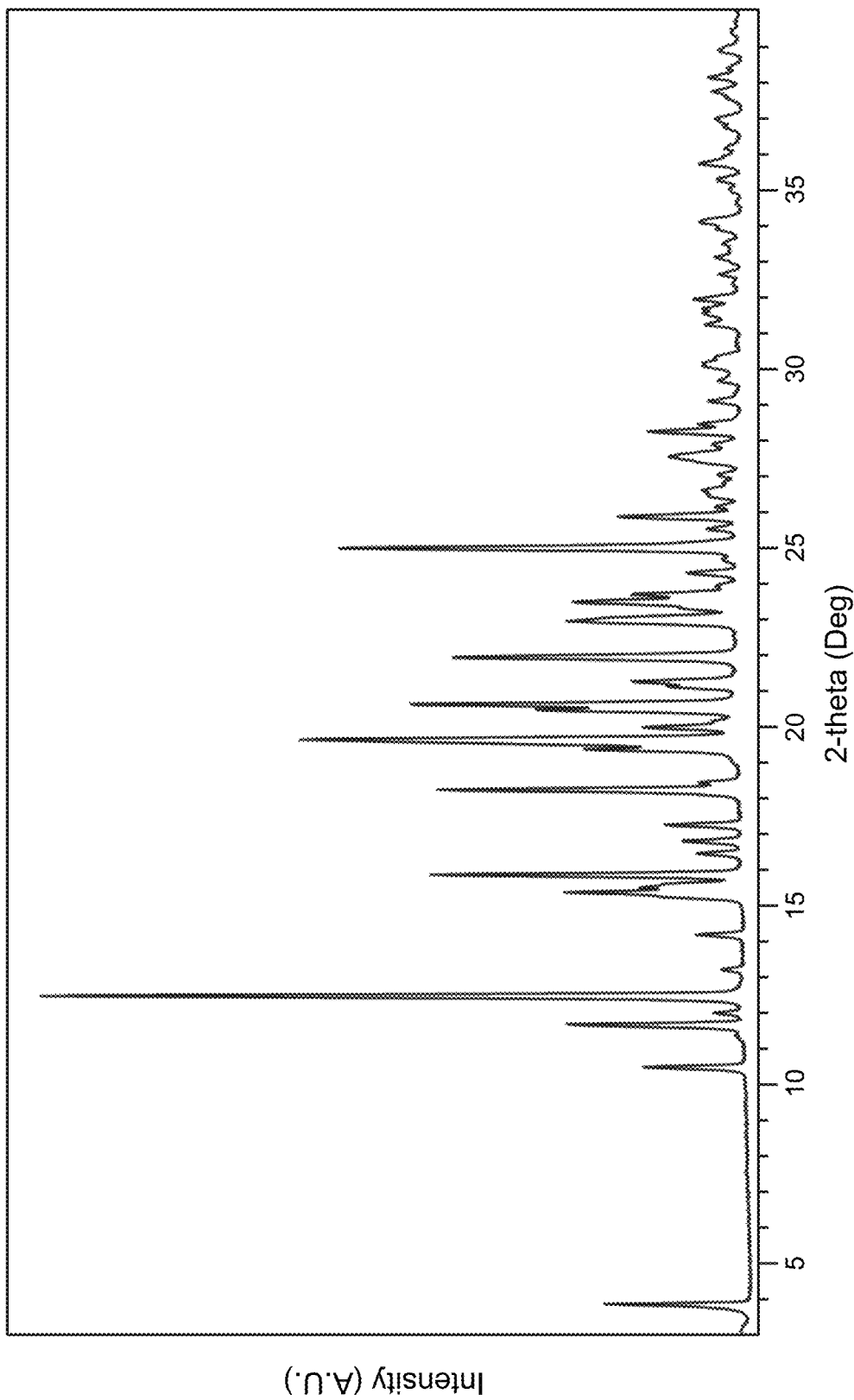
FIG. 16 depicts the XRPD pattern for Compound B Form F.

In one embodiment, a solid form provided herein, e.g., Form F, is a tartrate salt of Compound A, and is substantially crystalline, as indicated by X-ray powder diffraction pattern (XRPD) measurements. In one embodiment, the XRPD of a solid form provided herein, e.g., Form F, is substantially as shown in FIG. 16. In another embodiment, a solid form provided herein, e.g., Form F, has one or more characteristic XRPD peaks at approximately 3.92, 10.54, 11.72, 12.52, 14.22, 15.40, 15.54, 15.90, 16.48, 16.84, 17.29, 18.26, 18.47, 19.39, 19.66, 20.00, 20.50, 20.65, 21.16, 21.28, 21.95, 22.97, 23.49, 23.70, 23.94, 24.31, 24.67, or 24.99±0.1° 2θ, as depicted in, for example, FIG. 16 and as found in Table 20 herein. In still another embodiment, a solid form provided herein, e.g., Form F, has at least 3, at least 5, at least 7, or at least 10 characteristic XPRD peaks at approximately 3.92, 10.54, 11.72, 12.52, 14.22, 15.40, 15.54, 15.90, 16.48, 16.84, 17.29, 18.26, 18.47, 19.39, 19.66, 20.00, 20.50, 20.65, 21.16, 21.28, 21.95, 22.97, 23.49, 23.70, 23.94, 24.31, 24.67, or 24.99±0.1° 2θ, as depicted in, for example, FIG. 16 and as found in Table 20 herein. In yet another embodiment, a solid form described herein, e.g., Form F, has one, two, three, four, five, six, seven, eight, nine, ten, eleven, twelve, thirteen, fourteen, fifteen, twenty, twenty-five, or all of the characteristic XRPD peaks as set forth in Table 20.

In still another embodiment, a solid form provided herein, e.g., Form F, has one, two, three, four, five, six, seven, eight, nine, or ten characteristic XRPD peaks at approximately 12.52, 15.90, 19.66, 20.65, or 24.99±0.1° 2θ, as depicted in, for example, FIG. 16. In still another embodiment, a solid form provided herein, e.g., Form F, has one, two, three, four, or five characteristic XRPD peaks at approximately 12.52, 15.90, 19.66, 20.65, or 24.99±0.1° 2θ, as depicted in, for example, FIG. 16. In still another embodiment, a solid form provided herein, e.g., Form F, has one, two, three, four, or five characteristic XRPD peaks at approximately 12.52, 15.90, 19.66, 20.65, or 24.99±0.05° 2θ, as depicted in, for example, FIG. 16.

Figure 17:
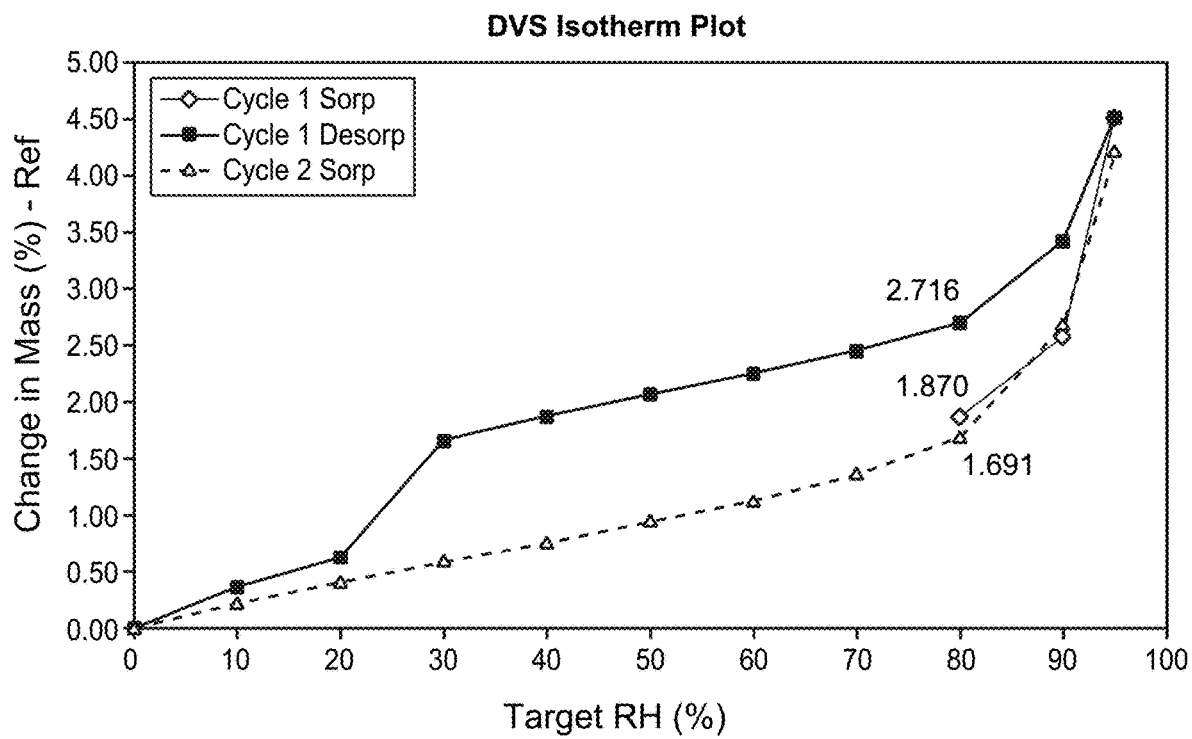
FIG. 17 depicts the DVS plot for Compound B Form F.

In one embodiment described herein, is a solid form, e.g., Form F, having a DVS isotherm plot corresponding substantially to the representative DVS isotherm plot as depicted in FIG. 17.

Figure 18:
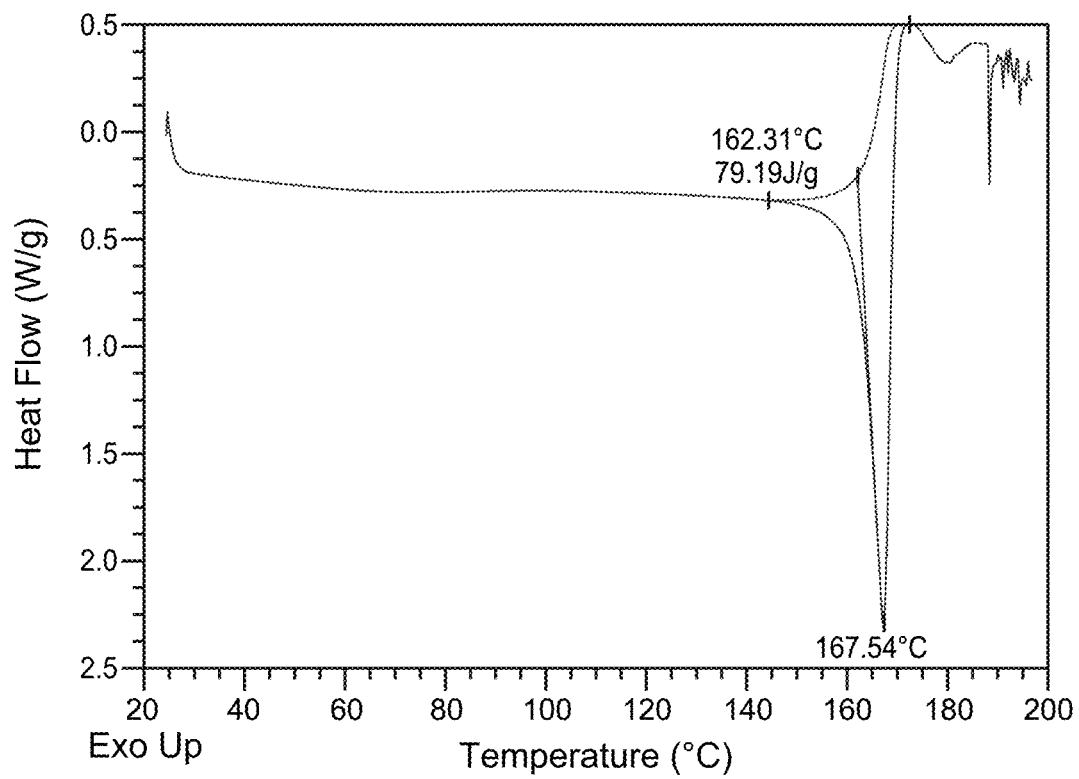
FIG. 18 depicts the DSC for Compound B Form F.

In another embodiment described herein, is a solid form, e.g., Form F, having a DSC thermogram substantially as depicted in FIG. 18 comprising an endothermic event with an onset temperature of about 162° C. and a peak maximum temperature of about 167° C.

In still another embodiment, Form F is pure. In certain embodiments, pure Form F is substantially free of other solid forms, e.g., amorphous solid. In certain embodiments, the purity of the Form F is no less than about 95%, no less than about 96%, no less than about 97%, no less than about 98%, no less than about 98.5%, no less than about 99%, no less than about 99.5%, or no less than about 99.9%.

Compound B, Form G

In certain embodiments, provided herein is a solid form of Compound B designated as Form G. Form G is a solid form of Compound B. In one embodiment, Form G is a methanol solvate of Compound B. In another embodiment, Form F is a methanol solvate tartrate salt of Compound A.

In one embodiment, Form G of Compound B is obtained by slurrying Compound B in methanol and slowly evaporating the methanol. The mixture can be filtered. Form G can be prepared according to the methods and examples described herein.

Figure 19:
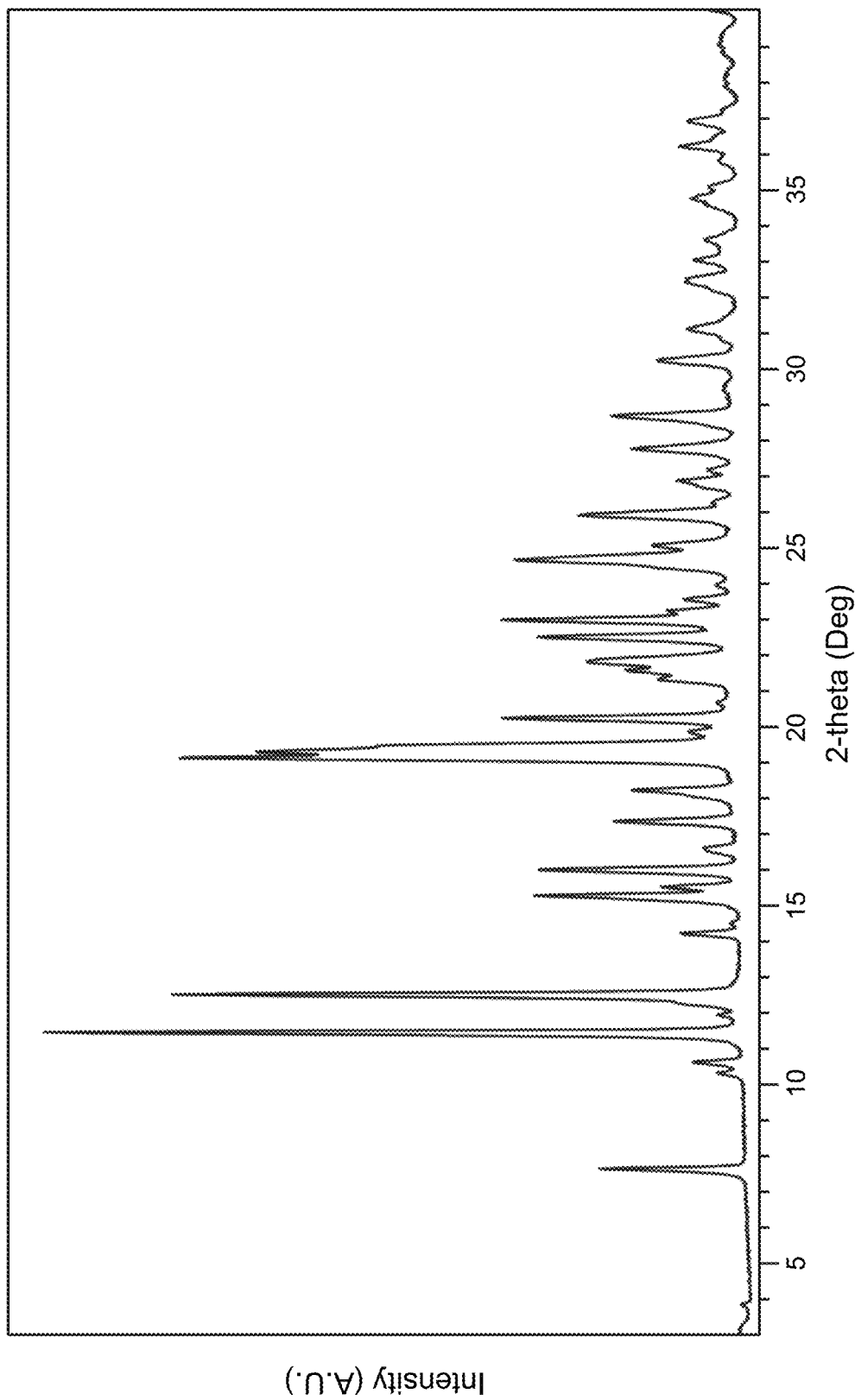
FIG. 19 depicts the XRPD pattern for Compound B Form G.

In one embodiment, a solid form provided herein, e.g., Form G, is a tartrate salt of Compound A, and is substantially crystalline, as indicated by X-ray powder diffraction pattern (XRPD) measurements. In one embodiment, the XRPD of a solid form provided herein, e.g., Form G, is substantially as shown in FIG. 19. In another embodiment, a solid form provided herein, e.g., Form G, has one or more characteristic XRPD peaks at approximately 7.65, 11.46, 12.51, 15.27, 15.51, 16.00, 17.34, 18.21, 19.11, 19.29, 19.42, 19.84, 20.23, 21.31, 21.57, 21.79, 22.49, 22.97, 23.22, 24.65, 25.04, or 25.88±0.1° 2θ, as depicted in, for example, FIG. 19 and as found in Table 21 herein. In still another embodiment, a solid form provided herein, e.g., Form G, has at least 3, at least 5, at least 7, or at least 10 characteristic XPRD peaks at approximately 7.65, 11.46, 12.51, 15.27, 15.51, 16.00, 17.34, 18.21, 19.11, 19.29, 19.42, 19.84, 20.23, 21.31, 21.57, 21.79, 22.49, 22.97, 23.22, 24.65, 25.04, or 25.88±0.1° 2θ, as depicted in, for example, FIG. 19 and as found in Table 21 herein. In yet another embodiment, a solid form described herein, e.g., Form G, has one, two, three, four, five, six, seven, eight, nine, ten, eleven, twelve, thirteen, fourteen, fifteen, twenty, or all of the characteristic XRPD peaks as set forth in Table 21.

In still another embodiment, a solid form provided herein, e.g., Form G, has one, two, three, four, five, six, seven, eight, nine, or ten characteristic XRPD peaks at approximately 11.46, 12.51, 15.27, 16.00, 19.29, 19.42, 20.23, 22.49, 22.97, or 24.65±0.1° 2θ, as depicted in, for example, FIG. 19. In still another embodiment, a solid form provided herein, e.g., Form G, has one, two, three, four, or five characteristic XRPD peaks at approximately 11.46, 12.51, 19.29, 19.42, or 20.23±0.1° 2θ, as depicted in, for example, FIG. 19. In still another embodiment, a solid form provided herein, e.g., Form G, has one, two, three, four, or five characteristic XRPD peaks at approximately 11.46, 12.51, 19.29, 19.42, or 20.23±0.05° 2θ, as depicted in, for example, FIG. 19.

Figure 20:
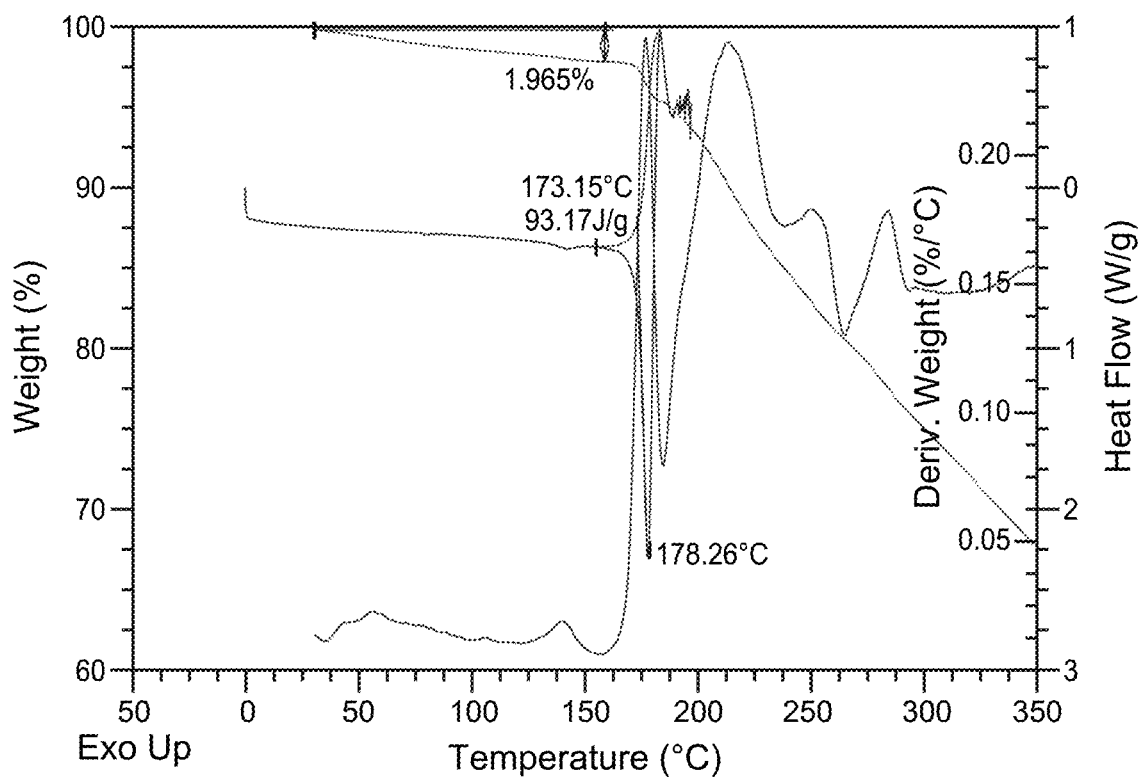
FIG. 20 depicts the TGA and DSC for Compound B Form G.

In one embodiment described herein, is a solid form, e.g., Form G, having a TGA thermograph corresponding substantially to the representative TGA thermogram as depicted in FIG. 20. In certain embodiments, the crystalline form exhibits a TGA thermogram comprising a total mass loss of approximately 2% of the total mass of the sample.

In another embodiment described herein, is a solid form, e.g., Form G, having a DSC thermogram substantially as depicted in FIG. 20 comprising an endothermic event with an onset temperature of about 173° C. and a peak maximum temperature of about 178° C.

In still another embodiment, Form G is pure. In certain embodiments, pure Form G is substantially free of other solid forms, e.g., amorphous solid. In certain embodiments, pure Form G is substantially free of Form B, Form D, or Form E. In certain embodiments, the purity of the Form G is no less than about 95%, no less than about 96%, no less than about 97%, no less than about 98%, no less than about 98.5%, no less than about 99%, no less than about 99.5%, or no less than about 99.9%.

Compound C, Form 1

In certain embodiments, provided herein is a solid form of Compound C designated as Form 1. Form 1 is a crystalline solid form of Compound C.

In one embodiment, Form 1 of Compound C is obtained by slurrying Compound C in isoamyl alcohol/water at about a 3:1 ratio for about 1.5 hours at about 55° C. The liquid of the mixture is then evaporated under flow of nitrogen and reduced pressure. In another embodiment, Form 1 of compound C is obtained by slurrying Compound C in ethanol/heptane at a ratio of about 3:8 at RT. In still another embodiment, Form 1 of compound C is obtained by slurrying Compound C in ethanol/heptane at a ratio of about 1:1 at RT. Form 1 can be prepared according to the methods and examples described herein.

Figure 27A:
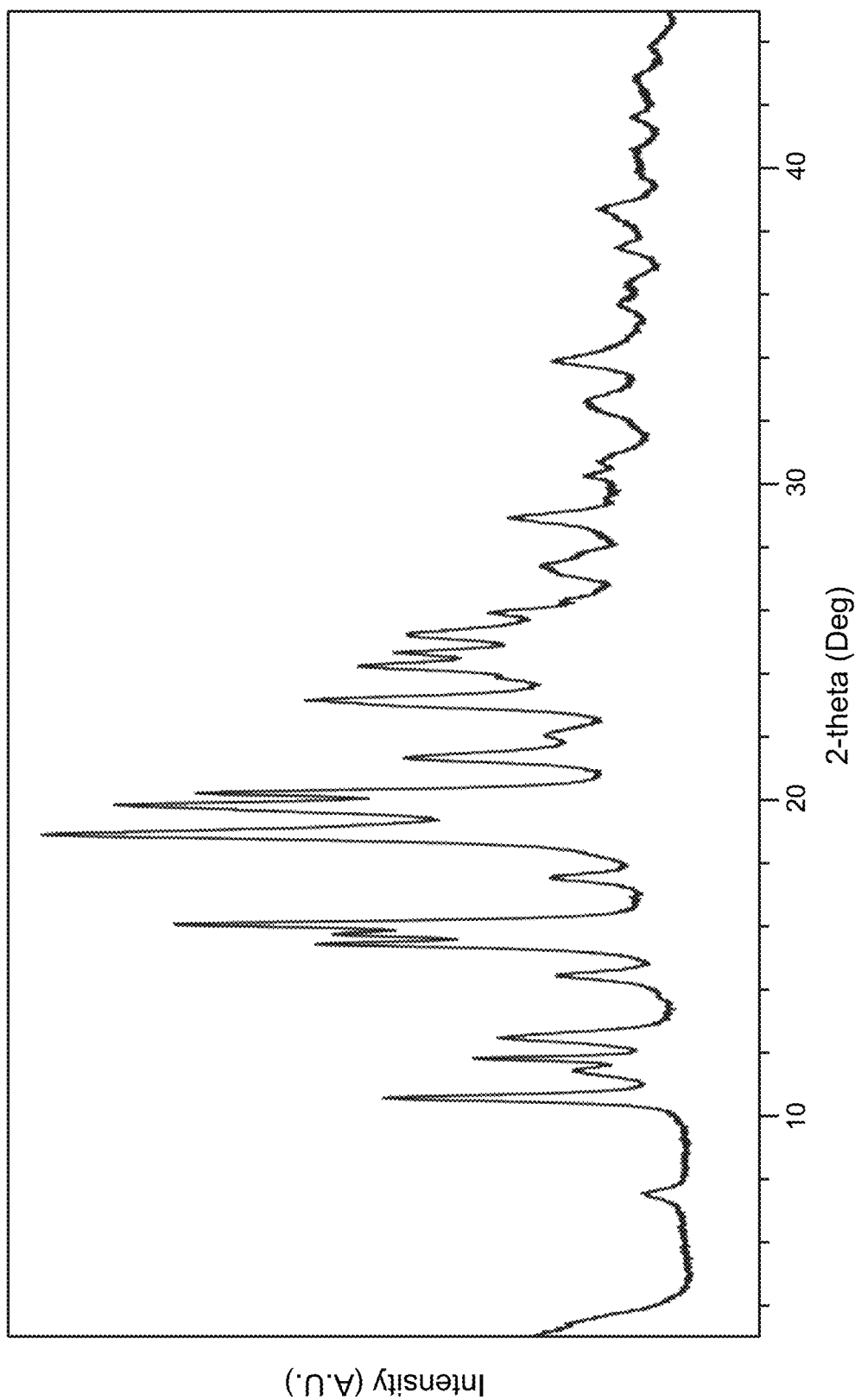
FIG. 27a depicts the XRPD pattern for Compound C Form 1.

In one embodiment, a solid form provided herein, e.g., Form 1, is fumarate salt of Compound A, and is substantially crystalline, as indicated by X-ray powder diffraction pattern (XRPD) measurements. In one embodiment, the XRPD is substantially as shown in FIG. 27a. In another embodiment, a solid form provided herein, e.g., Form 1, has one or more characteristic XRPD peaks at approximately 7.58, 10.59, 11.44, 11.84, 12.5, 14.44, 15.45, 15.78, 16.09, 17.55, 18.92, 19.69, 19.86, 20.23, 21.35, 22.04, 23.16, 23.89, 24.23, 24.67, 25.23, or 25.93±0.1° 2θ, as depicted in, for example, FIG. 27a and as found in Table 36 herein. In still another embodiment, a solid form provided herein, e.g., Form 1, has at least 3, at least 5, at least 7, or at least 10 characteristic XPRD peaks at approximately 7.58, 10.59, 11.44, 11.84, 12.5, 14.44, 15.45, 15.78, 16.09, 17.55, 18.92, 19.69, 19.86, 20.23, 21.35, 22.04, 23.16, 23.89, 24.23, 24.67, 25.23, or 25.93±0.1° 2θ, as depicted in, for example, FIG. 27a and as found in Table 36 herein. In yet another embodiment, a solid form described herein, e.g., Form 1, has one, two, three, four, five, six, seven, eight, nine, ten, eleven, twelve, thirteen, fourteen, fifteen, twenty, or all of the characteristic XRPD peaks as set forth in Table 36.

In still another embodiment, a solid form provided herein, e.g., Form 1, has one, two, three, four, five, six, seven, eight, nine, or ten characteristic XRPD peaks at approximately 10.59, 15.45, 15.78, 16.09, 18.92, 19.69, 19.86, 21.35, 23.16, or 24.23±0.1° 2θ, as depicted in, for example, FIG. 27a. In still another embodiment, a solid form provided herein, e.g., Form 1, has one, two, three, four, or five characteristic XRPD peaks at approximately 16.09, 18.92, 19.69, 19.86, or 23.16±0.1° 2θ as depicted in, for example, FIG. 27a. In still another embodiment, a solid form provided herein, e.g., Form 1, has one, two, three, four, or five characteristic XRPD peaks at approximately 16.09, 18.92, 19.69, 19.86, or 23.16±0.05° 2θ as depicted in, for example, FIG. 27a.

Figure 28:
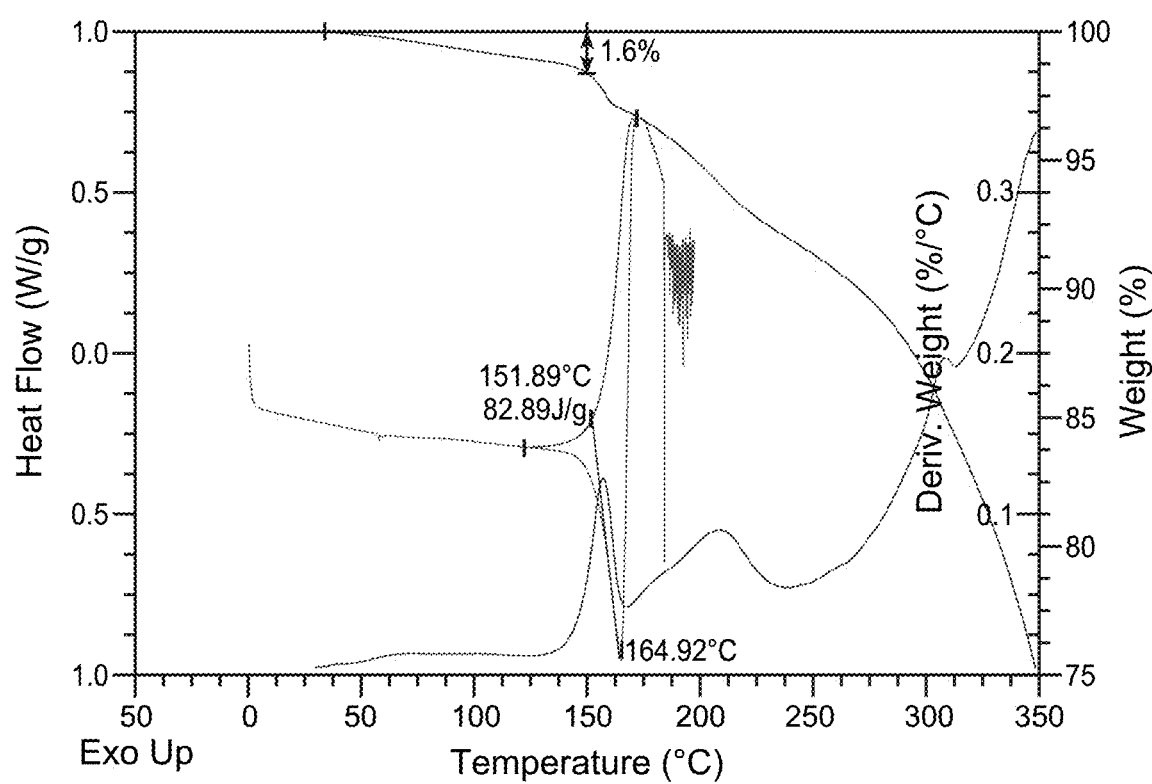
FIG. 28 depicts the TGA and DSC for Compound C Form 1.

In one embodiment described herein, is a solid form, e.g., Form 1, having a TGA thermograph corresponding substantially to the representative TGA thermogram as depicted in FIG. 28 depicts the TGA and DSC for Compound C Form 1.

Figure 29:
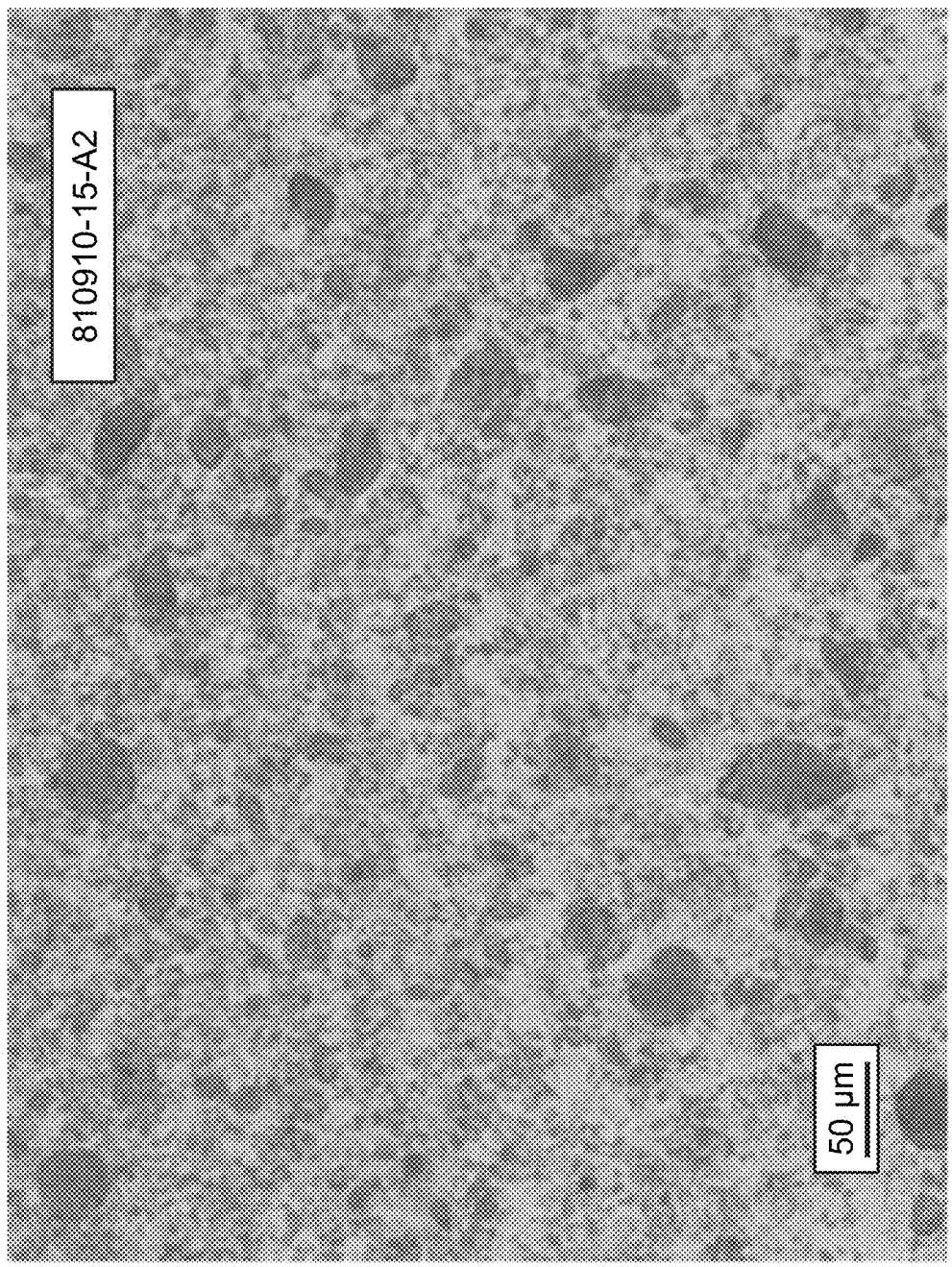
FIG. 29 depicts a PLM image for Compound C Form 1.

FIG. 29. In certain embodiments, the crystalline form exhibits a TGA thermogram comprising a total mass loss of approximately 2% of the total mass of the sample.

In another embodiment described herein, is a solid form, e.g., Form 1, having a DSC thermogram substantially as depicted in FIG. 28 depicts the TGA and DSC for Compound C Form 1.

FIG. 29 comprising an endothermic event with an onset temperature of about 167° C. and a peak maximum temperature of about 172° C.

In still another embodiment, Form 1 is pure. In certain embodiments, pure Form 1 is substantially free of other solid forms, e.g., amorphous solid. In certain embodiments, the purity of the Form 1 is no less than about 95%, no less than about 96%, no less than about 97%, no less than about 98%, no less than about 98.5%, no less than about 99%, no less than about 99.5%, or no less than about 99.9%.

Figure 30:
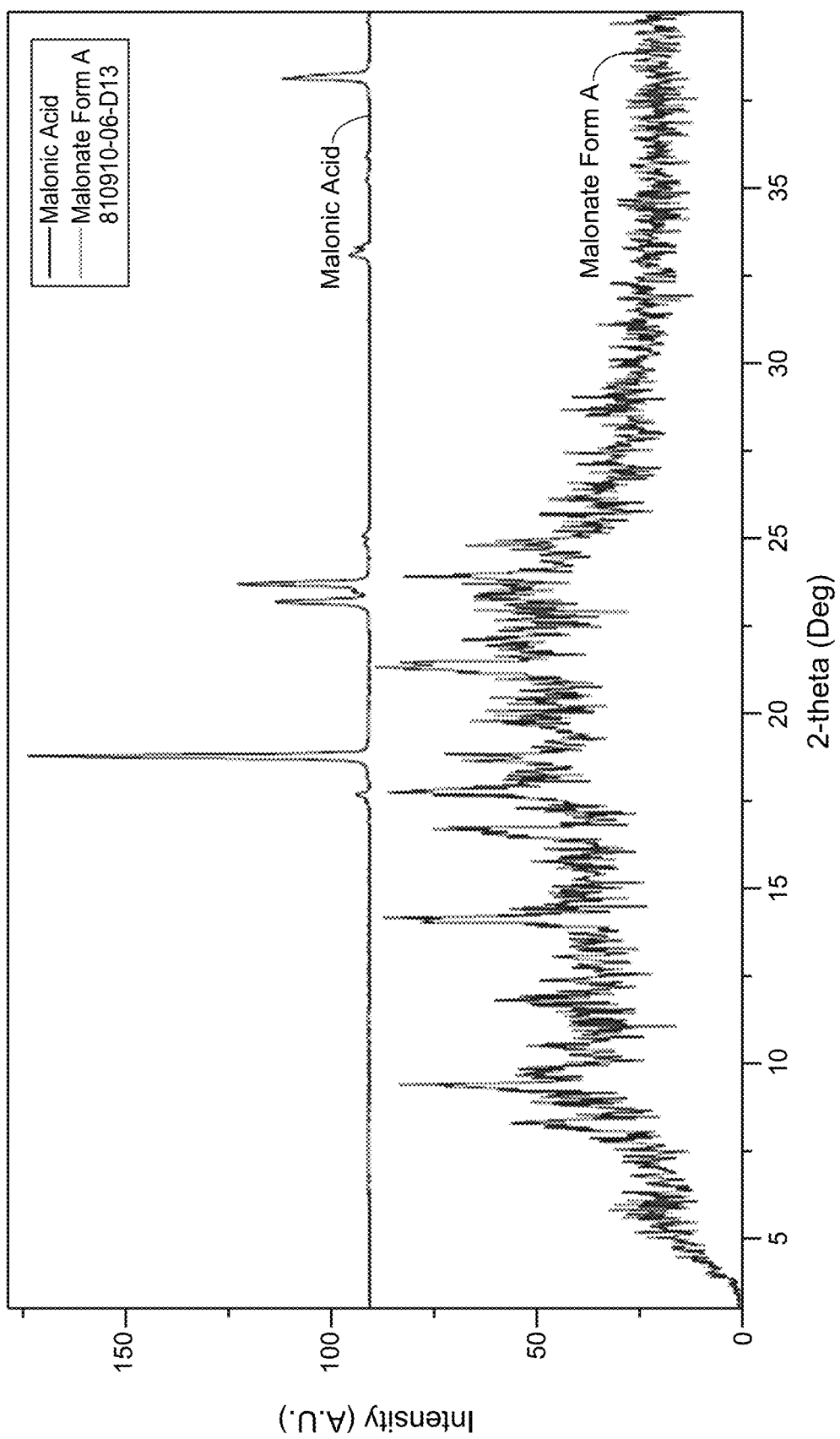
FIG. 30 depicts the XRPD pattern for Compound D Form M.

In another embodiment described herein, is a solid form, e.g., Form 1, having a PLM image as depicted in FIG. 30.

Compound C, Form 2

In certain embodiments, provided herein is a solid form of Compound C designated as Form 2. Form 2 is a crystalline solid form of Compound C.

Figure 27B:
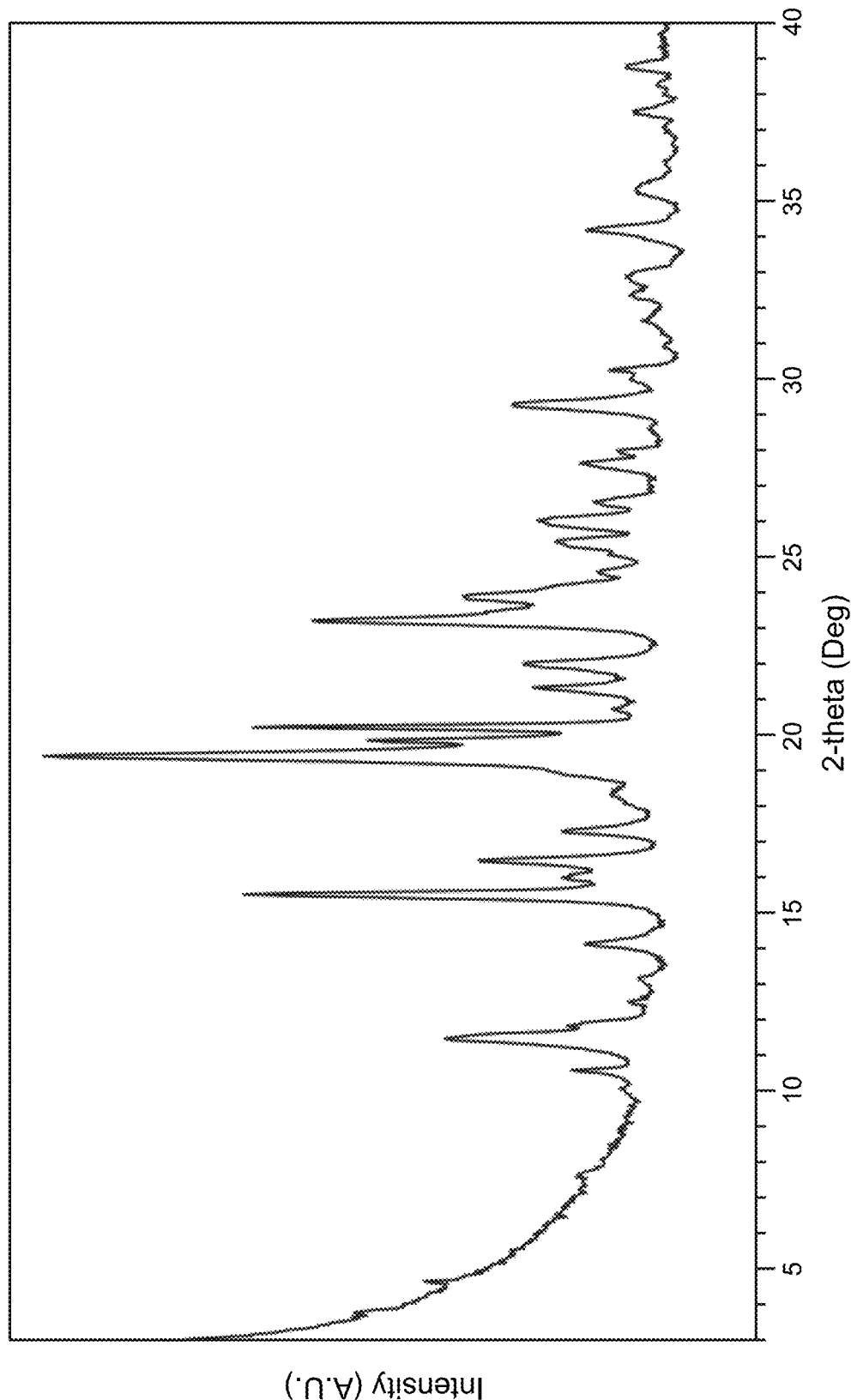
FIG. 27b depicts the XRPD pattern for Compound C Form 2.

In one embodiment, a solid form provided herein, e.g., Form 2, is fumarate salt of Compound A, and is substantially crystalline, as indicated by X-ray powder diffraction pattern (XRPD) measurements. In one embodiment, the XRPD is substantially as shown in FIG. 27b. In another embodiment, a solid form provided herein, e.g., Form 2, has one or more characteristic XRPD peaks at approximately 11.52, 11.87, 15.55, 16.04, 16.51, 17.32, 18.36, 19.00, 19.43, 19.87, 20.24, 21.35, 22.03, 23.23, 23.91, 25.43, or 26.03±0.1° 2θ, as depicted in, for example, FIG. 27b and as found in Table 37 herein. In still another embodiment, a solid form provided herein, e.g., Form 2, has at least 3, at least 5, at least 7, or at least 10 characteristic XPRD peaks at approximately 11.52, 11.87, 15.55, 16.04, 16.51, 17.32, 18.36, 19.00, 19.43, 19.87, 20.24, 21.35, 22.03, 23.23, 23.91, 25.43, or 26.03 0.1° 2θ, as depicted in, for example, FIG. 27b and as found in Table 37 herein. In yet another embodiment, a solid form described herein, e.g., Form 1, has one, two, three, four, five, six, seven, eight, nine, ten, eleven, twelve, thirteen, fourteen, fifteen, or all of the characteristic XRPD peaks as set forth in Table 37 herein.

In still another embodiment, a solid form provided herein, e.g., Form 1, has one, two, three, four, five, six, seven, eight, nine, or ten characteristic XRPD peaks at approximately 11.87, 15.55, 16.04, 16.51, 17.32, 19.43, 19.87, 20.24, 23.23, or 23.91±0.1° 2θ, as depicted in, for example, FIG. 27b. In still another embodiment, a solid form provided herein, e.g., Form 1, has one, two, three, four, or five characteristic XRPD peaks at approximately 15.55, 19.43, 19.87, 20.24, or 23.23±0.1° 2θ as depicted in, for example, FIG. 27b. In still another embodiment, a solid form provided herein, e.g., Form 1, has one, two, three, four, or five characteristic XRPD peaks at approximately 15.55, 19.43, 19.87, 20.24, or 23.23±0.05° 2θ as depicted in, for example, FIG. 27b.

Amorphous Form of Freebase Compound A

In certain embodiments, provided herein is an amorphous solid form of freebase Compound A.

Figure 33:
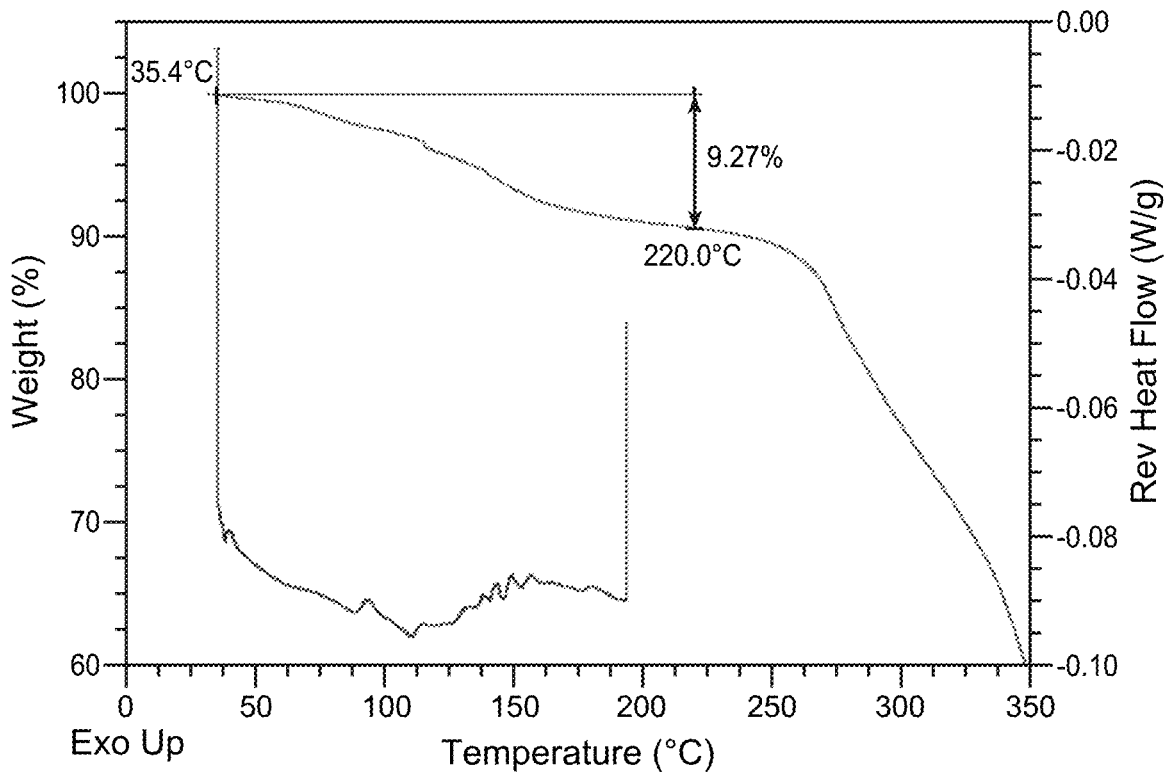
FIG. 33 depicts the TGA and DSC for the amorphous form of Compound A.

In one embodiment, is an amorphous solid form of freebase Compound A as indicated by X-ray powder diffraction pattern (XRPD) measurements. In one embodiment, the XRPD is substantially as shown in FIG. 33.

Figure 34:
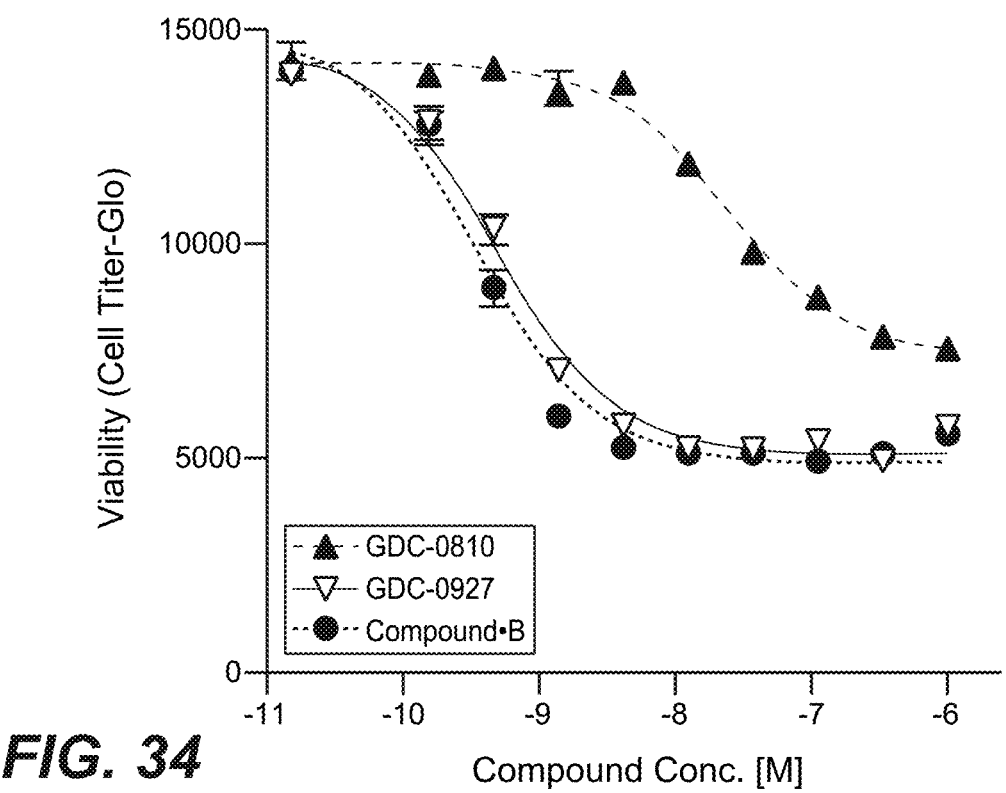
FIG. 34 depicts cell viability of ER+ breast cancer cell line for Compound B compared to GDC-0810 and GDC-0927.

In one embodiment described herein, is an amorphous solid form of freebase Compound A having a TGA thermograph corresponding substantially to the representative TGA and DSC thermogram as depicted in FIG. 34. In certain embodiments, the amorphous form exhibits a TGA thermogram comprising a total mass loss of approximately 9.3% of the total mass of the sample.

In still another embodiment, the amorphous solid form of Compound A is pure. In certain embodiments, pure amorphous solid form of Compound A is substantially free of other solid forms, e.g., crystalline solids as described herein. In certain embodiments, the purity is no less than about 95%, no less than about 96%, no less than about 97%, no less than about 98%, no less than about 98.5%, no less than about 99%, no less than about 99.5%, or no less than about 99.9%.

Pharmaceutical Compositions

The compounds described herein can be administered, for example, orally, intramuscularly, subcutaneously, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, intravitreally (e.g., by intravitreal injection), by eye drop, topically, transdermally, parenterally, by inhalation, by injection, by implantation, by infusion, by continuous infusion, by localized perfusion bathing target cells directly, by catheter, by lavage, in creams, or in lipid compositions. Compounds described herein can be formulated in pharmaceutical compositions as provided herein suitable for oral administration. In another embodiment, a compound described herein can be administered intramuscularly.

In one embodiment, compounds described herein are administered as pharmaceutical compositions capable of being administered to a subject orally or parenterally. Pharmaceutical compositions of the compounds described herein can be prepared as oral dosage forms such as, for example, capsules, microcapsules, tablets (coated and non-coated tablets), granules, powders, pills, or suppositories. The compounds described herein can be formulated for topical or parenteral use where the compound is dissolved or otherwise suspended in a solution suitable for injections, suspensions, syrups, creams, ointments, gels, sprays, solutions and emulsions.

Pharmaceutical compositions described herein include one or more pharmaceutically acceptable excipients such as, but not limited to: sucrose, starch, mannitol, sorbitol, lactose, glucose, cellulose, talc, calcium phosphate or calcium carbonate, cellulose, methylcellulose, hydroxymethylcellulose, hydroxypropylcellulose, carboxymethylcellulose, hydroxypropylstarch, polypropylpyrrolidone, polyvinylpyrrolidone, gelatin, gum arabic, polyethyleneglycol (PEG), starch, sodium bicarbonate, calcium citrate, magnesium stearate, sodium lauryl sulfate, sodium benzoate, sodium bisulfite, methylparaben, propylparaben, citric acid, sodium citrate or acetic acid, polyvinyl pyrroliclone, aluminum stearate), water, and cocoa butter. Uses as, for example, diluents, binders, lubricants and disintegrators of such excipients is well known in the art.

The pharmaceutical compositions described herein include an effective amount of the compound described herein (e.g. Compound A, Compound B, Compound C, Compound D, or a solid form thereof). The dose of the compound described herein can be a measure of a specific amount of the compound (e.g. a standard dose amount) or can be measured as a function of, for example, a patient's body weight. In one embodiment, a compound described herein is administered in an amount equivalent to about 0.1, 0.5, 0.75, 1, 2, 3, 4, 5, 10, 15, 20, 30, 50, 75, 100, 200, or 250 mg/kg. In another embodiment, a compound described herein is administered in an amount of about 0.1 mg/kg to about 1 mg/kg; about 0.5 mg/kg to about 2 mg/kg; about 1 mg/kg to about 5 mg/kg; about 3 mg/kg to about 10 mg/kg; about 8 mg/kg to about 15 mg/kg; or about 15 mg/kg to about 30 mg/kg. In still another embodiment, a compound described herein is administered in an amount less than about 100 mg/kg, less than about 50 mg/kg, less than about 30 mg/kg, less than about 10 mg/kg, or less than about 1 mg/kg.

In one embodiment, a compound described herein is administered at an amount of about 1, 5, 10, 20, 25, 30, 50, 60, 75, 90, 100, 120, 150, or 250 mg. In another embodiment, a compound described herein is administered in an amount of about 10 mg. In still another embodiment, a compound described herein is administered in an amount of about 30 mg. In still another embodiment, a compound described herein is administered in an amount of about 90 mg. In one embodiment, the pharmaceutical composition comprising the compound described herein is administered in an amount prescribed above once per day (QD). The compound can be Compound B, or a solid form thereof (e.g. Form A, Form B, Form C, Form D, Form E, Form F, or Form G). In another embodiment, the compound is a solid form of Compound B (e.g. Form B, Form D, or Form F). In one embodiment, the compound is Compound C or Compound C Form 1 or Form 2. In another embodiment, the compound is Compound D or a solid form described herein.

In another embodiment, a compound described herein is administered at an amount of about 1 mg to about 10 mg; about 10 mg to about 30 mg; about 10 mg to about 90 mg; about 30 mg to about 90 mg; or about 90 mg to about 250 mg. In one embodiment, the compound administered is Compound B at an amount of about 1, 10, 30, 50, 90, 100, or 150 mg. The doses of a compound described herein can be provided as a single dose (e.g. a single tablet or capsule of the given dosage amount) or can be provided as multiple doses given over a period of time (e.g. 2 or more tablets or capsules equating to the dosage amount). The compound can be Compound B, or a solid form thereof (e.g. Form A, Form B, Form C, Form D, Form E, Form F, or Form G). In another embodiment, the compound is a solid form of Compound B (e.g. Form B, Form D, or Form F). In one embodiment, the compound is Compound C or Compound C Form 1 or Form 2. In another embodiment, the compound is Compound D or a solid form described herein.

Pharmaceutical compositions described herein can be administered once daily (QD); twice daily (BID), thrice daily (TID), every other day (Q2D), every three days (Q3D), or once a week. Further, doses of pharmaceutical compositions provided herein comprising a compound described herein can be administered before food (ac), after food (pc), or with food. In one embodiment, a compound described herein is administered QD for a treatment period (a period of time where the drug is administered to a patient described herein) followed by a rest period (a period of time where the drug is not administered to a patient described herein). Rest periods may include administration of anti-cancer agents other than a compound described herein. In one embodiment, a compound described herein is formulated for oral administration as provided herein and is administered QD for 20-28 days followed by a 3-10 day rest period. In another embodiment, the compound is administered QD with no rest period.

Preferably a compound described herein is formulated for oral administration. Oral administration can promote patient compliance in taking the compound (e.g. formulated as a pharmaceutical composition), thereby increasing compliance and efficacy. Oral pharmaceutical compositions comprising a compound described herein include, but are not limited to, tablets (e.g. coated, non-coated and chewable) and capsules (e.g. hard gelatin capsules, soft gelatin capsules, enteric coated capsules, and sustained release capsules). Tablets can be prepared by direct compression, by wet granulation, or by dry granulation. Oral pharmaceutical compositions comprising a compound described herein can be formulated as understood in the art for delayed or prolonged release. In one embodiment, Compound B or a solid form described herein (e.g. Form B, Form D, or Form F) is formulated as a tablet or a capsule for oral administration in an amount set forth herein.

Further provided herein are compounds having the formulae:

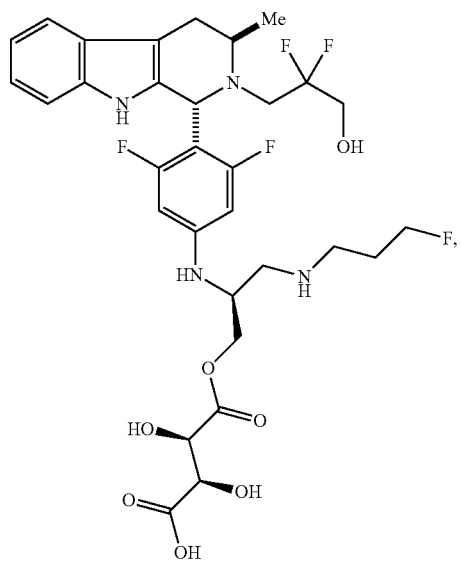

(M1)

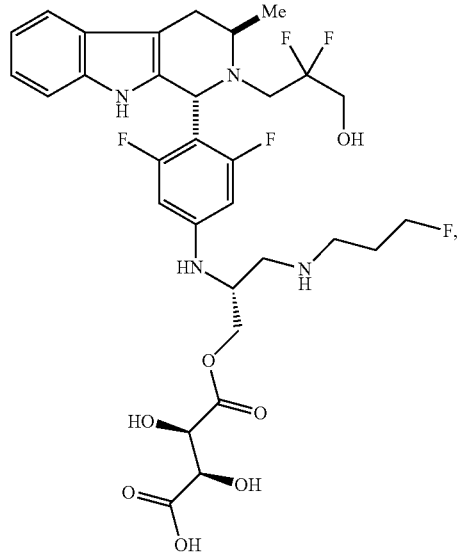

(M2)

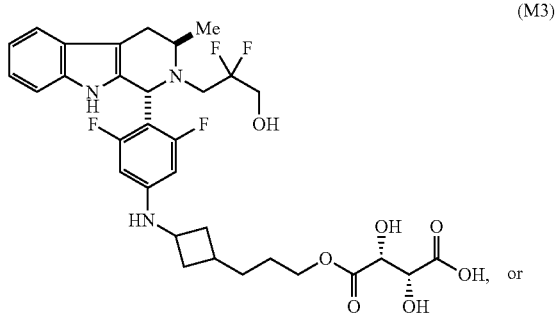

(M3)

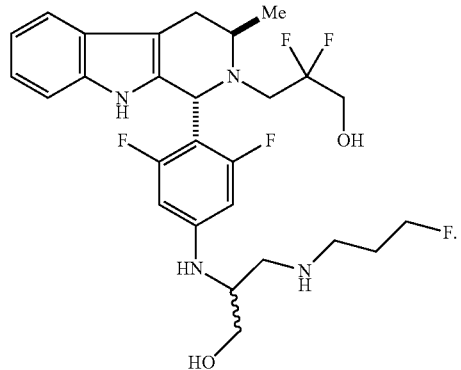

(M4)

Compounds M1, M2, M3, and M4 can be considered metabolites and/or degradants of Compound B, including solid forms described herein. In certain instances, such compounds can be found in compositions described herein where such compositions have been stored for a given period of time at a relative humidity (RH) of about 50%, 55%, 60%, 65%, 70%, 75%, 80% or more. Such compounds can also be found at elevated temperatures of about 30° C., 35° C., 40° C., 45° C., or about 50° C. In one embodiment, compound M1, M2, M3, or M4 is found in composition described herein where the composition comprises less than about 30 mg of Compound B or a solid form thereof. In certain instances, such compounds are found in compositions where the composition comprises an uncoated tablet as described herein.

In certain embodiments, compositions described herein comprising Compound B or a solid form of Compound B described herein (e.g. Form A, Form B, Form C, Form D, Form E, Form F, or Form G) comprise less than 0.01%, 0.02%, 0.03%, 0.04, 0.05, 0.1, 0.15, 0.75, 0.2, 0.225, 0.25, 0.3, 0.4, 0.5, 0.6, 0.7, 0.8, 0.9, or 1% w/w of one or more of M1, M2, M3, or M4. In one embodiment, a composition described herein comprises less than about 0.5% w/w of one or more of M1, M2, M3, or M4.

Methods of Treating Cancer

The compounds and solid forms described herein can be administered in an effective amount (e.g. an amount as described herein) for treating cancer. It is to be understood that the methods described herein also include treatment with a pharmaceutical composition as described herein comprising a compound (e.g. Compound B or a solid form thereof) described herein and one or more pharmaceutically acceptable excipients.

In one embodiment provided herein is a method of treating cancer by administering an effective amount of Compound B as described herein to a patient having cancer. In one embodiment, Compound B is a solid form as described herein (e.g. Form A, Form B, Form C, Form D, Form E, Form F, or Form G).

In another aspect provided herein Compound B, Form A can be administered as described herein to treat a patient having a cancer as set forth herein.

In another aspect provided herein Compound B, Form B can be administered as described herein to treat a patient having a cancer as set forth herein.

In another aspect provided herein Compound B, Form C can be administered as described herein to treat a patient having a cancer as set forth herein.

In another aspect provided herein Compound B, Form D can be administered as described herein to treat a patient having a cancer as set forth herein.

In another aspect provided herein Compound B, Form E can be administered as described herein to treat a patient having a cancer as set forth herein.

In another aspect provided herein Compound B, Form F can be administered as described herein to treat a patient having a cancer as set forth herein.

In another aspect provided herein Compound B, Form G can be administered as described herein to treat a patient having lung cancer, ovarian cancer, endometrial cancer, prostate cancer, uterine cancer, or breast cancer as set forth herein.

In another aspect provided herein an amorphous non-crystalline form of Compound A or Compound B can be administered as described herein to treat a patient having lung cancer, ovarian cancer, endometrial cancer, prostate cancer, uterine cancer, or breast cancer as set forth herein.

In another aspect provided herein is a method of treating lung cancer, ovarian cancer, endometrial cancer, prostate cancer, uterine cancer, or breast cancer by administering an effective amount of Compound B or a solid form as described herein to a patient having said cancer. In one embodiment, the cancer is ovarian cancer or endometrial cancer. In one embodiment, the cancer is breast cancer. In one embodiment of such methods, Compound B is a solid form as described herein (e.g. Form A, Form B, Form C, Form D, Form E, Form F, or Form G).

In a further aspect, Compound B, Form A can be administered as described herein to treat a patient having lung cancer, ovarian cancer, endometrial cancer, prostate cancer, uterine cancer, or breast cancer as set forth herein.

In a further aspect, Compound B, Form B can be administered as described herein to treat a patient having lung cancer, ovarian cancer, endometrial cancer, prostate cancer, uterine cancer, or breast cancer as set forth herein.

In a further aspect, Compound B, Form C can be administered as described herein to treat a patient having lung cancer, ovarian cancer, endometrial cancer, prostate cancer, uterine cancer, or breast cancer as set forth herein.

In a further aspect, Compound B, Form D can be administered as described herein to treat a patient having lung cancer, ovarian cancer, endometrial cancer, prostate cancer, uterine cancer, or breast cancer as set forth herein.

In a further aspect, Compound B, Form E can be administered as described herein to treat a patient having lung cancer, ovarian cancer, endometrial cancer, prostate cancer, uterine cancer, or breast cancer as set forth herein.

In a further aspect, Compound B, Form F can be administered as described herein to treat a patient having lung cancer, ovarian cancer, endometrial cancer, prostate cancer, uterine cancer, or breast cancer as set forth herein.

In a further aspect, Compound B, Form G can be administered as described herein to treat a patient having lung cancer, ovarian cancer, endometrial cancer, prostate cancer, uterine cancer, or breast cancer as set forth herein.

In a further aspect, an amorphous non-crystalline form of Compound A or Compound B can be administered as described herein to treat a patient having lung cancer, ovarian cancer, endometrial cancer, prostate cancer, uterine cancer, or breast cancer as set forth herein.

Further provided herein are methods of treating breast cancer in a patient having breast cancer by administering an effective amount of Compound B or a solid form of Compound B as described herein. In one embodiment is a method of treating breast cancer in such a patient by administering an effective amount of a solid form of Compound B as described herein. In one embodiment, the method comprises treating breast cancer in a patient having breast cancer by administering to the patient an effective amount of Compound B, Form B as described herein. In one embodiment, the method comprises treating breast cancer in a patient having breast cancer by administering to the patient an effective amount of pure Compound B (e.g. substantially free of another solid form described herein, e.g. substantially free of Form D and/or Form F). In another aspect the method comprises treating breast cancer in a patient having breast cancer by administering to the patient an effective amount of Compound B, Form D as described herein. In another aspect the method comprises treating breast cancer in a patient having breast cancer by administering to the patient an effective amount of Compound B, Form F as described herein. In still another aspect the method comprises treating breast cancer in a patient having breast cancer by administering to the patient an effective amount of Compound B, Form A as described herein. In still another aspect the method comprises treating breast cancer in a patient having breast cancer by administering to the patient an effective amount of Compound B, Form C as described herein. In still another aspect the method comprises treating breast cancer in a patient having breast cancer by administering to the patient an effective amount of Compound B, Form E as described herein. In still another aspect the method comprises treating breast cancer in a patient having breast cancer by administering to the patient an effective amount of Compound B, Form G, as described herein. In still another aspect the method comprises treating breast cancer in a patient having breast cancer by administering to the patient an effective amount of an amorphous non-crystalline form of Compound B as described herein.

The compounds described herein (e.g. Compound B or a solid form thereof as described herein) can be used in the manufacture of a medicament for use in treating breast cancer as described herein.

The methods of treating breast cancer provided herein comprise treatment where the breast cancer can be hormone receptor positive breast cancer (e.g. ER+ breast cancer), HER2-positive breast cancer, HER2-negative breast cancer, or triple negative breast cancer (TNBC).

In one embodiment, the breast cancer is HER2-negative breast cancer. HER2-negative breast cancer can be defined herein as, for example, a HER2 IHC score of 0 or 1+, or an IHC score of 2+ accompanied by a negative fluorescence, chromogenic, or silver in situ hybridization test indicating the absence of HER2-gene amplification, or a HER2/CEP17 ratio of <2.0, or local clinical guidelines. In one embodiment, the breast cancer is ER+/HER2- breast cancer. The breast cancer can be stage 0, I, II, III, or IV as understood in the art.

In another embodiment, the breast cancer is locally advanced or metastatic breast cancer (mBC).

In one embodiment, Compound B or a solid form thereof (e.g. Form B, Form D, or Form F) can be administered as a component of adjuvant therapy. In another embodiment, Compound B or a solid form thereof (e.g. Form B, Form D, or Form F) can be administered as a component of neoadjuvant therapy.

Breast cancer patients described herein may be premenopausal before treatment with a compound or solid form as described herein. Breast cancer patients described herein may be postmenopausal before treatment with a compound or solid for as described herein.

The methods provided herein include administering an effective amount of Compound B or a solid form as described herein to the patient at an amount as set forth herein. The effective amount can be, for example, an amount of about 10 mg, 30 mg, 50 mg, 90 mg, 100 mg, 125 mg, or 250 mg. In one embodiment of the methods provided herein, Compound B or a solid form described herein is administered orally. In one embodiment, Compound B or a solid form thereof is administered as a tablet (e.g. a coated or non-coated tablet). In another embodiment, Compound B or a solid form thereof is administered as a capsule. Thus, provided herein are compositions suitable for administration to a breast cancer patient where such compositions comprise an amount of Compound B or a solid form described herein of about 10 mg, 30 mg, 50 mg, 90 mg, 100 mg, 125 mg, or 250 mg in a tablet or capsule as set forth herein. When administered in accordance with the methods provided herein, Compound B or a solid form thereof can be pure as described herein.

Patients of the methods described above may have had previous treatment with one or more anti-cancer agents or radiation therapy. For example, in one embodiment, a patient may have been previously treated (e.g. with a 1 L, 2 L, 3 L or more line therapy) with doxorubicin, pegylated liposomal doxorubicin, epirubicin, paclitaxel, albumin-bound paclitaxel, docetaxel, 5-fluorouracil, cyclophosphamide, cisplatin, carboplatin, vinorelbine, capecitabine, gemcitabine, ixabepilone, eribulin, olaparib, methotrexate, anastrozole, exemestane, toremifene, letrozole, tamoxifen, 4-hydroxy tamoxifen, raloxifene, droloxifene, trioxifene, keoxifene, flutamide, nilutamide, bicalutamide, lapatinib, vinblastine, goserelin, leuprolide, pegfilgrastim, filgrastim, or venetoclax.

In another embodiment, a patient may have been previously treated (e.g. with a 1 L, 2 L, 3 L or more line therapy) with an AKT inhibitor, a CDK4/6 inhibitor, a PARP inhibitor, or an aromatase inhibitor. In one embodiment, the AKT inhibitor is ipatasertib (GDC-0068). In one embodiment, the CDK4/6 inhibitor is abemaciclib, ribociclib, or palbociclib. In certain instances, a patient may have been previously treated with: (1) abemaciclib, ribociclib, or palbociclib; (2) ipatasertib; (3) everolimus or fulvestrant; (4) -trastuzumab emtansine, trastuzumab, pertuzumab, or atezolizumab; or (5) alemtuzumab, bevacizumab, cetuximab, panitumumab, rituximab, tositumomab, or a combination thereof. Patients described herein may have had surgery prior to treatment with Compound B or the solid form thereof.

In another embodiment, a patient herein may be refractory to one or more anti-cancer therapies. For example, a patient herein may be refractory to aromatase inhibitors. In another example, a patient herein may be refractory to a selective estrogen receptor degrader (SERD) such as, for example, fulvestrant. In still another example, a patient may be refractory to one or more endocrine therapies such as, clomifene, toremifene, raloxifene, anordrin, bazedoxifene, broparoestrol, cyclofenil, lasofoxifene, ormeloxifene, acolbifene, elacestrant, brilanestrant, clomifenoxide, droloxifene, etacstil, or ospemifene. In another embodiment, a patient may be refractory to abemaciclib, anastrozole, exemestane, fulvestrant, goserelin, letrozole, leuprorelin, megestrol, palbociclib, tamoxifen, or toremifene. In another example, a patient may be refractory to treatment with trastuzumab emtansine, trastuzumab, pertuzumab, atezolizumab, pembrolizumab, durvalumab, avelumab, or nivolumab.

The compounds described herein can also be used in methods comprising inhibiting ERalpha in a patient. Such methods comprise administering an amount of a compound described herein (e.g. Compound A or Compound B, including solid forms thereof as described herein) to the patient.

Combination Therapies

The compounds and solid forms described herein can be administered in combination with one or more anti-cancer agents. Administration "in combination" as set forth herein includes sequential administration (in any order) of a compound described herein and one or more anti-cancer therapies as well as simultaneous administration. Accordingly, provided herein are methods of treating breast cancer in a patient having breast cancer, such methods comprising administering Compound B or a solid form as described herein in combination with one or more additional anti-cancer therapies. In one embodiment, the anti-cancer therapy comprises doxorubicin, pegylated liposomal doxorubicin, epirubicin, paclitaxel, albumin-bound paclitaxel, docetaxel, 5-fluorouracil, cyclophosphamide, cisplatin, carboplatin, vinorelbine, capecitabine, gemcitabine, ixabepilone, eribulin, olaparib, methotrexate, anastrozole, exemestane, toremifene, letrozole, tamoxifen, 4-hydroxy tamoxifen, raloxifene, droloxifene, trioxifene, keoxifene, flutamide, nilutamide, bicalutamide, lapatinib, vinblastine, goserelin, leuprolide, pegfilgrastim, filgrastim, or venetoclax.

In one embodiment provided herein is a method of treating breast cancer in a patient having breast cancer by administering an effective amount of Compound B or a solid form as described herein in combination with doxorubicin, pegylated liposomal doxorubicin, epirubicin, paclitaxel, albumin-bound paclitaxel, docetaxel, 5-fluorouracil, cyclophosphamide, cisplatin, carboplatin, vinorelbine, capecitabine, gemcitabine, ixabepilone, eribulin, olaparib, methotrexate, anastrozole, exemestane, toremifene, letrozole, tamoxifen, 4-hydroxy tamoxifen, raloxifene, droloxifene, trioxifene, keoxifene, flutamide, nilutamide, bicalutamide, lapatinib, vinblastine, goserelin, leuprolide, pegfilgrastim, filgrastim, or venetoclax.

In another aspect provided herein is a method of treating breast cancer in a patient having breast cancer by administering an effective amount of Compound B or a solid form as described herein in combination with paclitaxel, albumin-bound paclitaxel, methotrexate, anastrozole, exemestane, toremifene, letrozole, tamoxifen, 4-hydroxy tamoxifen, raloxifene, droloxifene, trioxifene, keoxifene, or venetoclax. In still another aspect provided herein is a method of treating breast cancer in a patient having breast cancer by administering an effective amount of Compound B or a solid form as described herein in combination with fulvestrant, paclitaxel, albumin-bound paclitaxel, clomifene, toremifene, raloxifene, anordrin, bazedoxifene, broparoestrol, cyclofenil, lasofoxifene, ormeloxifene, acolbifene, elacestrant, brilanestrant, clomifenoxide, droloxifene, etacstil, or ospemifene.

In still another aspect provided herein is a method of treating breast cancer in a patient having breast cancer by administering an effective amount of Compound B or a solid form as described herein in combination with a CDK4/6 inhibitor, a PARP inhibitor, or an aromatase inhibitor.

In a further aspect provided herein is a method of treating breast cancer in a patient having breast cancer as described herein where the method comprises administering an effective amount of Compound B or a solid form as described herein in combination with a CDK4/6 inhibitor where the CDK4/6 inhibitor is abemaciclib, ribociclib, or palbociclib. In a preferred embodiment, the method comprises administering Compound B or a solid form as described herein in combination with palbociclib. In still another embodiment, the method comprises administering Compound B or a solid form as described herein in combination with abemaciclib or ribociclib. In another aspect provided herein is a kit comprising (i) Compound B or a solid form thereof in a unit dosage form; (ii) a CDK4/6 inhibitor (e.g. palbociclib) in a second unit dosage form; and a container containing each dosage form.

The dose of abemaciclib may be 50 mg to 500 mg daily, or 150 mg to 450 mg daily and the dosing can be daily in 28 day cycles or less than 28 days per 28 day cycles such as 21 days per 28 day cycle or 14 days per 28 day cycle or 7 days per 28 day cycles. In one embodiment, abemaciclib is dosed once daily or preferably on a bid schedule where dosing is oral. In the case of bid dosing, the doses can be separated by 4 hours. 8 hours or 12 hours. In certain embodiments, abemaciclib is dosed at 150 mg orally bid where each dose is administered about 12 hr apart. In certain embodiments, the dose of abemaciclib is administered in accordance with a package insert.

The dose of ribociclib may be 200 mg to 1,000 mg daily; or 250 mg to 750 mg daily and the dosing can be daily in 28 day cycles or less than 28 days per 28 day cycles such as 21 days per 28 day cycle or 14 days per 28 day cycle or 7 days per 28 day cycles. In one embodiment, ribociclib is dosed once daily where dosing is oral. In certain embodiments, the dose of ribociclib is administered in accordance with a package insert.

The dose of palbociclib may be 25 mg to 250 mg daily or 50 mg to 125 mg daily or from 75 mg to 125 mg daily or 75 mg daily to 100 mg daily or 125 mg daily. The dosing can be daily in 28 day cycles or less than 28 days per 28 day cycles such as 21 days per 28 day cycle or 14 days per 28 day cycle or 7 days per 28 day cycles. In one embodiment, palbociclib is dosed once daily where dosing is oral. In certain embodiments, the dose of palbociclib is administered in accordance with a package insert.

In another aspect provided herein the methods described herein comprise administering an effective amount of Compound B or a solid form as described herein in combination with an aromatase inhibitor (AI), where the AI is letrozole, anastrozole, exemestane, or testolactone.

In yet another aspect provided herein is a method of treating breast cancer in a patient having breast cancer by administering an effective amount of Compound B or a solid form as described herein in combination with a cancer immunotherapy (e.g. an antibody). In one embodiment, Compound B or a solid form as described herein is administered in combination with trastuzumab emtansine, trastuzumab, pertuzumab, atezolizumab, pembrolizumab, durvalumab, avelumab, or nivolumab, or a combination thereof. In one embodiment, Compound B or a solid form as described herein is administered in combination with a cancer immunotherapy comprising PD-1 or PD-L1 inhibitor, where the cancer immunotherapy is atezolizumab, pembrolizumab, or nivolumab.

Administration of a compound described herein (e.g. Compound B or a solid form as described herein) results in patients having adverse effects (AEs) characterized as Grade 2 or lower. In one embodiment, a patient administered Compound B or a solid form as described herein has Grade 2 or lower AEs.

EXAMPLES

The following Examples are presented by way of illustration, not limitation.

Synthesis of Compounds described herein. All reagents and solvents were purchased from commercial suppliers and used with no additional purification. Anhydrous solvent (dichloromethane) was utilized. Commercially available solvents were not further purified.

All reactions were carried out in screw-cap vials equipped with a Teflon septa under a nitrogen atmosphere.

Flash column chromatography was performed using a teledyne Isco CombiFlash® Rf instrument with pre-packed RediSepRf Gold silica cartridges.

Unless otherwise indicated, reported yields are for isolated material and are corrected for residual solvents.

Compounds were characterized by one or more of $^1$H NMR, $^{13}$C NMR, melting point and HRMS, and HPLC analysis (e.g., for confirmation of purity).

$^1$H, and $^{13}$C Nuclear Magnetic Resonance Spectra were recorded on a Bruker 400 MHz instrument at ambient temperature. All $^1$H NMR spectra were measured in parts per million (ppm) relative to residual chloroform signal (7.26 ppm) or dimethyl sulfoxide (2.50 ppm) in the deuterated solvent unless otherwise stated. Data for $^1$H NMR are reported as follows: chemical shift, multiplicity (br=broad signal, overlap=overlapping, s=singlet, d=doublet, t=triplet, q=quartet, p=pentet, m=multiplet), coupling constants and integration. All $^{13}$C NMR spectra are reported in ppm relative to deuterochloroform (77.06 ppm) or deuterated dimethyl sulfoxide (39.53 ppm), and were obtained with complete $^1$H decoupling unless otherwise stated. HPLC analyses were performed on an Agilent 1260 Infinity HPLC system with a UV detector at 220 nm using an Ace Super C18 column. Melting points were obtained using a Buchi B-540 Melting Point Apparatus and are uncorrected. High resolution mass spectrometry (HRMS) data was acquired on a Thermo Scientific Orbitrap Fusion mass spectrometer.

Examples 1-3: Indole Alkylation

Indole alkylation was done by the sequence of Boc protection (Example 1), sulfamide formation (Example 2), and indole alkylation (Example 3)

Example 1: Boc Protection

Example 1: Boc Protection General Reaction Scheme

Boc protection was done according to the following general reaction scheme where $R_A$ and $R_B$ correspond to the various functional groups in the following Example 1 protection reactions, and wherein the asterisks represent a chiral center:

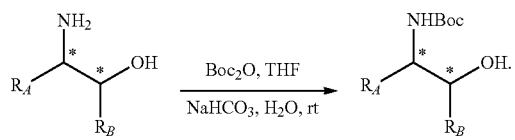

Example 1A: Preparation of tert-butyl (S)-(2-hydroxy-1-(4-methoxyphenyl)ethyl)carbamate

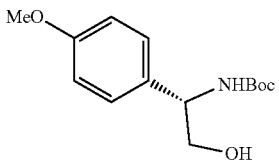 [SMILES: COc1ccc([C@@H](CO)NC(=O)OC(C)(C)C)cc1]

General reaction scheme 1 above was performed as follows. To a slurry of (S)-2-amino-2-(4-methoxyphenyl) ethan-1-ol hydrochloride (1.04 g, 5.10 mmol, 100 mol %) in THF (4.4 mL) was added Boc$_2$O (1.21 mL, 5.61 mmol, 110 mol %), NaHCO$_3$ (451 mg, 5.10 mmol, 100 mol %), and water (4.4 mL) at rt. The solution was stirred at rt for 18 h, and extracted with iPrOAc (20 mL×2). The organic layer was washed with saturated brine (20 mL), dried (Na$_2$SO$_4$), filtered, and concentrated under reduced pressure to provide the product without further purification. Example 1A yield is reported are corrected based on residual solvent from $^1$H NMR. The reaction yielded tert-butyl (S)-(2-hydroxy-1-(4-methoxyphenyl)ethyl)carbamate (1.36 g, 100% yield) as a white solid. mp: 139.0-139.9° C.; FTIR (neat, cm$^{-1}$) 3370, 2984, 2837, 1681, 1613, 1512, 1461; $^1$H NMR (400 MHz, CDCl$_3$): δ 7.24-7.20 (m, 2H), 6.92-6.86 (m, 2H), 5.10 (d, J=7.2 Hz, 1H), 4.72 (br, 1H), 3.82 (t, J=5.6 Hz, 2H), 3.80 (s, 3H), 2.35 (br, 1H), 1.43 (s, 9H); $^{13}$C NMR (100 MHz, CDCl$_3$): δ 159.1, 156.2, 131.6, 127.7, 114.2, 80.0, 66.8, 56.4, 55.3, 28.4.

Example 1B: Preparation of tert-butyl (R)-(1-cyclopropyl-2-hydroxyethyl)carbamate

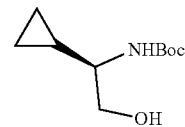 [SMILES: CC(C)(C)OC(=O)N[C@@H](CO)C1CC1]

The general reaction scheme as per Example 1A above was performed with (R)-2-amino-2-cyclopropylethan-1-ol (1.16 g, 11.5 mmol, 100 mol %) to yield tert-butyl (R)-(1-cyclopropyl-2-hydroxyethyl)carbamate (2.31 g, 100% yield) as a white solid. mp: 70.0-70.8° C.; FTIR (neat, cm$^{-1}$) 3358, 2974, 2937, 1682, 1521, 1366; $^1$H NMR (400 MHz, CDCl$_3$): δ 4.80 (br, 1H), 3.80 (ddd, J=10.8, 6.8, 3.2 Hz, 1H), 3.67 (ddd, J=10.8, 6.0, 4.8 Hz, 1H), 2.94 (dtd, J=9.6, 6.4, 3.2 Hz, 1H), 2.81 (br, 1H), 1.45 (s, 9H), 0.85 (dtt, J=9.6, 8.0, 4.8 Hz, 1H), 0.60-0.47 (m, 2H), 0.44-0.25 (m, 2H); $^{13}$C NMR (100 MHz, CDCl$_3$): δ 156.6, 79.7, 66.3, 57.9, 28.4, 13.0, 3.3, 2.9.

Example 1C: Preparation of tert-butyl ((1R,2S)-2-hydroxy-2,3-dihydro-1H-inden-1-yl)carbamate

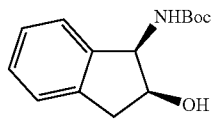 [SMILES: CC(C)(C)OC(=O)N[C@@H]1c2ccccc2C[C@@H]1O]

The general reaction scheme as per Example 1A above was performed with (1R,2S)-1-amino-2,3-dihydro-1H-inden-2-ol (5.15 g, 34.5 mmol, 100 mol %) to yield tert-butyl ((1R,2S)-2-hydroxy-2,3-dihydro-1H-inden-1-yl)carbamate (8.61 g, 100% yield) as a white solid. mp: 67.3-68.4° C.; FTIR (neat, cm$^{-1}$) 3428, 3350, 2983, 2933, 1688, 1509; $^1$H NMR (400 MHz, CDCl$_3$): δ 7.31-7.26 (m, 1H), 7.26-7.18 (m, 3H), 5.17 (br, 1H), 5.05 (br, 1H), 4.57 (ddd, J=7.2, 4.8, 2.0 Hz, 1H), 3.12 (dd, J=16.8, 5.2 Hz, 1H), 2.91 (dd, J=16.8, 2.4 Hz, 1H), 2.31 (d, J=4.8 Hz, 1H), 1.50 (s, 9H); $^{13}$C NMR (100 MHz, CDCl$_3$): δ 156.3, 140.9, 139.9, 128.2, 127.1, 125.3, 124.5, 79.9, 73.6, 58.9, 39.4, 28.4.

Example 1D: Preparation of tert-butyl (S)-(1-(3-fluorophenyl)-2-hydroxyethyl)carbamate

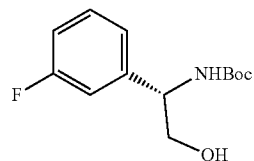 [SMILES: CC(C)(C)OC(=O)N[C@H](CO)c1cccc(F)c1]

The general reaction scheme as per Example 1A above was performed with (S)-2-amino-2-(3-fluorophenyl)ethan-1-ol (1.36 g, 8.73 mmol, 100 mol %) to yield tert-butyl (S)-(1-(3-fluorophenyl)-2-hydroxyethyl)carbamate (2.23 g, 100% yield) as a white solid. mp: 106.5-107.9° C.; FTIR (neat, cm$^{-1}$) 3251, 3059, 2977, 2901, 1671, 1587, 1543; $^1$H NMR (400 MHz, CDCl$_3$): δ 7.33 (ddd, J=7.6, 7.6, 6.0 Hz, 1H), 7.12-7.07 (m, 1H), 7.05-6.95 (m, 2H), 5.24 (br, 1H), 4.77 (br, 1H), 3.93-3.77 (m, 2H), 2.02 (br, 1H), 1.44 (s, 9H); $^{13}$C NMR (100 MHz, CDCl$_3$): δ 163.0 (d, $^1J_{CF}$=246 Hz), 156.0, 142.5, 130.2 (d, $^3J_{CF}$=9 Hz), 122.2 (d, $^4J_{CF}$=3 Hz), 114.5 (d, $^2J_{CF}$=21 Hz), 113.6 (d, $^2J_{CF}$=21 Hz), 80.2, 66.2, 56.3, 28.3; $^{19}$F NMR (CDCl$_3$, 376 MHz): δ −112.4.

Example 1E: Preparation of (S)-(1-(3-fluorophenyl)-2-hydroxyethyl)carbamate

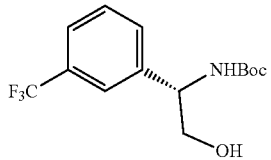

The general reaction scheme as per Example 1A above was performed with (S)-2-amino-2-(3-(trifluoromethyl)phenyl)ethan-1-ol hydrochloride (1.00 g, 4.12 mmol, 100 mol %) to yield (S)-(1-(3-fluorophenyl)-2-hydroxyethyl)carbamate (1.26 g, 100% yield) as a white solid. mp: 50.3-52.5° C.; FTIR (neat, cm$^{-1}$) 3368, 3254, 2979, 2939, 1691, 1510, 1453, 1333; $^1$H NMR (400 MHz, CDCl$_3$): δ 7.59-7.54 (m, 2H), 7.53-7.45 (m, 2H), 5.31 (d, J=6.4 Hz, 1H), 4.83 (br, 1H), 3.92 (ddd, J=11.2, 6.8, 4.0 Hz, 1H), 3.88-3.79 (m, 1H), 1.94 (br, 1H), 1.43 (s, 9H); $^{13}$C NMR (100 MHz, CDCl$_3$): δ 156.1, 141.1, 130.9 (q, $^2J_{CF}$=32 Hz), 130.1, 129.0, 124.3 (q, $^3J_{CF}$=4 Hz), 124.1 (q, $^1J_{CF}$=270 Hz), 123.4 (q, $^3J_{CF}$=4 Hz), 80.3, 65.8, 56.3, 28.2; $^{19}$F NMR (CDCl$_3$, 376 MHz): δ −62.6.

Example 2: Sulfamidate Formation

Example 2: Sulfamidate Formation General Reaction Scheme

Sulfamidate formation was done according to the following general reaction scheme where R$_A$ and R$_B$ correspond to the various functional groups in the following Example 2 reactions, and wherein the asterisks represent a chiral center:

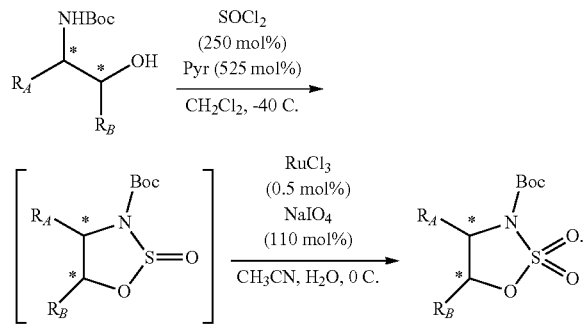

Example 2A: Preparation of tert-butyl (R)-4-benzyl-1,2,3-oxathiazolidine-3-carboxylate 2,2-dioxide

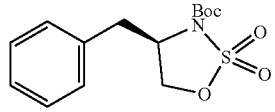 [SMILES: CC(C)(C)OC(=O)N1[C@H](Cc2ccccc2)COS1(=O)=O]

General reaction scheme 2 above was performed as follows. To a cold (−40° C.) solution of SOCl$_2$ (10.9 mL, 149 mmol, 250 mol %) in CH$_2$Cl$_2$ (60.0 mL) was added a solution of tert-butyl (R)-(1-hydroxy-3-phenylpropan-2-yl)carbamate (15.0 g, 59.7 mmol, 100 mol %) in CH$_2$Cl$_2$ (60.0 mL) over 60 min at −40° C. Pyridine (25.3 mL, 313 mmol, 525 mol %) was then added to the reaction mixture over 30 min at −40° C. The reaction mixture was stirred at −40° C. for 2 h, solvent swapped to CH$_2$Cl$_2$/iPrOAc (1:1) mixture, filtered. The filtrate was washed with saturated brine solution (20 mL), dried (Na$_2$SO$_4$), filtered, and concentrated under reduced pressure. The residue was dissolved in CH$_3$CN (60.0 mL) at 0° C. NaIO$_4$ (14.0 g, 65.7 mmol, 110 mol %), RuCl$_3$ (61.9 mg, 0.298 mmol, 0.5 mol %), and water (60.0 mL) were added into the reaction mixture at 0° C. and stirred for 15 min. The reaction mixture was then warmed to room temperature and stirred at room temperature for 2 h, extracted with iPrOAc (20 mL), washed with saturated NaHCO$_3$ solution (15 mL), saturated brine solution (15 mL), dried (Na$_2$SO$_4$), filtered, purified by chromatography on SiO$_2$. Specific gradient used for each sample is included in the characterization data. All the yields reported are corrected based on residual solvent from $^1$H NMR. Reaction 2A yielded tert-butyl (R)-4-benzyl-1,2,3-oxathiazolidine-3-carboxylate 2,2-dioxide (18.7 g, 56% yield) as a white solid. Column Gradient: 0 to 5% CH$_3$OH in CH$_2$Cl$_2$. mp: 134.4-135.0° C.; FTIR (neat, cm$^{-1}$) 3261, 2979, 2903, 1712, 1673, 1540; $^1$H NMR (400 MHz, CDCl$_3$): δ 7.38-7.20 (m, 5H), 4.49-4.40 (m, 2H), 4.35-4.28 (m, 1H), 3.37 (dd, J=14.0, 4.0 Hz, 1H), 2.98-2.87 (m, 1H), 1.56 (s, 9H); $^{13}$C NMR (100 MHz, CDCl$_3$): δ 148.5, 135.2, 129.5, 129.1, 127.5, 85.6, 68.8, 58.6, 37.9, 28.0.

Example 2B: Preparation of tert-butyl (S)-4-phenyl-1,2,3-oxathiazolidine-3-carboxylate 2,2-dioxide

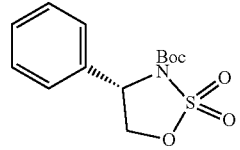 [SMILES: CC(C)(C)OC(=O)N1[C@@H](c2ccccc2)COS1(=O)=O]

The general reaction scheme as per Example 2A above was performed with tert-butyl (S)-(2-hydroxy-1-phenylethyl)carbamate (10.0 g, 42.1 mmol, 100 mol %) to yield compound tert-butyl (S)-4-phenyl-1,2,3-oxathiazolidine-3-carboxylate 2,2-dioxide (5.23 g, 42% yield) as a white solid. Column Gradient: 0 to 5% CH$_3$OH in CH$_2$Cl$_2$. mp: 144.3-145.0° C.; FTIR (neat, cm$^{-1}$) 2976, 1722, 1458, 1377; $^1$H NMR (400 MHz, CDCl$_3$): δ 7.44-7.35 (m, 5H), 5.28 (dd, J=6.4, 4.0 Hz, 1H), 4.87 (dd, J=9.2, 6.4 Hz, 1H), 4.39 (dd, J=9.2, 4.4 Hz, 1H), 1.42 (s, 9H); $^{13}$C NMR (100 MHz, CDCl$_3$): δ 148.3, 137.0, 129.2, 129.1, 126.2, 85.5, 71.8, 60.8, 27.8.

Example 2C: Preparation of tert-butyl (S)-4-(4-methoxyphenyl)-1,2,3-oxathiazolidine-3-carboxylate 2,2-dioxide

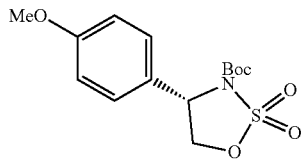 [SMILES: COc1ccc([C@H]2COS(=O)(=O)N2C(=O)OC(C)(C)C)cc1]

The general reaction scheme as per Example 2A above was performed with tert-butyl (S)-(2-hydroxy-1-(4-methoxyphenyl)ethyl) carbamate (1.45 g, 5.42 mmol, 100 mol %) to yield compound tert-butyl (S)-4-(4-methoxyphenyl)-1,2,3-oxathiazolidine-3-carboxylate 2,2-dioxide (1.05 g, 59% yield) as a white solid. Column Gradient: 0 to 5% CH$_3$OH in CH$_2$Cl$_2$. mp: 151.6-153.0° C.; FTIR (neat, cm$^{-1}$) 2979, 2933, 2838, 1721, 1636, 1510, 1457; $^1$H NMR (400 MHz, CDCl$_3$): δ 7.37-7.32 (m, 2H), 6.95-6.90 (m, 2H), 5.24 (dd, J=6.8, 4.4 Hz, 1H), 4.84 (dd, J=9.2, 6.8 Hz, 1H), 4.39 (dd, J=9.2, 4.4 Hz, 1H), 3.82 (s, 3H), 1.44 (s, 9H); $^{13}$C NMR (100 MHz, CDCl$_3$): δ 160.2, 148.3, 128.9, 127.7, 114.6, 85.5, 72.0, 60.5, 55.4, 27.9.

Example 2D: Preparation of tert-butyl (R)-4-methyl-1,2,3-oxathiazolidine-3-carboxylate 2,2-dioxide

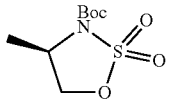

The general reaction scheme as per Example 2A above was performed with tert-butyl (R)-(1-hydroxypropan-2-yl)carbamate (5.00 g, 28.5 mmol, 100 mol %) to yield compound tert-butyl (R)-4-methyl-1,2,3-oxathiazolidine-3-carboxylate 2,2-dioxide (3.85 g, 57% yield) as a white solid. Column Gradient: 0 to 5% CH$_3$OH in CH$_2$Cl$_2$. FTIR (neat, cm$^{-1}$) 3245, 2982, 1719, 1402, 1329; $^1$H NMR (400 MHz, CDCl$_3$): δ 4.66 (dd, J=9.2, 6.0 Hz, 1H), 4.41 (qdd, J=6.4, 6.0, 2.8 Hz, 1H), 4.19 (dd, J=9.2, 2.8 Hz, 1H), 1.54 (s, 9H), 1.50 (d, J=6.4 Hz, 3H); $^{13}$C NMR (100 MHz, CDCl$_3$): δ 148.5, 85.4, 71.4, 53.8, 28.0, 18.3.

Example 2E: Preparation of tert-butyl (R)-4-isopropyl-1,2,3-oxathiazolidine-3-carboxylate 2,2-dioxide

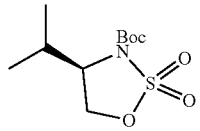 [SMILES: CC(C)[C@@H]1COS(=O)(=O)N1C(=O)OC(C)(C)C]

The general reaction scheme as per Example 2A above was performed with tert-butyl (R)-(1-hydroxy-3-methylbutan-2-yl)carbamate (5.00 g, 24.6 mmol, 100 mol %) to yield compound tert-butyl (R)-4-isopropyl-1,2,3-oxathiazolidine-3-carboxylate 2,2-dioxide (3.93 g, 60% yield) as a white solid. Column Gradient: 0 to 5% CH$_3$OH in CH$_2$Cl$_2$. mp: 104.8-105.8° C.; $^1$H NMR (400 MHz, CDCl$_3$): δ 4.55 (dd, J=9.6, 6.4 Hz, 1H), 4.38 (dd, J=9.6, 2.0 Hz, 1H), 4.17 (ddd, J=6.4, 5.2, 1.6 Hz, 1H), 2.24 (qqd, J=6.8, 6.8, 5.2 Hz, 1H), 1.53 (s, 9H), 1.00 (d, J=6.8 Hz, 3H), 0.95 (d, J=6.8 Hz, 3H); $^{13}$C NMR (100 MHz, CDCl$_3$): δ 149.1, 85.3, 67.0, 62.0, 30.0, 27.9, 18.0, 16.4.

Example 2F: Preparation of tert-butyl (R)-4-cyclopropyl-1,2,3-oxathiazolidine-3-carboxylate 2,2-dioxide

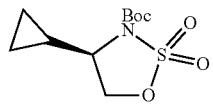 [SMILES: CC(C)(C)OC(=O)N1[C@H](C2CC2)COS1(=O)=O]

The general reaction scheme as per Example 2A above was performed with tert-butyl (R)-(1-cyclopropyl-2-hydroxyethyl)carbamate (2.31 g, 11.5 mmol, 100 mol %) to yield tert-butyl (R)-4-cyclopropyl-1,2,3-oxathiazolidine-3-carboxylate 2,2-dioxide (1.36 g, 45% yield) as a white solid. Column Gradient: 0 to 5% CH$_3$OH in CH$_2$Cl$_2$. mp: 52.7-55.7° C.; FTIR (neat, cm$^{-1}$) 2977, 1734, 1460, 1363; $^1$H NMR (400 MHz, CDCl$_3$): δ 4.64 (dd, J=9.2, 6.0 Hz, 1H), 4.40 (dd, J=8.8, 2.0 Hz, 1H), 3.77 (ddd, J=9.2, 6.0, 2.0 Hz, 1H), 1.54 (s, 9H), 1.35-1.23 (m, 1H), 0.74-0.65 (m, 2H), 0.63-0.54 (m, 1H), 0.29-0.20 (m, 1H); $^{13}$C NMR (100 MHz, CDCl$_3$): δ 148.9, 85.3, 71.1, 61.6, 27.9, 14.3, 4.4, 1.7.

Example 2G: Preparation of tert-butyl (3aR,8aS)-8,8a-dihydroindeno[1,2-d][1,2,3]oxathiazole-3(3aH)-carboxylate 2,2-dioxide

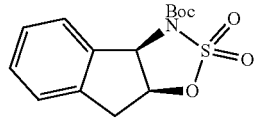 [SMILES: CC(C)(C)OC(=O)N1[C@@H]2c3ccccc3C[C@@H]2OS1(=O)=O]

The general reaction scheme as per Example 2A above was performed with tert-butyl ((1R,2S)-2-hydroxy-2,3-dihydro-1H-inden-1-yl)carbamate (9.12 g, 36.6 mmol, 100 mol %) to yield tert-butyl (3aR,8aS)-8,8a-dihydroindeno[1,2-d][1,2,3]oxathiazole-3(3aH)-carboxylate 2,2-dioxide (7.50 g, 66% yield) as a white solid. Column Gradient: 0 to 5% CH$_3$OH in CH$_2$Cl$_2$. mp: 134.2-135.0° C.; FTIR (neat, cm$^{-1}$) 2988, 2937, 1732, 1462, 1375; $^1$H NMR (400 MHz, CDCl$_3$): δ 7.62-7.57 (m, 1H), 7.39-7.24 (m, 3H), 5.71 (d, J=5.6 Hz, 1H), 5.50 (dt, J=6.0, 3.2 Hz, 1H), 3.38 (d, J=3.2 Hz, 1H), 1.62 (s, 9H); $^{13}$C NMR (100 MHz, CDCl$_3$): δ 149.6, 138.4, 137.9, 129.9, 128.4, 126.2, 125.2, 85.7, 82.2, 65.0, 36.5, 28.0.

Example 2H: Preparation of tert-butyl (S)-5-methyl-1,2,3-oxathiazolidine-3-carboxylate 2,2-dioxide

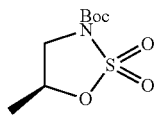

The general reaction scheme as per Example 2A above was performed with tert-butyl (S)-(2-hydroxypropyl)carbamate (6.25 g, 35.7 mmol, 100 mol %) to yield compound tert-butyl (S)-5-methyl-1,2,3-oxathiazolidine-3-carboxylate 2,2-dioxide (6.10 g, 72% yield) as a white solid. Column Gradient: 0 to 5% $CH_3OH$ in $CH_2Cl_2$. mp: 116.9-118.2° C.; FTIR (neat, cm$^{-1}$) 3370, 2956, 2938, 2837, 1681, 1512, 1461, 1366; $^1$H NMR (400 MHz, CDCl$_3$): δ 5.00-4.90 (m, 1H), 4.06 (dd, J=9.6, 5.6 Hz, 1H), 3.63 (dd, J=9.6, 9.2 Hz, 1H), 1.56 (d, J=6.4 Hz, 3H), 1.53 (s, 9H); $^{13}$C NMR (100 MHz, CDCl$_3$): δ 148.6, 85.3, 76.2, 51.7, 27.9, 18.0.

Example 2I: Preparation of tert-butyl (S)-4-(3-fluorophenyl)-1,2,3-oxathiazolidine-3-carboxylate 2,2-dioxide

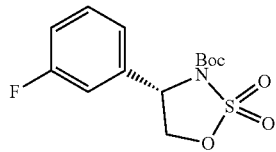

The general reaction scheme as per Example 2A above was performed with tert-butyl (S)-(1-(3-fluorophenyl)-2-hydroxyethyl)carbamate (1.45 g, 5.68 mmol, 100 mol %) to yield tert-butyl (S)-4-(3-fluorophenyl)-1,2,3-oxathiazolidine-3-carboxylate 2,2-dioxide (0.702 g, 39% yield) as a white solid. Column Gradient: 0 to 50% iPrOAc in Heptane. mp: 112.9-114.3° C.; FTIR (neat, cm$^{-1}$) 2976, 1722, 1636, 1594, 1458; $^1$H NMR (400 MHz, CDCl$_3$): δ 7.44-7.36 (m, 1H), 7.24-7.18 (m, 1H), 7.17-7.11 (m, 1H), 7.11-7.05 (m, 1H), 5.28 (dd, J=6.8, 3.6 Hz, 1H), 4.88 (dd, J=9.2, 6.8 Hz, 1H), 4.39 (dd, J=9.2, 3.6 Hz, 1H), 1.47 (s, 9H); $^{13}$C NMR (100 MHz, CDCl$_3$): δ 163.2 (d, $^1J_{CF}$=246 Hz), 148.2, 139.6 (d, $^3J_{CF}$=7 Hz), 131.1 (d, $^3J_{CF}$=8 Hz), 121.8 (d, $^4J_{CF}$=3 Hz), 116.2 (d, $^2J_{CF}$=21 Hz), 113.4 (d, $^2J_{CF}$=22 Hz), 86.0, 71.6, 60.2 (d, $^4J_{CF}$=3 Hz), 27.9; $^{19}$F NMR (CDCl$_3$, 376 MHz): δ −111.0.

Example 2J: Preparation of tert-butyl (S)-4-(3-(trifluoromethyl)phenyl)-1,2,3-oxathiazolidine-3-carboxylate 2,2-dioxide

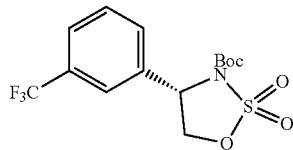 [SMILES: CC(C)(C)OC(=O)N1[C@@H](c2cccc(C(F)(F)F)c2)COS1(=O)=O]

The general reaction scheme as per Example 2A above was performed with tert-butyl (S)-(1-(3-fluorophenyl)-2-hydroxyethyl)carbamate (1.00 g, 3.28 mmol, 100 mol %) to yield tert-butyl (S)-4-(3-(trifluoromethyl)phenyl)-1,2,3-oxathiazolidine-3-carboxylate 2,2-dioxide (0.528 g, 44% yield) as a white solid. Column Gradient: 0 to 50% iPrOAc in Heptane. mp: 92.0-92.6° C.; FTIR (neat, cm$^{-1}$) 2989, 1720, 1463, 1373, 1325; $^1$H NMR (400 MHz, CDCl$_3$): δ 7.70-7.61 (m, 3H), 7.61-7.55 (m, 1H), 5.35 (dd, J=6.8, 4.0 Hz, 1H), 4.92 (dd, J=9.2, 6.8 Hz, 1H), 4.41 (dd, J=9.2, 3.6 Hz, 1H), 1.46 (s, 9H); $^{13}$C NMR (100 MHz, CDCl$_3$): δ 148.2, 138.2, 131.8 (q, $^2J_{CF}$=32 Hz), 130.1, 129.4, 126.1 (q, $^3J_{CF}$=4 Hz), 123.7 (q, $^1J_{CF}$=270 Hz), 123.4 (q, $^3J_{CF}$=4 Hz), 86.2, 71.4, 60.2, 27.8; $^{19}$F NMR (CDCl$_3$, 376 MHz): δ −62.8.

Example 2K: Preparation of tert-butyl (S)-4-phenyl-1,2,3-oxathiazinane-3-carboxylate 2,2-dioxide

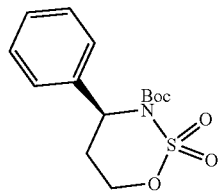 [SMILES: CC(C)(C)OC(=O)N1[C@H](c2ccccc2)CCOS1(=O)=O]

The general reaction scheme as per Example 2A above was performed with tert-butyl (S)-(3-hydroxy-1-phenylpropyl)carbamate (2.00 g, 7.96 mmol, 100 mol %) to yield tert-butyl (S)-4-phenyl-1,2,3-oxathiazinane-3-carboxylate 2,2-dioxide (1.26 g, 51% yield) as a white solid. Column Gradient: 0 to 50% iPrOAc. mp: 128.6-129.9° C.; FTIR (neat, cm$^{-1}$) 2986, 1727, 1449, 1367; $^1$H NMR (400 MHz, DMSO-d$_6$) (94:6 mixture of rotamers): δ 7.48-7.35 (m, 4H), 7.35-7.23 (m, 1H), 5.65 (dd, J=4.4, 4.4 Hz, 0.94H), 5.53 (dd, J=11.2, 4.4 Hz, 0.06H), 4.70 (ddd, J=10.4, 7.2, 2.8 Hz, 0.94H), 4.51 (ddd, J=8.8, 4.4, 4.4 Hz, 0.06H), 4.40 (ddd, J=10.4, 10.4, 6.8 Hz, 1H), 2.80-2.68 (m, 1H), 2.66-2.56 (m, 1H), 1.41 (s, 8.46H), 1.12 (s, 0.54H); $^{13}$C NMR (100 MHz, DMSO-d$_6$) (rotamers): δ 155.1, 143.0, 128.4 (128.6), 127.0 (127.3), 126.3 (125.4), 78.1 (84.3), 73.6 (70.9), 50.5 (60.0), 36.0, 28.2 (27.4).

Example 3: Indole Alkylation

Chiral tryptamines are frequently encountered in pharmacology due to their significant biological activities in the central nervous system. In addition, the chiral tryptamine moiety serves as synthetic precursor of many medicinally important indole alkaloids and found in numerous biologically active natural products and pharmaceuticals.

In particular, stereocontrolled synthesis of tetrahydro-β-carboline-containing compounds such as those described herein often relies on diastereoselective Pictet-Spengler reaction, which in turn requires enantiomerically pure tryptamines as starting material. The latter is typically prepared in a non-stereoselective manner via a multistep sequence involving hazardous nitroalkane reagents. Therefore, the development of a simple regioselective alkylation approach which involves readily available non-protected indoles as nucleophiles and chiral amine-derived electrophiles, such as chiral aziridines and cyclic sulfamidates, provided a convenient access to these valuable chiral scaffolds.

Aziridine electrophiles have been applied to provide C³-selective alkylation under Lewis acidic conditions; however, this method is only applicable to the synthesis of β-substituted tryptamines as the displacement occurs preferentially at the more substituted carbon. Discovered herein, low order cuprate of indoles in combination with chiral cyclic sulfamidates successfully provided a practical access to both α- and β-substituted chiral tryptamines having high regioselectivity.

It was found that the reaction with chiral aziridines as the electrophile always led to a mixture of α- and β-substituted tryptamines while reaction with cyclic sulfamidates as the electrophile unambiguously reacted to displace C—O bond.

Contrary to the literature precedence suggesting preferential alkylation at the C³-position when Grignard reagents were used as base, initial attempts resulted in lower than expected yields and poor site-selectivity. Without being bound by any particular theory, softer indole nucleophiles were tried as they would likely prefer to react as carbon-centered nucleophile. Various additives including Cu and Zn salts were surveyed. Interestingly, a mixed halide system such as MeMgCl in combination with CuBr or CuI, or MeMgBr in combination with CuCl was much less efficient than the chloride-only system. Other copper salts, such as $CuCl_2$, CuCN, CuTC, or Cu(SCN) were also inferior to CuCl.

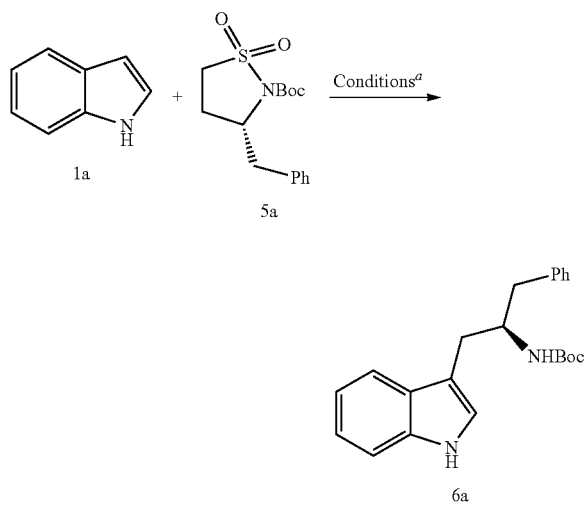

| entry | base/additive/temperature | isolated yield | C³/N¹ [b] |
|---|---|---|---|
| 1 | MeMgCl/None/−10° C. | 14% | 31/69 |
| 2 | MeMgCl/CuCl/−10° C. | 66% | 95/5 |
| 3 | MeMgCl/CuBr/−10° C. | 37% | 95/5 |
| 4 | MeMgCl/CuI/−10° C. | 26% | 90/10 |
| 5[c] | MeMgCl/CuCl/−10° C. | 38% | 67/33 |
| 6 | MeMgCl/ZnCl₂/−10° C. | 38% | 22/78 |
| 7 | MeMgCl/ZnBr₂/−10° C. | 28% | 37/63 |
| 8 | MeMgBr/CuCl/−10° C. | 26% | 45/54 |
| 9 | PhMgCl/CuCl/−10° C. | 66% | 96/4 |
| 10 | MeLi/CuCl/−10° C. | N.D. | 11/89 |
| 11 | MeMgCl/CuCl 1-40° C. | N.D. | 42/58 |
| 12[d] | MeMgCl/CuCl/−20° C. | 76% | 97/3 |
| 13 | MeMgCl/CuCl/0° C. | 65% | 95/5 |

| product | | | isolated yield | C³/N¹ ratio[b] |
|---|---|---|---|---|
| 6a | | | 76% (>99% ee) | 97:3 |
| 6b | R = Me | | 73% | 95.5 |
| 6c | | Ph | 82% | 97.3 |
| 6d | | Cl | 60% | 96.4 |
| 6e | | OMe | 92% | 97.3 |
| 6f | | CF₃ | 47% | 96.4 |
| 6g | | | 68% | 97.3 |
| 6h | R = Me | | 71% | 99.1 |
| 6i | | Ph | 51% | 98.2 |
| 6j | | | 8% | 98.2 |

A catalytic amount of CuCl was not tolerated and resulted in significant decrease in yield and selectivity. Notably, a reversal of regioselectivity was observed when zinc halides were used instead of CuCl (see above). The same was true when MeLi was used as base instead of MeMgCl, while the use of other Grignard reagent was well-tolerated. The effect of reaction temperature was evaluated and established that the displacement reaction performed optimally at around −20° C. At below −30° C., a significant drop in regioselectivity was observed presumably due to the incomplete cuprate formation.

The Cu-mediated indole alkylation tolerated a variety of substitution both on the indole nucleophile as well as on the cyclic sulfamidate providing the C³-alkylated indole products in moderate to good yield and excellent regioselectivity. For instance, indoles with either electron-donating or electron-withdrawing substituents participated in the reaction well (Exemplary compounds 6b-6g above), and sterically demanding substrates also worked reasonably well (Exemplary compounds 6h and 6i above).

On the other hand, azaindoles appear to be possible poor substrates. Under standard reaction conditions, 6-azaindole provided only 8% of the alkylation product albeit with comparable regioselectivity (see e.g. exemplary compound 6j above). Other azaindoles such as indazole and 7-azaindole failed to produce any desired alkylated products A variety of sulfamidates were tested in the reaction successfully. Both aryl- and alkyl-substituted sulfamidates, prepared in two step sequence from the corresponding amino alcohols, were converted smoothly to the respective α-substituted chiral tryptamines. Similarly, 6-membered cyclic sulfamidate also participated in the alkylation well producing a homologated tryptamine in good yield and regioselectivity. This alkylation process can be also applied to get access to β-substituted, and α,β-disubstituted tryptamines (see exemplary compounds 6s and 6t above). In these cases, the indole nucleophile added to the corresponding cyclic sulfamidate with the inversion of stereochemistry at the carbon bearing oxygen with complete stereospecificity. The utility of this alkylation process was demonstrated as provided herein.

Example 3: Indole Alkylation General Reaction Scheme

Indole alkylation was done according to the following general reaction scheme where $R_A$ and $R_B$ correspond to the various functional groups in the following Example 3 reactions, and wherein the asterisks represent a chiral center:

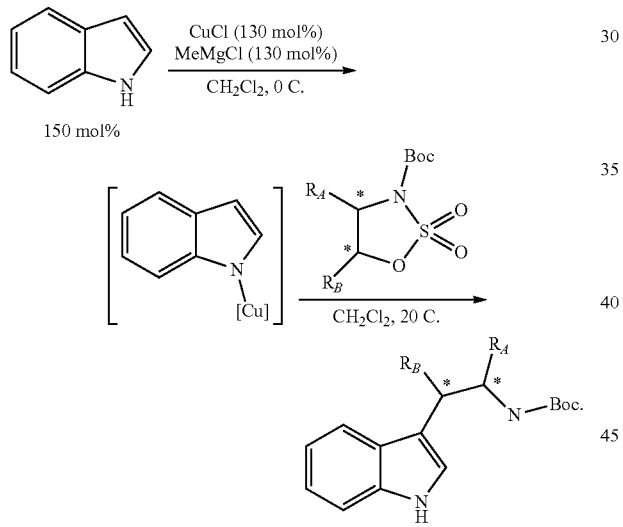

Example 3A: Preparation of tert-butyl (R)-(1-(1H-indol-3-yl)-3-phenylpropan-2-yl)carbamate

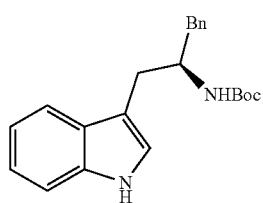 [SMILES: CC(C)(C)OC(=O)N[C@@H](Cc1c[nH]c2ccccc12)c1ccccc1]

General reaction scheme 3 above was performed as follows. To a cold (0° C.) mixture of indole (280 mg, 2.39 mmol, 150 mol %), and CuCl (193 mg, 1.95 mmol, 130 mol %) in CH$_2$Cl$_2$ (3.0 mL) was added MeMgCl (3.0 M in THF, 0.65 mL, 1.95 mmol, 130 mol %) over 10 min at 0° C. The reaction mixture was stirred at 0° C. for 1 h and cooled to −20° C. A solution of tert-butyl (R)-4-benzyl-1,2,3-oxathiazolidine-3-carboxylate 2,2-dioxide (500 mg, 1.60 mmol, 100 mol %) in CH$_2$Cl$_2$ (2.0 mL) was added into the reaction mixture over 30 min at −20° C. The reaction mixture was then stirred at −20° C. for 18 h, quenched with 10% aqueous citric acid (5.0 mL) at 0° C., filtered, extracted with CH$_2$Cl$_2$ (10.0 mL×2), washed with saturated brine (20.0 mL×2), dried (Na$_2$SO$_4$), filtered, purified by chromatography on SiO$_2$. Specific gradient used for each sample is included in the characterization data. All the yields reported are corrected based on residual solvent from $^1$H NMR. Reaction 3A yielded tert-butyl (R)-(1-(1H-indol-3-yl)-3-phenylpropan-2-yl)carbamate (424 mg, 76% yield) as a white solid. The $C^3/N^1$ ratio was 97:3. Column Gradient: 0 to 50% iPrOAc in Heptane. mp: 152.1-153.2° C.; FTIR (neat, cm$^{-1}$) 3418, 3402, 3376, 2974, 2911, 1684, 1522; $^1$H NMR (400 MHz, DMSO-d$_6$) (85:15 mixture of rotamers): δ 10.78 (br, 1H), 7.46 (d, J=8.0 Hz, 1H), 7.32 (d, J=8.0 Hz, 1H), 7.28-7.21 (m, 2H), 7.19-7.10 (m, 4H), 7.05 (ddd, J=8.4, 7.2, 1.2 Hz, 1H), 6.95 (ddd, J=8.0, 6.8, 1.2 Hz, 1H), 6.76 (d, J=8.4 Hz, 0.85H), 6.34 (d, J=9.2 Hz, 0.15H), 3.97-3.83 (m, 1H), 2.90-2.65 (m, 4H), 1.29 (s, 7.65H), 1.12 (s, 1.35H); $^{13}$C NMR (100 MHz, DMSO-d$_6$) (rotamers): δ 155.1, 139.6, 136.1, 129.0, 128.0, 127.5, 125.8, 123.2, 120.8, 118.3, 118.1, 111.4, 111.3, 77.3, 52.6, 39.9, 30.4, 28.2 (27.8).

Example 3B: Preparation of tert-butyl (S)-(2-(1H-indol-3-yl)-1-phenylethyl)carbamate

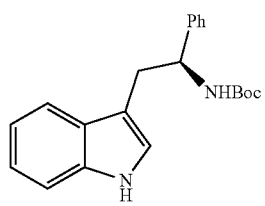

The general reaction as per Example 3A was performed between indole (294 mg, 2.51 mmol, 150 mol %) and tert-butyl (S)-4-phenyl-1,2,3-oxathiazolidine-3-carboxylate 2,2-dioxide (500 mg, 1.67 mmol, 100 mol %) to yield tert-butyl (S)-(2-(1H-indol-3-yl)-1-phenylethyl)carbamate (398 mg, 71% yield) as a white solid. The $C^3/N^1$ ratio was 97:3. Column Gradient: 0 to 50% iPrOAc in Heptane. mp: 134.6-135.2° C.; FTIR (neat, cm$^{-1}$) 3416, 3401, 3371, 2980, 2909, 1683, 1524; $^1$H NMR (400 MHz, DMSO-d$_6$) (85:15 mixture of rotamers): δ 10.74 (br, 1H), 7.54 (d, J=7.6 Hz, 1H), 7.41 (d, J=8.4 Hz, 1H), 7.38-7.25 (m, 5H), 7.20 (dd, J=6.8, 7.2 Hz, 1H), 7.06 (dd, J=7.6, 7.2 Hz, 1H), 7.02 (s, 1H), 6.98 (dd, J=7.6, 7.2 Hz, 1H), 4.89-4.74 (m, 1H), 3.08 (dd, J=14.8, 8.8 Hz, 1H), 2.99 (dd, J=14.4, 6.0 Hz, 1H), 1.31 (s, 7.65H), 1.08 (s, 1.35H); $^{13}$C NMR (100 MHz, DMSO-d$_6$): δ 155.0, 144.5, 136.0, 128.0, 127.3, 126.5, 126.4, 123.2, 120.8, 118.3, 118.2, 111.3, 111.3, 77.6, 55.0, 32.8, 28.2.

Example 3C: Preparation of tert-butyl (S)-(2-(1H-indol-3-yl)-1-(4-methoxyphenyl)ethyl)carbamate

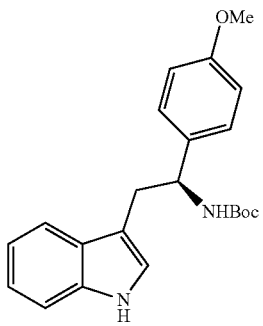 [SMILES: COc1ccc([C@H](Cc2c[nH]c3ccccc23)NC(=O)OC(C)(C)C)cc1]

The general reaction as per Example 3A was performed between indole (264 mg, 2.25 mmol, 150 mol %) and tert-butyl (S)-4-(4-methoxyphenyl)-1,2,3-oxathiazolidine-3-carboxylate 2,2-dioxide (495 mg, 1.50 mmol, 100 mol %) to yield tert-butyl (S)-(2-(1H-indol-3-yl)-1-(4-methoxyphenyl)ethyl)carbamate (378 mg, 69% yield) as a white solid. The $C^3/N^1$ ratio was 98:2. Column Gradient: 0 to 50% iPrOAc in Heptane. mp: 173.3-176.5° C.; FTIR (neat, cm$^{-1}$) 3402, 3326, 2979, 2925, 2904, 1690, 1611, 1506; $^1$H NMR (400 MHz, DMSO-d$_6$) (85:15 mixture of rotamers): δ 10.72 (br, 1H), 7.54 (d, J=8.0 Hz, 1H), 7.39-7.28 (m, 2H), 7.24 (d, J=8.8 Hz, 2H), 7.05 (ddd, J=8.4, 7.2, 1.2 Hz, 1H), 7.02-6.94 (m, 2H), 6.84 (d, J=8.4 Hz, 2H), 4.88-4.57 (m, 1H), 3.72 (s, 3H), 3.06 (dd, J=14.8, 8.4 Hz, 1H), 2.96 (dd, J=14.8, 6.4 Hz, 1H), 1.31 (s, 7.65H), 1.11 (s, 1.35H); $^{13}$C NMR (100 MHz, DMSO-d$_6$): δ 157.9, 154.9, 136.4, 136.0, 127.5, 127.3, 123.2, 120.7, 118.3, 118.1, 113.4, 111.4, 111.2, 77.5, 55.0, 54.4, 32.8, 28.2.

Example 3D: Preparation of tert-butyl (R)-(1-(1H-indol-3-yl)propan-2-yl)carbamate

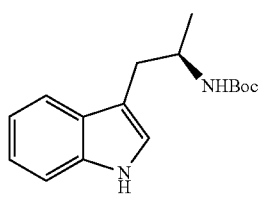 [SMILES: C[C@H](Cc1c[nH]c2ccccc12)NC(=O)OC(C)(C)C]

The general reaction as per Example 3A was performed between indole (370 mg, 3.16 mmol, 150 mol %) and tert-butyl (R)-4-methyl-1,2,3-oxathiazolidine-3-carboxylate 2,2-dioxide (500 mg, 2.11 mmol, 100 mol %) to yield tert-butyl (R)-(1-(1H-indol-3-yl)propan-2-yl)carbamate (406 mg, 70% yield) as a white solid. The $C^3/N^1$ ratio was 99:1. Column Gradient: 0 to 50% iPrOAc in Heptane. mp: 82.2-84.3° C.; FTIR (neat, cm$^{-1}$) 3416, 3401, 3366, 2974, 2963, 1684, 1524; $^1$H NMR (400 MHz, DMSO-d$_6$): δ 10.77 (br, 1H), 7.56 (d, J=7.6 Hz, 1H), 7.33 (ddd, J=8.0, 1.2, 0.8 Hz, 1H), 7.10 (d, J=2.4 Hz, 1H), 7.05 (ddd, J=8.0, 6.8, 1.2 Hz, 1H), 6.97 (ddd, J=8.0, 6.8, 1.2 Hz, 1H), 6.71 (d, J=8.4 Hz, 1H), 3.82-3.66 (m, 1H), 2.87 (dd, J=14.0, 6.0 Hz, 1H), 2.65 (dd, J=14.0, 7.6 Hz, 1H), 1.38 (s, 9H), 1.01 (d, J=6.8 Hz, 3H); $^{13}$C NMR (100 MHz, DMSO-d$_6$): δ 155.0, 136.1, 127.5, 123.1, 120.7, 118.4, 118.1, 111.6, 111.2, 77.3, 46.8, 32.2, 28.3, 20.1.

Example 3E: Preparation of tert-butyl (R)-(1-(1H-indol-3-yl)-3-methylbutan-2-yl)carbamate

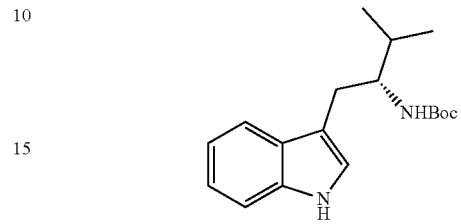

The general reaction as per Example 3A was performed between indole (331 mg, 2.83 mmol, 150 mol %) and tert-butyl (R)-4-isopropyl-1,2,3-oxathiazolidine-3-carboxylate 2,2-dioxide (500 mg, 1.88 mmol, 100 mol %) to yield tert-butyl (R)-(1-(1H-indol-3-yl)-3-methylbutan-2-yl)carbamate (335 mg, 59% yield) as a white solid. The $C^3/N^1$ ratio was 94:6. Column Gradient: 0 to 50% iPrOAc in Heptane. mp: 145.1-146.9° C.; FTIR (neat, cm$^{-1}$) 3417, 3402, 3362, 2978, 1686, 1526; $^1$H NMR (400 MHz, DMSO-d$_6$) (85:15 mixture of rotamers): δ 10.72 (br, 1H), 7.51 (d, J=8.0 Hz, 1H), 7.31 (ddd, J=8.0, 1.2, 0.8 Hz, 1H), 7.07 (d, J=2.0 Hz, 1H), 7.04 (ddd, J=8.0, 6.8, 1.2 Hz, 1H), 6.96 (ddd, J=8.0, 6.8, 1.2 Hz, 1H), 6.59 (d, J=9.2 Hz, 0.85H), 6.15 (d, J=10.0 Hz, 0.15H), 3.64-3.53 (m, 1H), 2.80 (dd, J=14.8, 5.2 Hz, 1H), 2.68 (dd, J=14.8, 8.8 Hz, 1H), 1.77-1.65 (m, 1H), 1.32 (s, 7.65H), 1.12 (s, 1.35H), 0.95-0.82 (m, 6H); $^{13}$C NMR (100 MHz, DMSO-d$_6$): δ 155.6, 136.1, 127.5, 122.7, 120.7, 118.3, 118.0, 112.0, 111.2, 77.1, 55.6, 31.4, 28.3, 27.1, 19.4, 17.7.

Example 3F: Preparation of tert-butyl (S)-(1-cyclopropyl-2-(1H-indol-3-yl)ethyl)carbamate

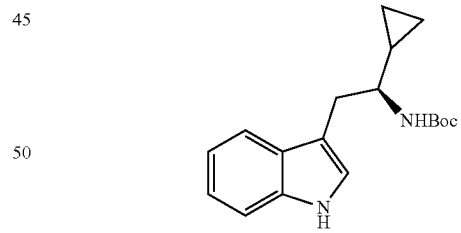

The general reaction as per Example 3A was performed between indole (264 mg, 2.25 mmol, 150 mol %) and tert-butyl (R)-4-cyclopropyl-1,2,3-oxathiazolidine-3-carboxylate 2,2-dioxide (395 mg, 1.50 mmol, 100 mol %) to yield tert-butyl (S)-(1-cyclopropyl-2-(1H-indol-3-yl)ethyl)carbamate (292 mg, 65% yield) as a white solid. The $C^3/N^1$ ratio was 99:1. Column Gradient: 0 to 50% iPrOAc in Heptane. mp: 128.8-130.5° C.; FTIR (neat, cm$^{-1}$) 3414, 3400, 3362, 2981, 2937, 1683, 1525; $^1$H NMR (400 MHz, DMSO-d$_6$) (9:1 mixture of rotamers): δ 10.73 (br, 1H), 7.52 (d, J=7.6 Hz, 1H), 7.31 (ddd, J=8.0, 1.2, 0.8 Hz, 1H), 7.07 (d, J=2.4 Hz, 1H), 7.04 (ddd, J=8.0, 6.8, 1.2 Hz, 1H), 6.95 (ddd, J=8.0, 6.8, 1.2 Hz, 1H), 6.66 (d, J=8.4 Hz, 0.9H), 6.26

(s, 0.1H), 3.30-3.18 (m, 1H), 2.91 (dd, J=14.4, 5.6 Hz, 1H), 2.85 (dd, J=14.4, 8.0 Hz, 1H), 1.33 (s, 8.1H), 1.17 (s, 0.9H), 0.96-0.83 (m, 1H), 0.42-0.32 (m, 1H), 0.32-0.24 (m, 2H), 0.15-0.01 (m, 1H); $^{13}$C NMR (100 MHz, DMSO-d$_6$): δ 155.3, 136.0, 127.7, 122.9, 120.6, 118.4, 118.0, 111.6, 111.2, 77.2, 54.2, 30.4, 28.2, 16.0, 3.0, 1.9.

Example 3G: Preparation of tert-butyl ((1S,2S)-2-(1H-indol-3-yl)-2,3-dihydro-1H-inden-1-yl)carbamate

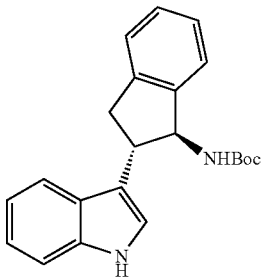 [SMILES: CC(C)(C)OC(=O)N[C@@H]1c2ccccc2C[C@H]1c1c[nH]c2ccccc12]

The general reaction as per Example 3A was performed between indole (282 mg, 2.41 mmol, 150 mol %) and tert-butyl (3aR,8aS)-8,8a-dihydroindeno[1,2-d][1,2,3]oxathiazole-3(3aH)-carboxylate 2,2-dioxide (500 mg, 1.61 mmol, 100 mol %) to yield tert-butyl ((1S,2S)-2-(1H-indol-3-yl)-2,3-dihydro-1H-inden-1-yl)carbamate (304 mg, 54% yield) as a white solid. The $C^3/N^1$ ratio was 95:5. Column Gradient: 0 to 50% iPrOAc in Heptane. mp: 155.7-157.1° C.; FTIR (neat, cm$^{-1}$) 3387, 3351, 2980, 2938, 1691, 1500; $^1$H NMR (400 MHz, DMSO-d$_6$) (87:13 mixture of rotamers): 10.85 (br, 1H), 7.61 (d, J=8.0 Hz, 1H), 7.42-7.32 (m, 2H), 7.30-7.20 (m, 4H), 7.17 (dd, J=8.0, 4.0 Hz, 1H), 7.07 (ddd, J=8.0, 6.8, 1.2 Hz, 1H), 6.97 (ddd, J=8.0, 6.8, 1.2 Hz, 1H), 5.18 (dd, J=9.2, 9.2 Hz, 1H), 3.69 (dd, J=18.4, 9.6 Hz, 0.87H), 3.64-3.53 (m, 0.13H), 3.37 (dd, J=15.2, 8.0 Hz, 0.87H), 3.30-3.23 (m, 0.13H), 3.13-3.04 (m, 0.13H), 2.99 (dd, J=15.2, 10.4 Hz, 0.87H), 1.38 (s, 7.83H), 1.12 (s, 1.17H); $^{13}$C NMR (100 MHz, DMSO-d$_6$) (rotamers): δ 155.9, 144.5, 141.3, 136.6, 127.2, 127.1, 126.4, 124.4, 123.3, 121.7, 120.9, 119.1, 118.2, 115.5, 111.4, 77.7, 60.8, 44.0, 37.2, 28.2 (27.7).

Example 3H: Preparation of tert-butyl (S)-(2-(1H-indol-3-yl)propyl)carbamate

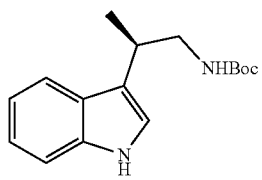 [SMILES: C[C@@H](CNC(=O)OC(C)(C)C)c1c[nH]c2ccccc12]

The general reaction as per Example 3A was performed between indole (264 mg, 2.25 mmol, 150 mol %) and tert-butyl (S)-5-methyl-1,2,3-oxathiazolidine-3-carboxylate 2,2-dioxide (356 mg, 1.50 mmol, 100 mol %) to yield tert-butyl (S)-(2-(1H-indol-3-yl)propyl)carbamate (319 mg, 78% yield) as a colorless liquid. The $C^3/N^1$ ratio was 93:7. Column Gradient: 0 to 50% iPrOAc in Heptane. FTIR (neat, cm$^{-1}$) 3412, 3327, 2971, 2930, 1685, 1508, 1456; $^1$H NMR (400 MHz, DMSO-d$_6$) (9:1 mixture of rotamers): δ 10.78 (br, 1H), 7.58 (d, J=7.6 Hz, 1H), 7.33 (ddd, J=8.0, 1.2, 0.8 Hz, 1H), 7.10 (d, J=2.0 Hz, 1H), 7.05 (ddd, J=8.0, 6.8, 1.2 Hz, 1H), 6.96 (ddd, J=8.0, 6.8, 1.2 Hz, 1H), 6.86 (dd, J=6.0, 6.0 Hz, 0.9H), 6.51 (s, 0.1H), 3.29 (ddd, J=13.2, 5.6, 5.6 Hz, 1H), 3.18-3.05 (m, 1H), 2.97 (ddd, J=13.2, 8.8, 6.0 Hz, 1H), 1.41 (s, 0.9H), 1.38 (s, 8.1H), 1.25 (d, J=6.8 Hz, 3H); $^{13}$C NMR (100 MHz, DMSO-d$_6$) (rotamers): δ 155.7, 136.4, 126.6, 121.0, 120.8, 118.6, 118.1, 117.9, 111.4, 77.4, 46.8, 30.9, 28.3 (28.2), 18.4 (18.2).

Example 3I: Preparation of tert-butyl (R)-(1-(3-fluorophenyl)-2-(1H-indol-3-yl)ethyl)carbamate

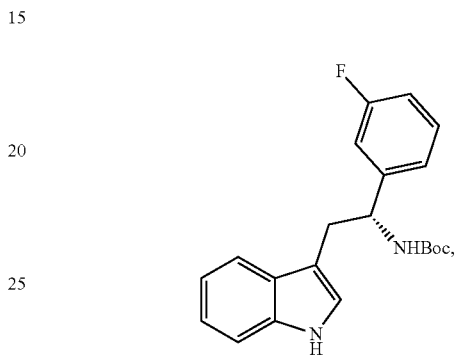

The general reaction as per Example 3A was performed between indole (263 mg, 2.25 mmol, 150 mol %) and tert-butyl (S)-4-(3-fluorophenyl)-1,2,3-oxathiazolidine-3-carboxylate 2,2-dioxide (475 mg, 1.50 mmol, 100 mol %) to yield tert-butyl (R)-(1-(3-fluorophenyl)-2-(1H-indol-3-yl)ethyl)carbamate (382 mg, 72% yield) as a white solid. The $C^3/N^1$ ratio was 99:1. Column Gradient: 0 to 50% iPrOAc in Heptane. mp: 148.6-151.2° C.; FTIR (neat, cm$^{-1}$) 3414, 3398, 3363, 3055, 2981, 1682, 1591, 1527; $^1$H NMR (400 MHz, DMSO-d$_6$) (9:1 mixture of rotamers): δ 10.75 (br, 1H), 7.53 (d, J=7.6 Hz, 1H), 7.44 (d, J=8.4 Hz, 1H), 7.37-7.26 (m, 2H), 7.20-7.11 (m, 2H), 7.08-6.93 (m, 4H), 4.85-4.65 (m, 1H), 3.06 (dd, J=14.4, 8.4 Hz, 1H), 2.98 (dd, J=14.4, 6.4 Hz, 1H), 1.30 (s, 8.1H), 1.08 (s, 0.9H); $^{13}$C NMR (100 MHz, DMSO-d$_6$): δ 162.2 (d, $^1J_{CF}$=243 Hz), 155.0, 147.5 (d, $^3J_{CF}$=7 Hz), 136.0, 129.9 (d, $^3J_{CF}$=8 Hz), 127.2, 123.3, 122.6, 120.8, 118.3, 118.2, 113.3 (d, $^2J_{CF}$=21 Hz), 113.0 (d, $^2J_{CF}$=21 Hz), 111.3, 111.0, 77.8, 54.7, 32.5, 28.2; $^{19}$F NMR (DMSO-d$_6$, 376 MHz): δ −113.6.

Example 3J: Preparation of tert-butyl (R)-(2-(1H-indol-3-yl)-1-(3-(trifluoromethyl)phenyl)ethyl) carbamate

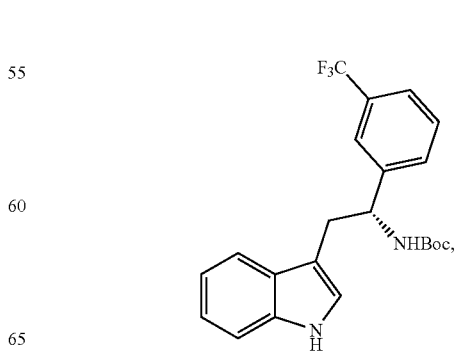

The general reaction as per Example 3A was performed between indole (176 mg, 1.50 mmol, 150 mol %) and tert-butyl (S)-4-(3-(trifluoromethyl)phenyl)-1,2,3-oxathiazolidine-3-carboxylate 2,2-dioxide (368 mg, 1.00 mmol, 100 mol %) to yield tert-butyl (R)-(2-(1H-indol-3-yl)-1-(3-(trifluoromethyl)phenyl)ethyl) carbamate (320 mg, 79% yield) as a white solid. The $C^3/N^1$ ratio was 98:2. Column Gradient: 0 to 50% iPrOAc in Heptane. mp: 99.3-101.4° C.; FTIR (neat, cm$^{-1}$) 3414, 3399, 3361, 2982, 2936, 1683, 1523; $^1$H NMR (400 MHz, DMSO-d$_6$) (88:12 mixture of rotamers): δ 10.76 (br, 1H), 7.80-7.45 (m, 6H), 7.31 (d, J=8.0 Hz, 1H), 7.08-7.00 (m, 2H), 6.96 (ddd, J=8.0, 7.2, 1.2 Hz, 1H), 5.11-4.69 (m, 1H), 3.09 (dd, J=14.4, 8.4 Hz, 1H), 3.00 (dd, J=14.4, 6.4 Hz, 1H), 1.30 (s, 7.9H), 1.07 (s, 1.1H); $^{13}$C NMR (100 MHz, DMSO-d$_6$): δ 155.1, 145.8, 136.1, 130.8, 129.0, 128.9 (q, $^2J_{CF}$=32 Hz), 127.3, 124.4 (q, $^1J_{CF}$=270 Hz), 123.3 (q, $^3J_{CF}$=4 Hz), 123.0, 122.8 (q, $^3J_{CF}$=4 Hz), 120.8, 118.3, 118.2, 111.3, 110.8, 77.9, 55.0, 32.5, 28.2; $^{19}$F NMR (DMSO-d$_6$, 376 MHz): δ −61.0.

Example 3K: Preparation of tert-butyl (S)-(3-(1H-indol-3-yl)-1-phenylpropyl)carbamate

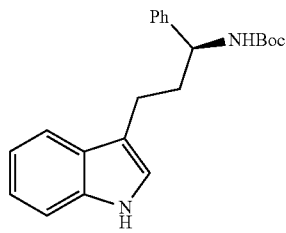 [SMILES: CC(C)(C)OC(=O)N[C@@H](CCc1c[nH]c2ccccc12)c1ccccc1]

The general reaction as per Example 3A was performed between indole (264 mg, 2.25 mmol, 150 mol %) and tert-butyl (S)-4-phenyl-1,2,3-oxathiazinane-3-carboxylate 2,2-dioxide (470 mg, 1.50 mmol, 100 mol %) to yield tert-butyl (S)-(3-(1H-indol-3-yl)-1-phenylpropyl)carbamate (401 mg, 73% yield) as a white solid. The $C^3/N^1$ ratio was 98:2. Column Gradient: 0 to 50% iPrOAc in Heptane. mp: 121.7-123.2° C.; FTIR (neat, cm$^{-1}$) 3390, 2979, 2929, 2859, 1681, 1507, 1457, 1364; $^1$H NMR (400 MHz, CDCl$_3$) (80:20 mixture of rotamers): δ 8.04 (br, 0.2H), 7.96 (br, 0.8H), 7.66 (d, J=8.0 Hz, 0.2H), 7.52 (d, J=8.0 Hz, 0.8H), 7.40-7.22 (m, 6H), 7.22-7.15 (m, 1H), 7.15-7.06 (m, 1H), 7.00 (br, 1H), 4.88 (br, 0.8H), 4.75 (br, 1H), 4.53 (br, 0.2H), 3.52-3.35 (m, 0.4H), 3.32-3.20 (m, 0.4H), 2.87-2.67 (m, 1.6H), 2.16 (d, J=8.8 Hz, 1.6H), 1.42 (s, 9H); $^{13}$C NMR (100 MHz, DMSO-d$_6$) (rotamers): δ 155.4 (156.2), 143.0, 136.4 (136.6), 128.6, 127.3, 127.2, 126.4, 121.8 (122.0), 121.5 (120.8), 119.0 (119.2), 118.7, 115.3, 111.2 (111.3), 79.5, 54.7 (46.7), 37.2 (31.6), 28.4 (29.7), 21.9 (18.7).

Example 3L: Preparation of tert-butyl (R)-(1-(5-methyl-1H-indol-3-yl)-3-phenylpropan-2-yl)carbamate

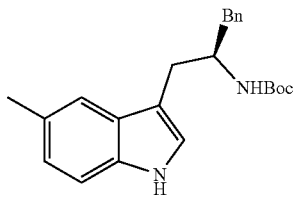 [SMILES: Cc1ccc2[nH]cc(C[C@@H](Cc3ccccc3)NC(=O)OC(C)(C)C)c2c1]

The general reaction as per Example 3A was performed between 5-methyl-1H-indole (295 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield of tert-butyl (R)-(1-(5-methyl-1H-indol-3-yl)-3-phenylpropan-2-yl)carbamate (401 mg, 73% yield) as a white solid. The $C^3/N^1$ ratio was 92:8. Column Gradient: 0 to 50% iPrOAc in Heptane. mp: 123.0-123.8° C.; FTIR (neat, cm$^{-1}$) 3413, 3368, 2974, 2927, 1685, 1524; $^1$H NMR (400 MHz, DMSO-d$_6$) (85:15 mixture of rotamers): δ 10.63 (br, 1H), 7.30-7.13 (m, 7H), 7.07 (d, J=2.0 Hz, 1H), 6.87 (dd, J=8.4, 1.6 Hz, 1H), 6.74 (d, J=8.8 Hz, 0.85H), 6.34 (d, J=7.6 Hz, 0.15H), 3.96-3.80 (m, 1H), 2.86-2.64 (m, 4H), 2.36 (s, 3H), 1.30 (s, 7.65H), 1.16 (s, 1.35H); $^{13}$C NMR (100 MHz, DMSO-d$_6$) (rotamers): δ 155.1, 139.6, 134.5, 129.1, 128.0, 127.7, 126.4, 125.8, 123.2, 122.3, 117.9, 111.0, 110.9, 77.2, 52.7, 40.0, 30.2, 28.2 (27.8), 21.3.

Example 3M: Preparation of tert-butyl (R)-(1-(7-methyl-1H-indol-3-yl)-3-phenylpropan-2-yl)carbamate

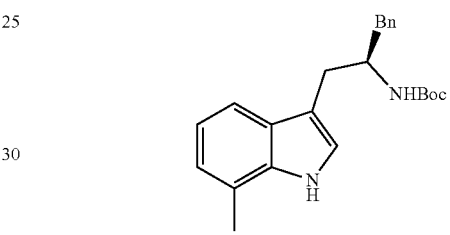

The general reaction as per Example 3A was performed between 7-methyl-1H-indole (295 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield tert-butyl (R)-(1-(7-methyl-1H-indol-3-yl)-3-phenylpropan-2-yl)carbamate (371 mg, 68% yield) as a white solid. The $C^3/N^1$ ratio was 97:3. Column Gradient: 0 to 50% iPrOAc in Heptane. mp: 124.4-125.9° C.; FTIR (neat, cm$^{-1}$) 3417, 3407, 3370, 2974, 2926, 1683, 1524; $^1$H NMR (400 MHz, DMSO-d$_6$) (85:15 mixture of rotamers): δ 10.75 (br d, J=2.0 Hz, 1H), 7.34-7.21 (m, 3H), 7.21-7.09 (m, 4H), 6.90-6.83 (m, 2H), 6.74 (d, J=8.8 Hz, 0.85H), 6.34 (d, J=7.6 Hz, 0.15H), 3.98-3.84 (m, 1H), 2.91-2.65 (m, 4H), 2.44 (s, 3H), 1.31 (s, 7.65H), 1.14 (s, 1.35H); $^{13}$C NMR (100 MHz, DMSO-d$_6$) (rotamers): δ 155.2, 139.6, 135.7, 129.0, 128.0, 127.2, 125.8, 122.9, 121.3, 120.3, 118.4, 115.9, 111.9, 77.3, 52.6, 39.9, 30.5, 28.2 (27.8), 16.7.

Example 3N: Preparation of tert-butyl (R)-(1-(5-chloro-1H-indol-3-yl)-3-phenylpropan-2-yl)carbamate

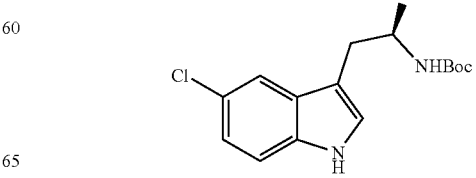

The general reaction as per Example 3A was performed between 5-chloro-1H-indole (341 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield tert-butyl (R)-(1-(5-chloro-1H-indol-3-yl)-3-phenylpropan-2-yl)carbamate (345 mg, 60% yield) as a white solid. The $C^3/N^1$ ratio was 96:4. Column Gradient: 0 to 50% iPrOAc in Heptane. mp: 70.5-73.9° C.; FTIR (neat, cm$^{-1}$) 3417, 3368, 2980, 2928, 1684, 1518; $^1$H NMR (400 MHz, DMSO-d$_6$) (85:15 mixture of rotamers): δ 10.99 (br, 1H), 7.49 (d, J=2.0 Hz, 1H), 7.34 (d, J=8.8 Hz, 1H), 7.30-7.22 (m, 2H), 7.22-7.13 (m, 4H), 7.04 (dd, J=8.4, 2.0 Hz, 1H), 6.77 (d, J=8.8 Hz, 0.85H), 6.34 (d, J=8.8 Hz, 0.15H), 3.90-3.76 (m, 1H), 2.83-2.62 (m, 4H), 1.27 (s, 7.65H), 1.10 (s, 1.35H); $^{13}$C NMR (100 MHz, DMSO-d$_6$) (rotamers): δ 155.1, 139.5, 134.6, 129.0, 128.8, 128.0, 125.8, 125.2, 122.9, 120.6, 117.7, 112.8, 111.5, 77.2, 52.9, 40.0, 30.1, 28.2 (27.7).

Example 3O: Preparation of tert-butyl (R)-(1-phenyl-3-(5-(trifluoromethyl)-1H-indol-3-yl)propan-2-yl)carbamate

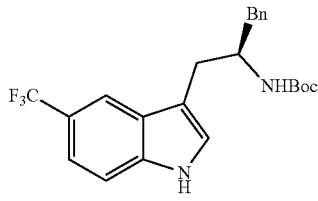 [SMILES: CC(C)(C)OC(=O)N[C@H](Cc1ccccc1)Cc1c[nH]c2ccc(C(F)(F)F)cc12]

The general reaction as per Example 3A was performed between 5-(trifluoromethyl)-1H-indole (417 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield tert-butyl (R)-(1-phenyl-3-(5-(trifluoromethyl)-1H-indol-3-yl)propan-2-yl)carbamate (297 mg, 47% yield) as a white solid. The $C^3/N^1$ ratio was 96:4. Column Gradient: 0 to 50% iPrOAc in Heptane. mp: 130.9-131.8° C.; FTIR (neat, cm$^{-1}$) 3417, 3368, 2980, 2929, 1684, 1519; $^1$H NMR (400 MHz, DMSO-d$_6$) (85:15 mixture of rotamers): 11.26 (br, 1H), 7.84 (s, 1H), 7.50 (d, J=8.4 Hz, 1H), 7.37-7.22 (m, 4H), 7.22-7.10 (m, 3H), 6.80 (d, J=8.8 Hz, 0.85H), 6.36 (d, J=9.2 Hz, 0.15H), 3.99-3.77 (m, 1H), 2.86 (d, J=6.8 Hz, 2H), 2.76 (d, J=6.8 Hz, 2H), 1.22 (s, 7.65H), 1.04 (s, 1.35H); $^{13}$C NMR (100 MHz, DMSO-d$_6$) (rotamers): δ 155.1 (154.6), 139.5, 137.6 (137.7), 129.1, 128.0, 126.9, 125.8, 125.7 (q, $^1J_{CF}$=269 Hz), 125.6, 119.1 (q, $^2J_{CF}$=32 Hz), 117.1 (q, $^3J_{CF}$=4 Hz), 116.1 (q, $^3J_{CF}$=4 Hz), 112.9, 111.9, 77.2, 53.0 (53.7), 40.3 (41.0), 29.9 (30.9), 28.1 (27.6); $^{19}$F NMR (DMSO-d$_6$, 376 MHz): δ −58.1.

Example 3P: Preparation of tert-butyl (R)-(1-(5-methoxy-1H-indol-3-yl)-3-phenylpropan-2-yl)carbamate

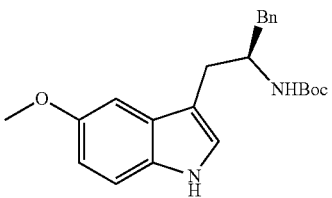 [SMILES: COc1ccc2[nH]cc(C[C@@H](Cc3ccccc3)NC(=O)OC(C)(C)C)c2c1]

The general reaction as per Example 3A was performed between 5-methoxy-1H-indole (331 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield tert-butyl (R)-(1-(5-methoxy-1H-indol-3-yl)-3-phenylpropan-2-yl)carbamate (523 mg, 92% yield) as a white solid. The $C^3/N^1$ ratio was 97:3. Column Gradient: 0 to 50% iPrOAc in Heptane. mp: 123.2-123.9° C.; FTIR (neat, cm$^{-1}$) 3368, 2975, 2933, 1692, 1680, 1516; $^1$H NMR (400 MHz, DMSO-d$_6$) (85:15 mixture of rotamers): δ 10.60 (s, 1H), 7.32-7.24 (m, 2H), 7.24-7.13 (m, 4H), 7.08 (d, J=2.4 Hz, 1H), 6.91 (d, J=2.4 Hz, 0.85H), 6.83 (br, 0.15H), 6.77 (d, J=8.8 Hz, 0.85H), 6.70 (dd, J=8.8, 2.4 Hz, 1H), 6.34 (d, J=9.2 Hz, 0.15H), 3.94-3.80 (m, 1H), 3.72 (s, 3H), 2.85-2.65 (m, 4H), 1.29 (s, 7.65H), 1.13 (s, 1.35H); $^{13}$C NMR (100 MHz, DMSO-d$_6$) (rotamers): δ 155.2, 152.9, 139.6, 131.3, 129.1, 128.0, 127.8, 125.8, 123.8, 111.9, 111.3, 110.8, 100.3, 77.3, 55.3, 52.8, 40.2, 30.2, 28.2 (27.8).

Example 3Q: Preparation of tert-butyl (R)-(1-phenyl-3-(5-phenyl-1H-indol-3-yl)propan-2-yl)carbamate

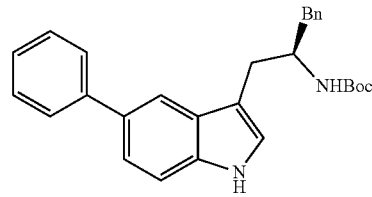 [SMILES: CC(C)(C)OC(=O)N[C@H](Cc1ccccc1)Cc1c[nH]c2ccc(-c3ccccc3)cc12]

The general reaction as per Example 3A was performed between 5-phenyl-1H-indole (435 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield tert-butyl (R)-(1-phenyl-3-(5-phenyl-1H-indol-3-yl)propan-2-yl)carbamate (523 mg, 82% yield) as a white solid. The $C^3/N^1$ ratio was 97:3. Column Gradient: 0 to 50% iPrOAc in Heptane. mp: 68.9-70.8° C.; FTIR (neat, cm$^{-1}$) 3427, 3411, 3392, 3310, 2977, 2929, 1715, 1696, 1506; $^1$H NMR (400 MHz, DMSO-d$_6$) (85:15 mixture of rotamers): δ 10.85 (br, 1H), 7.70 (s, 1H), 7.67-7.60 (m, 2H), 7.48-7.33 (m, 4H), 7.32-7.24 (m, 3H), 7.23-7.15 (m, 4H), 6.80 (d, J=8.8 Hz, 0.85H), 6.39 (d, J=9.2 Hz, 0.15H), 4.03-3.84 (m, 1H), 2.87 (d, J=6.8 Hz, 2H), 2.77 (d, J=6.8 Hz, 2H), 1.24 (s, 7.65H), 1.09 (s, 1.35H); $^{13}$C NMR (100 MHz, DMSO-d$_6$) (rotamers): δ 155.1, 142.0, 139.6, 135.8, 130.7, 129.1, 128.6, 128.1, 128.0, 126.6, 126.0, 125.8, 124.0, 120.1, 116.6, 112.2, 111.6, 77.2, 53.1, 40.4, 30.1, 28.2 (27.8).

Example 3R: Preparation of tert-butyl (R)-(1-(2-methyl-1H-indol-3-yl)-3-phenylpropan-2-yl)carbamate

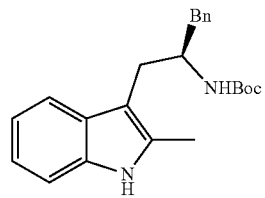 [SMILES: Cc1[nH]c2ccccc2c1C[C@@H](Cc1ccccc1)NC(=O)OC(C)(C)C]

The general reaction as per Example 3A was performed between 2-methyl-1H-indole (295 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield tert-butyl (R)-(1-(2-methyl-1H-indol-3-yl)-3-phenylpropan-2-yl)carbamate (386 mg, 71% yield) as a white solid. The $C^3/N^1$ ratio was 99:1. Column Gradient: 0 to 50% iPrOAc in Heptane. mp: 117.6-119.0° C.; FTIR (neat, cm$^{-1}$) 3440, 3385, 2984, 2930, 1684, 1524; $^1$H NMR (400 MHz, DMSO-d$_6$) (83:17 mixture of rotamers): δ 10.67 (br, 1H), 7.39 (d, J=7.6 Hz, 0.83H), 7.33 (d, J=8.0 Hz, 0.17H), 7.28-7.18 (m, 3H), 7.18-7.07 (m, 3H), 6.96 (ddd, J=8.0, 7.2, 1.2 Hz, 1H), 6.90 (ddd, J=8.0, 8.0, 1.2 Hz, 1H), 6.73 (d, J=8.8 Hz, 0.83H), 6.30 (d, J=8.8 Hz, 0.17H), 3.94-3.74 (m, 1H), 2.85 (dd, J=14.0, 6.4 Hz, 1H), 2.75-2.62 (m, 3H), 2.32 (s, 3H), 1.27 (s, 7.47H), 1.04 (s, 1.53H); $^{13}$C NMR (100 MHz, DMSO-d$_6$) (rotamers): 155.1, 139.8, 135.2, 132.4, 128.9, 128.7, 128.0, 125.7, 119.8, 118.0, 117.5, 110.2, 107.4, 77.2, 53.4, 39.4, 29.9, 28.2 (27.7), 11.4.

Example 3S: Preparation of tert-butyl (R)-(1-phenyl-3-(2-phenyl-1H-indol-3-yl)propan-2-yl)carbamate

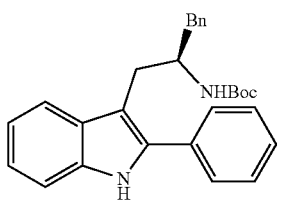 [SMILES: CC(C)(C)OC(=O)N[C@H](Cc1ccccc1)Cc1c(-c2ccccc2)[nH]c2ccccc12]

The general reaction as per Example 3A was performed between 2-phenyl-1H-indole (435 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield tert-butyl (R)-(1-phenyl-3-(2-phenyl-1H-indol-3-yl)propan-2-yl)carbamate (324 mg, 51% yield) as a white solid. The $C^3/N^1$ ratio was 98:2. Column Gradient: 0 to 50% iPrOAc in Heptane. mp: 178.5-178.8° C.; FTIR (neat, cm$^{-1}$) 3380, 3354, 3376, 2981, 2932, 1683, 1508; $^1$H NMR (400 MHz, DMSO-d$_6$) (82:18 mixture of rotamers): δ 11.14 (s, 1H), 7.69 (d, J=7.6 Hz, 1H), 7.60 (d, J=7.2 Hz, 2H), 7.44 (dd, J=7.2, 7.2 Hz, 2H), 7.35 (dd, J=7.2, 7.2 Hz, 2H), 7.21 (dd, J=7.2, 7.2 Hz, 2H), 7.17-6.97 (m, 5H), 6.79 (d, J=9.2 Hz, 0.82H), 6.38 (d, J=9.6 Hz, 0.18H), 4.15-3.90 (m, 1H), 3.06 (dd, J=14.0, 6.8 Hz, 1H), 2.96 (dd, J=14.4, 7.2 Hz, 1H), 2.64 (d, J=6.8 Hz, 2H), 1.21 (s, 7.40H), 0.97 (s, 1.60H); $^{13}$C NMR (100 MHz, DMSO-d$_6$) (rotamers): δ 155.0, 139.5, 136.0, 134.7, 133.0, 129.2, 128.9, 128.6, 128.0, 127.8, 127.1, 125.8, 121.3, 119.2, 118.5, 111.0, 109.2, 77.2, 53.4, 40.2, 28.1 (27.6).

Example 3T: Preparation of tert-butyl (R)-(1-phenyl-3-(1H-pyrrolo[2,3-c]pyridin-3-yl)propan-2-yl)carbamate

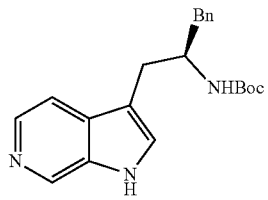 [SMILES: CC(C)(C)OC(=O)N[C@H](Cc1ccccc1)Cc1c[nH]c2cnccc12]

The general reaction as per Example 3A was performed between 1H-pyrrolo[2,3-c]pyridine (266 mg, 2.25 mmol, 150 mol %) and tert-butyl (R)-4-benzyl-1,2,3-oxathiazolidine-3-carboxylate 2,2-dioxide (470 mg, 1.50 mmol, 100 mol %) to yield tert-butyl (R)-(1-phenyl-3-(1H-pyrrolo[2,3-c]pyridin-3-yl)propan-2-yl)carbamate (40 mg, 8% yield) as a white solid. The $C^3/N^1$ ratio was 98:2. Column Gradient: 0 to 50% iPrOAc in Heptane. mp: 196.2-197.0° C.; FTIR (neat, cm$^{-1}$) 3360, 2978, 2931, 1685, 1625, 1524; $^1$H NMR (400 MHz, CDCl$_3$) (90:10 mixture of rotamers): δ 8.56 (br, 1H), 8.28 (s, 1H), 7.57 (d, J=6.4 Hz, 1H), 7.38-7.31 (m, 2H), 7.30-7.25 (m, 2H), 7.25-7.20 (m, 2H), 6.70 (br, 1H), 5.44 (br, 0.10H), 5.24 (d, J=5.6 Hz, 0.90H), 4.52 (dd, J=13.2, 8.4 Hz, 1H), 4.36 (dd, J=13.6, 4.8 Hz, 1H), 4.26-4.14 (m, 1H), 3.00 (dd, J=14.0, 7.6 Hz, 1H), 2.91 (dd, J=14.0, 6.8 Hz, 1H), 1.27 (s, 8.10H), 1.11 (s, 0.90H).

Example 4

Preparation of Azetidinyl-Amines

Preparation of compounds of formula (VII) were performed according to the general scheme below:

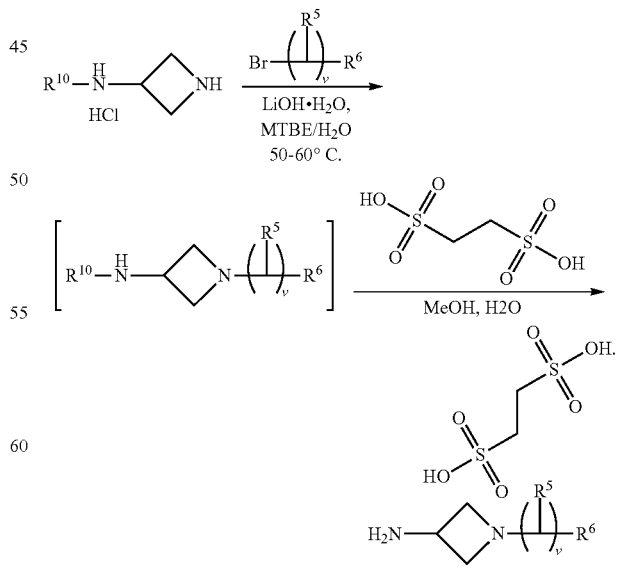

$R^5$, v, $R^6$, and $R^{10}$ are as described herein.

Example 4A

Preparation of 1-(3-fluoropropyl)azetidin-3-amine ethane-1,2-disulfonate 1-(3-fluoropropyl)azetidin-3-amine ethane-1,2-disulfonate was prepared according to the following reaction scheme:

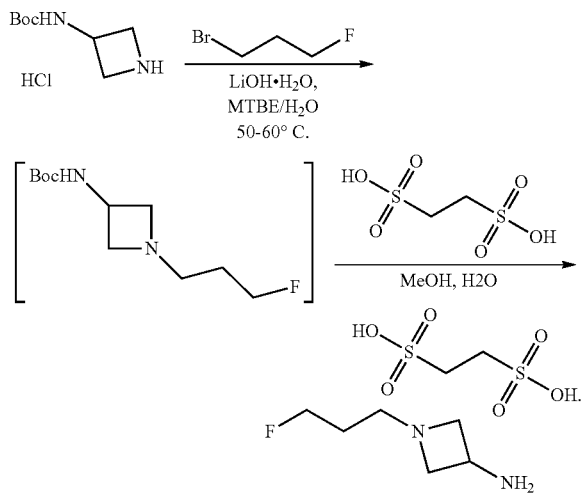

Tert-butyl azetidin-3-ylcarbamate hydrochloride (109.7 kg, 1.0 eq.) was dissolved in MTBE (793.4 kg), and 1-bromo-3-fluoropropane (82.3 kg) was added. MTBE (14 kg) and water (530 kg) were added followed by LiOH·H$_2$O (66.0 kg) at 15-25° C. followed by stirring at 50-60° C. After reaction completion, an organic phase was separated and then combined 1,2-ethanedisulfonic acid dihydrate aqueous solution (247.8 kg) at 0-5° C. The resulting mixture was stirred for 30 min at 15-20° C. An aqueous phase was separated, and 1,2-ethanedisulfonic acid dihydrate (56.85 kg) was added to the organic phase. The resulting mixture was stirred for 5 h at 35-40° C. until deprotection was complete. MeOH (884.1 kg) was then added at 35-40° C., and the mixture was stirred for 2 h at 35-40° C. After cooling to room temperature, the reaction mixture was stirred for 4 h. Solid was collected by filtration and rinsed with aq. MeOH. The washed solid was dried at 35-42° C. under reduced pressure to provide 106.8 kg of 1-(3-fluoropropyl)azetidin-3-amine ethane-1,2-disulfonate (63% yield). $^1$H NMR (400 MHz, DMSO-d$_6$) δ 9.92 (s, 0.7H), 9.63 (s, 0.3H), 8.35 (s, 3H), 4.52 (dt, J=47.1, 5.6 Hz, 2H), 4.43-4.08 (m, 5H), 3.36 (s, 3H), 2.74 (s, 4H), 2.06-1.77 (m, 2H).

Example 4B

Preparation of 1-(3-fluoropropyl)azetidin-3-amine ethane-1,2-disulfonate Via Strain Release Chemistry

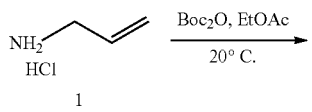

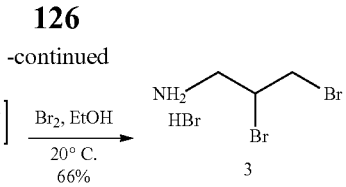

Preparation of 2,3-dibromopropan-1-amine hydrobromide (3)

To 1 (20.0 g, 1.0 equiv, 50 wt % in water) was added a solution of K$_2$CO$_3$ (29.55 g, 1.0 equiv) in water (100 mL) and a solution of Boc$_2$O (93.32 g, 2.0 equiv) in EtOAc (100 mL) at 0° C. The reaction mixture was stirred at 20° C. for 15 h. The organic layer was separated and solvent swapped to EtOH (100 mL) to provide a solution of 2 in EtOH. It was then added into a cold (0° C.) solution of Br$_2$ (71.74 g, 2.1 equiv) in EtOH (60 mL) at 0° C. The reaction mixture was stirred at 20° C. for 16 h, filtered, washed with MTBE (60 mL), dried under vacuum at 40° C. for 15 h to provide 3 as a colorless solid (43.01 g, 66%): $^1$H NMR (400 MHz, CD$_3$OD) δ 4.55-4.47 (m, 1H), 4.01 (dd, J=10.9, 4.6 Hz, 1H), 3.86 (dd, J=10.9, 8.7 Hz, 1H), 3.71 (dd, J=13.9, 3.2 Hz, 1H), 3.39-3.33 (m, 1H).

Preparation of N,N-dibenzyleazetidin-3-amine ethane-1,1disulfonate

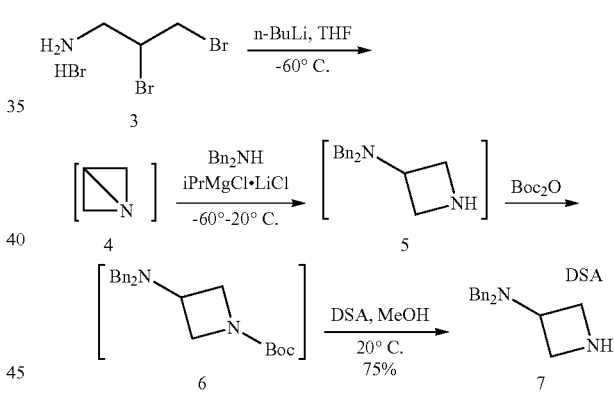

To a solution of Bn$_2$NH (33.12 g, 1.0 equiv) in THF (330 mL) was added iPrMgCl·LiCl (1.3 M in THF, 130 mL, 1.0 equiv) at 20° C. and stirred at 20° C. for 5 h to provide a solution of Bn$_2$NMgCl·LiCl in THF. In a separate reactor was charged 3 (50.0 g, 1.0 equiv) in THF (500 mL), cooled to −60° C. n-BuLi (201 mL, 2.5 M solution in n-hexane, 3.0 equiv) was added into the suspension at −60° C. and stirred at −60° C. for 2 h to provide a solution of 4 in THF. Bn$_2$NMgCl·LiCl solution was added into the 4 at −60° C., warmed to 20° C. and stirred at 20° C. for 12 h to provide a solution of 5 in THF. The reaction mixture was cooled to 0° C., a solution of Boc$_2$O (73.28 g, 2.0 equiv) in THF (200 mL) was added at 0° C., stirred at 20° C. for 2 h, cooled to 0° C., quenched with a solution of AcOH (20.16 g, 2.0 equiv) in H$_2$O (383 mL). The organic layer was washed 5% Na$_2$SO$_4$ (150 mL). The combined aqueous layer was back extracted with MTBE (100 mL×2) to provide a solution of 6. A solution of ethanedisulfonic acid (40.0 g, 1.5 equiv) in MeOH (225 mL) was added into the solution at 20° C. and stirred at 40° C. for 20 h. The slurry was filtered, washed with THF (100 mL), dried under the vacuum (40° C.) for 20 h to provide 7 (69.21 g, 75% yield) as a white solid: $^1$H NMR (400 MHz, D$_2$O) δ 7.57-7.44 (m, 10H), 4.66 (t, J=8.2 Hz, 1H), 4.36 (s, 4H), 4.10-3.95 (m, 4H), 3.22 (s, 4H). MS ([M+H]$^+$) calculated for C$_{17}$H$_{21}$N$_2$ 253.17, found 253.00.

Preparation of N,N-dibenzyl-1-(3-fluoropropyl)azetidin-3-amine (8)

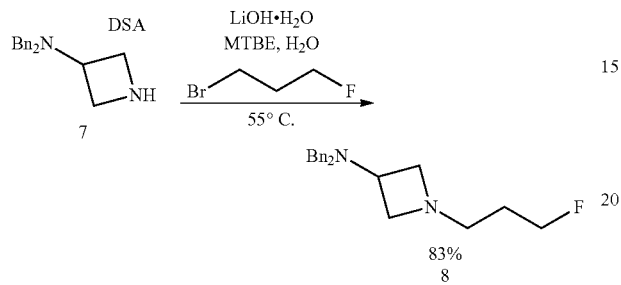

To a solution of 7 (40.0 g, 1.0 equiv) in MTBE (200 mL) and H$_2$O (200 mL) was added 1-bromo-3-fluoropropane (17.20 g, 1.5 equiv) and LiOH·H$_2$O (15.18 g, 4.0 equiv). The reaction mixture was heated to 55° C. and stirred at 55° C. for 20 h, cooled to 20° C. The organic layer was separated and washed with 5% Na$_2$SO$_4$ (120 mL×2). 8 can be obtained by concentration of MTBE solution under reduced vacuum as a white solid (22.3 g, 83% yield): $^1$H NMR (400 MHz, DMSO-d$_6$) δ 7.35-7.22 (m, 10H), 4.45 (t, J=6.0 Hz, 1H), 4.33 (t, J=6.0 Hz, 1H), 3.45-3.39 (m, 4H), 3.28-3.17 (m, 3H), 2.67-2.56 (m, 2H), 2.35 (t, J=7.0 Hz, 2H), 1.64-1.48 (m, 2H). MS ([M+H]$^+$) calculated for C$_{20}$H$_{26}$FN$_2$ 313.21, found 313.10.

Preparation of 1-(3-fluoropropyl)azetidin-3-amine ethane-1,2-disulfonate

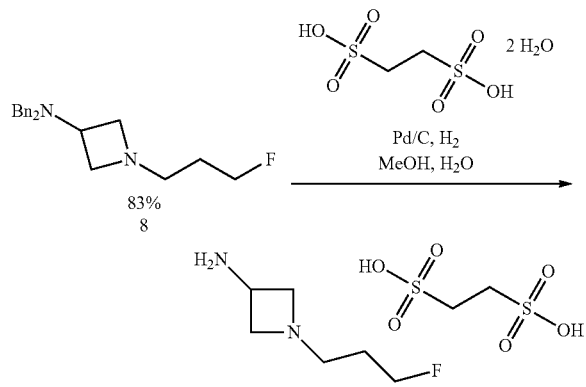

To a solution of 8 (2.00 g, 1.0 equiv) in MeOH (20.0 mL) was added a solution of ethanedisulfonic acid dihydrate (1.23 g, 1.0 equiv) in H$_2$O (10.0 mL) at 0° C. The reaction mixture was heated to 30° C., passed through charcoal cartridge. Pd/C (0.40 g, 0.20 equiv) was then charged into the reaction mixture, stirred at 45° C. with 40 psi H$_2$, filtered, concentrated to 5 mL, charged with MeOH (20.0 mL), stirred at 20° C. for 3 h, filtered, washed with MeOH (2 mL) to provide the title compound (1.36 g, 93% yield) as a white solid: $^1$H NMR (400 MHz, D$_2$O) δ 4.70-4.57 (m, 3H), 4.57-4.31 (m, 4H), 3.51 (t, J=7.2 Hz, 2H), 3.24 (s, 4H), 2.11-1.97 (m, 2H); $^{19}$F NMR (376 MHz, D$_2$O) δ −219.59.

Example 5

Preparation of (R)-1-(1H-indol-3-yl)propan-2-amine

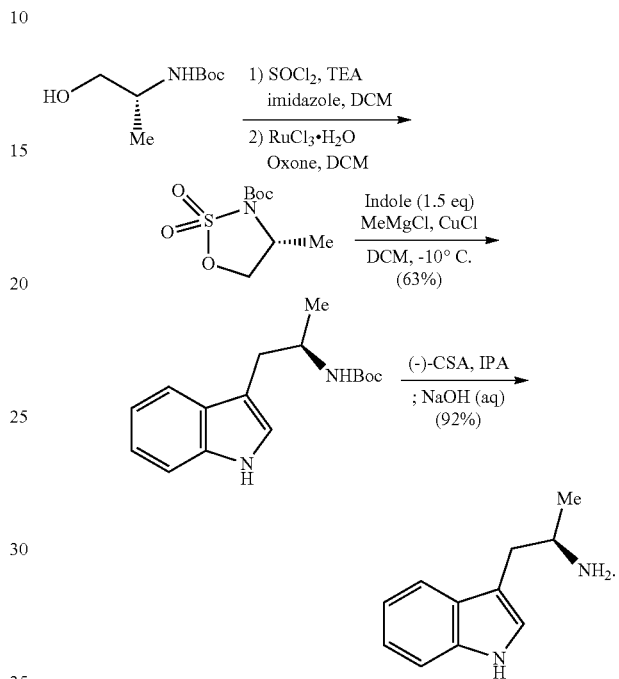

To a solution of imidazole (102.8 g, 1.51 mol, 1.5 equiv.) in DCM (1.33 L) was added SOCl$_2$ (179.3 g, 1.51 mol, 1.5 equiv.) dropwise at −5 to 0° C. under N$_2$ over 30 min. The reaction mixture was stirred for 0.5 h at −5 to 0° C. tert-butyl (R)-(1-hydroxypropan-2-yl)carbamate (Boc-alaninol) (177.7 g, 1.01 mol, 1.0 equiv.) in DCM (1.33 L, 7.5 vol.) was added dropwise at −5 to 0° C. over 1 h. The reaction mixture was stirred for 0.5 h at −2 to 0° C. followed by addition of triethylamine (204 g, 2.02 mol, 2 equiv.) dropwise at −5 to 0° C. The resulting mixture was stirred for 0.5 h or until N-Boc-alaninol was completely consumed as determined by GC analysis. Water was added to the reaction mixture (1.3 L) at 0~20° C. The phases were separated, and the aqueous phase was extracted with DCM (1.3 L). The organic phases were combined and washed with 10 w % citric acid (1.3 L), aq. NaHCO$_3$ (1.3 L), and brine (1 L) successively. The organic phase was cooled to 0~10° C., followed by addition of water (3.1 L) and RuCl$_3$·xH$_2$O (2.66 g), and then followed by addition of Oxone (927.1 g, 1.51 mol, 1.5 equiv.). The reaction mixture was warmed to 22° C. gradually, and held for 3.5 h or until the sulfamidate intermediate was completely consumed as determined by GC analysis. The phases were separated, and the aqueous phase was filtered through a pad of Celite (50 g) followed by rinsing with DCM (1.3 L). The filtrate was extracted with the DCM (1.3 L), and the organic phases were combined and then washed with sat. Na$_2$S$_2$O$_3$ (1.3 L) and brine (1 L×2). The organic phase was dried with Na$_2$SO$_4$ (50 g) and then filtered rinsing with DCM (200 mL). The combined filtrate and washes were concentrated under vacuum at 30° C. for 1 h, and then further dried under high vacuum to provide 220 g of tert-butyl (R)-4- methyl-1,2,3-oxathiazolidine-3-carboxylate 2,2-dioxide with >99 wt % in 91.8% isolated yield (corrected) over 2 steps. $^1$H NMR (400 MHz, CDCl$_3$): δ 4.66 (dd, J=9.2, 6.0 Hz, 1H), 4.41 (qdd, J=6.4, 6.0, 2.8 Hz, 1H), 4.19 (dd, J=9.2, 2.8 Hz, 1H), 1.54 (s, 9H), 1.50 (d, J=6.4 Hz, 3H).

Other oxidation reactions were run generally according to the procedure immediately above where the oxidant, catalyst, and solvent were varied. The results are reported in Table 1 below where "Exp." refers to experiment number, "Product" refers to tert-butyl (R)-4-methyl-1,2,3-oxathiazolidine-3-carboxylate 2,2-dioxide and "SM" refers to Boc-alaninol starting material, "LC A %" refers to area percent purity by liquid chromatography, and "ND" refers to not detected. The reaction temperature for experiments 1 and 3-9 was 0-25° C. and the reaction temperature for experiment 2 was 0-40° C. The reaction time for experiments 1-4 and 7 was 4 hours, the reaction time for experiments 5 and 6 was 8 hours, and the reaction time for experiments 8 and 9 was 18 hours.

TABLE 1

Oxidant Catalyst Conditions and Yields

| Exp. | Oxidant/Catalyst | Solvent | Product (LC A %) | SM (LC A %) |
|---|---|---|---|---|
| 6B | mCPBA (1.3 eq) | DCM (10 vol) | 3.2 | 94.4 |
| 6C | Oxone (1.5 eq) | MeCN/H$_2$O (1/1, 10 vol) | 4.1 | 46.6 |
| 6D | NaClO (5.26 eq)/NiCl$_2$ (2.6 mol %) | DCM/H$_2$O (1/1, 10 vol) | 0.5 | 94.6 |
| 6E | H$_2$O$_2$ (1.3 eq)/FeCl$_3$ (5 mol %) | H$_2$O (10 vol) | ND | 93.2 |
| 6F | NaClO (5.26 eq)/FeCl$_2$ (2.6 mol %) | DCM/H$_2$O (1/1, 10 vol) | ND | >95 |
| 6G | NaClO (5.26 eq)/FeCl$_3$ (2.6 mol %) | DCM/H$_2$O (1/1, 10 vol) | ND | >95 |
| 6H | NaClO (5.26 eq)/RuCl$_3$ (1.3 wt %) | DCM/H$_2$O (1/1, 10 vol) | 83.1 | ND |
| 6I | Oxone (2.0 eq)/RuCl$_3$ (1.3 wt %) | DCM/H$_2$O (1/1, 10 vol) | 83.8 | ND |
| 6J | Oxone (2.0 eq)/RuCl$_3$ (1.3 wt %) | MeCN/H$_2$O (1/1, 10 vol) | 70.7 | ND |

To a mixture of indole (7.4 g, 63.2 mmol, 1.5 equiv.) and CuCl (5.4 g, 54.7 mmol, 1.3 equiv.) in DCM (60 ml) was added MeMgCl (3.0 M in THF, 18.7 mL, 56 mmol, 1.33 equiv.) at −15° C. under N$_2$ over 10 min. The resulting light yellow mixture was stirred at −20° C. for 10 min, and then a solution of tert-butyl (R)-4-methyl-1,2,3-oxathiazolidine-3-carboxylate 2,2-dioxide (10.0 g, 42.1 mmol, 1.0 equiv.) in DCM (40 ml) was added dropwise at −10° C. under N$_2$ over 30 min. The mixture was stirred at −10° C. for 2 hours or until the reaction was complete as judged by TLC (PE/EA=5/1, disappearance of tert-butyl (R)-4-methyl-1,2,3-oxathiazolidine-3-carboxylate 2,2-dioxide) or by GC. The reaction was quenched by adding 10% citric acid (100 mL) while maintaining the internal temperature <5° C. The phases were separated, and the aqueous phase was extracted with DCM (100 mL×2). The organic phases were combined and washed with brine (100 mL×2), followed by addition to the organic phase of activated carbon (5 g) and Na$_2$SO$_4$ (10 g). The resulting mixture was stirred at room temperature for 30 min then filtered. The cake was washed with DCM (50 mL×2). The filtrate and wash were combined and concentrated under vacuum at 30° C. to provide crude tert-butyl (R)-(1-(1H-indol-3-yl)propan-2-yl)carbamate (16.9 g, 40.9 LCA %). Heptane (200 ml) was added to the crude tert-butyl (R)-(1-(1H-indol-3-yl)propan-2-yl)carbamate, and the mixture was stirred at room temperature for 1 hour, during which time, off-white solid precipitated gradually. The solid was collected by filtration, and the cake was washed with heptane (17 mL×3). The solid was dried under high vacuum at 25° C. to provide 7.0 g of tert-butyl (R)-(1-(1H-indol-3-yl)propan-2-yl)carbamate (25.5 mmol, 97 A %, 99 wt %). $^1$H NMR (400 MHz, DMSO-d$_6$) δ 10.76 (s, 1H), 7.55 (d, J=7.9 Hz, 1H), 7.32 (dt, J=8.1, 1.0 Hz, 1H), 7.09 (d, J=2.3 Hz, 1H), 7.05 (ddd, J=8.2, 7.0, 1.2 Hz, 1H), 6.96 (ddd, J=8.0, 6.9, 1.1 Hz, 1H), 6.71 (d, J=8.0 Hz, 1H), 3.76-3.69 (m, 1H), 2.86 (dd, J=13.9, 5.8 Hz, 1H), 2.64 (dd, J=14.1, 7.7 Hz, 1H), 1.37 (s, 9H), 1.00 (d, J=6.6 Hz, 3H).

Other indole alkylation reactions were run generally according to the procedure immediately above where the copper catalyst species and the stoichiometry of the Grignard reagent were varied. The results are reported in Table 2 below where "Exp." refers to experiment number, "CuX" refers to the copper catalyst species, "eq." refers to equivalents, "Prod" refers to tert-butyl (R)-(1-(1H-indol-3-yl)propan-2-yl)carbamate, "N1" refers to a by-product wherein the indole amine is alkylated, "BA" refers to a bisalkyl byproduct, and "AY" refers to LC Assay yield, "A %" refers to area percent purity by liquid chromatography, and "ND" refers to not detected.

TABLE 2

Indole Alkylation Reaction Conditions and Yields

| Entry | CuX | MgMeCl (eq.) | indole (eq.) | Prod (A %) | N1 (A %) | BA (A %) | AY (%) |
|---|---|---|---|---|---|---|---|
| 6K | CuCl | 1.1 | 1.2 | 82.9 | 1.2 | 6.5 | 72.2 |
| 6L | CuCl | 2.2 | 2.4 | 87.4 | 3.0 | 2.8 | 84.7 |
| 6M | CuI | 1.1 | 1.2 | 66.4 | 2.3 | 1.4 | 27.7 |
| 6N | CuI | 2.2 | 2.4 | 52.1 | 6.7 | nil | 12.8 |
| 6O | CuTC | 1.1 | 1.2 | 68.0 | 0.8 | 0.9 | 34.8 |
| 6P | CuTC | 2.2 | 2.4 | 59.3 | 16.2 | 0.4 | 28.1 |
| 6Q | CuCN | 1.1 | 1.2 | 70.2 | 16.7 | 1.6 | 22.3 |
| 6R | CuCN | 2.2 | 2.4 | 58.9 | 31.3 | 1.1 | 46.8 |
| 6S | CuSCN | 1.1 | 1.2 | 57.4 | 30.1 | 1.8 | 40.9 |
| 6T | CuSCN | 2.2 | 2.4 | 61.9 | 29.4 | 1.0 | 54.3 |

Other indole alkylation reactions were run generally according to the procedure immediately above where the reaction temperature was varied. The results are reported in Table 3 below where "Exp." refers to experiment number, "G temp" refers to the Grignard reagent addition temperature in ° C., "S temp" refers to the sulfamidate addition temperature in ° C., "Prod" refers to tert-butyl (R)-(1-(1H-indol-3-yl)propan-2-yl)carbamate, "N1" refers to a by-product wherein the indole amine is alkylated, "BA" refers to a bisalkyl byproduct, and "AY" refers to LC assay yield, and "A %" refers to area percent purity by liquid chromatography.

TABLE 3

Variable temperature indole alkylation experiments

| Exp | G Temp (° C.) | S Temp (° C.) | Prod (A %) | N1 (A %) | BA (A %) | AY (A %) |
|---|---|---|---|---|---|---|
| 6U | 15~20 | −10~−15 | 83.4 | 1.2 | 5.7 | 65.5 |
| 6V | −5~0 | −10~−15 | 87.6 | 1.6 | 6.0 | 72.1 |
| 6W | −10~−15 | −10~−15 | 85.8 | 1.1 | 6.3 | 80.4 |
| 6X | −20~−25 | −10~−15 | 89.0 | 1.3 | 6.4 | 80.3 |
| 6Y | −30~−35 | −10~−15 | 79.9 | 1.8 | 7.0 | 80.2 |
| 6Z | −40~−45 | −10~−15 | 82.8 | 3.2 | 6.6 | 78.9 |
| 6AA | −10~−15 | 15~20 | 85.4 | 2.5 | 3.9 | 75.7 |
| 6AB | −10~−15 | 5~10 | 89.4 | 2.0 | 5.7 | 81.7 |
| 6AC | −10~−15 | ~0 | 86.9 | 1.5 | 6.9 | 80.8 |
| 6AD | −10~−15 | −10~−15 | 85.8 | 1.1 | 6.3 | 80.4 |
| 6AE | −10~−15 | −20~−25 | 85.8 | 0.9 | 5.5 | 73.7 |
| 6AF | −10~−15 | −30~−35 | 88.4 | 0.8 | 5.1 | 70.6 |

To a solution of tert-butyl (R)-(1-(1H-indol-3-yl)propan-2-yl)carbamate (0.5 g, 1.8 mmol, 92 A %) in MeOH (5 mL, 10 vol.) was added HCl in MeOH (10 M, 1.8 mL, 18 mmol) dropwise at 0° C. under N$_2$ atmosphere over a period of 10 min. The resulting solution was stirred at 0° C. for 2 hrs, then at 25-30° C. for 1 h. The solution was concentrated under vacuum at 30° C., diluted with water (10 mL), and extracted with DCM (10 mL×2). The pH of the aqueous phase was adjusted to ~13 with 1 M aq. NaOH at 0-10° C. and then extracted with DCM (20 mL×4). The organic phase was dried over Na$_2$SO$_4$ (10 g). The desiccant was filtered, and the cake was washed with DCM (10 mL). The combined filtrate and wash was concentrated under vacuum at 30° C. to afford 0.31 g of crude (R)-1-(1H-indol-3-yl)propan-2-amine with 95.8 LCA % and 99.2% ee purity in 97% isolated yield. $^1$H NMR: 400 MHz (CDCl$_3$): δ 1.20 (d, J=6, 3H), 1.56 (s, br, 2H), 2.69 (dd, J=14, 8, 1H), 2.91 (dd, J=14, 4, 1H), 3.30-3.33 (m, 1H), 7.05 (s, 1H), 7.14 (t, J=7, 1H), 7.22 (t, J=7, 1H), 7.38 (d, J=8, 1H), 7.64 (d, J=8, 1H), 8.27 (s, 1H).

Example 6

Preparation of (R)-3-((1-(1H-indol-3-yl)propan-2-yl)amino)-2,2-difluoropropan-1-ol

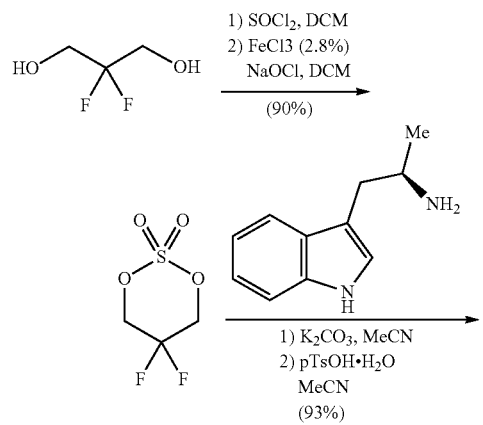

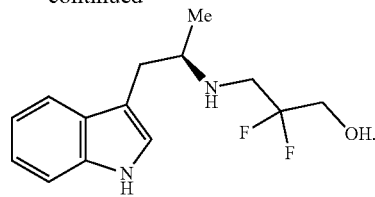

To a solution of 2,2-difluoropropane-1,3-diol (51 kg, 90 wt %, 409.5 mol, 1 eq.) in DCM (332 kg, 5 vol.) was added thionyl chloride (58.4 kg, 491.4 mol, 1.2 eq.) at 20-25° C. over 2 h. The reaction mixture was heated to 30-35° C., stirred for 2 h, and ice water (255 kg) was added to quench the reaction. The phases were separated, and the aqueous phase was extracted with DCM. The organic phases were combined and washed with water. To the crude organic phase was added water (255 kg) and FeCl$_3$ (1.6 kg), and the biphasic mixture was cooled to −3° C. Bleach [NaClO (8.1 wt %), 680 kg, 1556 mol, 3.8 equiv.] was then added dropwise during a period of 5 h at −5 to 1° C., and the reaction mixture was stirred for 1 h at 0° C. The reaction mixture was filtered through Celite. The phases were separated, and the aqueous phase was extracted with DCM. The organic phases were combined and washed with aq. solution of Na$_2$SO$_3$ and brine, then dried over Na$_2$SO$_4$. The desiccant was filtered off, and the filtrate was concentrated to ca. 100 L. Heptane (80 kg) was added to the resulting suspension, and the mixture was further concentrated to ca. 100 L. Solids were collected by filtration and dried under vacuum to afford 52.01 kg of 5,5-difluoro-1,3,2-dioxathiane 2,2-dioxide as an off-white crystal with (72% yield, two steps from 2,2-difluoropropane-1,3-diol). $^1$H NMR (400 MHz, DMSO-d$_6$) δ 5.14 (t, J=10.8 Hz, 1H).

Various other catalysts were evaluated for the preparation of 5,5-difluoro-1,3,2-dioxathiane 2,2-dioxide generally according to the procedure immediately above. The results are reported in Table 4 below where "Exp." refers to experiment number, "diol" refers to 2,2-difluoropropane-1,3-diol, "Prod" refers to 90 wt. % 5,5-difluoro-1,3,2-dioxathiane 2,2-dioxide and "Yield" refers to assay yield. Each reaction was quenched with 5 volumes of water.

TABLE 4

Conditions for preparation of 5,5-difluoro-1,3,2-dioxathiane 2,2-dioxide

| Exp | Diol | NaClO (eq.) | Catalyst (mol %) | Prod (Yield) |
|---|---|---|---|---|
| 7B | 50 g | 5.26 | NiCl$_2$ (2.8) | 78.6% |
| 7C | 50 g | 5.26 | RuCl$_3$ (2.8) | 67.1% |
| 7D | 10 g | 5.26 | RuCl$_3$ (2.0) | 57.1% |
| 7E | 10 g | 5.26 | RuCl$_3$ (2.8) | 64.3% |
| 7F | 10 g | 5.26 | CoCl$_2$ (2.8) | 65.7% |
| 7G | 10 g | 5.26 | FeCl$_3$ (2.8) | 71.4% |
| 7H | 10 g | 5.26 | FeCl$_2$ (2.8) | 75.7% |
| 7I | 10 g | 5.26 | MnCl$_2$ (2.8) | 60.7% |
| 7J | 100 g | 5.26 | NiCl$_2$ (2.8) | 78.3% |
| 7K | 100 g | 5.26 | FeCl$_3$ (2.8) | 79.5% |
| 7L | 500 g | 5.26 | FeCl$_3$ (2.8) | 76% |
| 7M | 50 g | 5.26 | NiCl$_2$ (2.8) | 78% |
| 7N | 32 g | 5.26 | FeCl$_3$ (2.8) | 76% |
| 7O | 32 g | 5.26 | None | 63% |

In a 2 L flask were placed (R)-1-(1H-indol-3-yl)propan-2-amine (99 wt %, 100 g, 568.2 mmol, 1 equiv.), 5,5-difluoro-1,3,2-dioxathiane 2,2-dioxide (97.9 wt %, 108 g, 608 mmol, 1.07 equiv.), K$_2$CO$_3$ (55 g, 398 mmol, 0.7 equiv.), and acetonitrile (1 L, 10 vol.). The resulting mixture was heated to 80° C. and stirred for 4 hrs. The reaction was cooled to 35° C. and filtered. The cake was washed with acetonitrile (100 mL×2), and p-TsOH monohydrate (119 g, 625.6 mmol, 1.1 equiv.) and water (100 mL, 1 vol) were added to the combined filtrate. The resulting biphasic mixture was heated to 80° C. and stirred for 3 hrs. The mixture was then poured into 1 L of ice-water, and the pH of the mixture was adjusted to 9 with saturated $Na_2CO_3$ (350 mL) at <5° C. The phases were separated, and the aqueous was extracted with i-PrOAc (500 mL×2). The organic phases were combined and washed with water (500 mL) and brine (500 mL×2), then dried over $Na_2SO_4$ (30 g). The desiccant was filtered off, and the cake was washed with i-PrOAc (100 mL×2). The filtrate and wash were combined concentrated under vacuum at 40° C. The residue was dissolved in i-PrOAc (200 mL) and heated to 60° C. Heptane (800 mL) was added dropwise at 60° C., and then the resulting mixture was stirred for 10 min. The mixture was cooled to 30-35° C. slowly over 2 hrs, and then further cooled to 0° C. After stirring for 10 min, solids were collected by filtration, and the cake was washed with heptane (100 mL×2). The solid thus obtained was dried under vacuum at 45° C. to afford (R)-3-((1-(1H-indol-3-yl)propan-2-yl)amino)-2,2-difluoropropan-1-ol (155 g, 99.2 LCA %, 96 wt %, 97.6% isolated yield). $^1$H NMR (400 MHz, DMSO-$d_6$) δ 10.79 (s, 1H), 7.51 (dd, J=7.9, 1.2 Hz, 1H), 7.33 (dt, J=8.2, 1.0 Hz, 1H), 7.13 (d, J=2.3 Hz, 1H), 7.05 (ddd, J=8.2, 6.9, 1.3 Hz, 1H), 6.96 (ddd, J=8.0, 6.9, 1.2 Hz, 1H), 5.35 (t, J=6.3 Hz, 1H), 3.61 (td, J=13.8, 5.2 Hz, 2H), 3.03-2.91 (m, 3H), 2.83 (dd, J=14.0, 5.7 Hz, 1H), 2.59 (dd, J=14.0, 7.2 Hz, 1H), 1.69 (s, 1H), 0.96 (d, J=6.2 Hz, 3H).

Example 7

Preparation of 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol (2R,3R)-2,3-dihydroxysuccinate

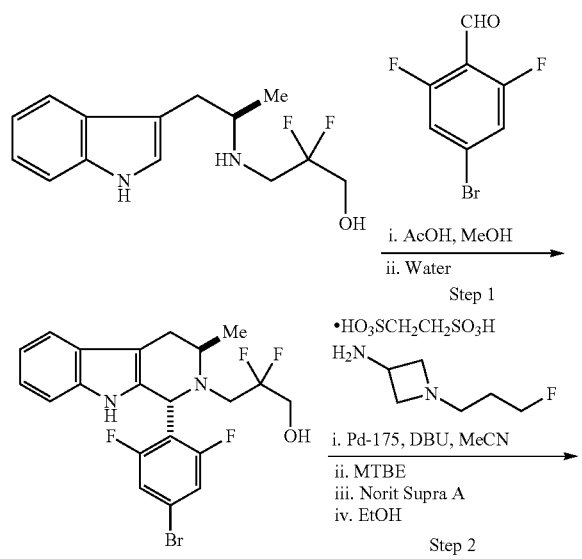

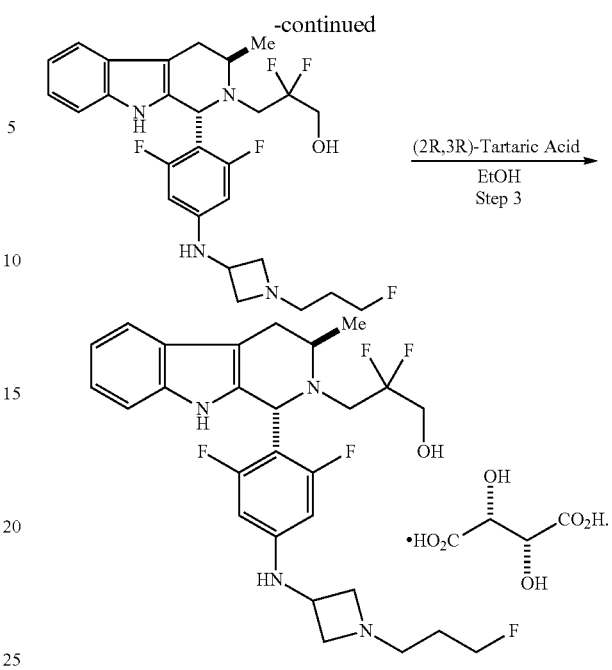

In step 1, to a flask with stirring apparatus was combined 4-bromo-2,6-difluorobenzaldehyde (131.79 g, 596.35 mmol), (R)-3-((1-(1H-indol-3-yl)propan-2-yl)amino)-2,2-difluoropropan-1-ol (160 g, 596.35 mmol), acetic acid (51.26 mL, 894.52 mmol), and toluene. The reaction was heated to 75° C. and held overnight, cooled, and then diluted with toluene. The resulting solution was then quenched with an aqueous potassium carbonate solution, washed with brine and water, and treated with activated charcoal. Following filtration, the solution was concentrated and crystallized from toluene/heptane to afford 3-((1R,3R)-1-(4-bromo-2,6-difluorophenyl)-3-methyl-1,3,4,9-tetrahydro-2H-pyrido[3,4-b]indol-2-yl)-2,2-difluoropropan-1-ol in 81% yield as a pale yellow solid. $^1$H NMR (400 MHz, DMSO-$d_6$) δ 10.59 (s, 1H), 7.45-7.36 (m, 3H), 7.20 (d, J=8.1 Hz, 1H), 7.05-6.92 (m, 2H), 5.29 (t, J=6.1 Hz, 1H), 5.21 (s, 1H), 3.71-3.55 (m, 1H), 3.53-3.38 (m, 2H), 3.17 (q, J=15.2 Hz, 1H), 2.89 (ddd, J=15.3, 4.8, 1.5 Hz, 1H), 2.71-2.55 (m, 2H), 1.08 (d, J=6.5 Hz, 3H). MS ([M+H]+) calculated for $C_{21}H_{19}BrF_4N_2O$ 470.06, found 470.80.

Alternatively, 4-bromo-2,6-difluorobenzaldehyde (67.2 g, 304 mmol), (R)-3-((1-(1H-indol-3-yl)propan-2-yl)amino)-2,2-difluoropropan-1-ol (80.0 g, 298 mmol), acetic acid (25.6 mL, 447 mmol), and methanol were combined in a stirred flask. The mixture was refluxed for 24 hours then cooled. Solids were precipitated from the resulting solution by addition of an aqueous solution of potassium carbonate. The resulting slurry was filtered and washed to afford 3-((1R,3R)-1-(4-bromo-2,6-difluorophenyl)-3-methyl-1,3,4,9-tetrahydro-2H-pyrido[3,4-b]indol-2-yl)-2,2-difluoropropan-1-ol in 97% yield as a pale yellow solid.

In steps 2 and 3, 3-((1R,3R)-1-(4-bromo-2,6-difluorophenyl)-3-methyl-1,3,4,9-tetrahydro-2H-pyrido[3,4-b]indol-2-yl)-2,2-difluoropropan-1-ol (100 g, 212.2 mmol), 1-(3-fluoropropyl)azetidin-3-amine ethane-1,2-disulfonate (82.09 g, 254.6 mmol), acetonitrile, DBU (1061 mmol 161.5 g 159.4 mL) were combined in a stirred flask followed by addition of Pd-175 (5.304 mmol 4.144 g). The reaction was heated to 75° C. for 2 hours, cooled, concentrated, and then diluted with methyl tert-butyl ether. This resulting solution was worked up with an aqueous solution of ammonium chloride, brine, and water, then scavenged with SiliaMetS Thiol. Following filtration, the solution was concentrated, diluted with ethanol, and crystallized with tartaric acid to afford 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol (2R,3R)-2,3-dihydroxysuccinate in a 90% yield as a yellow solid following filtration and washing. $^1$H NMR (400 MHz, DMSO-$d_6$) δ 10.52 (s, 1H), 7.38 (dd, J=7.5, 1.3 Hz, 1H), 7.21-7.16 (m, 1H), 7.02-6.90 (m, 2H), 6.82 (d, J=6.9 Hz, 1H), 6.18-6.08 (m, 2H), 5.07 (s, 1H), 4.53 (t, J=5.8 Hz, 1H), 4.42 (t, J=5.9 Hz, 1H), 4.18 (s, 2H), 4.14-4.05 (m, 1H), 3.93 (ddt, J=9.1, 7.0, 3.5 Hz, 2H), 3.74-3.60 (m, 1H), 3.51-3.32 (m, 2H), 3.21-3.02 (m, 3H), 2.88-2.73 (m, 3H), 2.70-2.51 (m, 2H), 1.83-1.66 (m, 2H), 1.09-1.05 (m, 3H). MS ([M+H]+) calculated for $C_{27}H_{31}F_5N_4O$ 522.24, found 523.00.

Example 8

Preparation of 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol (2R,3R)-2,3-dihydroxysuccinate

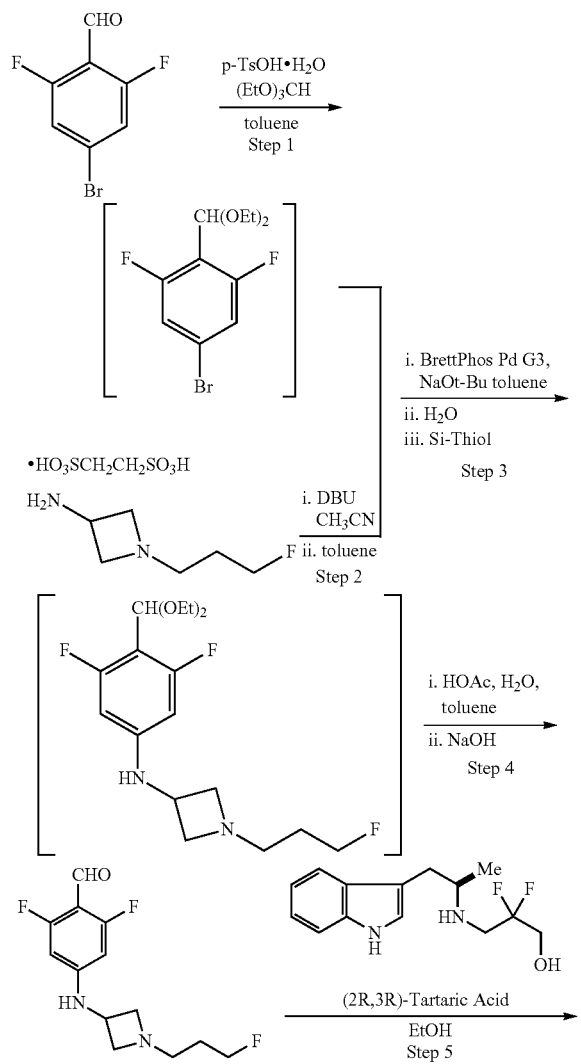

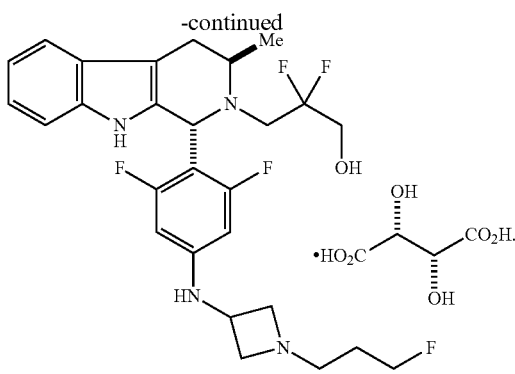

In steps 1-4, a reactor was charged with 4-bromo-2,6-difluorobenzaldehyde (75.0 g, 0.339 mol, 100 mol %), p-toluenesulfonic acid monohydrate (162 mg, 0.000849 mol, 0.250 mol %), and toluene (225 mL). Triethyl orthoformate (55.4 g, 62.1 mL, 0.373 mol, 110 mol %) was charged over 15 min at rt, the mixture was stirred at rt for 1 h, and the mixture was distilled to provide a toluene solution of 5-bromo-2-(diethoxymethyl)-1,3-difluorobenzene. Another reactor was charged with 1-(3-fluoropropyl)azetidin-3-amine 2-(trioxidanylthio)ethane-1-sulfonate (131.3 g, 0.407 mol, 120 mol %), and acetonitrile (656 mL). DBU (124.0 g, 122.8 mL, 0.814 mol, 240 mol %) was charged over 15 min at rt, and the mixture was stirred at rt for 2 h, distilled with toluene, and filtered to provide a toluene solution of 1-(3-fluoropropyl)azetidin-3-amine which was charged, along with NaOtBu (39.14 g, 0.407 mol, 120 mol %), to the toluene solution of 5-bromo-2-(diethoxymethyl)-1,3-difluorobenzene. The mixture was sparged, charged with BrettPhos Pd G3 (3.076 g, 0.00309 mol, 1.00 mol %), sparged, heated at 60° C. for 18 h, cooled, quenched with water, and washed with water twice. Siliamets Thiol (20.0 g) was charged and the mixture was heated at 50 C for 2 h, cooled, and filtered to provide a toluene solution of N-(4-(diethoxymethyl)-3,5-difluorophenyl)-1-(3-fluoropropyl)azetidin-3-amine. Acetic acid (21.4 mL, 0.373 mol, 110 mol %) and water (300 mL) were added and the mixture was held at rt for 2 h. An aqueous phase was separated, treated with aqueous NaOH (50 wt %, 21.5 mL, 0.407 mol, 120 mol %), and seeded with 2,6-difluoro-4-((1-(3-fluoropropyl)azetidin-3-yl)amino) benzaldehyde (923 mg, 0.00339 mol, 1.00 mol %). The resulting solids were filtered, washed with water, and dried to provide 2,6-difluoro-4-((1-(3-fluoropropyl)azetidin-3-yl)amino)benzaldehyde (77.9 g, 84.3% yield) as a white solid. $^1$H NMR (400 MHz, CDCl$_3$) δ 10.05 (dd, J=1.2 Hz, 1H), 6.05-5.97 (m, 2H), 5.03 (d, J=6.4 Hz, 1H), 4.54 (t, J=6.0 Hz, 1H), 4.42 (t, J=6.0 Hz, 1H), 4.14-4.03 (m, 1H), 3.70 (td, J=6.8, 1.6 Hz, 2H), 2.99-2.93 (m, 2H), 2.59 (t, J=7.2 Hz, 2H), 1.83-1.66 (m, 2H). MS: calcd for $C_{13}H_{15}F_3N_2O$ [M+H]$^+$=273.1, observed=273.0.

In step 5, a reactor was charged with (R)-3-((1-(1H-indol-3-yl)propan-2-yl)amino)-2,2-difluoropropan-1-ol (6.60 kg, 24.60 mol, 100 mol %), 2,6-difluoro-4-((1-(3-fluoropropyl)azetidin-3-yl)amino)benzaldehyde (6.70 kg, 24.60 mol, 100 mol %), L-tartaric acid (5.54 kg, 36.90 mol, 150 mol %), and ethanol (39.6 L). The reaction mixture was heated at 70° C. for 2 h, seeded with 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol (2R,3R)-2,3-dihydroxysuccinate (0.0827 kg, 0.123 mol, 0.5 mol %), agitated at 70° C. for 2 days, quenched with ethanol (26.4 L), cooled, and filtered to collect solid. The solid was washed with ethanol and dried under vacuum to provide 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol (2R,3R)-2,3-dihydroxysuccinate (12.7 kg, 78% yield) as an off white solid.

Various acids other than tartaric acid, as well as a comparative example with tartaric acid, were evaluated for the step 5 ring closure reaction generally according to the procedure immediately above. The results are reported in Table 5 below where "Exp." refers to experiment number, and "Conv" refers to the conversion to the fused tricyclic ring structure. The tartaric acid salt resulted in substantial increase in the final yield. Further, the tartaric acid salt minimized presence of byproduct oligomers formed during synthesis, resulting in purer product and less epimerization of the final compound product.

TABLE 5

Acids tested for ring closure for Compound A

| Exp. | Acid | Conv. | Comments |
|---|---|---|---|
| 9B | Acetic | 95% | 20% ring opening by-product |
| 9C | Trifluoroacetic | 20% | — |
| 9D | Methanesulfonic | 43% | — |
| 9E | Benzoic | 17% | — |
| 9F | Pivalic | 77% | 12% ring opening by-product |
| 9G | Diphenylphosphoric | 97% | 61% isolated yield and 6% oligomers |
| 9H | Triflic | 60% | — |
| 9I | Formic | 29% | — |
| 9J | Tartaric | 97% | 89% isolated yield and 0.3% oligomers |
| 9K | Fumaric | 92% | 70% isolated yield and 6% oligomers |

Example 9

Recrystallization of Compound B:

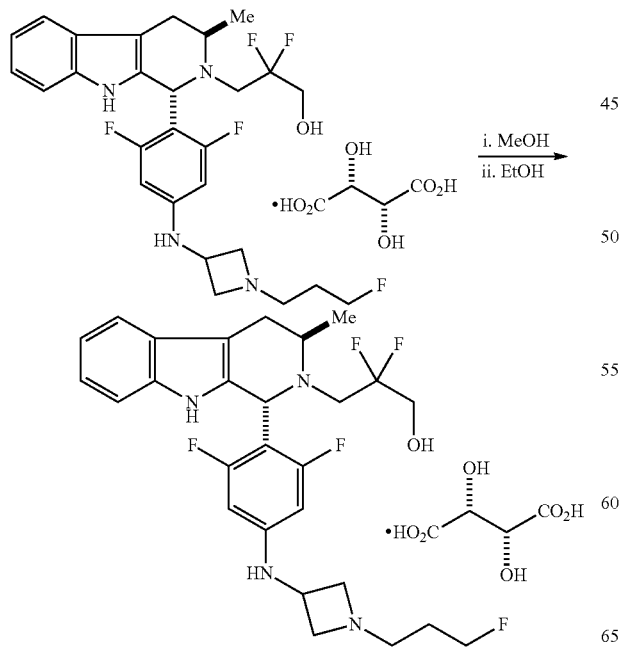

To a 250 mL reactor was charged crude Compound B (4.00 g, 5.95 mmol) in MeOH (90.0 mL) and EtOH (10.0 mL) mixture. The slurry was heated to 60° C. and became homogeneous. Compound B seeds (200 mg, 0.297 mmol, 5 mol %) were added into the solution. The slurry was distilled with EtOH, cooled to 25° C. over 1 h, held at 25° C. for 1 h, filtered, dried to provide Compound B (3.83 g, 91% yield) as an off white solid.

Example 10

Recrystallization of Compound B:

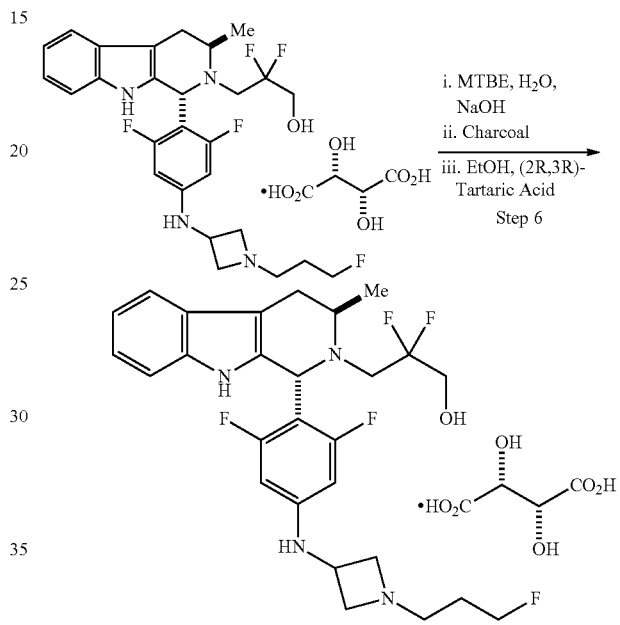

Example 10A: To a 30 L reactor was charged crude Compound B (1.26 kg, 1.88 mol, 100 mol %) and MTBE (6.30 L, 5.00 mL/g). A solution of NaOH (154 g, 3.85 mol, 205 mol %) in water (6.30 L, 5.00 mL/g) was added into the slurry. The reaction mixture was stirred at 20° C. for 30 min. The top organic layer was washed with water (2.53 L, 2.00 mL/g) twice, passed through charcoal cartridge, distilled with EtOH to provide Compound B freebase solution in EtOH.

Example 10B: To a 20 L reactor was charged with L-tartaric acid (296 g, 1.97 mol, 105 mol %), EtOH (2.52 L, 2.00 mL/g) and heated to 70° C. 20% of Compound B freebase solution was transferred into the 20 L reactor. Compound B seeds (25.2 g, 0.0375 mol, 2 mol %) were added into the solution. The rest of Compound B freebase solution was transferred into the 20 L reactor over 1 h, aged at 70° C. for 30 min, cooled to 20° C. over 5 h, aged at 20° C. for a minimum of 2 h, filtered, washed with EtOH (2.52 L, 2.00 mL/g) three times, dried to provide Compound B (1.12 kg, 89%) as an off white solid.

Example 11

Compounds provided herein were characterized by mass spectrometry and/or NMR techniques as understood in the art. The compounds of this example, unless otherwise noted, have verified stereochemistry.

Compound (M1)

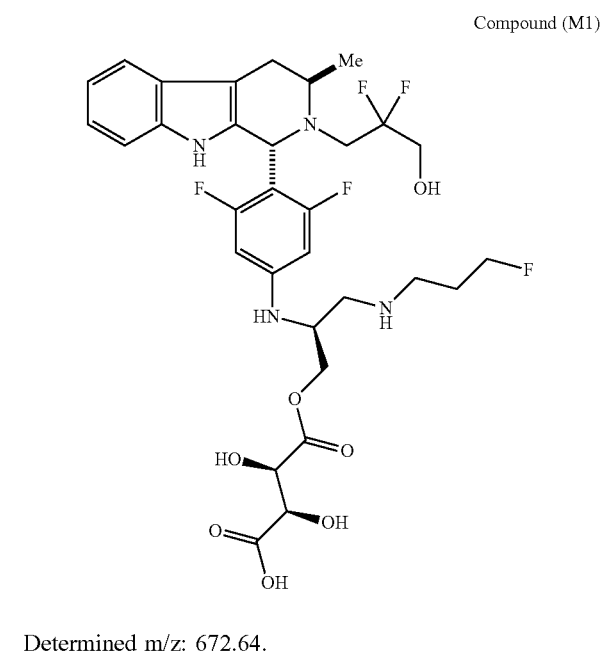

Determined m/z: 672.64.

Compound (M2)

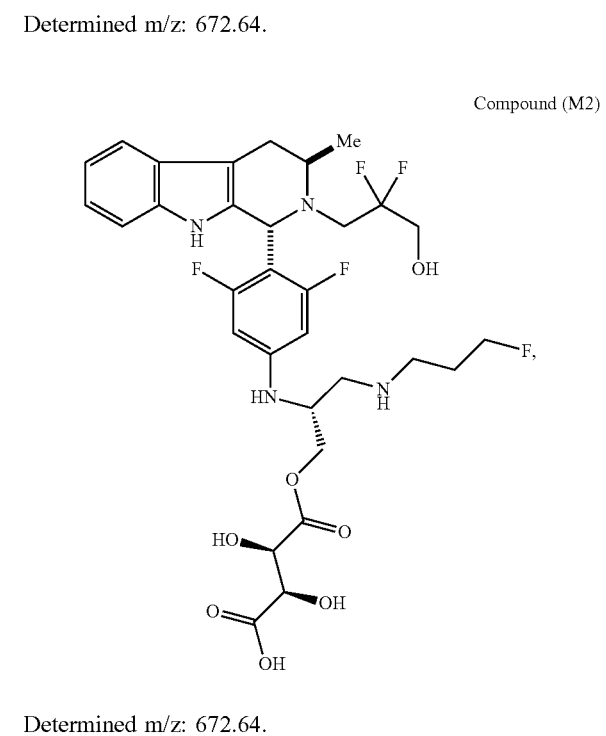

Determined m/z: 672.64.

Compound (M3)

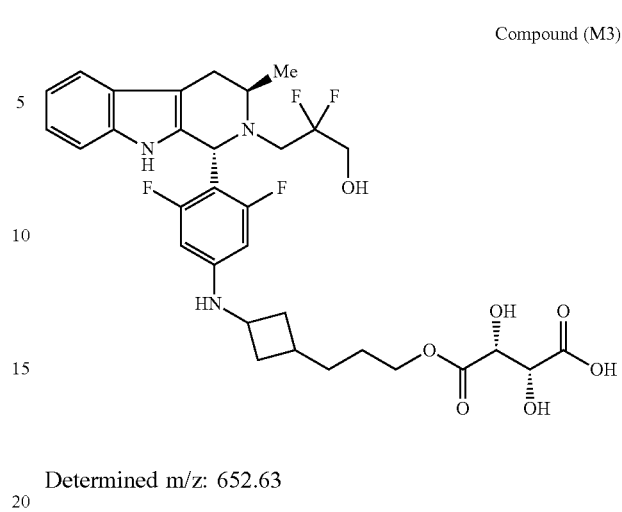

Determined m/z: 652.63

Compound (M4)

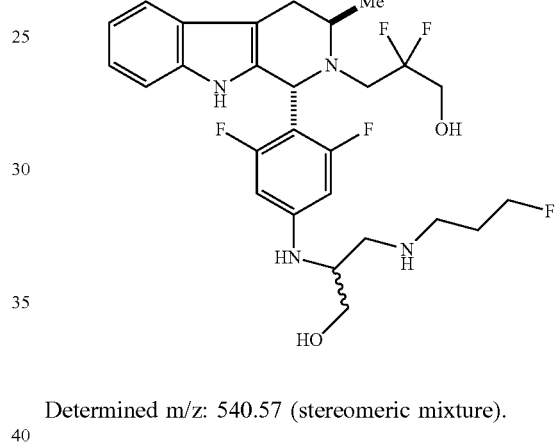

Determined m/z: 540.57 (stereomeric mixture).

Example 12

Enzymatic Transformations:

The screening of transaminases in the kinetic resolution mode of rac. alpa-methyltryptamine revealed enzymes possessing sufficient (R)-enantioselectivity for the asymmetric reductive amination approach and sufficient (S)-enantioselectivity for the kinetic resolution approach. Exemplary transaminases are listed in Table 6.

TABLE 6

| Enantioselective transaminases (TA): | |
|---|---|
| (R)-enantioselective TAs | (S)-enantioselectivity TAs |
| TA-P2-A01 (Codexis) | TA-P1-F03 [Codexis] |
| ESC-ATA01 (Libragen) | TA-P1-G05 [Codexis] |
| TA-P2-A07 (Codexis) | ATA47 [c-LEcta] |
| ATA117 (Codexis) | 3FCR_59F_87F_231G* |
| ESC-ATA03 (Libragen) | 3FCR_59W_87F_231A* |
|  | 3FCR_59F_86A_87F_152F_231A_234M_382M* |
|  | 3HMU_264V* |
|  | ATA12 |

Asymmetric reduction applying transaminase TA-P2-A07 was performed in buffer; iso-propyl amine and organic co-solvents such as DMSO or Acetonitrile on 5 g scale. Compound (XXI) was converted to compound (3) as described herein at a degree above 95% with an enantiomeric excess (EE) above 99% after 1 day.

The reductive amination was also performed in organic solvents containing small amounts of buffer and iso-propyl amine where the transaminase TA-P2-A07 was immobilized on the solid support. Compound (XXI) was converted to compound (3) at a conversion degree above 95% and an EE above 99% after 4 weeks. The organic solvent enabled higher substrates loadings up to 5% [w/w].

Kinetic resolution was performed in the presence of transaminase ATA12 in (1) whole cells; (2) cell free lysate or (3) crude lyophilisate in buffer containing pyruvate and organic cosolvent such as acetonitrile. Enantiomeric excess of >99% was achieved. Conversion to compound (3) was achieved at a degree equal to or above 50%. The undesired enantiomer was depleted by oxidative deamination towards the ketone.

```
Sequence Identification of select TAs:
3FCR Y59F/Y87F/T231G: amino acid
                                                              (SEQ ID NO: 1)
MLKNDQLDQW  DRDNFFHPST  HLAQHARGES  ANRVIKTASG  VFIEDRDGTK  LLDAFAGLFC    60

VNVGYGRQEI  AEAIADQARE  LAYYHSFVGH  GTEASITLAK  MILDRAPKNM  SKVYFGLGGS   120

DANETNVKLI  WYYNNILGRP  EKKKIISRWR  GYHGSGLVTG  SLTGLELFHK  KFDLPVEQVI   180

HTEAPYYFRR  EDLNQTEEQF  VAHCVAELEA  LIEREGADTI  AAFIGEPILG  GGGIVPPPAG   240

YWEAIQTVLN  KHDILLVADE  VVTGFGRLGT  MFGSDHYGLE  PDIITIAKGL  TSAYAPLSGS   300

IVSDKVWKVL  EQGTDENGPI  GHGWTYSAHP  IGAAAGVANL  KLLDELNLVS  NAGEVGAYLN   360

ATMAEALSQH  ANVGDVRGEG  LLCAVEFVKD  RDSRTFFDAA  DKIGPQISAK  LLEQDKIIAR   420

AMPQGDILGF  APPFCLTRAE  ADQVVEGTLR  AVKAVLG                              457

3FCR Y59W/Y87F/T231A: amino acid
                                                              (SEQ ID NO: 2)
MLKNDQLDQW  DRDNFFHPST  HLAQHARGES  ANRVIKTASG  VFIEDRDGTK  LLDAFAGLWC    60

VNVGYGRQEI  AEAIADQARE  LAYYHSFVGH  GTEASITLAK  MILDRAPKNM  SKVYFGLGGS   120

DANETNVKLI  WYYNNILGRP  EKKKIISRWR  GYHGSGLVTG  SLTGLELFHK  KFDLPVEQVI   180

HTEAPYYFRR  EDLNQTEEQF  VAHCVAELEA  LIEREGADTI  AAFIGEPILG  AGGIVPPPAG   240

YWEAIQTVLN  KHDILLVADE  VVTGFGRLGT  MFGSDHYGLE  PDIITIAKGL  TSAYAPLSGS   300

IVSDKVWKVL  EQGTDENGPI  GHGWTYSAHP  IGAAAGVANL  KLLDELNLVS  NAGEVGAYLN   360

ATMAEALSQH  ANVGDVRGEG  LLCAVEFVKD  RDSRTFFDAA  DKIGPQISAK  LLEQDKIIAR   420

AMPQGDILGF  APPFCLTRAE  ADQVVEGTLR  AVKAVLG                              457

3FCR Y59F/S86A/Y87F/Y152F/T231A/I234M/L382M: amino acid
                                                              (SEQ ID NO: 3)
MLKNDQLDQW  DRDNFFHPST  HLAQHARGES  ANRVIKTASG  VFIEDRDGTK  LLDAFAGLFC    60

VNVGYGRQEI  AEAIADQARE  LAYYHAFVGH  GTEASITLAK  MILDRAPKNM  SKVYFGLGGS   120

DANETNVKLI  WYYNNILGRP  EKKKIISRWR  GFHGSGLVTG  SLTGLELFHK  KFDLPVEQVI   180

HTEAPYYFRR  EDLNQTEEQF  VAHCVAELEA  LIEREGADTI  AAFIGEPILG  AGGMVPPPAG   240

YWEAIQTVLN  KHDILLVADE  VVTGFGRLGT  MFGSDHYGLE  PDIITIAKGL  TSAYAPLSGS   300

IVSDKVWKVL  EQGTDENGPI  GHGWTYSAHP  IGAAAGVANL  KLLDELNLVS  NAGEVGAYLN   360

ATMAEALSQH  ANVGDVRGEG  LMCAVEFVKD  RDSRTFFDAA  DKIGPQISAK  LLEQDKIIAR   420

AMPQGDILGF  APPFCLTRAE  ADQVVEGTLR  AVKAVLG                              457

3HMU I264V: amino acid
                                                              (SEQ ID NO: 4)
MATITNHMPT  AELQALDAAH  HLHPFSANNA  LGEEGTRVIT  RARGVWLNDS  ALAQKLAELA    60

GLWCVNIGYG  RDELAEVAAR  QMRELPYYNT  FFKTTHVPAI  ALAQKLAELA  PGDLNHVFFA   120

GGGSEANDTN  IRMVRTYWQN  KGQPEKTVII  SRKNAYHGST  VASSALGGMA  GMHAQSGLIP   180

DVHHINQPNW  WAEGGDMDPE  EFGLARAREL  EEAILELGEN  RVAAFIAEPV  QGAGGVIVAP   240

DSYWPEIQRI  CDKYDILLIA  DEVVCGFGRT  GNWFGTQTMG  IRPHIMTTAK  GLSSGYAPIG   300
```

```
-continued
GSIVCDEVAH VIGKDEFNHG YTYSGHPVAA AVALENLRIL EEENILDHVR NVAAPYLKEK    360

WEALTDHPLV GEAKIVGMMA SIALTPNKAS RAKFASEPGT IGYICRERCF ANNLIMRHVG    420

DRMIISPPLV ITPAEIDEMF VRIRKSLDEA QAEIEKQGLM KSAA                    464
```

Bolded and underline residues correspond to mutations to natural sequence.

Example 13

Freebase, Salt, and Polymorph Characterization of Compound A

Abbreviations

MIBK Methyl Isobutyl Ketone
ACN Acetonitrile
EtOAc Ethyl Acetate
EtOH Ethanol
MTBE Methyl Tert-butyl Ether
IPAc Isopropyl Acetate
MeTHF Methyl Tetrahydrofuran
CPME Cyclopentyl methyl ether
MeOH Methanol
THF Tetrahydrofuran
IPA Isopropyl Alcohol
DMSO Dimethyl Sulfoxide
DMC Dimethyl Carbonate
MEK Methyl Ethyl Ketone
DCM Dichloromethane Free-base Polymorph Screening. 96-well plate automated High-throughput Screening (HTS) using the Symyx CM2 system (Freeslate Inc., CA) was conducted to identify potential polymorphic forms for Compound A free base. Compound A was dispensed in each well (8 mg/well) using an automated powder dispensing accessory following which 800 µl of solvent (neat or mixture) was added and the slurry was stirred for 2 hours at 50° C. Compound A was initially dispensed in the slurry plate using either ethyl acetate (for tartrate) or MIBK (for fumarate) to maintain the solid form. From this master plate, the supernatant was filtered and distributed to three separate plates for evaporation, precipitation by anti-solvent addition and controlled cooling over 8-10 hrs from 50-20° C. In all cases residual solvents were either evaporated or siphoned off, and the solid was examined using polarized light microscopy and XRPD.

Example 14

Salt Screening. According to approximate solubility data of freebase and list of desired acids, five solvent systems were used in the screening. Approximately 20 mg of freebase amorphous compound was first dispersed in 0.5 mL of selected solvent in a glass vial and corresponding acid was then added with a 1:1 ratio of molar charge. An extra molar ratio of 2:1 (acid/freebase) was attempted for HCl, due to the two basic functional groups. The mixtures were stirred at RT overnight. Resulted solids were analyzed by XRPD. Clear solutions obtained after stirring were stirred at 5° C. for 2 days, then 0.5 mL of $H_2O$ was added into each of clear solutions in ACN/$H_2O$ (19:1, v/v) while 0.5 mL of n-heptane was added into each of the clear solutions in the other solvent systems followed by stirring at 5° C. for around 3 days, and the final clear solutions were transferred to slow evaporation at RT, in order to identify as many crystalline hits as possible.

The first round of screening identified the crystalline form hits as provided in Table 7. Tartrate and fumarate were further scaled up to 50 mg-1.5 g scale for further characterization. Testing in different solvent systems and conditions allowed for a) in-depth characterization of the different polymorphic forms obtained as hits in the screening and b) identifying conditions to inhibit and control cis-epimer formation. The epimer content varied from <1%-22% in different free base lots.

TABLE 7

Salt screening and crystalline form hits for Compound A.

| | Solvent | | | | |
|---|---|---|---|---|---|
| Acid | A Acetone | B IPA | C EtOAc | D THF | E ACN/H2O (19:1 v/v) |
| Blank | Yellow gel | Yellow gel | Yellow gel | Light yellow gel | Yellow gel |
| Acetic Acid | Yellow gel | Yellow gel | Yellow gel | Yellow gel | Yellow gel |
| Benzene Sulfonic Acid | Yellow oil | Yellow gel | Yellow gel | Yellow gel | Yellow gel |
| Citric Acid | Yellow oil | Yellow gel | Amorphous | Yellow gel | Yellow gel |
| Ethane sulfonic acid | Yellow oil | Yellow gel | Amorphous | Yellow gel | Yellow gel |
| 1,2-Ethanedisulfonic acid | Amorphous | Amorphous | Amorphous | Amorphous | Dark blue gel |
| Fumaric acid | Yellow oil | Yellow gel | Fumarate Form A | Fumarate Form A | Yellow gel |
| Formic acid | Yellow gel | Yellow gel | Yellow gel | Yellow gel | Yellow gel |
| Gentisic acid | Yellow oil | Yellow gel | Yellow gel | Yellow gel | Yellow gel |
| Glutamic acid | Glutamic acid | Glutamic acid | Glutamic acid | Glutamic acid | Yellow gel |
| Hydrochloric acid (1:1) | Yellow oil | Yellow gel | Yellow gel | Yellow gel | Yellow gel |
| Hydrochloric acid (2:1) | Yellow oil | Yellow gel | Yellow gel | Yellow gel | Yellow gel |
| Methanesulfonic acid | Yellow oil | Yellow gel | Yellow gel | Yellow gel | Yellow gel |
| Malonic acid | Yellow oil | Yellow gel | Yellow gel | Malonate Form A | Yellow gel |
| Maleic acid | Yellow gel | Yellow gel | Yellow gel | Yellow gel | Yellow gel |
| Phosphoric acid | Yellow oil | Yellow gel | Yellow gel | Yellow gel | Yellow gel |
| p-Toluene sulfonic acid | Yellow oil | Yellow gel | Yellow gel | Yellow gel | Yellow gel |

TABLE 7-continued

Salt screening and crystalline form hits for Compound A.

| | Solvent | | | | |
|---|---|---|---|---|---|
| Acid | A<br>Acetone | B<br>IPA | C<br>EtOAc | D<br>THF | E<br>ACN/H2O<br>(19:1 v/v) |
| Succinic acid | Yellow oil | Yellow gel | Yellow gel | Yellow gel | Yellow gel |
| Sulfuric acid | Yellow gel | Amorphous | Amorphous | Yellow gel | Yellow gel |
| L-Tartaric acid | Tartrate Form A | Yellow gel | Tartrate Form B | Tartrate Form C | Yellow gel |

Methods:

Ambient X-ray Powder Diffractometry (XRPD). XRPD patterns were collected using the PANalytical Empyrean powder X-ray diffractometer (PANalytical Inc., Lelyweg, Netherlands). The powder sample was packed in a zero-background silicon holder and run in reflection mode (Bragg Brentano configuration). The instrument was equipped a Cu Kα source with tube voltage and current of 45 kV and 40 mA respectively. Data was collected at ambient temperature from 3.0 to 40.0° 2θ using a step size of 0.0263°, with a revolution speed of 8 sec. The incident beam path was equipped with a 0.02° soller slit, a fixed 1° anti scatter slit, a fixed incident beam mask of 10 mm, and a programmable divergence slit in automatic mode. A beam knife for linear detectors was used. The diffracted beam was equipped with a 0.02° soller slit, a programmable anti scatter slit in automatic mode, and a nickel K-β filter. A PIXcel 1D detector was used in the scanning line detector (1D) mode. Data was analyzed using commercial software (JADE®, version 9, Materials Data Inc., Livermore, CA).

Water sorption analysis. About 5-6 mg of powder sample was placed in the sample pan of an automated water sorption analyzer (Q5000SA, TA instruments, New Castle, DE) at 25° C. and a nitrogen flow rate of 200 mL/min. The sample was initially "dried" at 0% RH for a total of 400 minutes (at 60 followed by 25° C.), following which it was subjected to progressive increase in RH from 0-90%, in increments of 10% with a dwell time of 200 minutes at every RH. This was followed by a progressive decrease in RH in decrements of 10% back to 0% RH, using the same protocol.

Differential Scanning Calorimetry (DSC). Approximately 3-8 mg of powder sample was analyzed using a DSC Q2000™ (TA instruments, New Castle, DE) equipped with a refrigerated cooling accessory. Samples were packed in non-hermetically pans (Tzero™, aluminum pans) and typically heated from 0-200° C. at 10° C./min under dry nitrogen purge. The instrument was calibrated using sapphire (baseline) and indium (temperature and cell constant). The data was analyzed using commercial software (Universal Analysis 2000, version 4.7A, TA Instruments).

Thermogravimetry (TGA). In a thermogravimetric analyzer (Discovery TGA, TA instruments), 3-5 mg of Compound A samples were heated in an open aluminum pan from RT to 350° C. at a heating rate of 10° C./min under dry nitrogen purge. Temperature calibration was performed using Alumel® and Nickel. Standard weights of 100 mg and 1 gm were used for weight calibration.

Polarized Light Microscopy (PLM). Samples were dispersed in silicon oil and observed under cross polarizers of a video enhanced Leica DM 4000B microscope equipped with a high resolution CCD camera and motorized stage (Clemex Technologies Inc., Longueuil, Quebec, Canada) at 200× magnification. Photomicrographs were acquired using the Clemex Vision PE software (Clemex Technologies Inc., Longueuil, Quebec, Canada).

Scanning electron microscopy (SEM). Powder sample sputter coated on SEM stub and then examined using a benchtop Phenom SEM (Nanoscience Instruments, Inc., AZ). Micrographs were acquired at different magnifications.

Particle size distribution (PSD). Particle size analysis was performed using a Malvern Mastersizer 2000 instrument equipped with a Hydros 2000SM wet dispersion attachment (Malvern Instruments Ltd., Malvern, UK). ~40 mg of API was weighed into a vial and 1 mL of 0.1% Span 85 in heptane was added. The vial was sonicated for 10 seconds, about 0.5 mL was added to the sampler at a stir speed of 1500 rpm, and a PSD was performed at an obscuration of 10-20%. Owing to presence of large clusters in the sample that were settling rapidly out of the suspension, the dispersant was changed to 0.2% Span 85 in heptane to stabilize the suspension. External sonication of 2 followed by two 5 minute duration was applied to break the clusters and PLM images were acquired before and after sonication. The aliquot was mixed in the sampler for 2 minutes prior to data collection to ensure homogeneity. The instrument was rinsed twice with isopropyl alcohol (IPA) and once with heptane before being filled with 0.1% Span 85 in heptane for each sample. After the last sample had run, the instrument was rinsed with IPA once. Data for replicates with 5 minute sonication has been reported.

BET Surface area analysis. Surface area measurement was conducted using a Micromeritics ASAP 2460 with a Micromeritics Smart VacPrep attachment (Micromeritics Instrument Corp., GA). A sample of 500 mg-1 g was weighed into an empty ASAP 2460 tube and placed on the Smart VacPrep, degassed for 24 hours under ambient conditions and then exposed to Krypton gas adsorption at 25° C. and 100 mm Hg hold pressure. An 11 point measurement was made in the relative pressure range of 0.050-0.300 and the data was analyzed using MicroActive software provided by the vendor.

Solid-state Nuclear Magnetic Resonance Spectroscopy (SSNMR). All $^{13}$C (@ 8 kHz spinning speed) SSNMR experiments were conducted using the 500 Mhz Bruker instrument (Bruker BioSpin GmbH, Karlsruhe, Germany) $^{13}$C data were acquired using a CP/TOSS sequence. 1-2 K scans were collected for signal averaging. A contact time of 2-ms and a recycle delay of 5 seconds was used. Spinal 64 sequence was used for decoupling with a pulse length of 5.3 microseconds. $^{1}$H 90 degree pulse length of 2.9 microseconds was employed. All $^{19}$F (@ 14 kHz spinning speed) SSNMR experiments were conducted using the 500 Mhz Bruker instrument. $^{19}$F data were acquired using a CP and direct polarization sequences. 64-256 K scans were collected for signal averaging. A contact time of 750 microseconds and a recycle delay of 7 seconds was used. ¹H 90 degree pulse length of 3.54 microseconds was employed.

Example 15

Preliminary characterization of Compound A free base. Compound A free base was found to be amorphous. The starting material free base Compound A was characterized by XRPD, TGA and mDSC before screening). As shown by the characterization results in FIG. 33 and FIG. 34, Compound A starting material was amorphous with a weight loss of 9.3% up to 220° C. in TGA and no substantial glass transition signal in mDSC. White solids of freebase Compound A were obtained by anti-solvent addition in MeOH/$H_2O$ (3:20, v/v) with shaking and air dried for ~7 days.

Polymorph Screening. The solubility of freebase Compound A was estimated in 16 solvents at RT. (Table 8). Polymorph screening experiments were performed using different solution crystallization or solid phase transition methods. The methods uses and crystal forms identified are summarized in Table 9.

TABLE 8

Approximate solubility of freebase Compound A

| Solvent | Solubility (mg/mL) | Solvent | Solubility (mg/mL) |
| --- | --- | --- | --- |
| Acetone | S > 60.0 | MIBK | S > 60.0 |
| 2-propanol | S > 60.0 | MTBE | S > 60.0 |
| EtOAc | S > 60.0 | IPAc | S > 60.0 |
| ACN | S > 60.0 | MeTHF | S > 60.0 |
| $H_2O$ | S < 1.9* | CPME | S > 44.0* |
| 1,4-Dioxane | S > 60.0 | n-Heptane | S < 2.1* |
| EtOH | S > 60.0 | Cyclohexanes | S < 1.9* |
| Toluene | S > 60.0 | Iso-butanol | S > 40.0* |

TABLE 9

Summary of polymorph screening of freebase Compound A

| Method | No. of Experiments | Final Results |
| --- | --- | --- |
| Solid Vapor Diffusion | 13 | Amorphous |
| Slurry at RT | 25 | Amorphous |
| Anti-solvent Addition | 15 | Amorphous |
| Liquid Vapor Diffusion | 14 | Amorphous |
| Slow Evaporation | 12 | Gel |
| Total | 79 | Amorphous |

Solid Vapor Diffusion. Solid vapor diffusion experiments were conducted using 13 different kinds of solvent. For each experiment, about 15 mg of starting material was weighed into a 3-mL vial, which was placed into a 20-mL vial with 2 mL of corresponding volatile solvent. The 20-mL vial was sealed with a cap and kept at RT for 11 days to allow the solvent vapor to interact with the solid sample. The isolated solids were tested by XRPD. As summarized in Table 10, only oil or amorphous was obtained.

TABLE 10

Summary of solid vapor diffusion experiments

| Solvent | Final Results |
| --- | --- |
| $H_2O$ | Amorphous |
| DCM | N/A |
| EtOH | Oil |
| MeOH | Oil |

TABLE 10-continued

Summary of solid vapor diffusion experiments

| Solvent | Final Results |
| --- | --- |
| ACN | Oil |
| THF | N/A |
| $CHCl_3$ | Oil |
| Acetone | N/A |
| DMF | Oil |
| EtOAc | N/A |
| 1,4-Dioxane | N/A |
| IPA | Oil |
| DMSO | Oil |

Slurry Conversion at RT. Slurry conversion experiments were conducted at RT in different solvent systems. About 40 mg of starting material was suspended in 0.3 mL of solvent in a 1.5-mL glass vial. After stirring, all the clear solutions were transferred to 5° C., followed by slow evaporation at RT after 3 days. Results summarized in Table 11 indicated that only amorphous, gel or oil was obtained.

TABLE 11

Summary of slurry conversion experiments for freebase Compound A

| Solvent, v:v | Final Results |
| --- | --- |
| MeOH | Gel |
| EtOH | Gel |
| IPA | Gel |
| ACN | Gel |
| Acetone | Gel |
| THF | Gel |
| EtOAc | Gel |
| 2-MeTHF | Gel |
| DCM | Gel |
| CPME | Gel |
| Acetic acid | Gel |
| DMC | Gel |
| Triethylamine | N/A |
| MIBK | Gel |
| MTBE | Gel |
| Iso-butanol | Gel |
| Acetone/$H_2O$ (1:1) | Oil |
| ACN/$H_2O$ (1:1) | Oil |
| EtOH/$H_2O$ (1:1) | Gel |
| EtOH/n-heptane (1:1) | Gel |
| Xylene | N/A* |
| Cumene | N/A* |
| Cyclohexane | Amorphous** |
| N-heptane | Amorphous** |
| $H_2O$ | Amorphous** |

*no slow evaporation was applied
**solids were centrifuged and analyzed by XRPD after stirring at RT for 4 days
N/A: no solid obtained Anti-solvent Addition. A total of 15 anti-solvent addition experiments were carried out. About 30 mg of starting material was weighed into a 20-mL glass vial and dissolved in 0.15 mL of corresponding solvent at RT. Anti-solvent was added stepwise till the precipitation appeared or the total amount of anti-solvent reached 12 mL, with the sample being stirred magnetically. The precipitate was isolated for XRPD analysis. If no solid was observed, the clear solutions were stirred magnetically at 5° C. overnight and then evaporated at RT. Results in Table 12 showed that only amorphous or gel was generated.

TABLE 12

Summary of anti-solvent additions
experiments for freebase Compound A

| Solvent | Anti-solvent (v:v) | Final Results |
|---|---|---|
| MeOH | H₂O | Amorphous |
| EtOH |  | Amorphous |
| Acetone |  | Gel |
| THF |  | Gel |
| ACN |  | Gel |
| EtOH | Cyclohexane | Gel |
| Acetone |  | Gel |
| EtOAc |  | Gel |
| THF |  | Gel |
| EtOH | n-Heptane | Gel |
| Acetone |  | Gel |
| EtOAc |  | Gel |
| THF |  | Gel |
| MeOH | MeOH/H₂O (1:8) | Amorphous |
| EtOH | EtOH/H₂O (1:8) | Amorphous |

Liquid Vapor Diffusion. Liquid vapor diffusion experiments were conducted under 14 conditions (Table 13). About 30 mg of starting material was weighed into each 3-mL glass vial. The corresponding solvent was added to get a solution. The vial was sealed into the 20-mL glass vial with 3-mL of corresponding anti-solvent and kept at RT, allowing about 11 days for the vapor to interact with solution. The precipitates were isolated for XRPD analysis. Clear solutions were transferred to evaporation at RT.

TABLE 13

Summary of liquid vapor diffusion
experiments for freebase Compound A

| Solvent | Anti-solvent | Final Results |
|---|---|---|
| n-Butanol | Cyclohexane | Gel |
|  | n-Heptane | Gel |
| Xylene | Cyclohexane | Amorphous |
|  | n-Heptane | Amorphous |
| Cumene | Cyclohexane | Amorphous |
|  | n-Heptane | Amorphous |
| MEK | Cyclohexane | Gel |
|  | n-Heptane | Gel |
| IPAc | Cyclohexane | Gel |
|  | n-Heptane | Gel |
| THF | H₂O | Amorphous |
|  | Cyclohexane | Amorphous |
|  | n-Heptane | Amorphous |
| ACN | H₂O | Gel |

Slow Evaporation. Slow evaporation experiments were performed under 12 conditions. For each experiment, around 20 mg of starting material was weighed into a 3-mL glass vial, followed by the addition of corresponding solvent or solvent mixture to get a clear solution. Subsequently, the vial was covered with parafilm with 3~4 pinholes, and kept at 4° C. to allow the solution to evaporate slowly. Only gel was obtained, as summarized in Table 14.

TABLE 14

Summary of slow evaporation experiments
for freebase Compound A

| Solvent (v/v) | Final Results |
|---|---|
| Xylene | Gel |
| Cumene | Gel |
| IPAc | Gel |
| MIBK | Gel |

TABLE 14-continued

Summary of slow evaporation experiments
for freebase Compound A

| Solvent (v/v) | Final Results |
|---|---|
| MTBE | Gel |
| DCM/n-heptane (1:1) | Gel |
| THF/n-heptane (1:1) | Gel |
| Acetone/H₂O (1:1) | Gel |
| IPAc/cyclohexane (1:1) | Gel |
| MTBE/cyclohexane (1:1) | Gel |
| EtOH/H₂O (1:1) | Gel |
| EtOH/n-heptane (1:1) | Gel |

Table 15 summarizes the forms that were obtained via manual screening as described herein.

TABLE 15

Polymorphic forms of Compound A

| Form | Type |
|---|---|
| Polymorph screening: Compound A free base | |
| N/A | No crystalline hits identified |
| Salt screening: Compound A free base | |
| A-tartrate | Acetone solvate |
| B-tartrate | Anhydrate |
| C-tartrate | THF solvate |
| A-malonate | THF solvate |
| A-fumarate | Anhydrate |
| Polymorph screening: Compound A tartrate | |
| D | Hydrate |
| E | DMSO solvate |
| F | Anhydrate |
| G | Methanol solvate |

Example 16

Figure 2A:
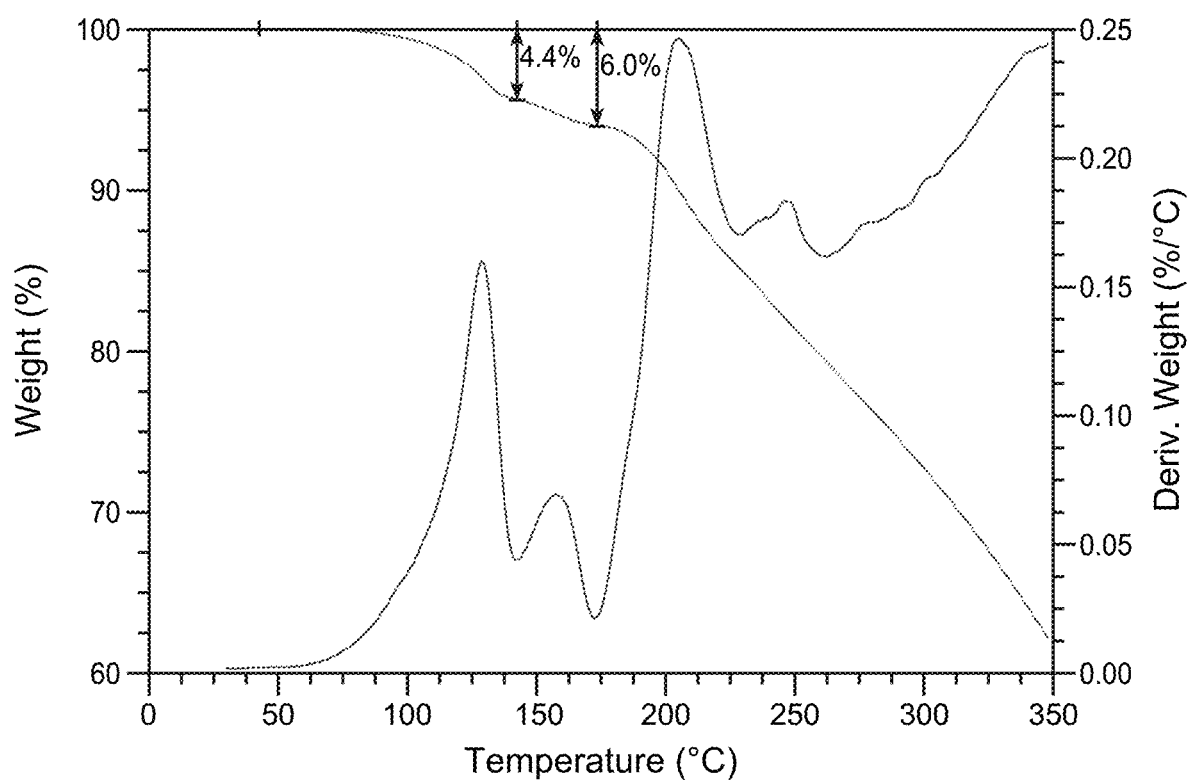
FIG. 2A depicts the TGA and FIG. 2B depicts the DSC for Compound B Form A.
Figure 2B:
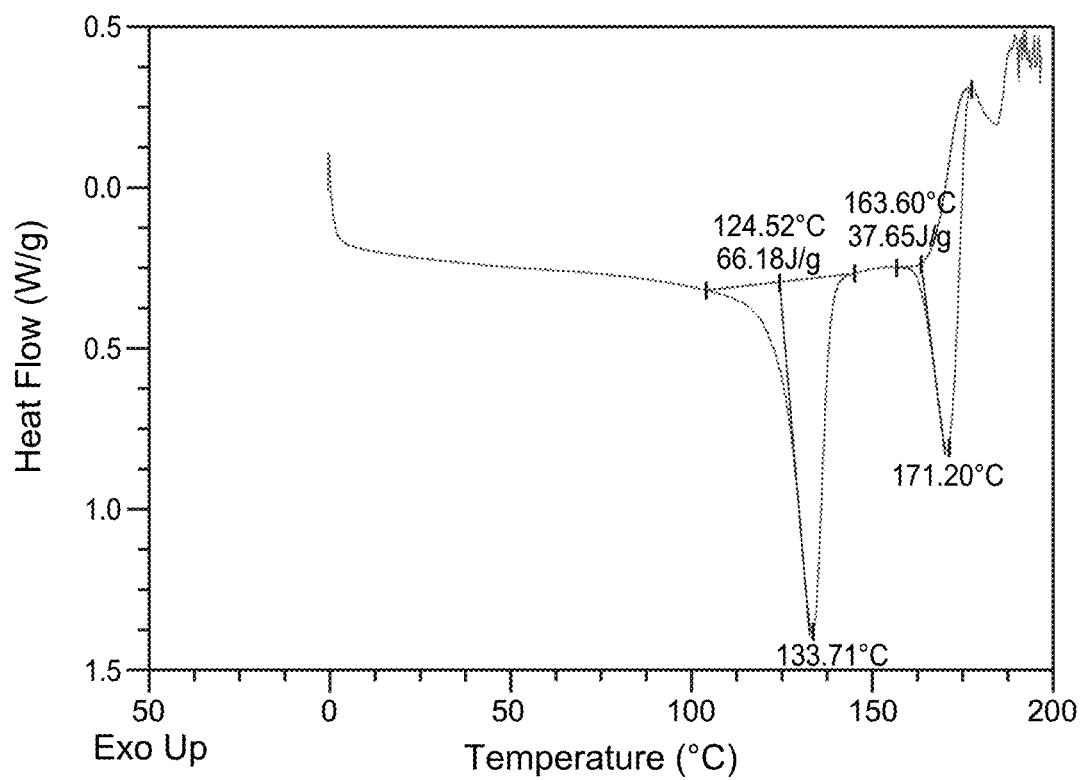

Characterization of Compound B Form A. Compound B Form A was prepared at 200-mg scale via solution reactive crystallization in acetone, as evidenced by XRPD (FIG. 1). As shown in FIG. 2a and FIG. 2b, weight loss of about 7.2% up to 125° C. was observed in TGA and DSC result showed one endotherm at 124.3° C. (onset temperature). ¹H NMR showed that its molar ratio was 0.98 (acid/freebase) and 5.6% acetone (a molar ratio of 0.69 to freebase) was detected. Heating experiments were conducted to further identify Form A. No form change was observed after Form A was heated to 90° C., but the sample turned to amorphous after being heated to 140° C. A considerable amount of acetone (4.5%) was still observed after heating Form A sample to 90° C. The Form A sample was composed primarily of fine particles and some aggregates (FIG. 3). Based on the data collected, Compound B Form A is an acetone solvate and that the loss of solvent is concomitant with melting.

TABLE 16

Representative XRPD Peaks for Compound B Form A:

| 2-Theta (°2θ) | d(Å) |
|---|---|
| 4.643 | 19.0147 |
| 8.263 | 10.6916 |
| 9.286 | 9.5157 |
| 11.183 | 7.9057 |

TABLE 16-continued

Representative XRPD Peaks for Compound B Form A:

| 2-Theta (°2θ) | d(Å) |
| --- | --- |
| 11.495 | 7.6916 |
| 11.969 | 7.3884 |
| 12.543 | 7.0515 |
| 13.776 | 6.4228 |
| 14.226 | 6.2207 |
| 14.619 | 6.0545 |
| 15.092 | 5.8656 |
| 15.564 | 5.689 |
| 16.013 | 5.5302 |
| 17.354 | 5.1058 |
| 18.559 | 4.777 |
| 18.847 | 4.7046 |
| 19.321 | 4.5903 |
| 19.821 | 4.4757 |
| 20.265 | 4.3785 |
| 21.343 | 4.1597 |
| 21.631 | 4.105 |
| 21.92 | 4.0515 |
| 22.524 | 3.9443 |
| 22.97 | 3.8686 |
| 23.285 | 3.8171 |
| 23.549 | 3.7748 |
| 23.942 | 3.7138 |
| 24.81 | 3.5858 |
| 25.964 | 3.4289 |

Preparation of Compound B Form A. About 57.5 mg of tartaric acid was weighed into a 5-mL glass vial, and 2.0 mL acetone was added to get a clear solution. The clear acid solution was added to 2.0 mL freebase stock solution in acetone (~100 mg/mL) into the 5-mL vial with a molar ratio of 1:1, and stirred at RT. About 1 mg of Compound B Form A seed was added, and the solution turned cloudy. The sample was stirred overnight before taking XRPD measurements as described herein. The pattern conformed to Compound B Form A. The suspension was then stirred at RT for another 24 hours and the cake dried at 50° C. for 1.5 hrs. Yield: 170.4 mg, with a yield of ~65.3%.

Example 17

Characterization of Compound B Form B. Compound B Form B was prepared at 200-mg scale via solution reactive crystallization in EtOAc, as evidenced by XRPD (FIG. 4). As shown in FIG. 5a and FIG. 5b, a limited weight loss of about 1.3% up to 140° C. was observed in TGA and DSC result showed a melting endothermic peak at 156.7° C. (onset temperature). Stoichiometry was determined to be 1.08 (acid/freebase) and 1.4% EtOAc (a molar ratio of 0.11 to freebase) was detected by $^1$H NMR. Based on the characterization data collected, Compound B Form B is an anhydrate.

The solid-state characterization data indicates that Form B is substantially crystalline (XRPD), and TGA indicates presence of some surface solvent of ~2% by an early onset of weight loss from RT-100° C.) with a melting onset of ~163° C. The melting onset, following a shallow endotherm (vaporization of residual solvent) is at 163° C. Based on the derivative weight loss curve, a very early onset of weight loss (2.4% w/w) was detected up to 100° C., which may be attributed to surface solvent. The total weight loss, including that at the melt is 3.5% w/w. Form B was found to be slightly hygroscopic with a moisture pick up of 1.2% w/w at 90% RH, 25° C. as shown by the water sorption-desorption profile in FIG. 8. The $^{13}$C (FIG. 6) and $^{19}$F SSNMR spectra (FIG. 7) further indicated formation of Form B. SEM (FIG. 9a, 500× magnification) and PLM (FIG. 9b, 200× magnifications) images of Compound B show Form B comprises of dense spherical aggregates.

TABLE 17

Representative XRPD Peaks for Compound B Form B:

| 2-Theta (°2θ) | d(Å) |
| --- | --- |
| 7.684 | 11.4966 |
| 11.491 | 7.6942 |
| 12.54 | 7.053 |
| 14.245 | 6.2123 |
| 15.303 | 5.7851 |
| 15.557 | 5.6912 |
| 16.014 | 5.5301 |
| 16.634 | 5.3252 |
| 17.371 | 5.1009 |
| 18.242 | 4.8593 |
| 19.163 | 4.6278 |
| 19.424 | 4.5662 |
| 19.892 | 4.4597 |
| 20.243 | 4.3833 |
| 21.817 | 4.0705 |
| 22.524 | 3.9442 |
| 22.996 | 3.8644 |
| 23.253 | 3.8223 |
| 23.573 | 3.7711 |
| 24.676 | 3.6049 |
| 25.073 | 3.5487 |
| 25.915 | 3.4353 |

Preliminary stress stability analysis of Compound B Form B. The XRPD patterns of Compound A salts (fumarate and tartrate) exposed to 40° C./75% RH for one month under open conditions. The solid form did not change under these conditions.

Although no correlation was observed between epimer content ranging from 0.56-0.72% and the solid-state properties of the different salt forms, the SSNMR, XRPD and DSC data indicate that the possibility of obtaining a mixture of forms existed from fumarate salts and that form control in either salt required a substantial amount of effort downstream, given the variability in structural data and melting points with change in crystallization conditions. The tartrate salt lacked the impurities found in the fumarate salt sample at 0.18% upon exposure to 40° C./75% RH for one month.

Compression analysis of Compound B Form B. FIG. 22, FIG. 23, and FIG. 24 demonstrate the effect of compression on Compound B tartrate Form B. 250 mg compacts of neat Compound B Form B were analyzed. Both SSNMR and XRPD (FIG. 23 and FIG. 22, respectively) show that the form remains unchanged upon compression. A lowering of the $^{19}$F T$_1$ relaxation time was observed upon compression which is attributable to generation of disorder, albeit very minor as evident from $^{19}$F SSNMR spectra of the compressed Compound B Form B in FIG. 23. $^{19}$F T$_1$ relaxation values are included in Table 18 for as is and compressed Compound B Form B. Compression did not affect the melting point of Compound B Form B, as seen in the DSC thermogram (FIG. 24). Comparative XRPD collected before and after exposure to accelerated stability conditions of 30° C./65% RH and 40° C./75% RH for up to 6 months (open) demonstrated that Compound A Form B remains unchanged upon exposure to these conditions.

TABLE 18

$^{19}$F T$_1$ relaxation times for Compound B Form B

| Sample | T$_1$ (s) for peaks at −96 to −125 ppm | T$_1$ (s) for peaks at −214 to −230 ppm |
|---|---|---|
| Uncompressed (As-is) | 12.5 | 11 |
| Compressed | 10.2 | 9 |

XRPD of one-month stability sample. The XRPD of Compound B Form B exposed to 40° C./75% RH for one month shows the Compound B Form B remains unchanged under stress stability conditions including elevated temperature and moisture.

Preparation of Compound B Form B. About 58.0 mg of tartaric acid was weighed into a 5-mL glass vial, and 2.0 mL EtOAc was added. The acid remained undissolved. About 2.0 mL freebase stock solution in EtOAc (~100 mg/mL) was added into the 5-mL vial with a molar ratio of 1:1, and the solution was stirred at RT. About 1 mg of Form B seed was added and the solution remained clear. The solution was stirred overnight and sampled by XRPD. The pattern conformed to Compound B Form B. The suspension was stirred at 50° C. for 2 more days. The suspension was centrifuged and the cake dried at 50° C. for 2 hrs. Yield: 144.5 mg, with a yield of ~56.1%.

Example 18

Preparation of Compound B Form C. Form C was prepared at 200-mg scale via solution reactive crystallization in THF, as evidenced by XRPD (FIG. 10). As shown in FIG. 11a and FIG. 11b, a weight loss of 6.8% up to 130° C. was observed in TGA and DSC showed one endotherm at 118.1° C. (onset temperature). The stoichiometric ratio was determined to be 1.02 (acid/freebase) and 9.7%

Preparation of Compound B Form C. About 56.9 mg of tartaric acid was added into a 3-mL glass vial, and added 1.0 mL THF to get a clear solution. The clear acid solution was added to 2.0 mL freebase stock solution in THF (~100 mg/mL) with a molar ratio of 1:1, and stirred at RT. About 1 mg of Form C seed was added, and the solution turned a little turbid. The suspension was stirred overnight and sampled by XRPD. The pattern conformed to Form C. The suspension was stirred at RT for another 24 hours, the cake dried at 50° C. for 1.5 hours. The suspension was centrifuged to collect the solids. Yield: 161.4 mg, with a yield of ~62.7%.

Example 19

Preparation of Compound B Form D. Form D samples were obtained via fast evaporation in MeOH/DCM and slurry in H$_2$O at RT, respectively. The XRPD pattern for Form D is shown in FIG. 12. TGA and DSC results of Form D sample are provided in FIG. 13a and FIG. 13b, respectively, and show a weight loss of 3.5% before 150° C. and an endotherm at 73.0° C. before melting/decomposition at 163.9° C. (onset temperature). The form change to Form F was observed after Form D was heated to 150° C., cooled to 30° C. under protection of nitrogen, and then exposed to ambient condition. No significant amount of process solvent MeOH or DCM was detected by $^1$H NMR and further determined the stoichiometric ratio of L-tartaric acid to freebase to be 1.0. Form D is a hydrate.

To evaluate the physical stability of Form D under different humidity, DVS data of Form D sample was collected at 25° C. after the sample was equilibrated at ambient humidity (80% RH). A platform from 20% RH (2.25% water uptake) to 80% RH (2.72% water uptake) was observed during desorption in DVS test of Form D, suggesting the dehydration of hydrous Form D occurred when relevant humidity value was less than 20%. Furthermore, as the theoretical water content of a monohydrate is 2.6%. Form D is therefore likely to be a mono-hydrate.

TABLE 19

Representative XRPD Peaks for Compound B Form D:

| 2-Theta (°2θ) | d(Å) |
|---|---|
| 7.322 | 12.0634 |
| 10.992 | 8.0426 |
| 11.312 | 7.8161 |
| 12.182 | 7.2597 |
| 13.234 | 6.6847 |
| 13.487 | 6.5601 |
| 14.114 | 6.2697 |
| 14.668 | 6.0342 |
| 15.145 | 5.8453 |
| 15.702 | 5.6393 |
| 16.036 | 5.5225 |
| 16.217 | 5.4611 |
| 16.542 | 5.3546 |
| 17.249 | 5.1369 |
| 17.637 | 5.0246 |
| 18.113 | 4.8935 |
| 18.349 | 4.8311 |
| 19.108 | 4.641 |
| 20.209 | 4.3905 |
| 20.583 | 4.3115 |
| 21.163 | 4.1948 |
| 21.472 | 4.135 |
| 21.891 | 4.0569 |
| 22.762 | 3.9036 |
| 23.334 | 3.8091 |
| 23.569 | 3.7717 |

Example 20

Preparation of Compound B Form E. Form E was obtained via DMSO-mediated crystallization by adding IPAc into DMSO solution, and its XRPD is shown in FIG. 14. TGA and DSC curves (FIG. 15a and FIG. 15b, respectively) showed a considerable weight loss of 8.3% before 140° C. and an endotherm at 126.3° C. before melting/decomposition at 142.6° C. (onset temperature). The $^1$H NMR spectrum indicated a 0.7 equivalent of DMSO (~9.4 wt %) and no significant amount of IPAc were detected. The stoichiometric ratio of L-tartaric acid to freebase was determined to be 1.0. Form E is a DMSO solvate.

Example 21

Preparation of Compound B Form F. Form F was obtained via heating a Form D sample to 150° C., cooling to 30° C. under protection of nitrogen, and exposed to ambient conditions. The XRPD pattern of Form F is provided in FIG. 16. DSC analysis (FIG. 18) indicated that Form F was crystalline with an endothermic peak at 164.2° C. (onset temperature). $^1$H NMR determined a stoichiometric ratio of L-tartaric acid to freebase to be 1.0 and no significant solvent signal was detected.

TABLE 20

Representative XRPD Peaks for Compound B Form F:

| 2-Theta (°2θ) | d(Å) |
| --- | --- |
| 3.925 | 22.4935 |
| 10.54 | 8.3864 |
| 11.724 | 7.5419 |
| 12.52 | 7.0646 |
| 14.227 | 6.2205 |
| 15.407 | 5.7466 |
| 15.54 | 5.6976 |
| 15.902 | 5.5687 |
| 16.488 | 5.3721 |
| 16.844 | 5.2594 |
| 17.294 | 5.1235 |
| 18.267 | 4.8526 |
| 18.473 | 4.799 |
| 19.399 | 4.572 |
| 19.661 | 4.5117 |
| 20.005 | 4.4348 |
| 20.501 | 4.3286 |
| 20.655 | 4.2968 |
| 21.161 | 4.1952 |
| 21.287 | 4.1706 |
| 21.951 | 4.0458 |
| 22.972 | 3.8683 |
| 23.498 | 3.783 |
| 23.708 | 3.7499 |
| 23.943 | 3.7137 |
| 24.31 | 3.6584 |
| 24.679 | 3.6044 |
| 24.997 | 3.5594 |

To further characterize Form F, variable temperature XRPD (VT-XRPD) was conducted on Form D where the temperature increased to 150° C. and back to 30° C. under protection of nitrogen. Under such conditions, Form F was observed after dehydration of Form D sample at elevated temperatures, indicating Form F was an anhydrate.

To evaluate the physical stability of Form F under different humidity, dynamic vapor sorption (DVS) data of Form F was collected at 25° C. after the sample was equilibrated at ambient humidity (80% RH). A water uptake of ~1.9% was observed up to 80% RH, suggesting Form F is slightly hygroscopic.

Preparation of Compound B Form G. Form G was obtained by slow evaporation in MeOH at RT. The Form G XRPD is provided in FIG. 19. TGA and DSC results are provided in FIG. 20a and FIG. 20b, respectively, and demonstrated a weight loss of 3.3% before 150° C. and a melting/decomposition peak at 170.4° C. (onset temperature). The $^1$H NMR spectrum showed a 0.49 equivalent of MeOH (equal to ~3.0 wt %). The stoichiometric ratio of L-tartaric acid to freebase was determined to be 1.0. Form G is a MeOH solvate.

TABLE 21

Representative XRPD Peaks of Compound B Form G:

| 2-Theta (°2θ) | d(Å) |
| --- | --- |
| 7.654 | 11.5416 |
| 11.462 | 7.7139 |
| 12.517 | 7.0663 |
| 15.275 | 5.796 |
| 15.514 | 5.7072 |
| 16.007 | 5.5323 |
| 17.349 | 5.1072 |
| 18.217 | 4.8658 |
| 19.114 | 4.6395 |
| 19.294 | 4.5966 |
| 19.424 | 4.5661 |
| 19.845 | 4.4702 |
| 20.236 | 4.3846 |
| 21.317 | 4.1647 |
| 21.577 | 4.1152 |
| 21.791 | 4.0752 |
| 22.497 | 3.9489 |
| 22.971 | 3.8685 |
| 23.228 | 3.8263 |
| 24.651 | 3.6085 |
| 25.046 | 3.5525 |
| 25.888 | 3.4388 |

Example 22

Polymorph Screening of L-Tartrate. The solubility of Compound B Form B material was estimated in 20 solvents at RT. (Table 22). Approximately 2 mg solids were added into a 3-mL glass vial. Solvents in Table 6-7 were then added into the vials stepwise until the solids were dissolved or a total volume of 1 mL was reached. Results of Table 22 were used to guide the solvent selection in polymorph screening. Polymorph screening experiments were performed using different solution crystallization or solid phase transition methods. The methods utilized and crystal forms identified are summarized in Table 23.

TABLE 22

Compound B solubilities

| Solvent | Solubility (mg/mL) | Solvent | Solubility (mg/mL) |
| --- | --- | --- | --- |
| DMSO | S > 38.0 | Anisole | S < 1.9 |
| MeOH | 6.7 < S < 20.0 | MTBE | S < 2.1 |
| THF | 2.1 < S < 7.0 | 2-MeTHF | S < 1.9 |
| Acetone | 2.1 < S < 7.0 | 1,4-Dioxane | S < 2.2 |
| EtOH | S < 1.9 | CPME | S < 2.1 |
| IPA | S < 2.1 | ACN | S < 2.1 |
| MEK | S < 2.0 | n-Heptane | S < 2.0 |
| MIBK | S < 1.9 | Toluene | S < 1.9 |
| EtOAc | S < 1.9 | H$_2$O | S < 1.9 |
| IPAc | S < 1.9 | DCM | S < 2.0 |

TABLE 23

Summary of polymorph screenings

| Method | No. of Experiments | Isolated Solid Forms |
| --- | --- | --- |
| Anti-solvent addition | 14 | Form B, D, E |
| Slurry conversion | 34 | Form B, D, G |
| Slow evaporation | 9 | Form G |
| Solid vapor diffusion | 11 | Form B |
| Liquid vapor diffusion | 12 | Form B, Form B + G, Form B + D |
| Slow cooling | 10 | N/A |
| Total | 84 | Form B, D, E, G, B + G, B + D |

Example 23

Anti-solvent Addition. A total of 14 anti-solvent addition experiments were carried out. For each experiment, about 15 mg of Compound B Form B was weighed into a 20-mL glass vial, followed by the addition of 0.3-1.0 mL corresponding solvent. The mixture was then magnetically stirred at the speed of 500 RPM to get a clear solution at RT. Subsequently, the corresponding anti-solvent was added to the solution to induce precipitation or until the total amount of anti-solvent reached 10.0 mL. The clear solutions were transferred to slurry at 5° C. If no precipitation occurs, the solution was then transferred to fast evaporation at RT. The solids were isolated for XRPD analysis. Results summarized in Table 24 showed that Compound B Forms B, D, and E were obtained.

TABLE 24

Summary of anti-solvent addition experiments

| Solvent | Anti-Solvent | Final Results |
|---|---|---|
| MIBK | MeOH | Form D* |
| EtOAc | | Form D** |
| DCM | | Form D** |
| IPA | | Form D** |
| 1,4-Dioxane | | Amorphous |
| ACN | | Amorphous |
| THF | | Form B* |
| Toluene | DMSO | Form E |
| MEK | | N/A |
| IPAc | | Form E |
| 2-MeTHF | | N/A |
| CPME | | Yellow oil |
| $H_2O$ | | N/A |
| EtOH | | N/A |

*solid was obtained via stirring at 5° C.
**solid was obtained via fast evaporation at RT
N/A: no solid was obtained Example 24

Slurry Conversion at RT. Slurry conversion experiments were conducted at RT in different solvent systems. For each experiment, about 20 mg of Compound B Form B was suspended in 0.3 mL corresponding solvent in a 1.5-mL glass vial. After the suspension was magnetically stirred for 17 days at RT, the remaining solids were isolated for XRPD analysis. Results summarized in Table 25 showed that Compound B Forms B, D, and G were obtained.

TABLE 25

Summary of slurry conversion experiments at RT.

| Solvent (v:v) | Final Results |
|---|---|
| MeOH | Form G |
| EtOAc | Form B |
| Acetone | Form B |
| Anisole | Form B |
| MTBE | Form B |
| CPME | Form B |
| 2-MeTHF | Form B |
| ACN | Form B |
| Toluene | Form B |
| DCM | Form B |
| $H_2O$ | Form D* |
| EtOH | Form B |
| IPAc/DMSO, 9:1 | Form E |
| MIBK/MeOH, 9:1 | Form B |
| EtOH/$H_2O$, 97:3, $a_w$ = 0.2 | Form B |
| EtOH/$H_2O$, 92.7:7.3, $a_w$ = 0.4 | Form B |
| EtOH/$H_2O$, 86:14, $a_w$ = 0.6 | Form B |
| EtOH/$H_2O$, 71:29, $a_w$ = 0.8 | Form D |

*heating-cooling was performed on the sample after being stirred for 17 days.

Example 25

Slurry Conversion at Elevated Temperatures. Slurry conversion experiments were conducted at 50° C. and 70° C. in different solvent systems. For each experiment, about 20 mg of Compound B Form B was suspended in 0.3 mL corresponding solvent in a 1.5-mL glass vial. After the suspension was magnetically stirred for 17 days at 50° C. and 70° C., the remaining solids were isolated for XRPD analysis. Results summarized in Table 26 indicated that Compound B Form B was obtained.

TABLE 26

Summary of slurry conversion experiments at elevated temperatures

| Solvent, v:v | Temperature, ° C. | Final Results |
|---|---|---|
| $H_2O$ | 50 | Form B |
| MeOH | | Form B |
| Acetone | | Form B |
| THF | | Form B |
| MEK | | Form B |
| EtOAc | | Form B |
| $CHCl_3$ | | Form B |
| ACN | | Form B |
| EtOH | | Form B |
| MTBE | | Form B |
| IPA | 70 | Form B |
| 1-Butanol | | Form B |
| MIBK | | Form B |
| IPAc | | Form B |
| Anisole | | Form B |
| Toluene | | Form B |

Example 26

Slow Evaporation. Slow evaporation experiments were performed under 9 conditions. For each experiment, around 15 mg of Compound B Form B was weighed into a 3-mL glass vial, followed by the addition of corresponding solvent or solvent mixture to get a clear solution. Subsequently, the vial was covered with parafilm with 3~4 pinholes, and kept at RT to allow the solution to evaporate slowly. The isolated solids were tested by XRPD. As summarized in Table 27, Compound B Form G was generated.

TABLE 27

Summary of slow evaporation experiments

| Solvent (v:v) | Final Results |
|---|---|
| MeOH | Form G |
| Acetone | Yellow gel |
| EtOH | Yellow gel |
| 2-MeTHF | Yellow gel |
| THF | Yellow gel |
| ACN/MeOH, 1:3 | Yellow gel |
| EtOAc/MeOH, 1:3 | Form G |
| DCM/MeOH, 1:3 | Form G |
| Anisole/MeOH, 1:3 | Yellow gel |

Example 27

Solid Vapor Diffusion. Solid vapor diffusion experiments were conducted using 11 solvents. For each experiment, about 15 mg of Compound B Form B was weighed into a 3-mL vial, which was placed into a 20-mL vial with 4 mL of corresponding solvent. The 20-mL vial was sealed with a cap and kept at RT for 14 days to allow the solvent vapor to interact with the solid sample. The isolated solids were tested by XRPD. The results summarized in Table 28 indicated that Compound B Form B was obtained.

TABLE 28

Summary of solid vapor diffusion experiments.

| Solvent | Final Results |
|---|---|
| $H_2O$ | Form B |
| DCM | Form B |
| EtOH | Form B |
| MeOH | Form B |
| ACN | Form B |
| THF | Form B |
| $CHCl_3$ | Form B |
| Acetone | Form B |
| EtOAc | Form B |
| 1,4-Dioxane | Form B |
| IPA | Form B |

Example 28

Liquid Vapor Diffusion. Twelve liquid vapor diffusion experiments were conducted. For each experiment, about 15 mg of Compound B Form B was dissolved in 0.5-1.0 mL of corresponding solvent to obtain a clear solution in a 3-mL vial. Subsequently, the solution was placed into a 20-mL vial with 4 mL of corresponding anti-solvent. The 20-mL vial was sealed with a cap and kept at RT, allowing sufficient time for solvent vapor to interact with the solution. Solids were isolated for XRPD analysis. Results summarized in Table 29 showed that Compound B Form B and a mixture of Form B+G/B+D were obtained.

TABLE 29

Summary of liquid vapor diffusion experiments.

| Anti-solvent | Solvent | Final Results |
|---|---|---|
| 1,4-Dioxane | MeOH | Form B |
| MeOH | | Form B + G |
| Acetone | | Form B + G |
| ACN | | Form B + G |
| THF | | Form B + D |
| EtOAc | | Form B + G |
| $CHCl_3$ | DMSO | N/A |
| MTBE | | N/A |
| 2-MeTHF | | N/A |
| DMC | | N/A |
| IPAc | | N/A |
| Anisole | | N/A |

N/A: no solid obtained

Example 29

Slow Cooling. Slow cooling experiments were conducted in 10 solvent systems. For each experiment, about 20 mg of Compound B Form B was suspended in 1.0 mL of corresponding solvent in a 3-mL glass vial at RT. The suspension was transferred to slurry at 50° C. with a magnetic stirrer at the speed of 500 RPM. The sample was equilibrated at 50° C. for 2 hrs and filtered using a 0.45 m Nylon membrane. Subsequently, the filtrate was slowly cooled down from 50° C. to 5° C. at a rate of 0.1° C./min. The results summarized in Table 30 indicated that no solid was observed.

TABLE 30

Summary of slow cooling experiments.

| Solvent, v:v | Final Results |
|---|---|
| MeOH | N/A |
| EtOH | N/A |
| Acetone | N/A |
| MEK | N/A |
| THF | N/A |
| 2-MeTHF | N/A |
| $H_2O$ | N/A |
| ACN/DMSO, 4:1 | N/A |
| Toluene/MeOH, 3:1 | N/A |
| EtOAc/MeOH, 3:1 | N/A |

Example 30

Figure 21:
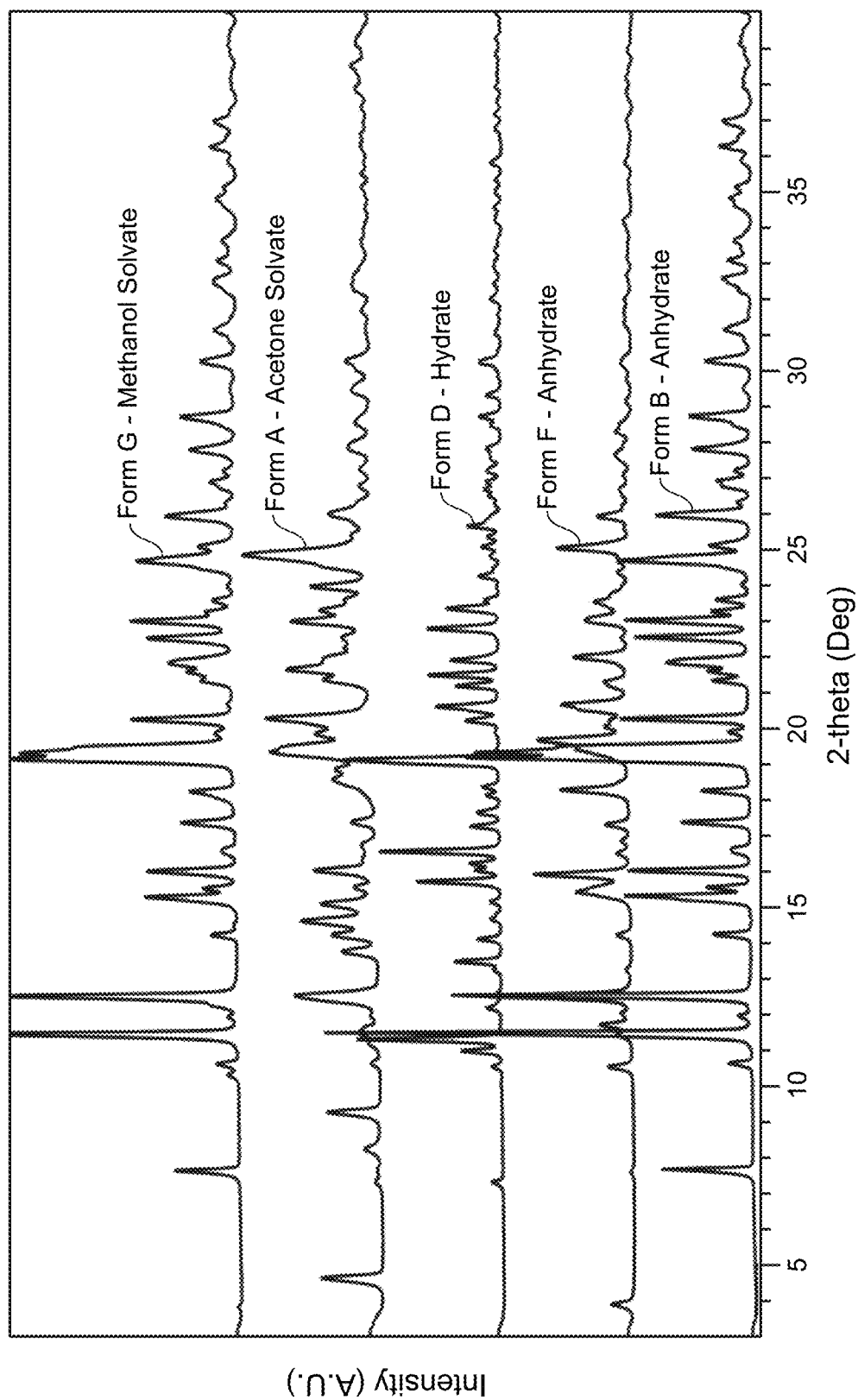
FIG. 21 depicts the XRPD pattern overlay for Compound B Form A, Form B, Form C, Form D, Form F, and Form G.

Phase transformation. Crystallization of Compound B from solvents such as ethyl acetate, ethanol, acetone or and aqueous mixture of these may result in the formation of one more of the following forms: anhydrous Form B, anhydrous Form F, monohydrate Form D, and acetone solvate Form A. The XRPD patterns of these four solid forms are shown in FIG. 21. It was therefore important to know the physical stability of these forms to determine the complete phase transformation landscape and control crystallization to obtain the desired Form B. Owing to the close proximity of melting points of Forms F and B (160-164° C. onset for Form F vs 166-175° C. for Form B), form conversion was slow in competitive slurry bridging experiments at RT and a mixture of both forms was obtained. As a result, equilibrium solubility studies were conducted for both forms in ethanol over 17 hrs at 25, 35 and 50° C. to determine their thermodynamic stability relationship.

Form F was found to have higher solubility at these three temperatures, confirming Form B to be the thermodynamically stable form from 25-50° C. The Van't Hoff plot of solubility of Forms B and F vs temperature showed that the two anhydrates were related enantiotropically with a transition temperature at ~19° C. In case of hydrate-anhydrate stability, it was found that Form B remained stable at water activity ($a_w$) $a_w$<0.2 (RT), above which the hydrate Form D was stable. However, Form B was found to be kinetically stable up to $a_w$ of 0.4 (RT) in slurry bridging experiments for up to 36 days. This suggests that although the critical $a_w$ value for form conversion to hydrate is low, there is a large kinetic barrier for the conversion of Form B to Form D.

Slurry and crystallization samples. Form B+Form A 1:1 mixtures of Compound B lots comprising (1) mixture of Form A/acetone solvate and Form B) and (2) Form B were made and added to 100% acetone and aqueous mixtures of acetone water (90% acetone, 95, 96, 97, 98 and 99% acetone v/v). Samples were slurried at RT for 120 hrs, filtered and then analyzed by XRPD.

Form F

Form F was slurried in 100% ethanol at RT and 50° C. overnight. One of the suspensions was seeded at RT with Form B while the other was left unseeded. The suspension stirred at 50° C. was seeded with Form B. Samples were filtered and analysed by XRPD. Samples of Form F were slurried separately at RT in 100% DI water, 1:1 acetone/water and 100% acetone. Slurries of Form F in neat solvents were maintained at RT whereas a solution of Form F was obtained in the 1:1 acetone:water mixture which was thus agitated at 5° C. for cooling crystallization/precipitation. After 24 hrs, all samples were filtered and analyzed by XRPD. Form F was also slurried in 95:5 acetone:water and 97:3 acetone:water mixtures at 50° C. for 2 hrs after which the slurries were cooled to RT, filtered and analyzed by XRPD. Finally, Form F was recrystallized from 95:5 acetone:water seeded with Form B at 50° C.

Form D

Form D was slurried at RT for 48 hrs in 100% ethanol. The sample was subsequently filtered and analyzed by XRPD.

Results

Development of calorimetric method to estimate purity. Switching from ethanol to acetone/water as the crystallization solvent saw a marked improvement in purity, with oligomer content dropping by an average of 5% w/w, with acceptable yield. The change in oligomer content as well as yield was a function of slurry solvent composition. An increase in the water content improved purity but lowered the yield. For a given solvent composition, the melting point onset and % oligomer content consistently showed opposing results, indicating that purity is likely to affect the melting point, with greater % oligomer depressing the melting point and vice versa. Based on this observation, several slurry lots obtained from acetone/water were analyzed using DSC and tested for oligomer content by SEC and a correlation curve was developed. XRPD data was collected for all these samples to ensure that they conformed to Compound B Form B. Using the exponential fit to the data, purity estimates were made for several lots, including a 20 gm scale up and IPC sample. An $R^2$ value of 0.96 was obtained for the linear fit between experimental and predicted oligomer content. Given that these were solid/powder samples with inherent issues of sample homogeneity, this high $R^2$ value provided confidence in the robustness of the correlation determined between melting point onset and purity.

Compound B Form B was consistently obtained from 100% ethanol (slurry or crystallization). Further conditions were conducted including slurry or crystallizations from ethanol/water and slurry in acetone/water (≥95% acetone). Depending on the slurry and crystallization parameters, several other solid forms of Compound B were obtained, namely Form F (ethanol/water) Form A/acetone solvent (≥95% acetone) and mixtures of Form A and B or Form A and F. In conditions where Form F was obtained, the formation of an intermediate hydrate (Form D) was postulated since $a_w$ values of ethanol/water mixtures employed for these samples were well above 0.2 (RT), where the hydrate is thermodynamically stable. Table 31 shows the crystallization conditions with the form obtained. Since mixtures of forms were obtained in several cases, a form control strategy was implemented to obtain Form B in the final solid phase.

TABLE 31

Crystallization conditions and corresponding solid forms

| Crystallization condition | Form identified (XRPD) |
|---|---|
| Acetone/water(96:4), 5 vol, 50 C. for 6 h | Form A + Form B |
| Acetone/water(95:5) | Form A + Form B |
| Acetone/water(99:1), 5 vol, 50 C. for 2 h | Form A + Form B |
| crystallize GMP batch: 4 vol acetone/water 90:10, 8 vol acetone anti-solvent with 1% Form B seeds | Form A + Form F |
| Seeded crystallization in ethanol/water 65:35 | Form F |

Since acetone/water system was the most effective in purging oligomers from Compound B, a competitive slurry bridging experiment was conducted using 1:1 mixtures of two separate lots of Compound B: one that was predominantly Form A with some Form B and a second that was slurried in acetone/water mixtures of various compositions at RT for 120 hrs. Acetone solvate was obtained as the stable form at ≥95% acetone while a mixture of Form B and Form D hydrate was obtained at 90% acetone. As the desired acetone level was between 96 and 95% (to oligomer levels), there was a possibility of obtaining any of Forms A, B, or D from the final crystallization.

Form control strategy: conversion of Forms A and F to Form B. FIG. 2b shows the DSC thermograms of Form A acetone solvate. The first endotherm at 124° C. indicates solvent loss and vaporization while the second endotherm at 164° C. denotes the melting of the corresponding anhydrate. XRPD confirmed this anhydrate to be Form B when Form A was heated to 152° C. Form A was re-slurried in 100% ethanol overnight for conversion to Form B. Thus a two-step slurry process was proposed to aid form control for Compound B to obtain Form B in the event that the first slurry in acetone/water produces either Form A or a mixture for Form A and B, depending on the slurry conditions. This would ensure that irrespective of a change in form during the first slurry, Form B would be the final Compound B form that is isolated after the second slurry step.

Unlike the acetone solvate, Form F obtained from a 65:35 ethanol:water crystallization seeded with Form B showed only one melting endotherm at 162° C. Owing to near identical solubility values of Forms F and B in ethanol at 25° C. (0.23 mg/mL for Form B vs 0.26 mg/mL for Form F), the thermodynamic driving force for conversion of metastable Form F to stable Form B is less and thus Form F→Form B conversion rate would be slow, even in the presence of Form B as seeds. Irrespective of seeding and temperature, Form F→Form B conversion is slow and a mixture of both forms is obtained after 12 hours.

Figure 25:
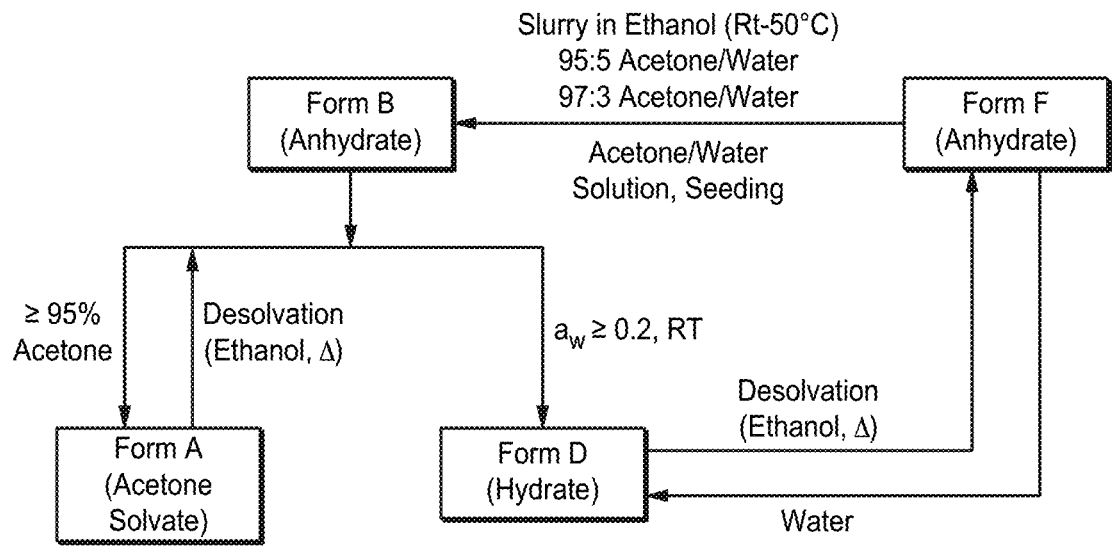
FIG. 25 depicts phase transformation pathways for Compound B Forms A, B, D, and F.
Figure 26:
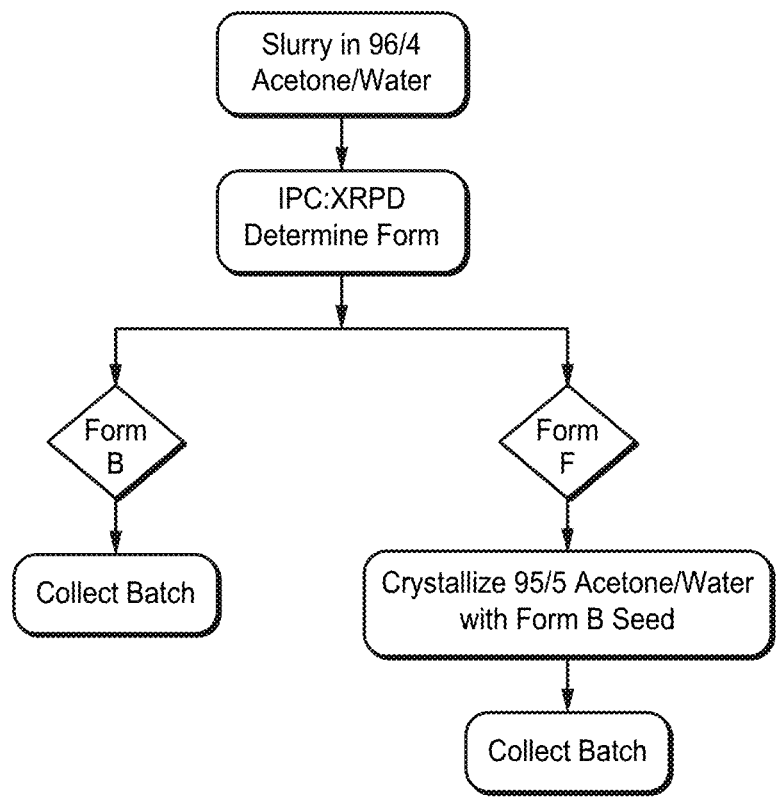
FIG. 26 depicts phase transformation pathways to obtain Compound B Form B from Form F.

To facilitate Form F→Form B conversion in shorter timescales, a solvate route was adopted wherein Form F would be converted to Form B via acetone solvate or hydrate formation, which would subsequently be desolvated to Form B. Form F was slurried overnight in neat water, acetone and 1:1 acetone:water mixture, without any seeding. Form F remains unchanged in 100% acetone but converts to hydrate (Form D) in presence of water. When the hydrate is slurried in neat ethanol, a mixture of Form D and Form F results, thus indicating the propensity of the hydrate to desolvate to the metastable anhydrous form. Form F slurried in 95:5 acetone:water and 97:3 acetone:water at 50° C. demonstrated that Form B appears but the conversion is incomplete. Recrystallization of Form F from 95:5 acetone:water using Form B seeds at 50° C. resulted in complete conversion Form F→Form B. FIG. 25 and FIG. 26 provide schematics of form conversion between Forms A, B, D and F.

Thermodynamic Relationship between Anhydrous Form B and Form F by slurry competition between anhydrous Form B and F. To determine the thermodynamic stability between Form B and F, competitive slurry experiments were conducted in solvent systems of acetone/EtOH/EtOAc at RT (25±3° C.) and 50° C. as listed in Table 32. A mixture of Form B and F with equal mass ratio was suspended in saturated acetone/EtOH/EtOAc solutions of Form B and then magnetically stirred at targeted temperature. After slurry for about 4-11 days, remaining solids were isolated for XRPD characterization. A mixture of Form B and F was observed, indicating slow transition between Form B and F.

TABLE 32

Slurry competition conditions for thermodynamic relationship between Compound B Form B and Form F.

| Starting Form | Solvent | Temperature (° C.) | Solid Form |
|---|---|---|---|
| Form B + F | Acetone | 50 | Form B + F (sampled after 5 days) |
| | EtOH | RT | Form B + F (sampled after 4 days) |
| | | 50 | Form B + F (sampled after 11 days) |
| | EtOAc | RT | Form B + F (sampled after 8 days) |

The thermodynamic stability relationship between anhydrous Form B and F was determined via slurry competition and equilibrium solubility measurement. As a result, a mixture of Form B and F was observed in all the slurry competition experiments, indicating slow transition between Form B and F. Without being bound by any particular theory, Form B and Form F low solubility may be caused by their low solubility in tested solvents (acetone/EtOH/EtOAc). Therefore, equilibrium solubility (17 hours) was measured in EtOH at 25° C., 35° C. and 50° C., respectively, to determine their thermodynamic stability relationship. Compared with Form B, Form F showed higher solubility under all the three tested temperatures in EtOH, indicating Form B is thermodynamically more stable than Form F from 25° C. to 50° C.

The $a_w$ between anhydrous Form B and hydrous Form D was determined via slurry competition under various water activity conditions at RT. Form D was observed in $a_w$ of 0.6 and 0.8 after one week and in water after 36 days. Form B was observed in EtOH ($a_w$<0.2) after one week. A mixture of Form D and B was observed in $a_w$ of 0.2 and 0.4 systems after stirring at RT for 36 days. To further confirm the thermodynamic stability relationship between Form B and Form D in $a_w$ of 0.2 and 0.4 systems at RT, their equilibrium solubility (24 hours) under the corresponding conditions was collected. Compared with that of samples that started with Form B, lower solubility was observed in samples that started with Form D (crystal forms of the final limited solids were not checked) in both $a_w$ of 0.2 and 0.4 systems.

Equilibrium Solubility Measurement of Anhydrous Form B and F. To further determine the thermodynamic stability between Form B and F, equilibrium solubility measurement experiments were conducted in EtOH at 25° C., 35° C. and 50° C., respectively. Detailed procedures are summarized as follows: solids of Form B and F were suspended in 0.4 mL of EtOH at targeted temperatures and magnetically stirred for 17 hrs (750 rpm). After centrifugation, the concentration and HPLC purity of freebase in the filtrate was tested. The crystal form of remaining solids was checked by XRPD.

Compared with Form B, Form F showed higher solubility at 25° C., 35° C. and 50° C. in EtOH (Table 33). Based on the XRPD results, no form change was observed after solubility test, indicating Form B is likely thermodynamically more stable than Form F from 25° C. to 50° C.

TABLE 33

Summary of equilibrium solubility measurements of Form B and Form F in EtOH

| Starting Form | Temperature (° C.) | Final Form | Solubility (mg/mL)* |
|---|---|---|---|
| Form B | 25 | Form B | 0.23 |
| Form F | | Form F | 0.26 |
| Form B | 35 | Form B | 0.30 |
| Form F | | Form F | 0.36 |
| Form B | 50 | Form B | 0.49 |
| Form F | | Form F | 0.82 |

Critical Water Activity Determination between Form B and D. To determine critical water activity between anhydrous Form B and hydrous Form D, slurry competition was performed in various water activity conditions at RT as listed in Table 34. A mixture of Form B and D with equal mass ratio was suspended in saturated EtOH-water (with various $a_w$) solutions of Form B and then magnetically stirred at RT. After slurry for about 7~36 days, remaining solids were isolated for XRPD characterization.

TABLE 34

Summary of slurry competition of Form B and Form D under various $a_w$ conditions

| Starting Form | Solvent (v:v, $a_w$) | Sample Time (d) | Solid Form |
|---|---|---|---|
| Form B + D | EtOH | 7 | Form B |
| | EtOH:H$_2$O (97:3, 0.2) | 36 | Form D + B |
| | EtOH:H$_2$O (92.7:7.3, 0.4) | 36 | Form D + B |
| | EtOH:H$_2$O (86:14, 0.6) | 7 | Form D |
| | EtOH:H$_2$O (71:29, 0.8) | 7 | Form D |
| | H$_2$O | 36 | Form D |

Form D was observed in $a_w$ of 0.6 and 0.8 after slurry for one week and in water after 36 days. Form B was observed in EtOH after slurry for one week. A mixture of Form D and B was observed in $a_w$ of 0.2 and 0.4 systems after stirring at RT for 36 days.

Solubility Measurement of Form B and D. To further confirm the thermodynamic stability relationship between Form B and Form D under $a_w$ of 0.2 and 0.4 conditions at RT, equilibrium solubility under the conditions set forth in Table 35 was collected.

TABLE 35

Summary for equilibrium solubility measurement of Form B and D in $a_w$ = 0.2/0.4 systems

| Starting Form | $A_w$, solvent system | Solubility (mg/mL) |
|---|---|---|
| Form B | 0.2, | 24.4 |
| Form D | EtOH:H$_2$O (97:3, v/v) | 21.7 |
| Form B | 0.4, | 27.5 |
| Form D | EtOH:H$_2$O (92.7:7.3, v/v) | 18.6 |

Solids of anhydrous Form B and hydrous Form D were suspended in 0.5 mL of target solvent system ($a_w$=0.2/0.4), respectively, and magnetically stirred for 24 hrs (750 rpm). The suspension was filtered and the concentration of freebase in the filtrate was tested. Lower solubility was observed in samples that started with Form D. Hydrous Form D appears thermodynamically more stable than anhydrous Form B when $a_w$≥0.2 at RT (25±3° C.).

Example 31

Malonate Form M

Figure 31:
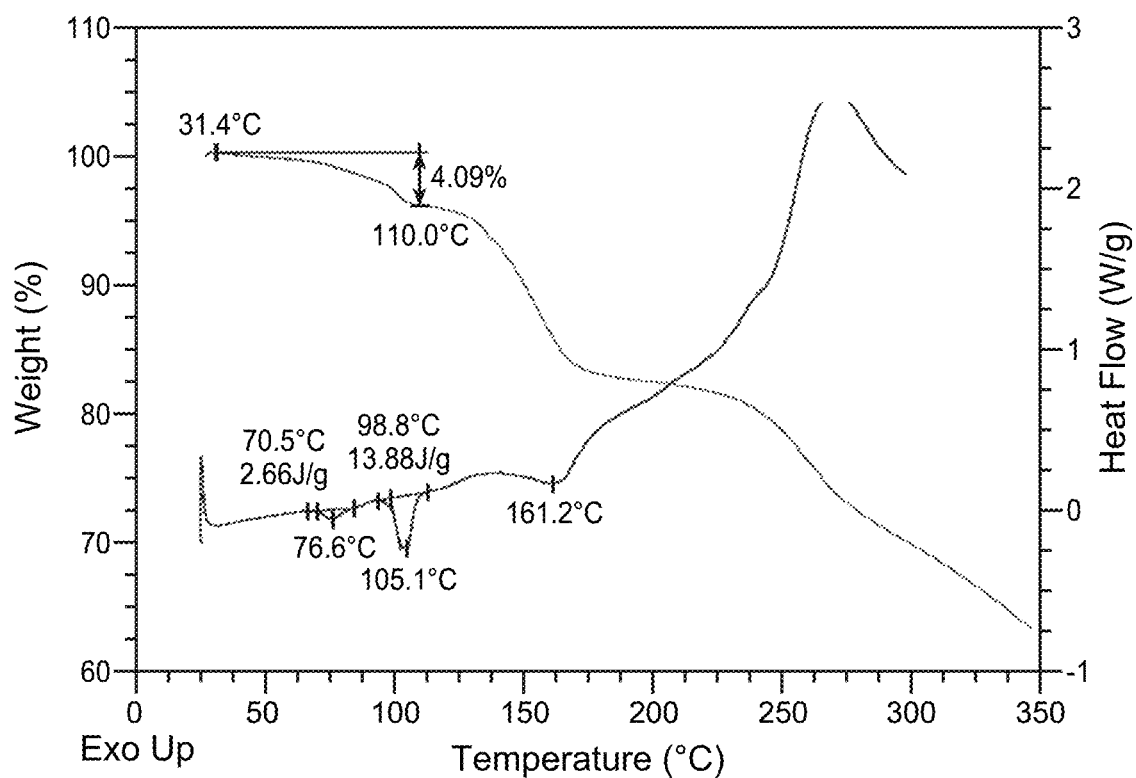
FIG. 31 depicts the TGA and DSC for Compound D Form M.
Figure 32:
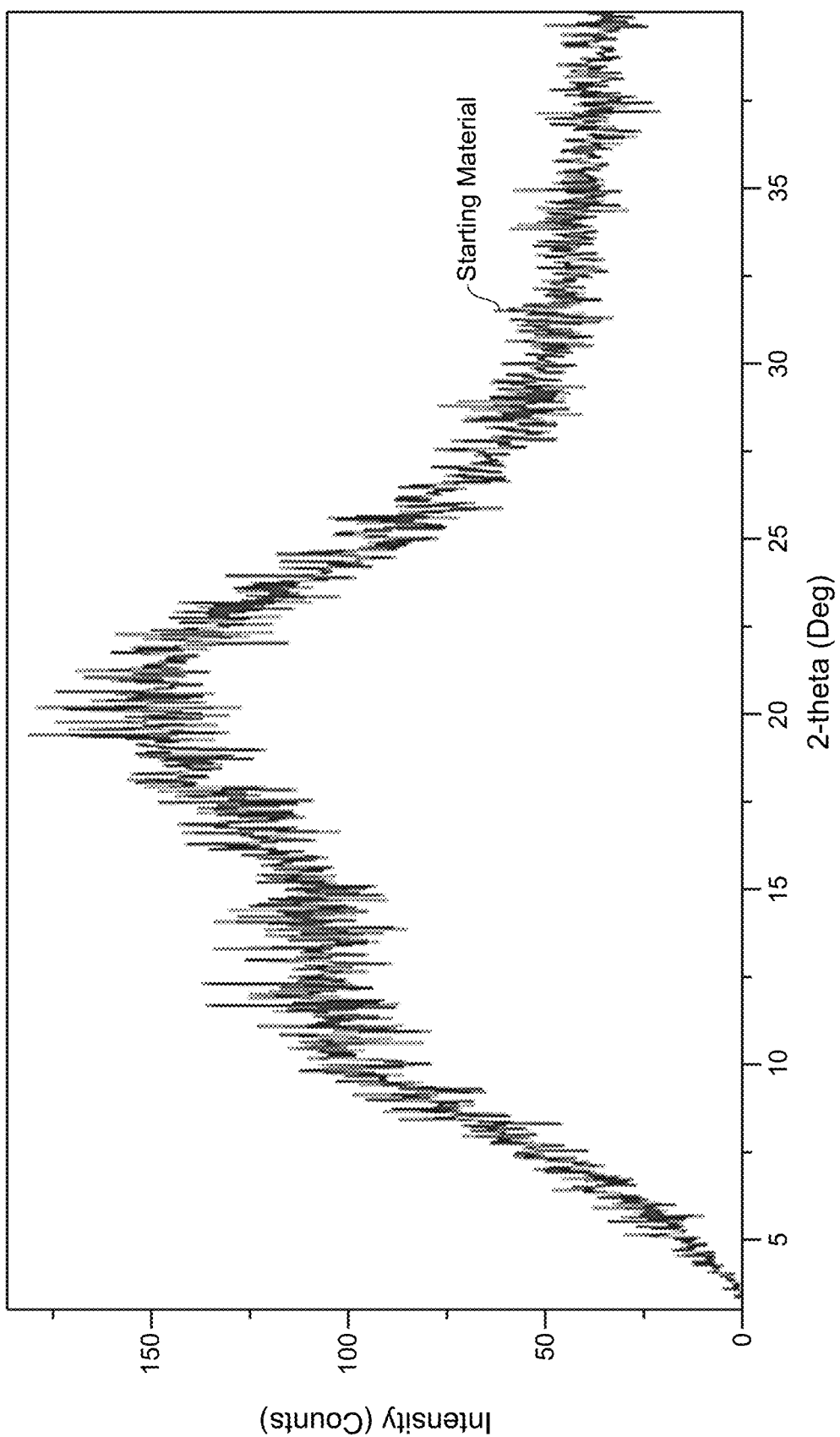
FIG. 32 depicts the XRPD pattern for the amorphous form of Compound A.

One malonate hit with low crystallinity, malonate Form M, was obtained from screening. Its XRPD pattern is shown in FIG. 31. A weight loss of 4.1% up to 110° C. was observed in TGA and DSC result showed multiple endotherms (FIG. 32). Stoichiometry was determined to be 0.50 (acid/freebase) and 6.2% THF (a molar ratio of 0.58 to freebase) was detected by $^1$H NMR. Since multiple endotherms and considerable amount of THF are observed, malonate Form M is a THF solvate, but no further characterization was conducted due to its low crystallinity.

Example 32

Fumarate Form 1

One crystalline fumarate hit, fumarate Form 1, was obtained from screening. A weight loss of 0.9% up to 150° C. was observed in TGA and DSC (FIG. 28 depicts the TGA and DSC for Compound C Form 1.

FIG. 29) result showed one melting endothermic peak at 164.3° C. (onset temperature). Stoichiometry was determined to be 0.88 (acid/freebase) and 1.5% EtOAc (a molar ratio of 0.11 to freebase) was detected by $^1$H NMR.

Preparation of Fumarate Form 1. About 44.7 mg of fumaric acid was weighed into a 5-mL glass vial, and 2.0 mL EtOAc was added. The acid remained undissolved. About 2.0 mL of freebase stock solution in EtOAc (~100 mg/mL) was added into the 5-mL vial with a molar ratio of 1:1, and stirred at RT. About 3 mg of fumarate Form 1 seed was added, and the solution turned cloudy. The suspension was stirred overnight and sampled by XRPD (FIG. 27) with a confirmed pattern conformed to fumarate Form 1. The suspension was stirred at 50° C. for 3 more days to increase the crystallinity followed by centrifugation. The cake was dried at 50° C. for 4 hrs. Yield: 186.6 mg, with a yield of ~76.2%.

TABLE 36

Representative XRPD Peaks for Compound C Form 1.

| 2-Theta (°2θ) | d(Å) |
|---|---|
| 7.589 | 11.6401 |
| 10.596 | 8.3423 |
| 11.449 | 7.7224 |
| 11.844 | 7.4662 |
| 12.5 | 7.0758 |
| 14.444 | 6.1275 |
| 15.454 | 5.729 |
| 15.782 | 5.6107 |
| 16.097 | 5.5017 |
| 17.555 | 5.0479 |
| 18.921 | 4.6865 |
| 19.696 | 4.5038 |
| 19.866 | 4.4657 |
| 20.233 | 4.3853 |
| 21.35 | 4.1585 |
| 22.046 | 4.0288 |
| 23.162 | 3.837 |
| 23.897 | 3.7206 |
| 24.238 | 3.669 |
| 24.672 | 3.6055 |
| 25.236 | 3.5261 |
| 25.932 | 3.4331 |

TABLE 37

Representative XRPD Peaks for Compound C Form 2.

| 2-Theta (°2θ) | d(Å) |
|---|---|
| 11.521 | 7.6744 |
| 11.879 | 7.4439 |
| 15.558 | 5.691 |
| 16.04 | 5.5211 |
| 16.515 | 5.3633 |
| 17.324 | 5.1146 |
| 18.361 | 4.8281 |
| 19.004 | 4.6662 |
| 19.439 | 4.5628 |
| 19.876 | 4.4634 |
| 20.244 | 4.383 |
| 21.355 | 4.1574 |
| 22.035 | 4.0306 |
| 23.238 | 3.8246 |
| 23.917 | 3.7175 |
| 25.439 | 3.4985 |
| 26.039 | 3.4193 |

Summary Compound A freebase was identified as an amorphous solid form with <0.5% weight loss before decomposition and a melting point of about 87° C. It's hygroscopicity at 95% RH was <1% and had an epimer content of <1%. It's solubility at 37° C. was about 6.6 mg/mL. The XRPD pattern for the amorphous form is provided in FIG. 33. Compound C Form 1 was a crystalline solid with <0.5% weight loss before decomposition and a melting point of about 165-174° C. Multiple forms of Compound C were obtained dependent upon the solvent. It's hygroscopicity at 95% RH was <1.5% and had an epimer content of <1%. It's solubility at 37° C. was about 6.6 mg/mL. The Compound B Form B was a crystalline solid with <0.5% weight loss before decomposition and a melting point of about 168° C. A single form was present in anhydrous Form B. It's hygroscopicity at 95% RH was <1% and had an epimer content of <2.5%. It's solubility at 37° C. was about 5.9 mg/mL. The anhydrous form of Compound B Form B was found to be a stable pure crystalline form with properties more favorable than Forms D, E, and F as described herein.

Example 33

Evaluation of safety, pharmacokinetics, and activity of Compound B. Breast cancer is the most frequent cancer diagnosed in women, with an estimated global incidence of 1.67 million new cases reported in 2012 (Ferlay et al. 2013). Breast cancer accounts for approximately 15% (approximately 522,000 cases) of all cancer deaths.

Approximately 80% of all breast cancers express the estrogen receptor (ER) factor, and the vast majority of these are dependent on ER for tumor growth and progression. Modulation of estrogen activity and/or synthesis is the mainstay of therapeutic approaches in women with ER-positive breast cancer. However, despite the effectiveness of available endocrine therapies such as ER antagonists (e.g., tamoxifen), aromatase inhibitors (e.g., anastrozole, letrozole, and exemestane) and full ER antagonists/degraders (e.g., fulvestrant), many patients ultimately relapse or develop resistance to these agents and therefore require further treatment for optimal disease control.

Despite becoming refractory to aromatase inhibitors or tamoxifen, growth and survival of resistant tumor cells remain dependent on ER signaling; therefore, patients with ER-positive breast cancer can still respond to second- or third-line endocrine treatment after progression on prior therapy (Di Leo et al. 2010; Baselga et al. 2012). There is growing evidence that in the endocrine resistant state, ER can signal in a ligand-independent manner via input from other signaling pathways (Miller et al. 2010; Van Tine et al. 2011). Without being bound by any particular theory, an agent with a dual mechanism of action (ER antagonism plus degradation) has the potential to target both ligand-dependent and ligand-independent ER signaling and, consequently, improve treatment outcomes in late-stage ER-positive breast cancer. Furthermore, recent studies have identified mutations in ESR1 (i.e., the gene that encodes for ERa) affecting the ligand-binding domain (LBD) of the ER (Segal and Dowsett 2014). In nonclinical models, mutant ER can drive transcription and proliferation in the absence of estrogen, suggesting that LBD-mutant forms of ER may be involved in mediating clinical resistance to some endocrine therapies (Li et al. 2013; Robinson et al. 2013; Toy et al. 2013). ER antagonists that are efficacious against these ligand-independent, constitutively-active ER-mutated receptors may possess substantial therapeutic benefit.

As such, there is a need for new ER-targeting therapies with increased anti-tumor activity to further delay disease progression and/or overcome resistance to the currently available endocrine therapies and ultimately prolong survival in women with ER-positive breast cancer.

Compound B is a potent, orally bioavailable, small-molecule therapeutic agent that is being developed for the treatment of patients with ER-positive breast cancer. As provided herein Compound B, including its solid forms (e.g. Form B) are stable compounds with favorable properties for continued pharmaceutical development. Without being bound by any particular theory, Compound B appears to antagonize the effects of estrogens via competitive binding to the LBD of both wild-type and mutant ER with nanomolar potency. Upon binding, and without being bound by any particular theory, Compound B induces an inactive conformation to the ER LBD, as measured by displacement of co-activator peptides. In addition to its direct antagonist properties, without being bound by any particular theory, the mechanism of action of Compound B includes reducing levels of ERα protein through proteasome-mediated degradation. Degradation of ER is hypothesized to enable full suppression of ER signaling, which is not achieved by first-generation ER therapeutics such as tamoxifen, which display partial agonism. Compound B potently inhibits the proliferation of multiple ER-positive breast cancer cell lines in vitro, including cells engineered to express clinically relevant mutations in ER.

In vivo, Compound B exhibited dose-dependent anti-tumor activity in xenograft models of ER-positive breast cancer, including in a patient-derived xenograft model that harbors an ESR1 mutation (ER.Y537S). The efficacious dose range was found to be 0.1-10 mg/kg/day, and all doses were well tolerated. Fulvestrant, when dosed according to a clinically relevant dosing scheme, was less efficacious than Compound B in the assessed xenograft models. Thus, Compound B demonstrated robust nonclinical activity in ER-positive breast cancer models of ESR1-wildtype- and ESR1-mutation-bearing disease.

Example 34

Figure 35:
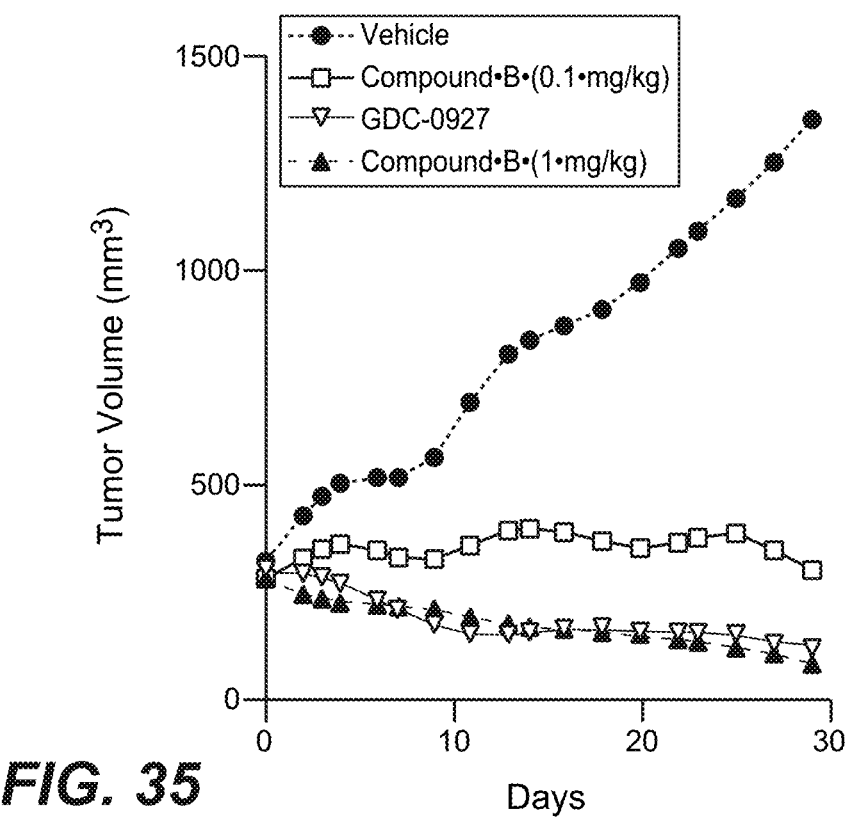
FIG. 35 depicts effect on tumor volume of Compound B at 0.1 mg/kg and 1 mg/kg compared to GDC-0927 at 100 mg/kg.

In vitro and in vivo efficacy analysis of Compound B. Compound B displays superior ER degradation & ER pathway suppression when compared to both GDC-0927 GDC-0810. Further, Compound B has better DMPK properties than both GDC-0927 and GDC-0810—resulting in same in vivo efficacy as GDC-0927 but at 100× lower doses (e.g. 1 mg or 10 mg dose). (See FIG. 34 and FIG. 35).

Pharmacokinetics and Metabolism. After a single IV administration to rats, dogs, and monkeys, Compound B was found to have a low to moderate clearance, a large volume of distribution, and a terminal elimination half-life of 7-24 hours. Oral bioavailability was moderate in rats and dogs (41%-55%) and low (17%) in monkeys. In vitro data showed that plasma protein binding of Compound B was high across all species, ranging from 98% to 99% bound.

In vitro metabolite identification experiments showed that UGT1A4-mediated glucuronidation was the major in vitro metabolic pathway of Compound B. The contribution from CYP450 isoforms was minor and included both CYP3A4 and CYP2C9. In vitro CYP inhibition studies in human liver microsomes and induction studies in human hepatocytes suggested a low-to-moderate potential for drug-drug interactions. Compound B directly inhibited CYP3A4 with 50% inhibitory concentration ($IC_{50}$) values of 6.5 µM (midazolam 1'-hydroxylation) and 26 µM (testosterone 6β-hydroxylation); $IC_{50}$ for CYP2B6 and CYP2C8 inhibition were 13 µM and 21 µM, respectively. Compound B showed weak metabolism dependent inhibition of CYP2C9.

Toxicology. Four-week Good Laboratory Practice (GLP) repeat-dose oral toxicity studies in female rats and monkeys with integrated assessments of neurologic (rats, monkey), respiratory (monkey), and cardiovascular (monkey) function were conducted to characterize the nonclinical safety profile of Compound B.

In the rat study, Compound B was tolerated at the exemplary dose levels (10, 30, and 100 mg/kg) with adverse effects predominantly in the kidneys and liver at 100 mg/kg. In the monkey study (20, 60, and 200 mg/kg), the maximum tolerated dose (MTD) was considered to be 60 mg/kg as the high dose of 200 mg/kg was not tolerated. Adverse effects were primarily observed at the high dose level of 200 mg/kg, and lack of tolerability was attributed to kidney and liver injury and inanition.

In both rats and monkeys, there was a dose-dependent PLD observed in numerous organs at exposures that were higher than those anticipated at the human starting dose in Phase I (at least 44-fold and 6-fold based on area under the concentration-time curve [AUC], respectively), with adverse organ effects largely confined to the kidney and liver. In rats, PLD was not noted at 10 mg/kg (18-fold exposure factor), but increased in incidence and severity from 30 to 100 mg/kg. In monkeys, dose-responsive PLD was present at all doses but was limited to minimal changes in the lung at 20 mg/kg (6-fold exposure factor). These exposure multiples provide evidence that the risk of PLD-associated toxicity to humans in the Phase I starting dose is low.

The translatability of PLD from nonclinical species to patients is not certain but can be reasoned (Reasor et al. 2006). Drugs such as tamoxifen and palbociclib have not demonstrated any clinical concerns in spite of their PLD findings in nonclinical studies. Although Compound B was associated with PLD in multiple tissues in both rats and monkeys, there was no light microscopic evidence of involvement of critical organs such as heart, eyes, or neurons in these studies (Chatman et al. 2009).

Following 28-day oral administration to rats and monkeys, the increases in systemic exposure of Compound B were dose proportional. Based on the nature and reversibility of clinical signs, clinical pathology, and histopathology findings, the severely toxic dose for 10% of animals ($STD_{10}$) for rats was defined as 100 mg/kg, with corresponding maximum plasma concentration ($C_{max}$) and AUC from 0 to 24 hours ($AUC_{0-24}$) values of 6560 ng/mL and 143,000 ng·hr/mL, respectively. In monkeys, the highest non-severely toxic dose was defined as 60 mg/kg/day, with corresponding $C_{max}$ and $AUC_{0-24}$ values of 841 ng/mL and 16,200 ng·hr/mL, respectively, due to the clinical signs and moribundities present at 200 mg/kg/day.

In summary, results from the nonclinical toxicity and safety pharmacology studies completed to date provide a robust characterization of the toxicity profile of Compound B and support administration to cancer patients in a Phase I trial.

Administration of Compound B as a Single Agent Monotherapy. Compound B demonstrated robust nonclinical activity in ER-positive breast cancer models of ESR1-wildtype and ESR1-mutation bearing disease. The safety, pharmacokinetic (PK), pharmacodynamic (PD) activity and preliminary anti-tumor activity of Compound B as a single agent was analyzed in a Phase Ia/Ib, multicenter, open-label study in patients with locally advanced or metastatic ER-positive breast cancer. Patients were enrolled in a dose-escalation stage with enrollment in an expansion stage to follow. During the single-agent dose escalation, cohorts were evaluated at escalating dose levels to determine the MTD or maximum administered dose (MAD).

Once the single-agent MTD or MAD has been established, an escalation cohort treated with Compound B (at or below the MTD or MAD) or Compound B in combination with palbociclib may be enrolled. Additionally, patients will be enrolled in the expansion stage and treated at or below the single-agent MTD or MAD of Compound B alone or in combination with palbociclib and/or LHRH agonist. The single-agent dose expansions may evaluate two different dose levels of Compound B with and without a LHRH agonist.

Patients were monitored for adverse events during a dose-limiting toxicity (DLT) assessment window, defined as Days −7 to 28 of Cycle 1 (single-agent cohorts). For DLT evaluation, toxicity was graded according to the National Cancer Institute Common Terminology Criteria for Adverse Events, Version 4.0 (NCI CTCAE v4.0).

Patients enrolled in the single-agent Compound B dose-escalation stage, which consists of a screening period, a PK lead-in period, a treatment period, and a safety follow-up period. Continuous once daily dosing was commenced during the treatment period starting on Cycle 1 Day 1. The starting dose of single-agent Compound B was 10 mg, administered by mouth to patients in the first cohort continuously in 28-day cycles. The dose will be increased by up to 200% of the preceding dose level for each successive cohort, until a safety finding of concern (i.e., either a DLT, any patient with Grade ≥2 clinically significant toxicity or overall adverse event profile inappropriate for 200% increments) is observed. Once safety findings of concern are observed, dose escalation will not exceed 100% increments.

Compound B has half-life of about 40 hours. As noted above, exposures of Compound B increased proportionally from 10 to 30 mg with normal variability.

Six patients were initiated in the initial dose of 10 mg QD on 28-day cycles as described herein. As noted in Table 38 below, all treated patients with FES-PET had qualitative near-complete (NC) or complete responses (CR). There were no observed DLTs, SAEs, AESIs, or clinically significant laboratory abnormalities in the treated patients. All related AEs were Grade 1 or Grade 2 events.

TABLE 38

Patient response to treatment with Compound B:

| Patient | Cohort (Dose) | Days (status) | BL disease (SLD) | Response |
| --- | --- | --- | --- | --- |
| C3 | 3 (90 mg) | 15 (active) | Bone-only (NM) | NA |
| C2 | 3 (90 mg) | 36 (active) | Lung, liver, LN, bone (>100 mm) | NA |
| C1 | 3 (90 mg) | 57 (active) | Bone-only (NM) | NA |
| B6 | 2-BF (30 mg) | 2 (active) | LN, Bone (87 mm) | NA |
| B5 | 2-BF (30 mg) | 28 (active) | LN, Bone (35 mm) | NA |
| B4 | 2-BF (30 mg) | 29 (active) | Bone-only (NM) | NA |
| B3 | 2 (30 mg) | 62 (PD) | Liver (30 mm) | PD |
| B2 | 2 (30 mg) | 119 (active) | Pulm/hilar (38 mm) | SD (−9%) |
| B1 | 2 (30 mg) | 127 (active) | Bone-only (NM) | SD (NM) |
| A6 | 1-BF (10 mg) | 64 (Clinical PD) | Liver, LN, Bone (62 mm) | SD (NM) |
| A5 | 1-BF (10 mg) | 21 (Clinical PD) | Liver, LN, Bone (13 mm) | cPD |
| A4 | 1-BF (10 mg) | 45 (Clinical PD) | Bone-only (NM) | cPD |
| A3 | 1 (10 mg) | 183 (active) | Breast (50 mm) | uPR (−40%) |
| A2 | 1 (10 mg) | 183 (active) | Pulmonary (36 mm) | SD (−27%) |
| A1 | 1 (10 mg) | 64 (PD) | Bone-only (NM) | PD |

Figure 36B:
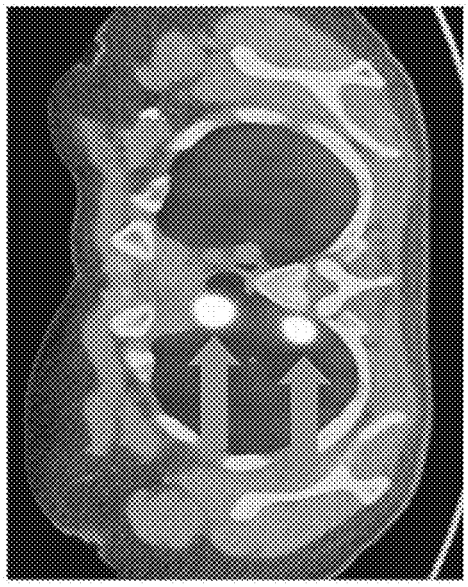
FIG. 36a depicts CT scanning and FIG. 36b depicts FES-PET scanning of a breast cancer patient treated with Compound B.
Figure 36B:
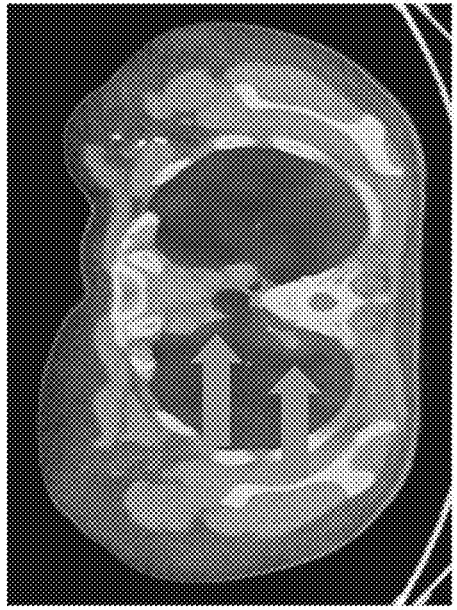
Figure 36A:
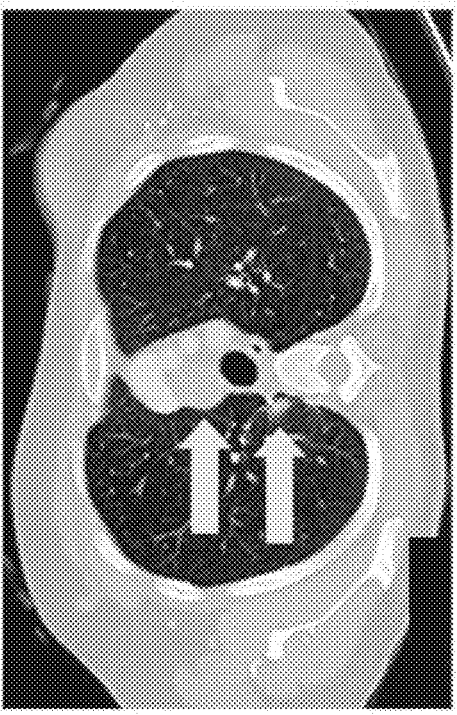
Figure 36A:
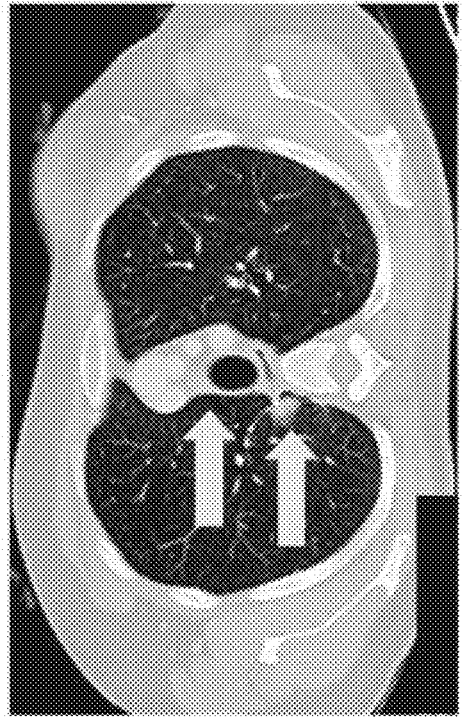

One treated patient was diagnosed with ER+PR+ breast cancer. The patient had undergone previous surgery and previous treatment with anti-cancer agents, including SERM therapy and AI therapy prior to enrollment and treatment. The patient was treated with Compound B at 10 mg and showed response to the treatment after 3 cycles as indicated in FIG. 36a and FIG. 36b.

Figures 37A, 37B:
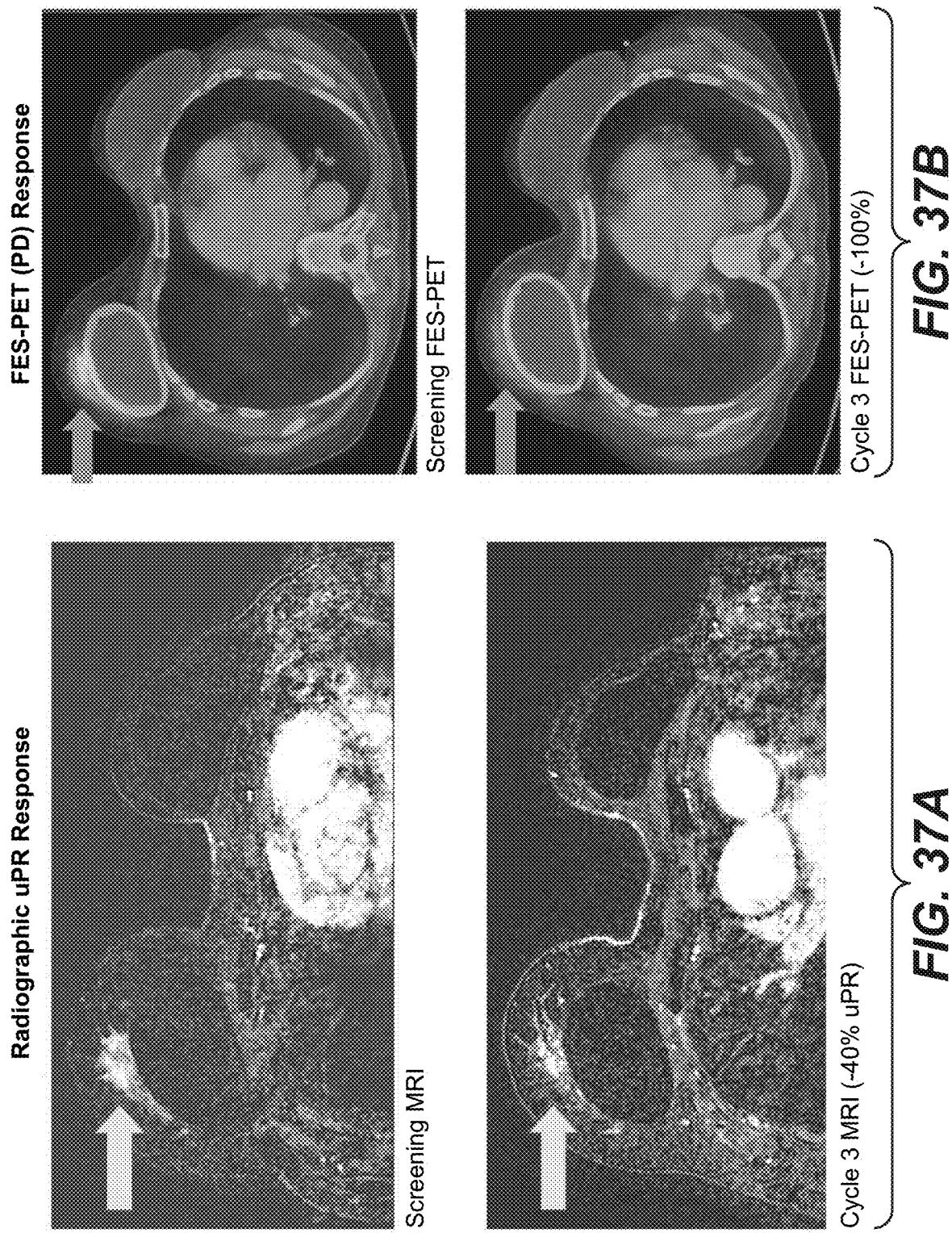
FIG. 37a depicts CT scanning and FIG. 37b depicts FES-PET scanning of a second breast cancer patient treated with Compound B.

Another patient was diagnosed with early stage HR+ breast cancer and had received prior surgery and treatment with anti-cancer agents, including cytotoxics, CDK4/6 inhibitors, and AIs. The patient was treated with Compound B at 10 mg and showed response to the treatment after 3 cycles as indicated in FIG. 37a and FIG. 37b. was enrolled on our trial at 10 mg in March 2018.

The treated patients to-date demonstrate that administration of Compound B is well-tolerated at 10 mg and 30 mg, with only Grade 1 and 2 AEs. In general, plasma exposures of Compound B increased proportionally with doses from 10 to 30 mg after single dose. The steady state exposures appeared to increase in a higher than dose proportional manner from 10 mg to 30 mg. The estimated half-life of about 40 hours supports once-daily dosing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A process for preparing a compound of formula (VIII) or a salt thereof, the process comprising:
   (a) reacting a reaction mixture comprising a compound of formula (IV), a compound of formula (V) or a compound of formula (X), and an organic solvent to form a compound of formula (VI) according to step 1 below

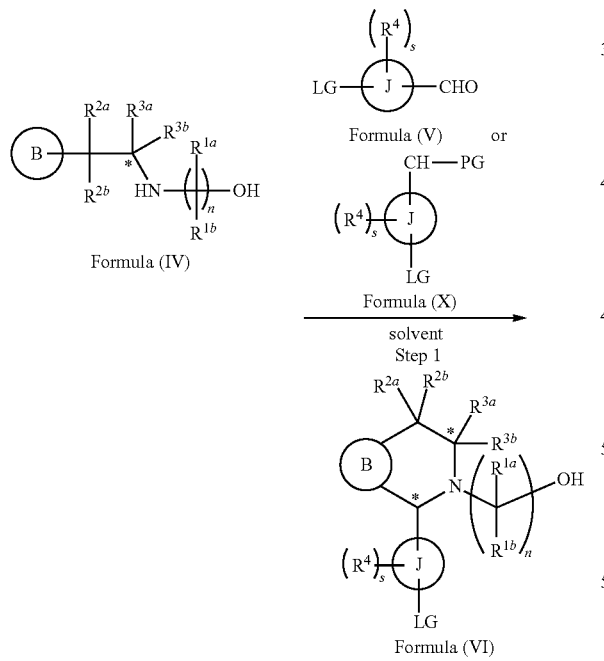

wherein
B is substituted or unsubstituted indolyl, benzofuranyl, benzothiophenyl, aza-indolyl, indazolyl, benzimidazolyl, pyrrolopyridinyl, furopyridinyl, thienopyridinyl, pyrrolopyridazinyl, pyrrolopyrimidinyl, pyrrolopyrazinyl, thienopyridazinyl, thienopyrimidinyl, thienopyrazinyl, furopyridazinyl, furopyrimidinyl, or furopyrazinyl;

each of $R^{1a}$ and $R^{1b}$ is independently hydrogen, fluorine, chlorine, —OH, $C_{1-3}$ alkyl, $C_{1-3}$ haloalkyl, $C_{1-3}$ alkoxy, $C_{1-3}$ hydroxyalkyl, and —CN, $C_{3-6}$ cycloalkyl, or $C_{3-6}$ spirocycloalkyl, n is an integer of 2 or 3, each of $R^{2a}$ and $R^{2b}$ is independently hydrogen, halogen, —OH, $C_{1-3}$ alkyl, $C_{1-3}$ haloalkyl, $C_{1-3}$ alkoxy, $C_{1-3}$ hydroxyalkyl, —CN, $C_{3-6}$ cycloalkyl, or $C_{3-6}$ spirocycloalkyl, $R^{3a}$ and $R^{3b}$ are independently hydrogen, $C_{1-3}$ alkyl, $C_{1-3}$ haloalkyl, $C_{1-3}$ alkoxy, —CN, $C_{3-6}$ cycloalkyl, $C_{3-6}$ heterocycloalkyl, phenyl, $C_{3-6}$ heteroaryl, or $C_{3-6}$ spirocycloalkyl, J is phenyl or pyridinyl;

each $R^4$ is independently hydrogen, halogen or $C_{1-3}$ alkyl, s is an integer from 0 to 2, LG is a leaving group, LG and CHO are located in the para position with respect to each other on J on the compound of formula (V), PG is an aldehyde protecting group, LG and CH-PG are located in the para position with respect to each other on J on the compound formula (X), and each asterisk independently represents a chiral center wherein the carbon bearing $R^{3a}$ and $R^{3b}$ is a chiral center when $R^{3a}$ and $R^{3b}$ are different; and (b) reacting a reaction mixture comprising the compound of formula (VI), an organic solvent, and a compound of formula (VII) or a salt thereof to form a compound of formula (VIII) or a salt thereof according to step 2 below Formula (VI)

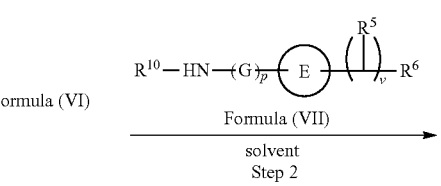

Formula (VII)

solvent
Step 2

183

-continued

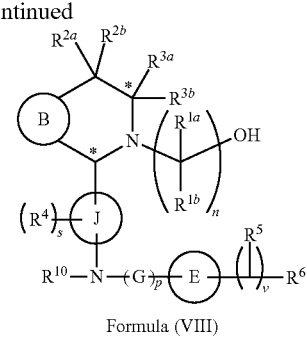

Formula (VIII)

wherein

G is $C_{1-3}$ alkyl, p is 0 or 1,

E is substituted or unsubstituted azetidinyl or pyrrolidinyl, each $R^5$ is independently hydrogen, halogen, —OH, —CN, $C_{1-5}$ alkoxy, or $C_{1-5}$ hydroxyalkyl, v is an integer from 1 to 5, and $R^6$ is halogen or —CN;

$R^{10}$ is hydrogen or $C_{1-3}$ alkyl.

2. The process of claim 1, wherein B is a substituted or unsubstituted indolyl, benzofuranyl, or benzothiophenyl.

3. The process of claim 2, wherein B is a substituted or unsubstituted indolyl.

4. The process wherein 1, is a substituted or unsubstituted pyrrolopyridazinyl, pyrrolopyrimidinyl, or pyrrolopyrazinyl.

5. The process of claim 1, wherein B is substituted with one or two substituents independently selected from fluorine, chlorine, $C_{1-3}$ alkyl, $C_{1-3}$ haloalkyl, —CN, —OH, $C_{1-3}$ alkoxy, or $C_{1-3}$ hydroxyalkyl.

6. The process of claim 1, wherein each of $R^{1a}$ and $R^{1b}$ is independently hydrogen, —F, —Cl, —OH, —CN, —CH$_3$, —CF$_3$, —CHF$_2$, —CH$_2$F, or spirocyclopropyl.

7. The process of claim 1, wherein n is 3.

8. The process of claim 1, wherein:

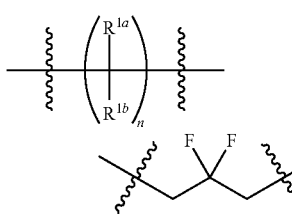

is of the formula

9. The process of claim 1, wherein each of $R^{2a}$ and $R^{2b}$ is hydrogen.

10. The process of claim 1, wherein $R^{3a}$ and $R^{3b}$ are independently hydrogen or —CH$_3$.

11. The process of claim 1, wherein each $R^4$ is fluorine.

12. The process of claim 1, wherein s is 2.

13. The process of claim 1, wherein the leaving group is bromine.

14. The process of claim 1, wherein p is 0.

15. The process of claim 1, wherein the structure of the moiety of formula

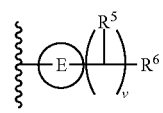

of Compound (VII) and Compound (VIII) is:

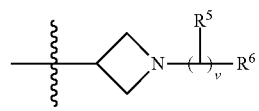

wherein each $R^5$ is hydrogen.

16. The process of claim 1, wherein v is 3.

17. The process of claim 1, wherein $R^6$ is fluorine.

18. The process of claim 1, wherein the compound of formula (VII) is a salt of an acid.

19. The process of claim 1, wherein step 1 further comprises an acid catalyst.

20. The process of claim 1, wherein step 2 further comprises a transition metal catalyst.

21. The process of claim 1, wherein the compound of formula (IV) is:

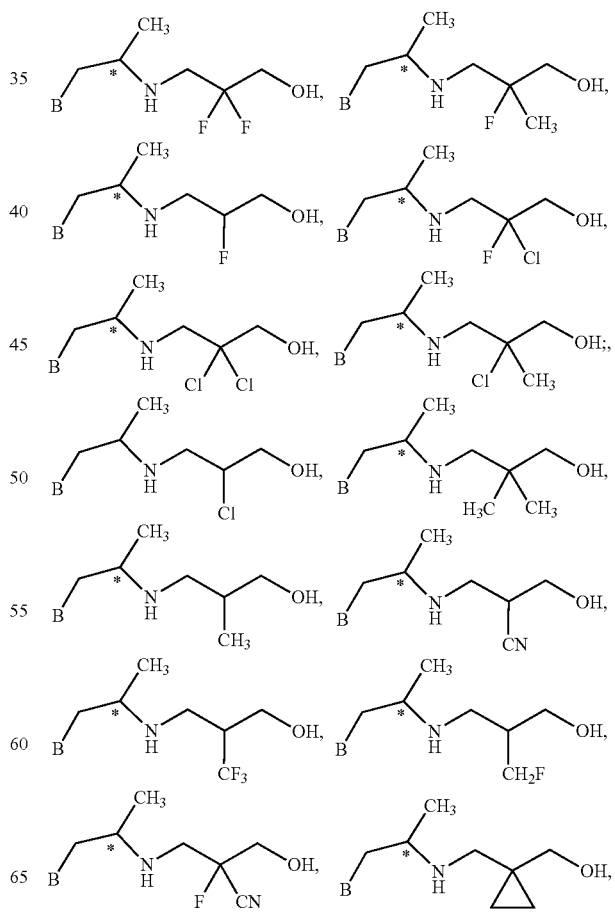

-continued
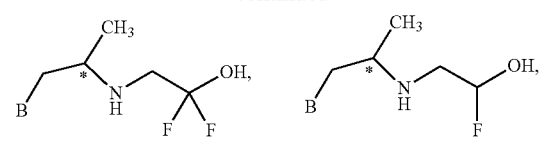
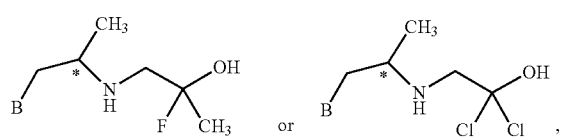
or salt thereof, including stereoisomers thereof.
22. The process of claim 1, wherein the compound of formula (V) is:
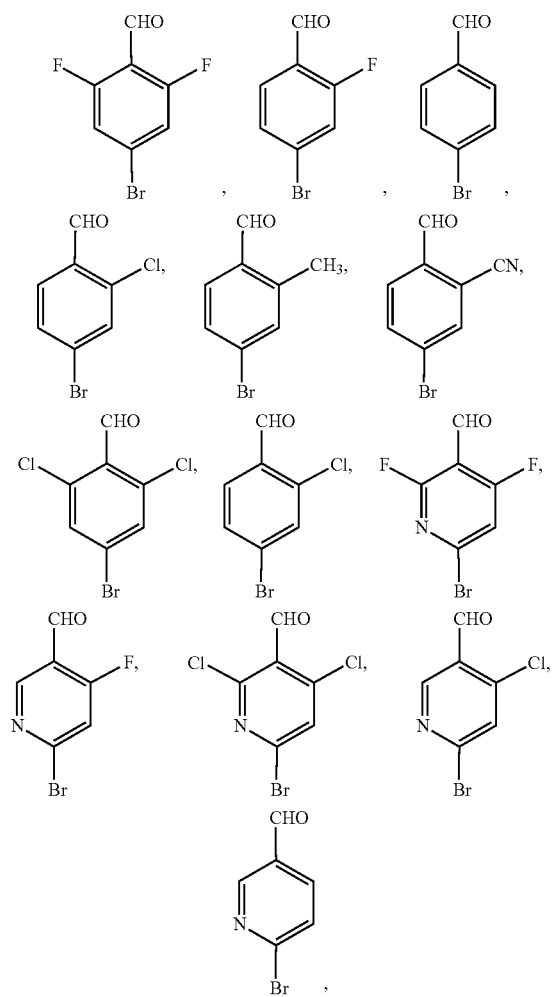
or a salt thereof.
23. The process of claim 1, wherein the compound of formula (X) is:
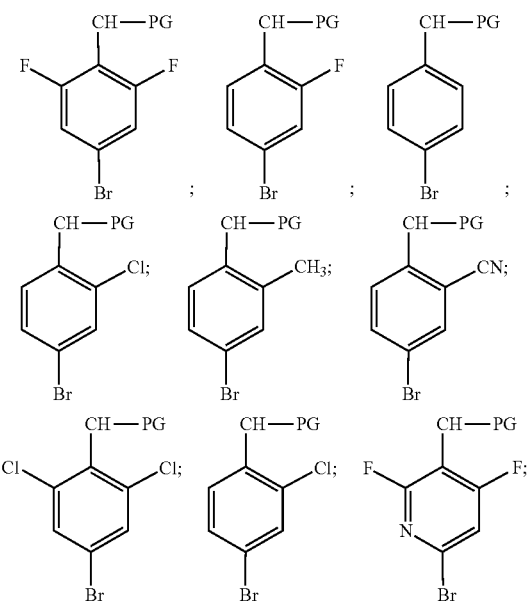
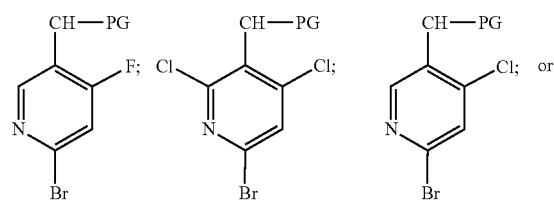
24. The process of claim 1, wherein the compound of formula (VI) is:
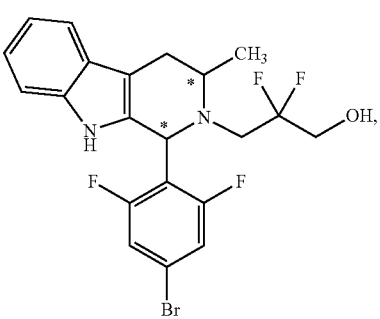

187                                              188
-continued                                      -continued
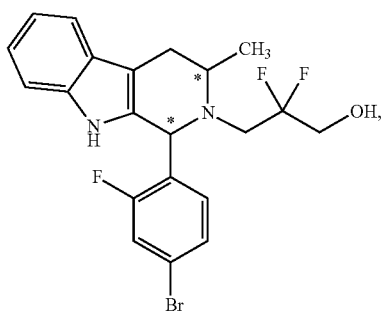
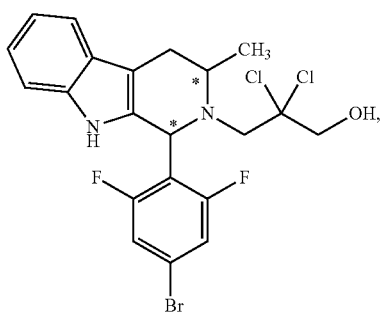

189
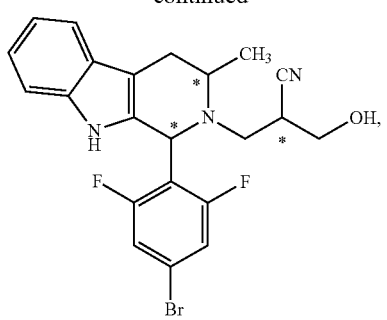
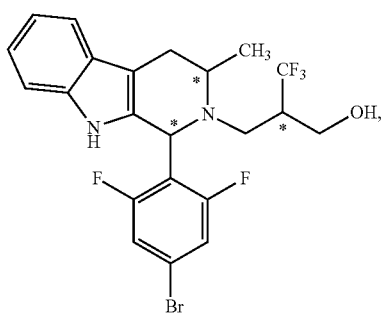
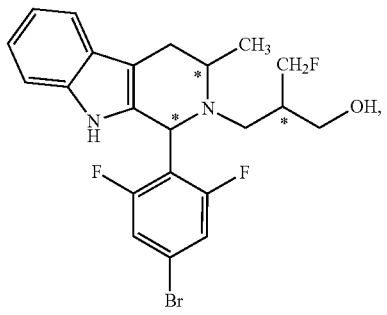
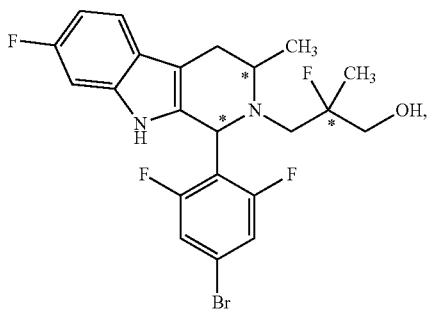
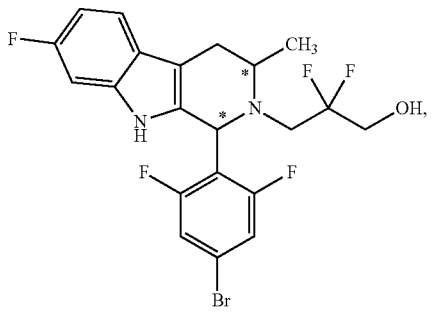
190
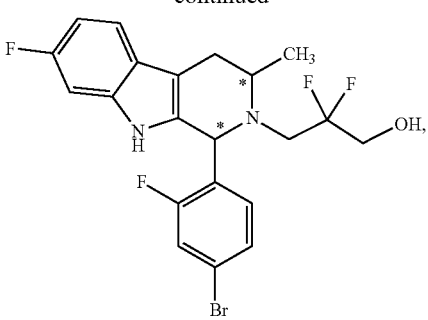
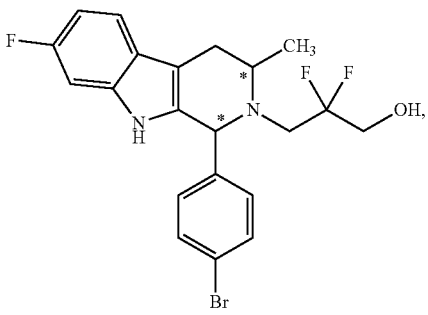
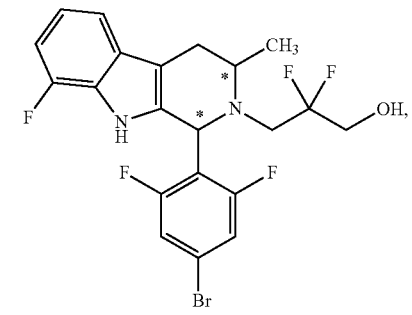
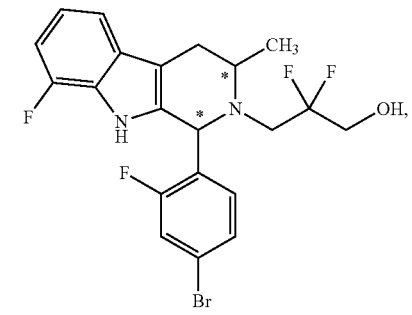
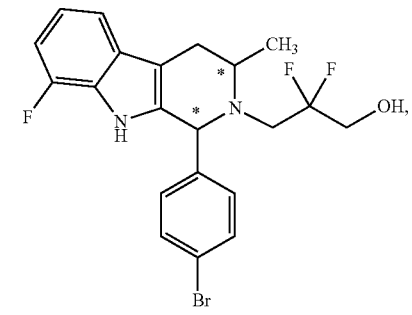

191
-continued
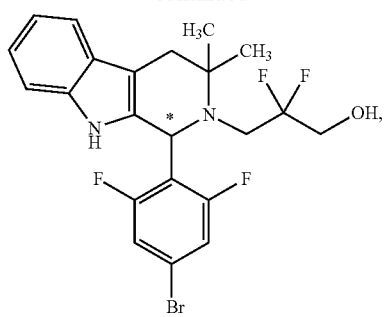
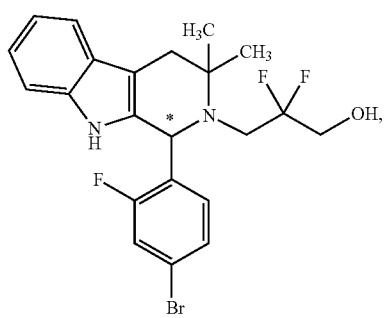
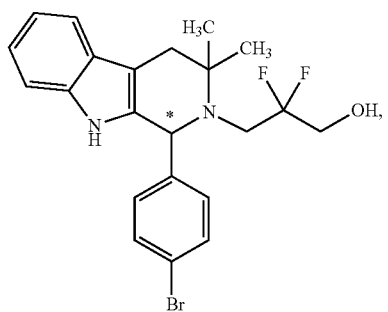
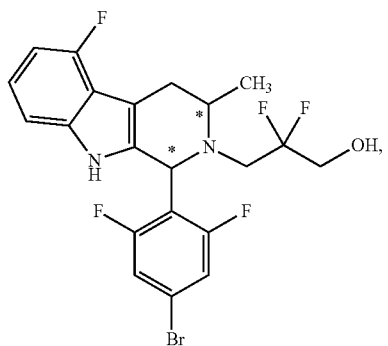
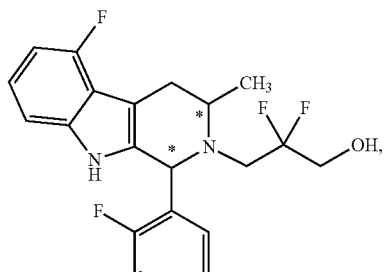
192
-continued
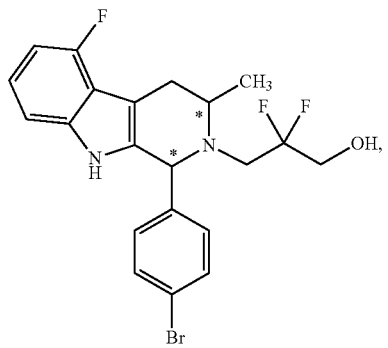
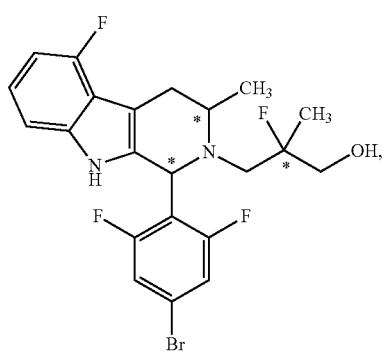
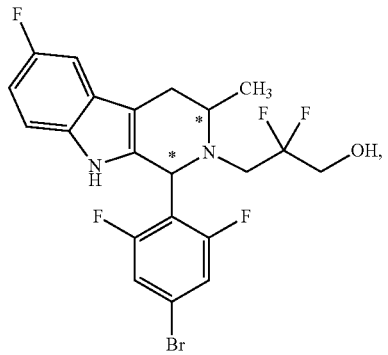
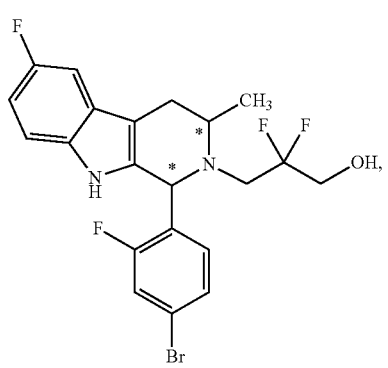

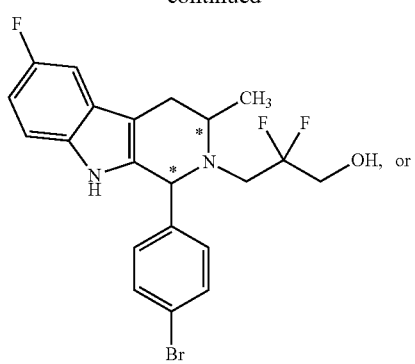
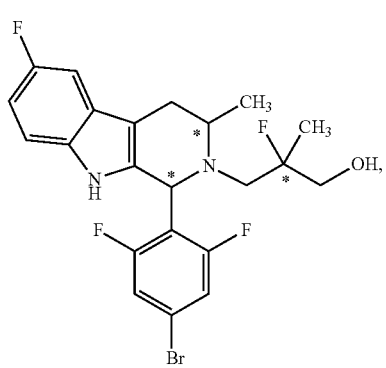
or a salt thereof, including stereoisomers thereof.
25. The process of claim 1, wherein the compound of formula (VII) is:
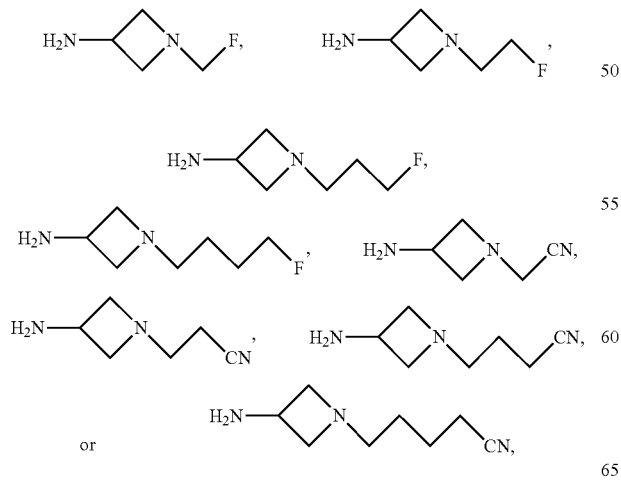
or a salt thereof.
26. The process of claim 1, wherein the compound of formula (VIII) is:
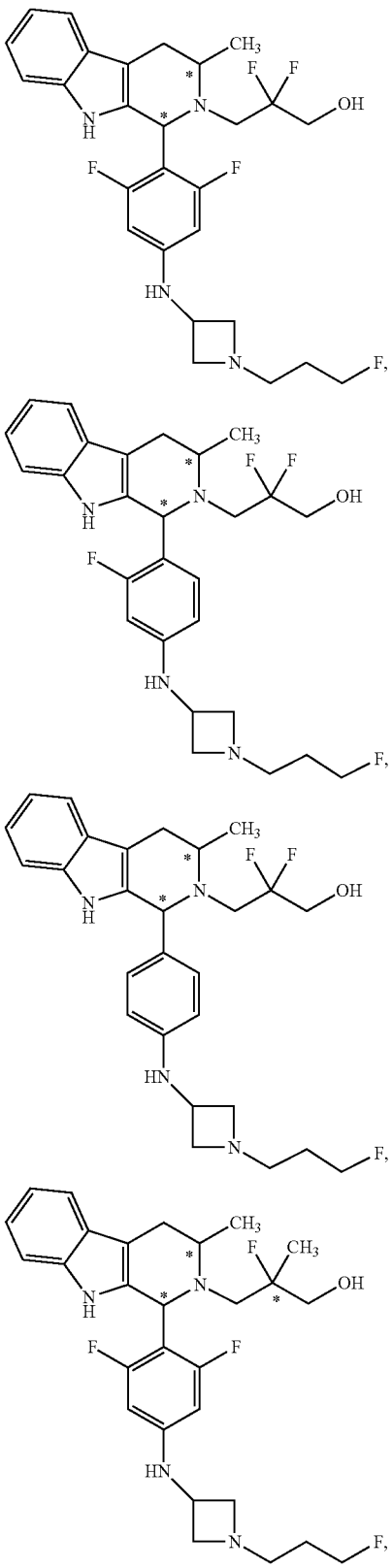 [SMILES: CC1Cc2c([nH]c3ccccc23)C(c2c(F)cc(NC3CN(CCCF)C3)cc2F)N1CC(Cl)CO ; CC1Cc2c([nH]c3ccccc23)C(c2c(F)cc(NC3CN(CCCF)C3)cc2F)N1CC(C)(C)CO ; CC(CO)CN1C(C)Cc2c([nH]c3ccccc23)C1c1c(F)cc(NC2CN(CCCF)C2)cc1F ; CC1Cc2c([nH]c3ccccc23)C(c2c(F)cc(NC3CN(CCCF)C3)cc2F)N1CC(C#N)CO]

195
-continued
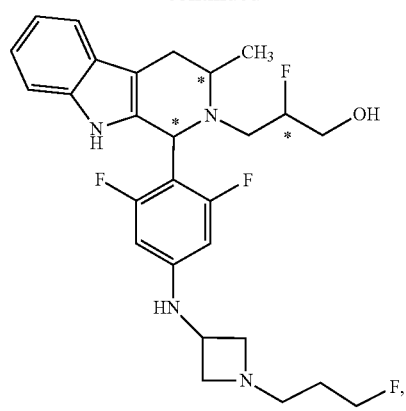
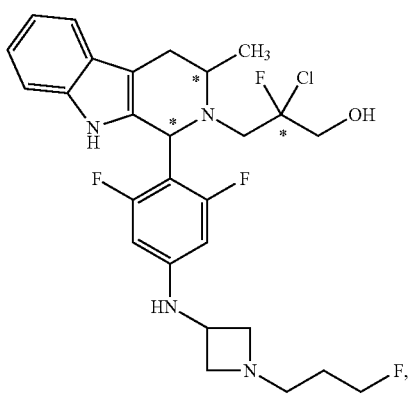
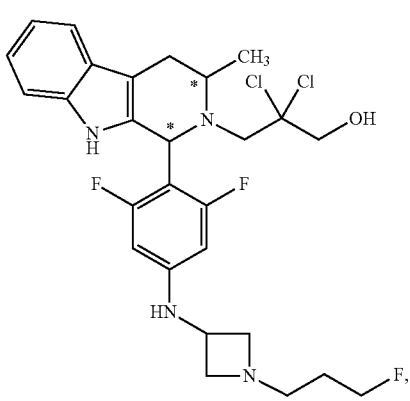
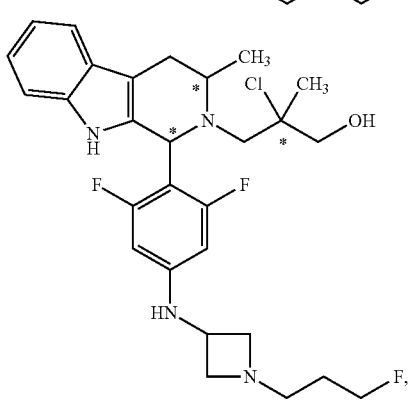
196
-continued
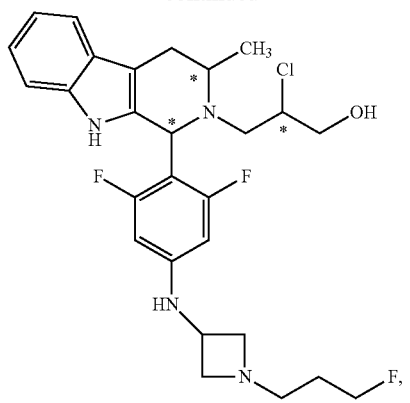
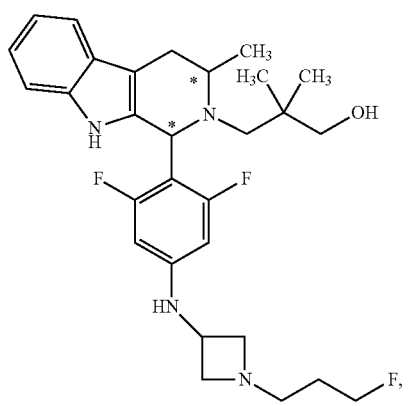
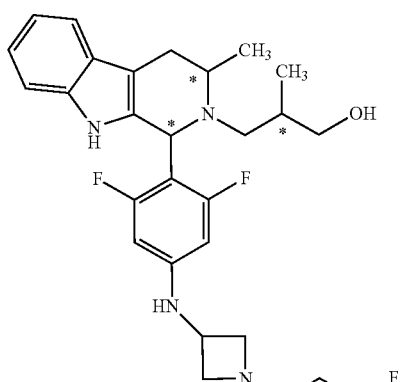
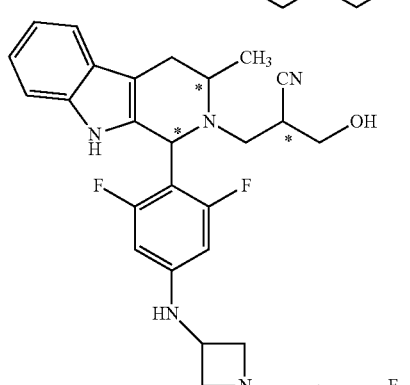

197
-continued
198
-continued
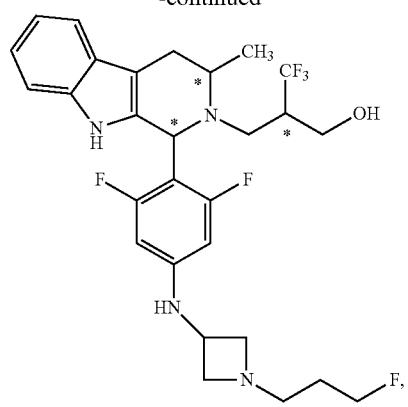
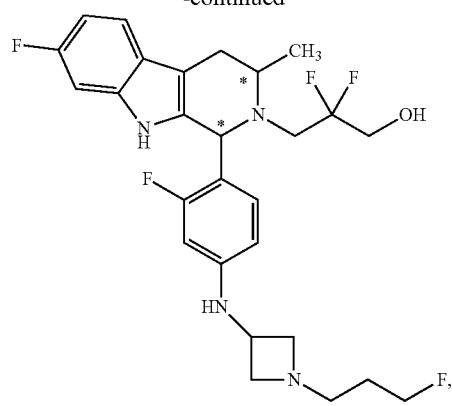
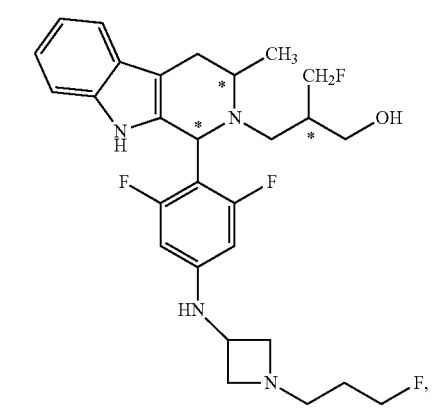
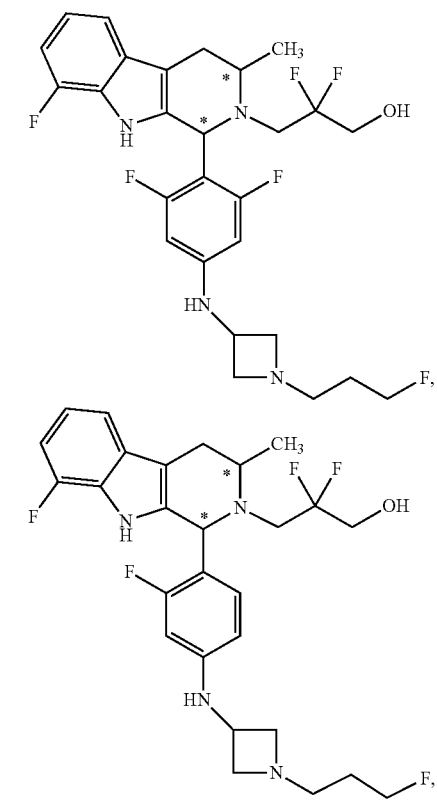

199
-continued
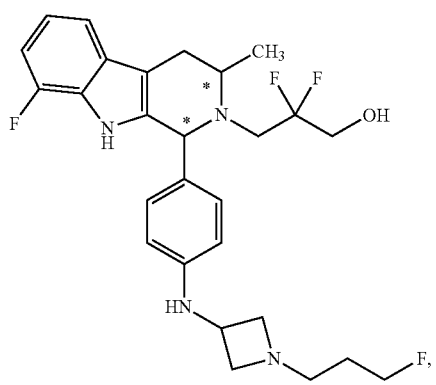
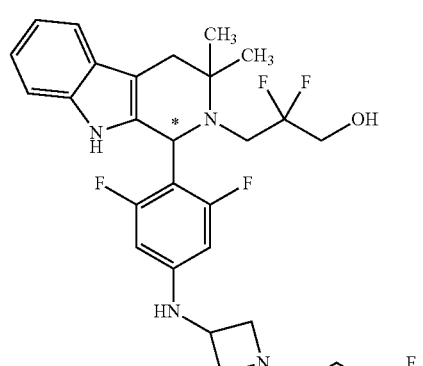
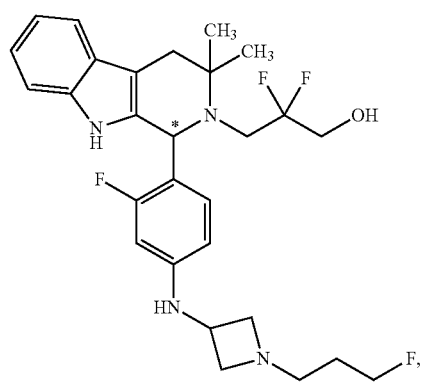
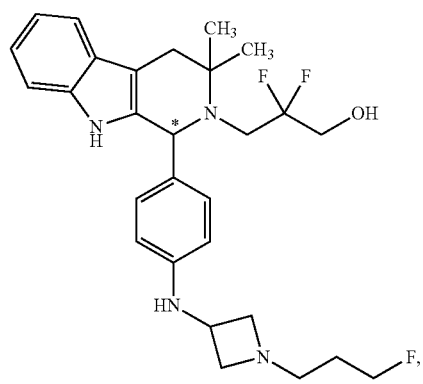
200
-continued
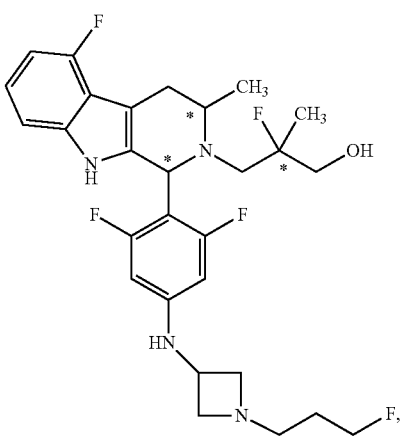

201
-continued

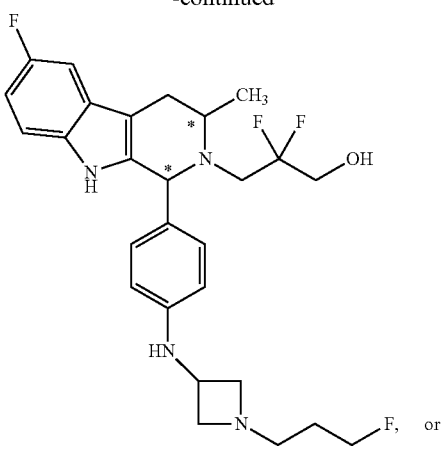

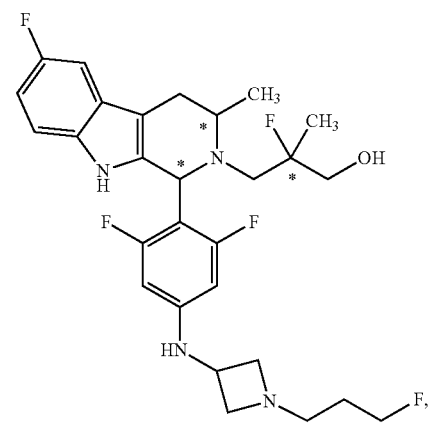 [SMILES: CC1Cc2c([nH]c3ccc(F)cc23)C(c2c(F)cc(NC3CN(CCCF)C3)cc2F)N1CC(C)(F)CO]

or a pharmaceutically acceptable salt thereof including stereoisomers thereof.

27. The process of claim 26, further comprising contacting the compound of formula (VIII) with (2R-3R)-tartaric acid in the presence of an organic solvent.

28. The process of claim 1, wherein the compound of formula (VIII) is:

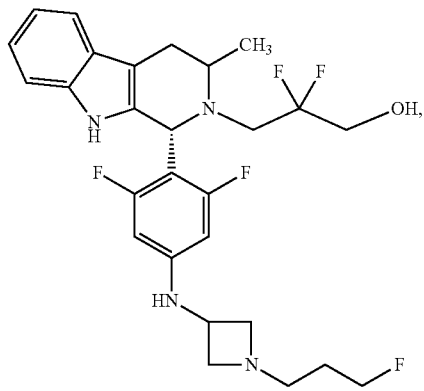 [SMILES: CC1Cc2c([nH]c3ccccc23)[C@@H](c2c(F)cc(NC3CN(CCCF)C3)cc2F)N1CC(F)(F)CO]

or a pharmaceutically acceptable salt thereof.

202

29. The process of claim 28, wherein the compound of formula (VIII) is:

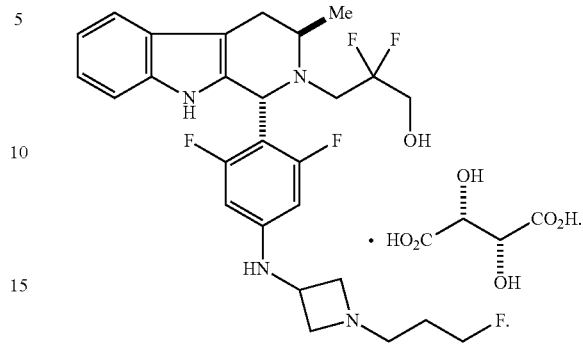

30. The process of claim 1, further comprising crystallizing the compound of formula (VIII) as the tartaric acid salt thereof.

31. A process for preparing a compound of formula (VIII) or a salt thereof, the process comprising reacting a reaction mixture comprising a compound of formula (IX) or a compound of formula (XI), a compound of formula (IV) and an organic solvent to form the compound of formula (VIII) or a salt thereof according to step 1 below

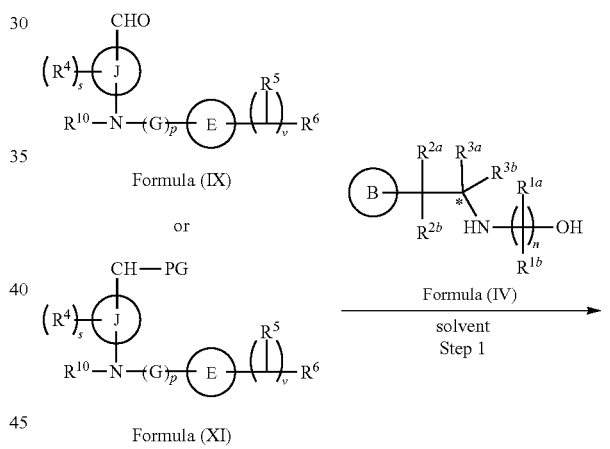

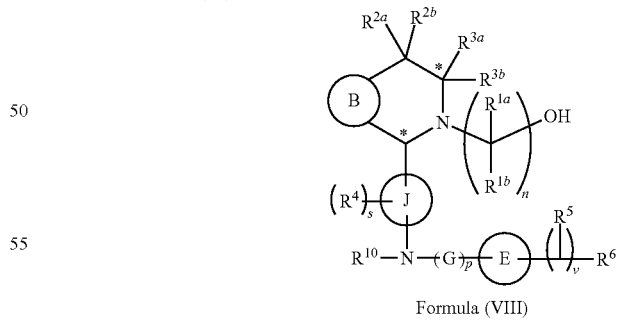

wherein:
B is substituted or unsubstituted indolyl, benzofuranyl, benzothiophenyl, aza-indolyl, indazolyl, benzimidazolyl, pyrrolopyridinyl, furopyridinyl, thienopyridinyl, pyrrolopyridazinyl, pyrrolopyrimidinyl, pyrrolopyrazinyl, thienopyridazinyl, thienopyrimidinyl, thienopyrazinyl, furopyridazinyl, furopyrimidinyl, or furopyrazinyl;

each of $R^{1a}$ and $R^{1b}$ is independently hydrogen, halogen, —OH, $C_{1-3}$ alkyl, $C_{1-3}$ haloalkyl, $C_{1-3}$ alkoxy, $C_{1-3}$ hydroxyalkyl, and —CN, $C_{3-6}$ cycloalkyl, or $C_{3-6}$ spirocycloalkyl;

n is an integer of 2 or 3;

each of $R^{2a}$ and $R^{2b}$ is independently hydrogen, halogen, —OH, $C_{1-3}$ alkyl, $C_{1-3}$ haloalkyl, $C_{1-3}$ alkoxy, $C_{1-3}$ hydroxyalkyl, —CN, $C_{3-6}$ cycloalkyl, or $C_{3-6}$ spirocycloalkyl;

$R^{3a}$ and $R^{3b}$ are independently hydrogen, halogen, —OH, $C_{1-3}$ alkyl, $C_{1-3}$ haloalkyl, $C_{1-3}$ alkoxy, $C_{1-3}$ hydroxyalkyl, —CN, $C_{3-6}$ cycloalkyl, or $C_{3-6}$ spirocycloalkyl;

J is phenyl or pyridinyl;

each $R^4$ is independently hydrogen, halogen or $C_{1-3}$ alkyl;

s is an integer from 0 to 2;

G is $C_{1-3}$ alkyl;

p is 0 or 1;

E is substituted or unsubstituted azetidinyl or pyrrolidinyl;

each $R^5$ is independently hydrogen, halogen, —OH, —CN, $C_{1-5}$ alkoxy or $C_{1-5}$ hydroxyalkyl;

v is an integer from 1 to 5;

$R^6$ is halogen or —CN;

$R^{10}$ is H or $C_{1-3}$ alkyl;

the CHO moiety and the nitrogen atom linking J and G are located in the para position with respect to each other on J on the compound of formula (IX);

PG is an aldehyde protecting group,

CH-PG and the nitrogen atom linking J and G are located in the para position with respect to each other on J on the compound of formula (XI); and each asterisk independently represents a chiral center wherein the carbon bearing $R^{3a}$ and $R^{3b}$ is a chiral center when $R^{3a}$ and $R^{3b}$ are different.

32. The process of claim 31, wherein B is a substituted or unsubstituted indolyl, benzofuranyl, or benzothiophenyl.

33. The process of claim 32, wherein B is a substituted or unsubstituted indolyl.

34. The process of claim 31, wherein B is a substituted or unsubstituted pyrrolopyridazinyl, pyrrolopyrimidinyl, or pyrrolopyrazinyl.

35. The process of claim 31, wherein B is substituted with one or two substituents independently fluorine, chlorine, $C_{1-3}$ alkyl, $C_{1-3}$ haloalkyl, —CN, —OH, $C_{1-3}$ alkoxy or $C_{1-3}$ hydroxyalkyl.

36. The process of claim 31, wherein each of $R^{1a}$ and $R^{1b}$ is independently hydrogen, F, —Cl, —OH, —CN, —CH$_3$, —CF$_3$, —CHF$_2$, —CH$_2$F, or spirocyclopropyl.

37. The process of claim 31, wherein n is 3.

38. The process of claim 31, wherein:

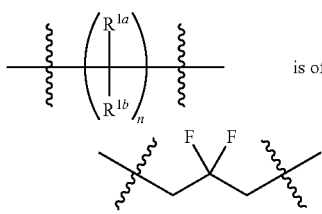

is of the formula

39. The process of claim 31, wherein each of $R^{2a}$ and $R^{2b}$ is hydrogen.

40. The process of claim 31, wherein $R^{3a}$ and $R^{3b}$ are independently hydrogen or —CH$_3$.

41. The process of claim 31, wherein J is phenyl.

42. The process of claim 31, wherein the structure of the moiety of formula

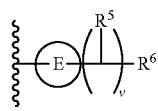

of Compound (VIII), Compound (IX), and Compound (XI) is:

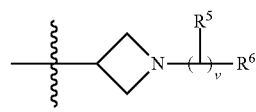

wherein each $R^5$ is hydrogen.

43. The process of claim 31, wherein each $R^4$ is fluorine.

44. The process of claim 31, wherein s is 2.

45. The process of claim 31, wherein p is 0.

46. The process of claim 31, wherein v is 3.

47. The process of claim 31, wherein $R^6$ is fluorine.

48. The process of claim 31, wherein the compound of formula (IV) is:

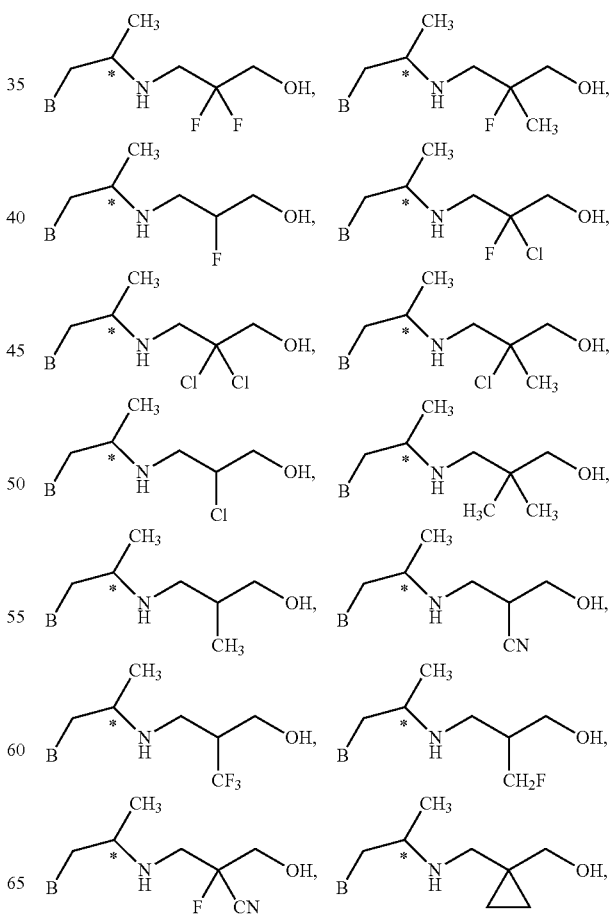

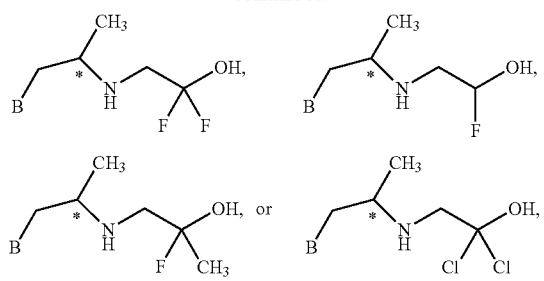
or salt thereof, including stereoisomers thereof.
49. The process of claim 31, wherein the compound of formula (IX) is:
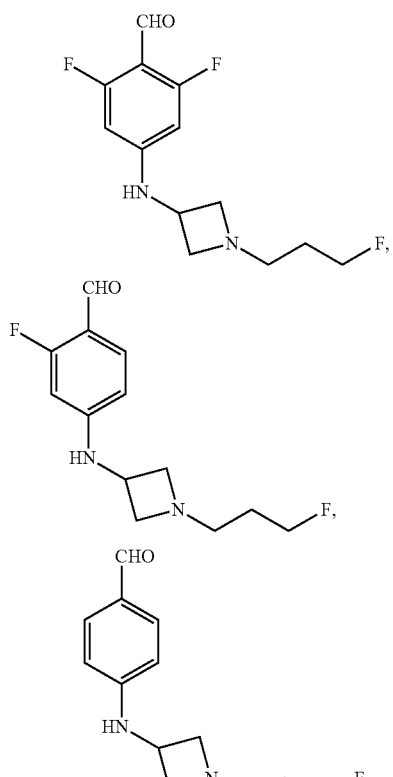
or a salt thereof.
50. The process of claim 31, wherein the compound of formula (XI) is:
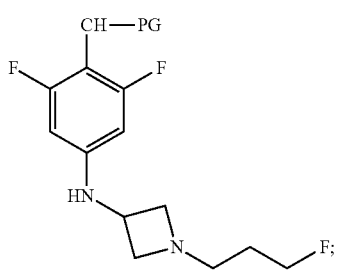
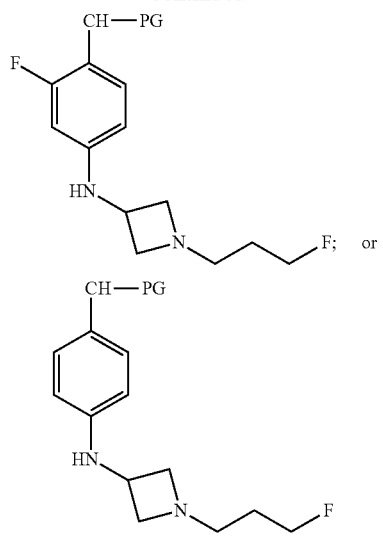
or a salt thereof.
51. The process of claim 31, wherein the compound of formula (VIII) is:
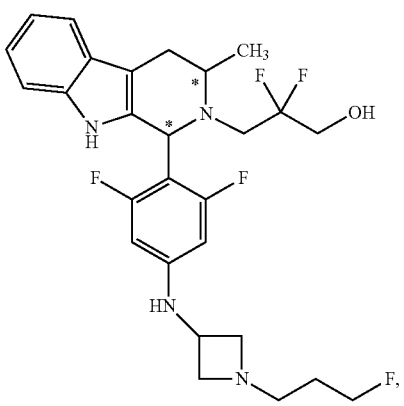
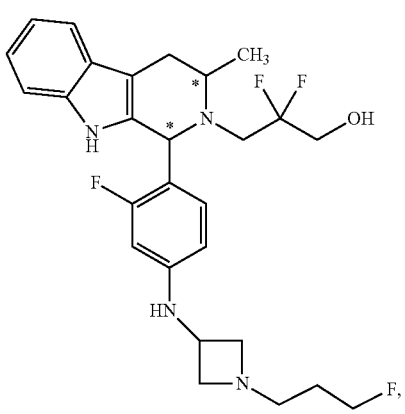

207
-continued
208
-continued
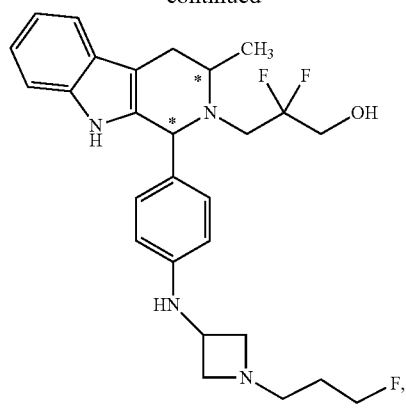
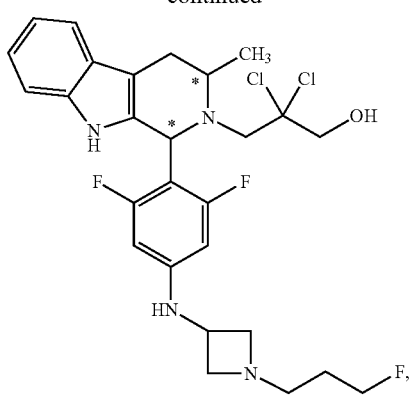
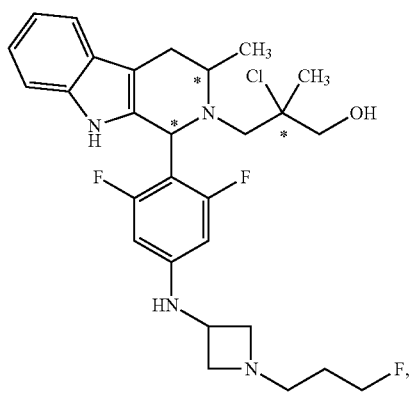
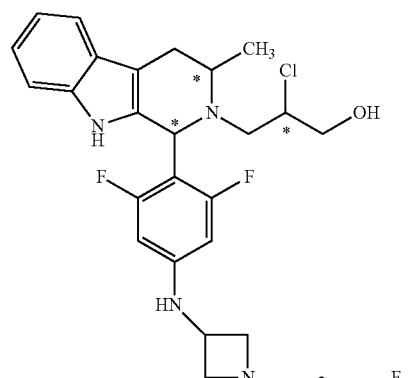
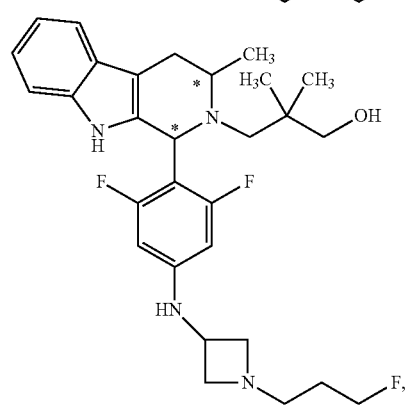

209
-continued
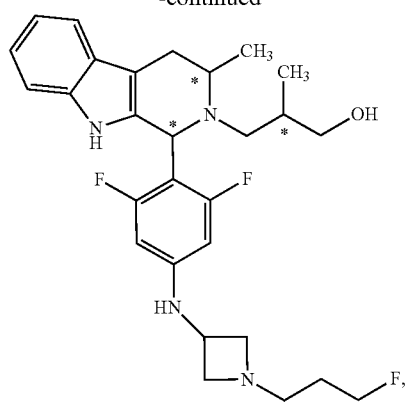
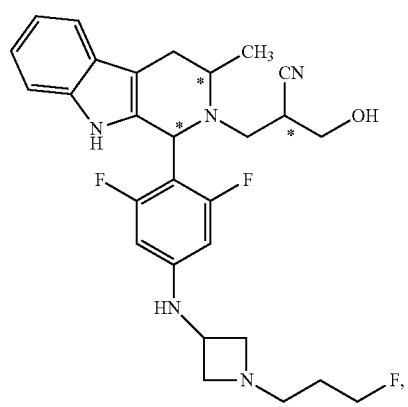
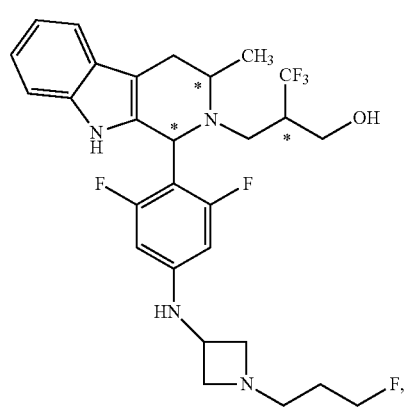
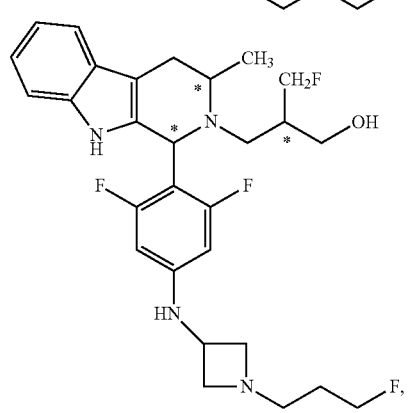
210
-continued
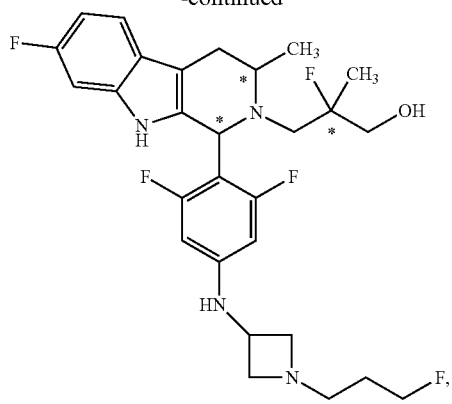
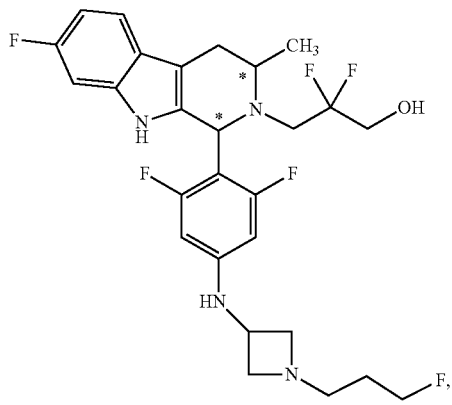
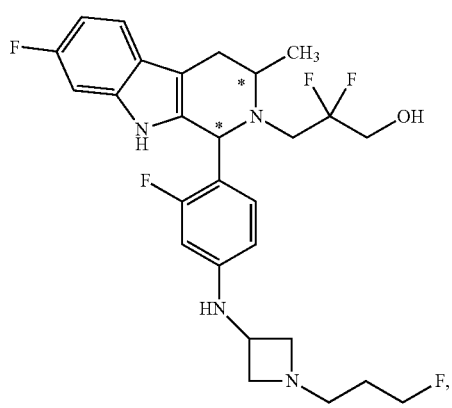
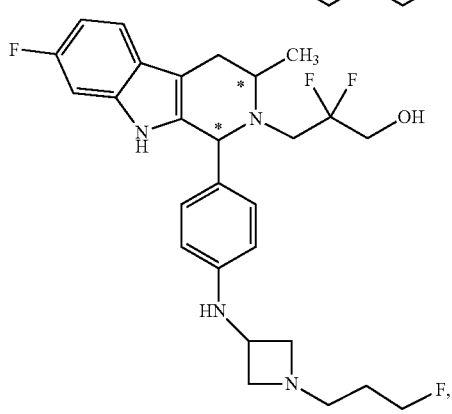

211
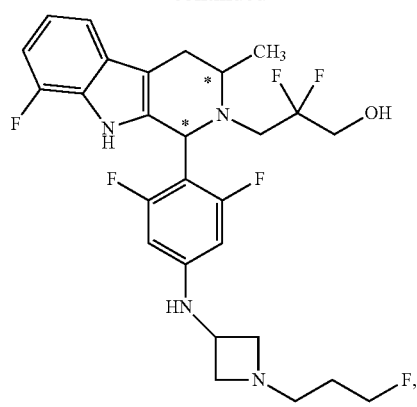
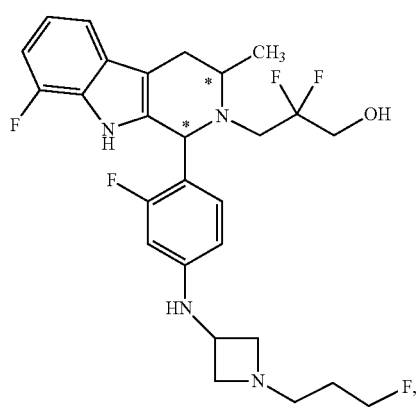
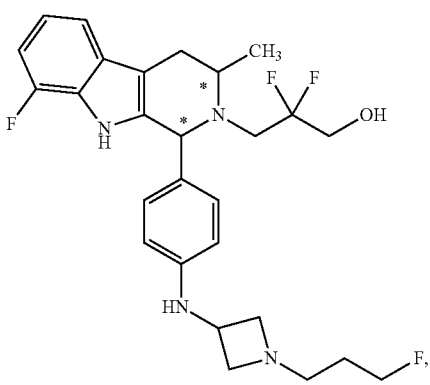
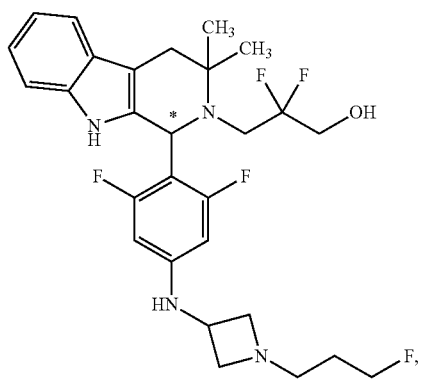
212
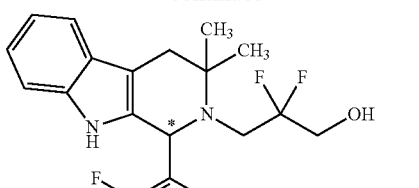
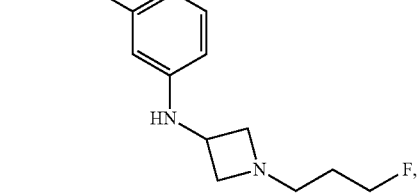
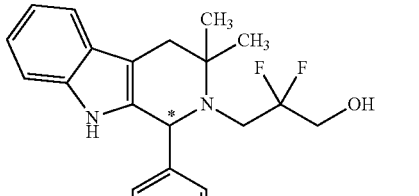
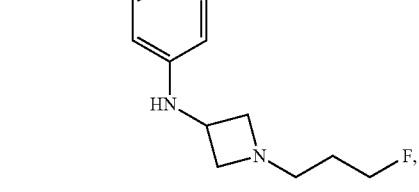

-continued

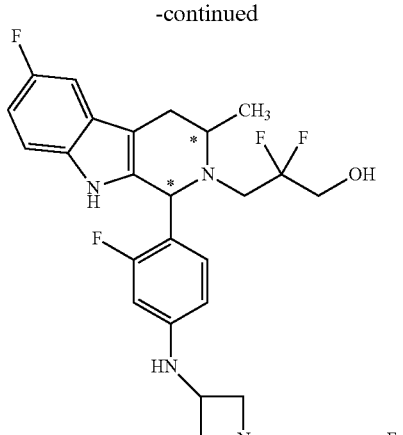

or a pharmaceutically acceptable salt thereof including stereoisomers thereof.

52. The process of claim 31, further comprising contacting the compound of formula (VIII) with (2R-3R)-tartaric acid in the presence of an organic solvent.

53. The process of claim 31, wherein the compound of formula (VIII) is:

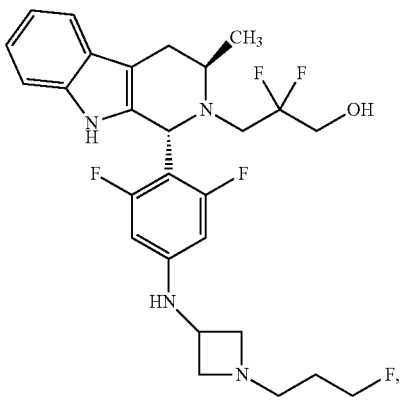 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

54. The process of claim 53, wherein the compound of formula (VIII) is:

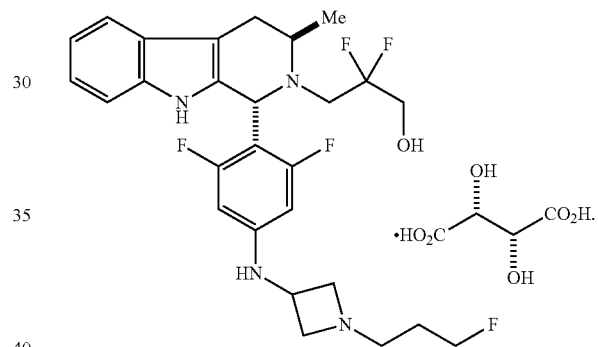

55. The process of claim 31, further comprising crystallizing the compound of formula (VIII) as the tartaric acid salt thereof.

56. A process for preparing a compound of formula (IX) or a salt thereof, the process comprising:

(1) reacting a reaction mixture comprising a compound of formula (X), an ethane-1,2-disulfonate salt of a compound of formula (VII), an organic solvent and a catalyst to form a compound of formula (XI) according to step 1 below

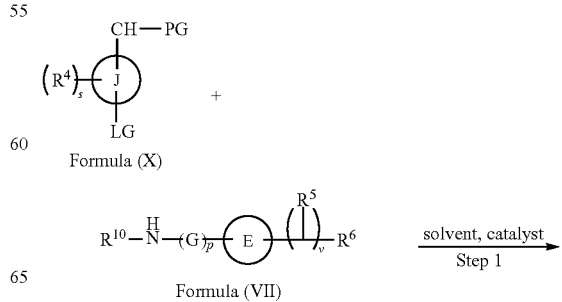

215

-continued

Formula (XI)

wherein
J is phenyl or pyridinyl;
each $R^4$ is independently hydrogen, halogen or $C_{1-3}$ alkyl,
s is an integer from 0 to 2,
LG is a leaving group, h
PG is an aldehyde protecting group,
LG and CH-PG are located in the para position with respect to each other on J,
G is $C_{1-3}$ alkyl,
p is 0 or 1,
E is substituted or unsubstituted azetidinyl or pyrrolidinyl,
each $R^5$ is independently hydrogen, halogen, —OH, —CN, $C_{1-5}$ alkoxy or $C_{1-5}$ hydroxyalkyl,
v is an integer from 1 to 5,
$R^6$ is halogen or —CN, and
$R^{10}$ is hydrogen or $C_1$-$C_3$ alkyl; and (2) deprotecting the compound of formula (XI) to form the compound of formula (IX) according to step 2 below Formula (XI) →(solvent, Step 2)→ Formula (IX).

57. The process of claim 56, wherein J is phenyl.
58. The process of claim 56, wherein each $R^4$ is fluorine.
59. The process of claim 56, wherein s is 2.
60. The process of claim 56, wherein the leaving group is bromine.
61. The process of claim 56, wherein p is 0.
62. The process of claim 56, wherein the structure of the moiety of formula of Compound (VIII), Compound (IX), and Compound (XI) is:

wherein each $R^5$ is hydrogen.
63. The process of claim 56, wherein v is 3.
64. The process of claim 56, wherein $R^6$ is fluorine.

216

65. The process of claim 56, wherein the compound of formula (VII) is a salt of an acid.
66. The process of claim 56, wherein the aldehyde protecting group is a trialkylorthoformate.
67. The process of claim 56, wherein the step 1 catalyst is a transition metal catalyst.
68. The process of claim 56, wherein the compound of formula (XI) is deprotected by contact with an acid.
69. The process of claim 56, wherein the compound of formula (IX) is:

or a salt thereof.

70. A process for the preparation of Compound B, (B)

wherein the process comprises the steps of:

step (1): contacting a compound

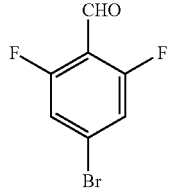

with p-toluenesulfonic acid (p-TsOH) and triethyl orthoformate ((EtO)₃CH) in a solvent comprising toluene to yield a compound of formula

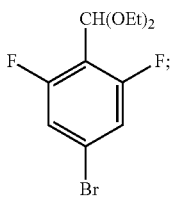

step (2): contacting the compound of formula

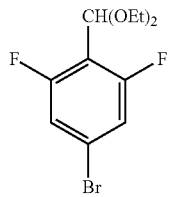

from step 1 with a compound of formula

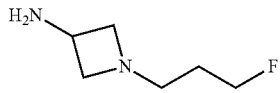

and NaOt-Bu followed by BrettPhos Pd G3, in a solvent comprising toluene to yield a compound of formula

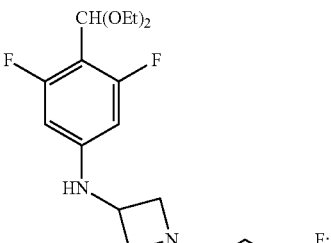

step (3): contacting the compound of formula

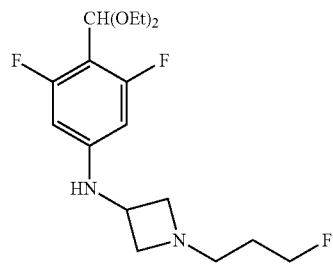 [SMILES: O=Cc1c(F)cc(NC2CN(CCCF)C2)cc1F]

of step 2 with acetic acid in water to yield a compound of formula

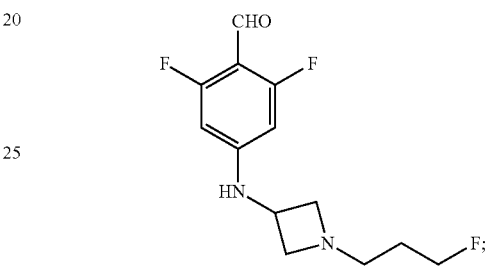

step (4): contacting the compound of formula

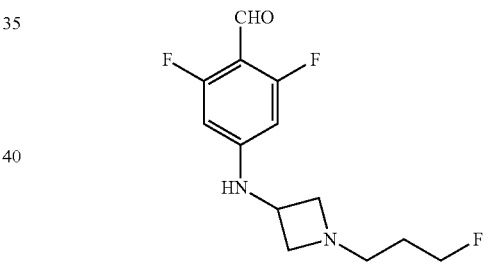

of step (3) with a compound of formula

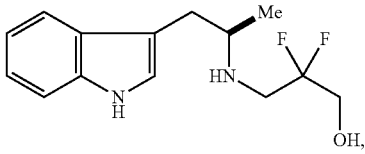 [SMILES: C[C@H](Cc1c[nH]c2ccccc12)NCC(F)(F)CO]

(4), wherein the compound of formula (4) is prepared according to the process:

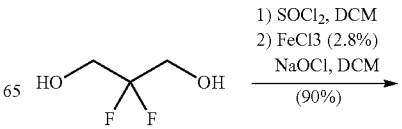

219
-continued
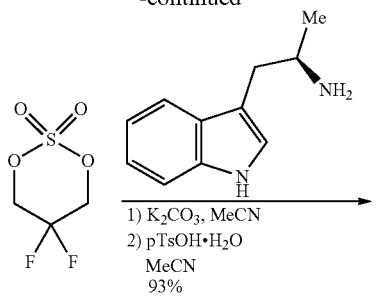
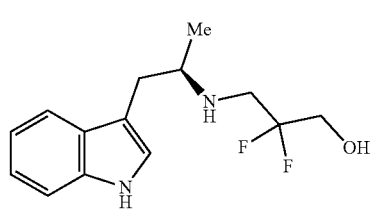
and L-Tartaric Acid in ethanol to yield the compound of formula (B).
71. The process of claim 70, wherein the process further comprises recrystallization of Compound B in methanol and ethanol;
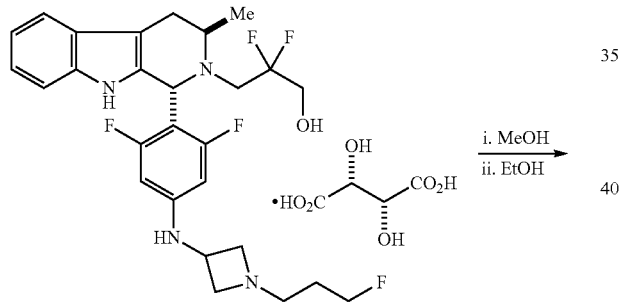
220
-continued
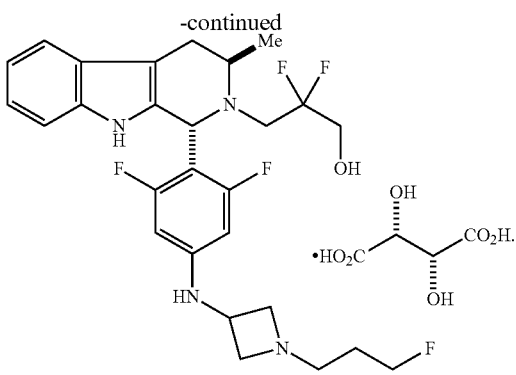
72. The process of claim 70, wherein the process further comprises recrystallization of Compound B in MTBE, water, NaOH and ethanol;
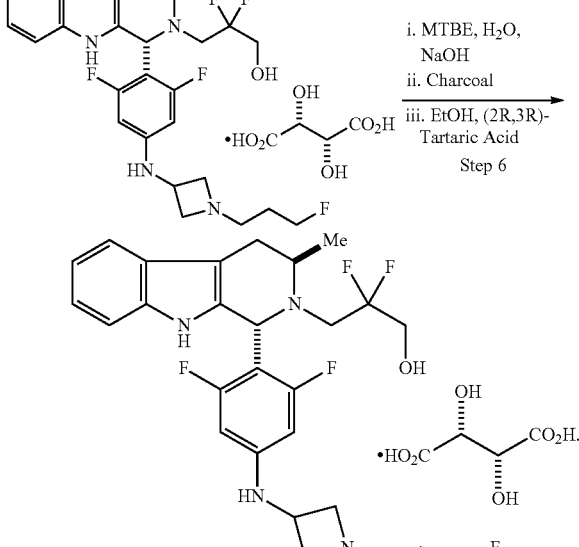
* * * * *

SEQUENCE LISTING

```
<160> NUMBER OF SEQ ID NOS: 4

<210> SEQ ID NO 1
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Phe Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Gly Gly Gly Ile Val Pro Pro Pro Ala Gly
```

```
                225                 230                 235                 240

Tyr Trp Glu Ala Ile Gln Thr Val Leu Asn Lys His Asp Ile Leu Leu
                    245                 250                 255

Val Ala Asp Glu Val Val Thr Gly Phe Gly Arg Leu Gly Thr Met Phe
                260                 265                 270

Gly Ser Asp His Tyr Gly Leu Glu Pro Asp Ile Ile Thr Ile Ala Lys
                275                 280                 285

Gly Leu Thr Ser Ala Tyr Ala Pro Leu Ser Gly Ser Ile Val Ser Asp
            290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
                340                 345                 350

Gly Glu Val Gly Ala Tyr Leu Asn Ala Thr Met Ala Glu Ala Leu Ser
            355                 360                 365

Gln His Ala Asn Val Gly Asp Val Arg Gly Glu Gly Leu Leu Cys Ala
        370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
                420                 425                 430

Pro Phe Cys Leu Thr Arg Ala Glu Ala Asp Gln Val Val Glu Gly Thr
            435                 440                 445

Leu Arg Ala Val Lys Ala Val Leu Gly
            450                 455

<210> SEQ ID NO 2
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
                20                  25                  30

Arg Val Ile Lys Thr Ala Ser Gly Val Phe Ile Glu Asp Arg Asp Gly
            35                  40                  45

Thr Lys Leu Leu Asp Ala Phe Ala Gly Leu Trp Cys Val Asn Val Gly
        50                  55                  60

Tyr Gly Arg Gln Glu Ile Ala Glu Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125
```

-continued

```
Leu Ile Trp Tyr Tyr Asn Asn Ile Leu Gly Arg Pro Glu Lys Lys
            130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
210                 215                 220

Gly Glu Pro Ile Leu Gly Ala Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
        355                 360                 365

Gln His Ala Asn Val Gly Asp Val Arg Gly Glu Gly Leu Leu Cys Ala
370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
        435                 440                 445

Leu Arg Ala Val Lys Ala Val Leu Gly
    450                 455

<210> SEQ ID NO 3
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Leu Lys Asn Asp Gln Leu Asp Gln Trp Asp Arg Asp Asn Phe Phe
1               5                   10                  15
```

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Phe Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ala Phe Val Gly His Gly Thr Glu Ala Ser Ile
            85                  90                  95

Thr Leu Ala Lys Met Ile Leu Asp Arg Ala Pro Lys Asn Met Ser Lys
        100                 105                 110

Val Tyr Phe Gly Leu Gly Gly Ser Asp Ala Asn Glu Thr Asn Val Lys
    115                 120                 125

Leu Ile Trp Tyr Tyr Asn Asn Ile Leu Gly Arg Pro Glu Lys Lys Lys
130                 135                 140

Ile Ile Ser Arg Trp Arg Gly Phe His Gly Ser Gly Leu Val Thr Gly
145                 150                 155                 160

Ser Leu Thr Gly Leu Glu Leu Phe His Lys Lys Phe Asp Leu Pro Val
            165                 170                 175

Glu Gln Val Ile His Thr Glu Ala Pro Tyr Tyr Phe Arg Arg Glu Asp
        180                 185                 190

Leu Asn Gln Thr Glu Glu Gln Phe Val Ala His Cys Val Ala Glu Leu
    195                 200                 205

Glu Ala Leu Ile Glu Arg Glu Gly Ala Asp Thr Ile Ala Ala Phe Ile
210                 215                 220

Gly Glu Pro Ile Leu Gly Ala Gly Gly Met Val Pro Pro Ala Gly
225                 230                 235                 240

Tyr Trp Glu Ala Ile Gln Thr Val Leu Asn Lys His Asp Ile Leu Leu
            245                 250                 255

Val Ala Asp Glu Val Val Thr Gly Phe Gly Arg Leu Gly Thr Met Phe
        260                 265                 270

Gly Ser Asp His Tyr Gly Leu Glu Pro Asp Ile Ile Thr Ile Ala Lys
    275                 280                 285

Gly Leu Thr Ser Ala Tyr Ala Pro Leu Ser Gly Ser Ile Val Ser Asp
290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
            325                 330                 335

Val Ala Asn Leu Lys Leu Leu Asp Glu Leu Asn Leu Val Ser Asn Ala
        340                 345                 350

Gly Glu Val Gly Ala Tyr Leu Asn Ala Thr Met Ala Glu Ala Leu Ser
    355                 360                 365

Gln His Ala Asn Val Gly Asp Val Arg Gly Glu Gly Leu Met Cys Ala
370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
            405                 410                 415

Ile Ile Ala Arg Ala Met Pro Gln Gly Asp Ile Leu Gly Phe Ala Pro
        420                 425                 430

Pro Phe Cys Leu Thr Arg Ala Glu Ala Asp Gln Val Val Glu Gly Thr

```
              435                 440                 445
Leu Arg Ala Val Lys Ala Val Leu Gly
    450                 455

<210> SEQ ID NO 4
<211> LENGTH: 464
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Ala Thr Ile Thr Asn His Met Pro Thr Ala Glu Leu Gln Ala Leu
1               5                   10                  15

Asp Ala Ala His His Leu His Pro Phe Ser Ala Asn Asn Ala Leu Gly
            20                  25                  30

Glu Glu Gly Thr Arg Val Ile Thr Arg Ala Arg Gly Val Trp Leu Asn
        35                  40                  45

Asp Ser Ala Leu Ala Gln Lys Leu Ala Glu Leu Ala Gly Leu Trp Cys
    50                  55                  60

Val Asn Ile Gly Tyr Gly Arg Asp Glu Leu Ala Glu Val Ala Ala Arg
65                  70                  75                  80

Gln Met Arg Glu Leu Pro Tyr Tyr Asn Thr Phe Phe Lys Thr Thr His
                85                  90                  95

Val Pro Ala Ile Ala Leu Ala Gln Lys Leu Ala Glu Leu Ala Pro Gly
            100                 105                 110

Asp Leu Asn His Val Phe Phe Ala Gly Gly Ser Glu Ala Asn Asp
        115                 120                 125

Thr Asn Ile Arg Met Val Arg Thr Tyr Trp Gln Asn Lys Gly Gln Pro
    130                 135                 140

Glu Lys Thr Val Ile Ile Ser Arg Lys Asn Ala Tyr His Gly Ser Thr
145                 150                 155                 160

Val Ala Ser Ser Ala Leu Gly Gly Met Ala Gly Met His Ala Gln Ser
                165                 170                 175

Gly Leu Ile Pro Asp Val His His Ile Asn Gln Pro Asn Trp Trp Ala
            180                 185                 190

Glu Gly Gly Asp Met Asp Pro Glu Glu Phe Gly Leu Ala Arg Ala Arg
        195                 200                 205

Glu Leu Glu Glu Ala Ile Leu Glu Leu Gly Glu Asn Arg Val Ala Ala
    210                 215                 220

Phe Ile Ala Glu Pro Val Gln Gly Ala Gly Gly Val Ile Val Ala Pro
225                 230                 235                 240

Asp Ser Tyr Trp Pro Glu Ile Gln Arg Ile Cys Asp Lys Tyr Asp Ile
                245                 250                 255

Leu Leu Ile Ala Asp Glu Val Val Cys Gly Phe Gly Arg Thr Gly Asn
            260                 265                 270

Trp Phe Gly Thr Gln Thr Met Gly Ile Arg Pro His Ile Met Thr Ile
        275                 280                 285

Ala Lys Gly Leu Ser Ser Gly Tyr Ala Pro Ile Gly Gly Ser Ile Val
    290                 295                 300

Cys Asp Glu Val Ala His Val Ile Gly Lys Asp Glu Phe Asn His Gly
305                 310                 315                 320

Tyr Thr Tyr Ser Gly His Pro Val Ala Ala Ala Val Ala Leu Glu Asn
                325                 330                 335
```

```
Leu Arg Ile Leu Glu Glu Asn Ile Leu Asp His Val Arg Asn Val
        340             345             350

Ala Ala Pro Tyr Leu Lys Glu Lys Trp Glu Ala Leu Thr Asp His Pro
            355             360             365

Leu Val Gly Glu Ala Lys Ile Val Gly Met Met Ala Ser Ile Ala Leu
    370             375             380

Thr Pro Asn Lys Ala Ser Arg Ala Lys Phe Ala Ser Glu Pro Gly Thr
385             390             395             400

Ile Gly Tyr Ile Cys Arg Glu Arg Cys Phe Ala Asn Asn Leu Ile Met
                405             410             415

Arg His Val Gly Asp Arg Met Ile Ile Ser Pro Pro Leu Val Ile Thr
            420             425             430

Pro Ala Glu Ile Asp Glu Met Phe Val Arg Ile Arg Lys Ser Leu Asp
        435             440             445

Glu Ala Gln Ala Glu Ile Glu Lys Gln Gly Leu Met Lys Ser Ala Ala
        450             455             460
```